(12) United States Patent
Shoji et al.

(10) Patent No.: US 12,286,440 B2
(45) Date of Patent: Apr. 29, 2025

(54) PENAM DERIVATIVE OR SALT THEREOF, PHARMACEUTICAL COMPOSITION, AND APPLICATIONS THEREOF

(71) Applicant: FUJIFILM Corporation, Tokyo (JP)

(72) Inventors: Muneo Shoji, Toyama (JP); Kentaro Furuya, Toyama (JP); Kei Matsuura, Toyama (JP); Tomofumi Nakae, Toyama (JP)

(73) Assignee: FUJIFILM Corporation, Tokyo (JP)

( * ) Notice: Subject to any disclaimer, the term of this patent is extended or adjusted under 35 U.S.C. 154(b) by 1142 days.

(21) Appl. No.: 17/063,110

(22) Filed: Oct. 5, 2020

(65) Prior Publication Data

US 2021/0024543 A1    Jan. 28, 2021

Related U.S. Application Data

(63) Continuation of application No. PCT/JP2019/015176, filed on Apr. 5, 2019.

(30) Foreign Application Priority Data

Apr. 6, 2018    (JP) ................. 2018-073568

(51) Int. Cl.
*C07D 499/897* (2006.01)
*A61P 31/04* (2006.01)

(52) U.S. Cl.
CPC .......... *C07D 499/897* (2013.01); *A61P 31/04* (2018.01)

(58) Field of Classification Search
CPC ................... C07D 499/897; C07D 499/70
See application file for complete search history.

(56) References Cited

U.S. PATENT DOCUMENTS

| 5,185,330 A | 2/1993 | Ochiai et al. |
| 5,300,497 A | 4/1994 | Ochiai et al. |

FOREIGN PATENT DOCUMENTS

| JP | 63-183588 A | 7/1988 |
| JP | 4-74182 A | 3/1992 |
| JP | 7-2870 A | 1/1995 |
| JP | 10-130272 A | 5/1998 |
| WO | 2013/052568 A1 | 4/2013 |
| WO | 2017/096472 A1 | 6/2017 |

OTHER PUBLICATIONS

Notice of Reasons for Refusal dated Oct. 12, 2021 from the Japanese Patent Office in Japanese Application No. 2020-512335.
Office Action dated Apr. 1, 2023 in Chinese Application No. 201980024184.6.
Office Action dated Oct. 10, 2022 from the China National Intellectual Property Administration in CN Application No. 201980024184.6.
Office Action dated Oct. 14, 2022 from the Taiwanese Intellectual Property Office in TW Application No. 108111972.
Office Action dated May 31, 2021 from the Australian Intellectual Property Office in AU Application No. 2019249008.
Giske et al., "Clinical and Economic Impact of Common Multidrug-Resistant Gram-Negative Bacilli", Antimicrobial Agents and Chemotherapy, Mar. 2008, vol. 52, No. 3, pp. 813-821 (9 pages total).
Brandt et al., "In silico serine β-lactamases analysis reveals a huge potential resistome in environmental and pathogenic species", Scientific Reports, 2017, vol. 7, No. 43232, pp. 1-13 (13 pages total).
Farrell et al., "Ceftolozane/tazobactam activity tested against Gram-negative bacterial isolates from hospitalised patients with pneumonia in US and European medical centres (2012)", International Journal of Antimicrobial Agents, 2014, vol. 43, pp. 533-539 (7 pages total).
International Search Report issued Jul. 9, 2019 in International Application No. PCT/JP2019/015176.
Written Opinion of the International Searching Authority issued Jul. 9, 2019 in International Application No. PCT/JP2019/015176.
International Preliminary Report on Patentability issued Oct. 6, 2020 in International Application No. PCT/JP2019/015176.

*Primary Examiner* — Susanna Moore
(74) *Attorney, Agent, or Firm* — Sughrue Mion, PLLC

(57) ABSTRACT

An object of the present invention is to provide a compound and a pharmaceutical composition which exhibit strong antibacterial activity against Gram-negative bacteria and drug-resistant Gram-negative bacteria. A compound represented by General Formula [1](the reference signs in Formula have the same definitions as those described in the present specification) or a salt thereof has strong antibacterial activity against Gram-negative bacteria such as *Pseudomonas aeruginosa* and drug-resistant Gram-negative bacteria including multidrug-resistant *Pseudomonas aeruginosa*, and the pharmaceutical composition containing the compound or a salt thereof is useful as an antibacterial agent.

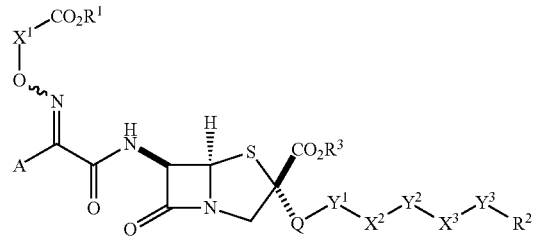

[1]

15 Claims, No Drawings

PENAM DERIVATIVE OR SALT THEREOF, PHARMACEUTICAL COMPOSITION, AND APPLICATIONS THEREOF

CROSS-REFERENCE TO RELATED APPLICATIONS

This application is a Continuation of PCT International Application No. PCT/JP2019/015176 filed on Apr. 5, 2019, which claims priority under 35 U.S.C § 119(a) to Japanese Patent Application No. 2018-073568 filed on Apr. 6, 2018. Each of the above application(s) is hereby expressly incorporated by reference, in its entirety, into the present application.

BACKGROUND OF THE INVENTION

1. Field of the Invention

The present invention relates to a novel penam derivative or a salt thereof exhibiting strong antibacterial activity against Gram-negative bacteria, particularly, *Pseudomonas aeruginosa*, and a pharmaceutical composition containing the novel penam derivative and a salt thereof.

2. Description of the Related Art

β-lactam-based drugs are clinically very important antibacterial agents, and various β-lactam-based drugs have been developed so far. Meanwhile, Gram-negative bacteria highly resistant to many β-lactam-based drugs such as cephalosporin-based drugs and/or carbapenem-based drugs have been isolated. The infections caused by these resistant bacteria have a high fatality rate and tend to result in a long hospital stay for patients, which are major clinical and economical issues (Antimicrobial Agents and Chemotherapy, 2008, No. 52, pp. 813-821).

As a resistance mechanism of β-lactam-based drugs, β-lactamase that decomposes β-lactam-based drugs is known. According to the Ambler's molecular classification method, the β-lactamase is roughly classified into Class A (such as TEM, SHV, CTX-M, KPC, and GES-type β-lactamases), Class B (such as IMP, VIM, and NDM-type β-lactamases), Class C (such as AmpC-type β-lactamase), and class D (OXA-type β-lactamase), which decompose β-lactam-based drugs with different substrate specificities (Scientific Reports, 2017, No. 24, Article No. 43232). Particularly, each type of β-lactamase of class B and KPC, GES, and OXA-type β-lactamases are called carbapenemase, and many of these exhibit high resistance to almost all β-lactam-based drugs including carbapenem-based drugs.

Furthermore, in recent years, *Pseudomonas aeruginosa* strains have been isolated which exhibit high resistance to ceftolozane/tazobactam and ceftazidime/avibactam that are newly developed cephalosporin-based combination medicines (International Journal of Antimicrobial Agents, 2014, No. 43, pp. 533-539).

SUMMARY OF THE INVENTION

Infections caused by multidrug-resistant *Pseudomonas aeruginosa* have few effective therapeutic agents and are a major problem worldwide as intractable diseases.

There is a need for the provision of compounds and pharmaceutical compositions that exhibit strong antibacterial activity against Gram-negative bacteria and drug-resistant Gram-negative bacteria.

Particularly, there is a desperate need for the provision of a compound and a pharmaceutical composition that exhibit strong antibacterial activity against enterobacteria or *Pseudomonas aeruginosa* producing carbapenemase.

Under these circumstances, the inventors of the present invention have conducted intensive studies and have found that a compound represented by General Formula [1] or a salt thereof has excellent solubility in water and exhibits strong antibacterial activity against Gram-negative bacteria such as *Pseudomonas aeruginosa* and drug-resistant Gram-negative bacteria including multidrug-resistant *Pseudomonas aeruginosa*, for example, enterobacteria or *Pseudomonas aeruginosa* producing carbapenemase. Based on this finding, the inventors have accomplished the present invention.

The present invention provides the following.

<1> A compound represented by General Formula [1] or a salt thereof.

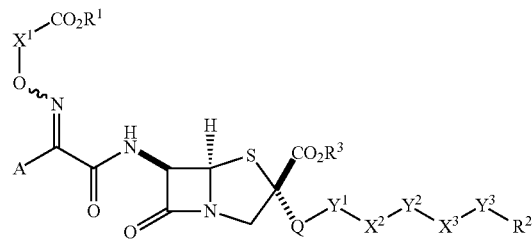

[1]

"In the formula, $R^1$ represents a hydrogen atom or a carboxyl protecting group;

$R^2$ represents an aryl group which may be substituted or a heterocyclic group which may be substituted;

$R^3$ represents a hydrogen atom or a carboxyl protecting group;

$X^1$ represents a $C_{1-6}$ alkylene group which may be substituted, a $C_{2-6}$ alkenylene group which may be substituted, a $C_{2-6}$ alkynylene group which may be substituted, a divalent cyclic hydrocarbon group which may be substituted, or a divalent monocyclic saturated heterocyclic group which may be substituted;

A represents a heterocyclic group which may be substituted;

Q represents a divalent cyclic amino group which may be substituted or a divalent heterocyclic group which may be substituted;

$Y^1$ represents a $C_{1-6}$ alkylene group which may be substituted, a $C_{2-6}$ alkenylene group which may be substituted, a $C_{2-6}$ alkynylene group which may be substituted, a group represented by Formula —N=CH—CH=N—, a group represented by Formula —N=CH—CH=N—O—, a group represented by Formula —N=CH—CH$_2$—, a group represented by Formula —N=CHC(=O)—, a group represented by Formula —NHC(=O)—, a group represented by Formula —NHC(=O)CH$_2$—, a group represented by Formula —NHC(=O)NH—, a group represented by Formula —NHC(=O)NH—O—, a group represented by Formula —NHC(=O)C(=O)NH—, a group represented by Formula —NHC(=O)C(=O)N(OH)—, a group represented by Formula —NHCH$_2$C(=O)—, a group represented by Formula —NHS(=O)$_2$NHC (=O)—, a group represented by Formula —NHC(=O)NHS(=O)$_2$—, or a bond;

X$^2$ represents a group represented by General Formula —NR$^4$— (where R$^4$ represents a hydrogen atom, a carbamoyl group, a C$_{1-6}$ alkyl group which may be substituted, or a hydroxyl group which may be protected), a group represented by General Formula —N$^+$R$^5$R$^6$— (where R$^5$ and R$^6$ are the same as or different from each other and each represent a C$_{1-6}$ alkyl group which may be substituted, or in combination represent a C$_{2-6}$ alkylene group which may be substituted or a C$_{2-6}$ alkenylene group which may be substituted), a group represented by General Formula —NR$^7$—C(=O)—NR$^8$— (where R$^7$ and R$^8$ are the same as or different from each other and each represent a hydrogen atom, a C$_{1-6}$ alkyl group which may be substituted, or a hydroxyl group which may be protected), a divalent cyclic amino group which may be substituted, a divalent heterocyclic group which may be substituted, or a bond;

Y$^2$ represents a C$_{1-6}$ alkylene group which may be substituted, a C2-6 alkenylene group which may be substituted, a C$_{2-6}$ alkynylene group which may be substituted, or a bond;

X$^3$ represents a group represented by General Formula —NR$^9$— (where R$^9$ represents a hydrogen atom, a C$_{1-6}$ alkyl group which may be substituted, or a hydroxyl group which may be protected) or a bond; and Y$^3$ represents a group represented by Formula —C(=O)—, a group represented by Formula —C(=O)—C(=O)—, a group represented by Formula —C(=O)—CH(—OH)—, a group represented by General Formula —C(=O)—C(=NR$^{10}$)— (where R$^{10}$ represents a hydrogen atom, a C$_{1-6}$ alkyl group which may be substituted, a C$_{1-6}$ alkoxy group which may be substituted, a C$_{1-6}$ alkylamino group which may be substituted, a di(C$_{1-6}$ alkyl)amino group which may be substituted, a cyclic amino group which may be substituted, an amino group which may be substituted, an amino group which may be protected, a hydroxyl group which may be protected, a carbamoyl group which may be substituted, a carboxyl group which may be protected, or a ureido group), or a group represents by —N=CR$^{11}$ (where R$^{11}$ represents a hydrogen atom, a carbamoyl group which may be substituted, or a carboxyl group which may be protected".

<2>
The compound or a salt thereof described in <1>, in which R$^2$ represents an aryl group which may be substituted.
<3>
The compound or a salt thereof described in <1> or <2>, in which A represents a monocyclic heterocyclic group which may be substituted.
<4>
The compound or a salt thereof described in any one of <1> to <3>, in which X$^1$ represents a C$_{1-6}$ alkylene group which may be substituted or a divalent cyclic hydrocarbon group which may be substituted.
<5>
The compound or a salt thereof described in any one of <1> to <4>, in which Q represents a divalent heterocyclic group which may be substituted.
<6>
The compound or a salt thereof described in any one of <1> to <5>, in which Y$^1$ represents a C$_{1-6}$ alkylene group which may be substituted, a group represented by Formula —N=CH—CH=N—, a group represented by Formula —N=CH—CH$_2$—, a group represented by Formula —N=CHC(=O)—, a group represented by Formula —NHC(=O)—, a group represented by Formula —NHC(=O)CH$_2$—, a group represented by Formula —NHC(=O)NH—, a group represented by Formula —NHC(=O)NH—O—, a group represented by Formula —NHC(=O)C(=O)NH—, a group represented by Formula —NHCH$_2$C(=O)—, or a bond.
<7>
The compound or a salt thereof described in any one of <1> to <6>, in which X$^2$ represents a group represented by General Formula —NR$^{4a}$— (where R$^{4a}$ represents a hydrogen atom or a carbamoyl group), a group represented by General Formula —N$^+$R$^{5a}$R$^{6a}$— (where R$^{5a}$ and R$^{6a}$ in combination represent a C$_{2-6}$ alkylene group which may be substituted), a group represented by General Formula —NR$^{7a}$—C(=O)—NR$^{8a}$— (where R$^{7a}$ and R$^{8a}$ each represent a hydrogen atom), a divalent cyclic amino group which may be substituted, a divalent heterocyclic group which may be substituted, or a bond.
<8>
The compound or a salt thereof described in any one of <1> to <7>, in which Y$^2$ represents a C$_{1-6}$ alkylene group which may be substituted or a bond.
<9>
The compound or a salt thereof described in any one of <1> to <8>, in which X$^3$ represents a group represented by General Formula —NR$^{9a}$— (where R$^{9a}$ represents a hydrogen atom) or a bond.
<10>
The compound or a salt thereof described in any one of <1> to <9>, in which Y$^3$ represents a group represented by Formula —C(=O)—, a group represented by Formula —C(=O)—C(=O)—, a group represented by General Formula —C(=O)—C(=NR$^{10a}$)— (where R$^{10a}$ represents a C$_{1-6}$ alkoxy group which may be substituted, a hydroxyl group which may be protected, or a ureido group), or a group represented by Formula —N=CR$^{11a}$— (where R$^{11a}$ represents a carbamoyl group which may be substituted or a carboxyl group which may be protected).
<11>
The compound or a salt thereof described in any one of <1> to <10>, in which R$^3$ represents a hydrogen atom.
<12>
The compound or a salt thereof described in any one of <1> to <11>, in which R$^1$ represents a hydrogen atom.
<13>
The compound or a salt thereof described in any one of <1> to <12>, in which R$^2$ represents a phenyl group which may be substituted;
  A represents a monocyclic nitrogen and sulfur-containing heterocyclic group which may be substituted;
  Q represents a divalent monocyclic heterocyclic group which may be substituted;
  Y$^1$ represents a group represented by Formula —NHC(=O)—, a group represented by Formula —NHC(=O)C(=O)NH—, or a bond;
  X$^2$ represents a group represented by General Formula —NR$^{4b}$— (where R$^{4b}$ represents a hydrogen atom) or a bond;
  Y$^2$ represents a C$_{1-3}$ alkylene group or a bond; and
  Y$^3$ represents a group represented by Formula —C(=O)— or a group represented by Formula —C(=O)—C(=O)—.
<14>
The compound or a salt thereof described in <1>, in which the compound is a compound selected from (3R,5R,6R)-6-

((Z)-2-(2-aminothiazol-4-yl)-2-((1-carboxycyclobutoxy)imino)acetamido)-3-(3-(2-(2-chloro-3,4-dihydroxyphenyl)-2-oxoacetamido)-2-oxoimidazolidin-1-yl)-7-oxo-4-thia-1-azabicyclo[3.2.0]heptane-3-carboxylate, (3R,5R,6R)-6-((Z)-2-(2-aminothiazol-4-yl)-2-(((2-carboxypropan-2-yl)oxy)imino)acetamido)-3-(3-(2-(2-chloro-3,4-dihydroxyphenyl)-2-oxoacetamido)-2-oxoimidazolidin-1-yl)-7-oxo-4-thia-1-azabicyclo[3.2.0]heptane-3-carboxylate, (3R,5R,6R)-6-((Z)-2-(2-amino-5-chlorothiazol-4-yl)-2-(((2-carboxypropan-2-yl)oxy)imino)acetamido)-3-(3-(2-(2-chloro-3,4-dihydroxyphenyl)-2-oxoacetamido)-2-oxoimidazolidin-1-yl)-7-oxo-4-thia-1-azabicyclo[3.2.0]heptane-3-carboxylate, (3R,5R,6R)-6-((Z)-2-(2-aminothiazol-4-yl)-2-(((2-carboxypropan-2-yl)oxy)imino)acetamido)-3-((S)-3-(2-(2-chloro-3,4-dihydroxyphenyl)-2-oxoacetamido)-2-oxopyrrolidin-1-yl)-7-oxo-4-thia-1-azabicyclo[3.2.0]heptane-3-carboxylate, (3R,5R,6R)-6-((Z)-2-(2-aminothiazol-4-yl)-2-(((2-carboxypropan-2-yl)oxy)imino)acetamido)-3-((R)-3-(2-(2-chloro-3,4-dihydroxyphenyl)-2-oxoacetamido)-2-oxopyrrolidin-1-yl)-7-oxo-4-thia-1-azabicyclo[3.2.0]heptane-3-carboxylate, (3R,5R,6R)-6-((Z)-2-(2-aminothiazol-4-yl)-2-(((2-carboxypropan-2-yl)oxy)imino)acetamido)-3-(4-(2-(2-chloro-3,4-dihydroxyphenyl)-2-oxoacetatamido)-2,3-dioxopiperazin-1-yl)-7-oxo-4-thia-1-azabicyclo[3.2.0]heptane-3-carboxylate, and (3R,5R,6R)-6-((Z)-2-(2-amino-5-chlorothiazol-4-yl)-2-(((2-carboxypropan-2-yl)oxy)imino)acetamido)-3-(3-(2-(2-(2-chloro-3,4-dihydroxyphenyl)-2-oxoacetyl)hydradienyl)-2-oxoacetamido)-2-oxoimidazolidin-1-yl)-7-oxo-4-thia-1-azabicyclo[3.2.0]heptane-3-carboxylate.

<15>
A pharmaceutical composition containing the compound or a salt thereof described in any one of <1> to <14>.

<A>
A method for treating infections caused by Gram-negative bacteria or drug-resistant Gram-negative bacteria, including administering the compound or a salt thereof described in any one of <1> to <14> to a subject.

<B>
The compound or a salt thereof described in any one of <1> to <14> that is used for treating infections caused by Gram-negative bacteria or drug-resistant Gram-negative bacteria.

<C>
Use of the compound or a salt thereof described in any one of <1> to <14> for manufacturing a pharmaceutical composition.

<D>
Use of the compound or a salt thereof described in any one of <1> to <14> for manufacturing a pharmaceutical composition for treating infections caused by Gram-negative bacteria or drug-resistant Gram-negative bacteria.

The compound or a salt thereof according to an embodiment of the present invention exhibits strong antibacterial activity against Gram-negative bacteria and drug-resistant Gram-negative bacteria such as enterobacteria or *Pseudomonas aeruginosa* producing carbapenemase. Therefore, the compound or a salt thereof is useful as a medicine. The pharmaceutical composition according to an embodiment of the present invention exhibits strong antibacterial activity against Gram-negative bacteria and drug-resistant Gram-negative bacteria.

Furthermore, the pharmaceutical composition according to an embodiment of the present invention is useful for treating infections caused by Gram-negative bacteria or drug-resistant Gram-negative bacteria.

DESCRIPTION OF THE PREFERRED EMBODIMENTS

Hereinafter, the present invention will be specifically described.

In the present specification, unless otherwise specified, "%" means "% by mass".

In the present specification, unless otherwise specified, each term has the following meaning.

The halogen atom means a fluorine atom, a chlorine atom, a bromine atom, or an iodine atom.

The $C_{1-6}$ alkyl group means, for example, a linear or branched $C_{1-6}$ alkyl group such as a methyl, ethyl, propyl, isopropyl, butyl, sec-butyl, isobutyl, tert-butyl, pentyl, isopentyl, or hexyl group.

The $C_{1-3}$ alkyl group means a methyl, ethyl, propyl, or isopropyl group.

The $C_{2-6}$ alkenyl group means, for example, a linear or branched $C_{2-6}$ alkenyl group such as a vinyl, allyl, propenyl, isopropenyl, butenyl, isobutenyl, 1,3-butadienyl, pentenyl, or hexenyl group.

The $C_{2-6}$ alkynyl group means a linear or branched $C_{2-6}$ alkynyl group such as an ethynyl, propynyl, butynyl, pentynyl, or hexynyl group.

The $C_{3-8}$ cycloalkyl group means a $C_{3-8}$ cycloalkyl group such as a cyclopropyl, cyclobutyl, cyclopentyl, or cyclohexyl group.

The aryl group means, for example, a $C_{6-18}$ aryl group such as a phenyl or naphthyl group.

The aryl $C_{1-6}$ alkyl group means, for example, an aryl $C_{1-6}$ alkyl group such as a benzyl, diphenylmethyl, trityl, phenethyl, or naphthylmethyl group.

The $C_{1-6}$ alkylene group means a linear or branched $C_{1-6}$ alkylene group such as a methylene, ethylene, propylene, butylene, or hexylene group.

The $C_{1-3}$ alkylene group means a methylene, ethylene, or propylene group.

The $C_{2-6}$ alkylene group means a linear or branched $C_{1-6}$ alkylene group such as an ethylene, propylene, butylene, or hexylene group.

The $C_{2-6}$ alkenylene group means a linear or branched $C_{2-6}$ alkenylene group such as a vinylene, propenylene, butenylene, or pentenylene group.

The $C_{2-6}$ alkynylene group means a linear or branched $C_{2-6}$ alkynylene group such as an ethynylene, propynylene, butynylene, or pentynylene group.

The $C_{1-6}$ alkoxy group means, for example, a linear or branched $C_{1-6}$ alkyloxy group such as a methoxy, ethoxy, propoxy, isopropoxy, butoxy, isobutoxy, sec-butoxy, tert-butoxy, pentyloxy, or hexyloxy group.

The $C_{1-6}$ alkoxy $C_{1-6}$ alkyl group means, for example, a $C_{1-6}$ alkyloxy $C_{1-6}$ alkyl group such as a methoxymethyl or 1-ethoxyethyl group.

The $C_{2-12}$ alkanoyl group means, for example, a linear or branched $C_{2-12}$ alkanoyl group such as an acetyl, propionyl, valeryl, isovaleryl, or pivaloyl group.

The aroyl group means, for example, a benzoyl or naphthoyl group.

The acyl group means, for example, a formyl group, a succinyl group, a glutaryl group, a maleoyl group, a phthaloyl group, a $C_{2-12}$ alkanoyl group, or an aroyl group.

The $C_{1-6}$ alkoxycarbonyl group means, for example, a linear or branched $C_{1-6}$ alkyloxycarbonyl group such as a methoxycarbonyl, ethoxycarbonyl, isopropoxycarbonyl, tert-butoxycarbonyl, or 1,1-dimethylpropoxycarbonyl group.

The aryl $C_{1-6}$ alkoxycarbonyl group means, for example, an ar $C_{1-6}$ alkyloxycarbonyl group such as a benzyloxycarbonyl or phenethyloxycarbonyl group.

The aryloxycarbonyl group means, for example, a phenyloxycarbonyl or naphthyloxycarbonyl group.

The $C_{1-6}$ alkylamino group means a linear or branched $C_{1-6}$ alkylamino group such as a methylamino, ethylamino, propylamino, isopropylamino, butylamino, sec-butylamino, tert-butylamino, pentylamino, or hexylamino group.

The di($C_{1-6}$ alkyl) amino group means a linear or branched di($C_{1-6}$ alkyl) amino group such as a dimethylamino, diethylamino, dipropylamino, diisopropylamino, dibutylamino, di(tert-butyl) amino, dipentylamino, dihexylamino, (ethyl)(methyl) amino, or (methyl)(propyl) amino group.

The $C_{1-6}$ alkylthio group means, for example, a $C_{1-6}$ alkylthio group such as a methylthio, ethylthio, or propylthio group.

The $C_{1-6}$ alkylsulfonyl group means, for example, a $C_{1-6}$ alkylsulfonyl group such as a methylsulfonyl, ethylsulfonyl, or propylsulfonyl group.

The arylsulfonyl group means, for example, a benzenesulfonyl, p-toluenesulfonyl, or naphthalenesulfonyl group.

The $C_{1-6}$ alkylsulfonyloxy group means, for example, a $C_{1-6}$ alkylsulfonyloxy group such as a methylsulfonyloxy an ethylsulfonyloxy group.

The arylsulfonyloxy group means a benzenesulfonyloxy or p-toluenesulfonyloxy group.

The silyl group means, for example, a trimethylsilyl, triethylsilyl, or tributylsilyl group.

The cyclic amino group means a cyclic amino group which contains one or more nitrogen atoms as hetero atoms forming a ring, such as a aziridinyl, azetidinyl, pyrrolyl, dihydropyrrolyl, pyrrolidinyl, tetrahydropyridyl, piperidinyl, homopiperidinyl, pyrazolyl, pyrazolinyl, pyrazolidinyl, imidazolyl, imidazolinyl, imidazolidinyl, thiazolinyl, thiazolidinyl, dihydrothiadiazolyl, piperazinyl, homopiperazinyl, morpholinyl, homomorpholinyl, or thiomorpholinyl group, and may further contain one or more oxygen atoms or sulfur atoms.

The monocyclic nitrogen-containing heterocyclic group means a monocyclic nitrogen-containing heterocyclic group containing only nitrogen atoms as hetero atoms forming a ring. Examples of the monocyclic nitrogen-containing heterocyclic group include an azetidinyl group; a 5-membered nitrogen-containing heterocyclic group such as a pyrrolidinyl, pyrrolinyl, pyrrolyl, imidazolidinyl, imidazolinyl, imidazolyl, pyrazolidinyl, pyrazolinyl, pyrazolyl, triazolyl, or tetrazolyl group; a 6-membered nitrogen-containing heterocyclic group such as a piperidyl, tetrahydropyridyl, pyridyl, piperazinyl, pyrazinyl, pyridazinyl, pyrimidinyl, tetrahydropyrimidyl, or homopiperazinyl group; a 7-membered nitrogen-containing heterocyclic group such as a homopiperidinyl group; and an 8-membered nitrogen-containing heterocyclic group such as an octahydroazocinyl group.

The monocyclic oxygen-containing heterocyclic group means a monocyclic oxygen-containing heterocyclic group containing only oxygen atoms as hetero atoms forming a ring. Examples of the monocyclic oxygen-containing heterocyclic group include a 5-membered oxygen-containing heterocyclic group such as a tetrahydrofuranyl or furanyl group; and a 6-membered oxygen-containing heterocyclic group such as a tetrahydropyranyl or pyranyl group.

The monocyclic sulfur-containing heterocyclic group means a thienyl group or the like.

The monocyclic nitrogen and oxygen-containing heterocyclic group means a monocyclic nitrogen and oxygen-containing heterocyclic group containing only a nitrogen atom and an oxygen atom as hetero atoms forming a ring. Examples of the monocyclic nitrogen and oxygen-containing heterocyclic group include a 5-membered nitrogen and oxygen-containing heterocyclic group such as an oxazolyl, oxazolidinyl, isoxazolyl, or oxadiazolyl group; and a 6-membered nitrogen and oxygen-containing heterocyclic group such as a homomorpholinyl group.

The monocyclic nitrogen and sulfur-containing heterocyclic group means a monocyclic nitrogen and sulfur-containing heterocyclic group containing only a nitrogen atom and a sulfur atom as hetero atoms forming a ring. Examples of the monocyclic nitrogen and sulfur-containing heterocyclic group include a 5-membered nitrogen and sulfur-containing heterocyclic group such as a thiazolyl, isothiazolyl, or thiadiazolyl group; and a 6-membered nitrogen and sulfur-containing heterocyclic group such as a thiomorpholinyl, 1-oxidethiomorpholinyl, or 1,1-dioxidethiomorpholinyl group.

The monocyclic heterocyclic group means a monocyclic nitrogen-containing heterocyclic group, a monocyclic oxygen-containing heterocyclic group, a monocyclic sulfur-containing heterocyclic group, a monocyclic nitrogen and oxygen-containing heterocyclic group, or a monocyclic nitrogen and sulfur-containing heterocyclic group.

The monocyclic saturated heterocyclic group means a monocyclic heterocyclic group not containing a multiple bond. Examples of the monocyclic saturated heterocyclic group include aziridinyl, azetidinyl, pyrrolidinyl, piperidinyl, imidazolidinyl, pyrazolidinyl, piperazinyl, oxazolidinyl, tetrahydropyrimidyl, tetrahydrofuranyl, tetrahydropyranyl, and morpholinyl groups.

The bicyclic nitrogen-containing heterocyclic group means a bicyclic nitrogen-containing heterocyclic group which contains only nitrogen atoms as hetero atoms forming a ring such as an indolinyl, indolyl, isoindolinyl, isoindolyl, benzimidazolyl, indazolyl, benzotriazolyl, quinolyl, tetrahydroquinolinyl, quinolyl, tetrahydroisoquinolinyl, isoquinolinyl, quinolizinyl, cinnolinyl, phthalazinyl, quinazolinyl, dihydroquinoxalinyl, quinoxalinyl, naphthyridinyl, purinyl, pyrrolopyridinyl, dihydrocyclopentapyridinyl, pteridinyl, or quinuclidinyl group.

The bicyclic oxygen-containing heterocyclic group means a bicyclic oxygen-containing heterocyclic group containing only oxygen atoms as hetero atoms forming a ring such as a 2,3-dihydrobenzofuranyl, benzofuranyl, isobenzofuranyl, chromanyl, chromenyl, isochromanyl, 1,3-benzodioxolyl, 1,3-benzodioxanyl, or 1,4-benzodioxanyl group.

The bicyclic sulfur-containing heterocyclic group means a bicyclic sulfur-containing heterocyclic group containing only sulfur atoms as hetero atoms forming a ring such as a 2,3-dihydrobenzothienyl or benzothienyl group.

The bicyclic nitrogen and oxygen-containing heterocyclic group means a bicyclic nitrogen and oxygen-containing heterocyclic group containing only a nitrogen atom and an oxygen atom as hetero atoms forming a ring such as a benzoxazolyl, benzisoxazolyl, benzoxadiazolyl, benzomorpholinyl, dihydropyranopyridyl, dihydrodioxynopyridyl, or dihydropyridoxazinyl group.

The bicyclic nitrogen and sulfur-containing heterocyclic group means a bicyclic nitrogen and sulfur-containing heterocyclic group containing a nitrogen atom and a sulfur atom as hetero atoms forming a ring such as a benzothiazolyl, benzisothiazolyl, or benzothiadiazolyl group.

The bicyclic heterocyclic group means a bicyclic nitrogen-containing heterocyclic group, a bicyclic oxygen-containing heterocyclic group, a bicyclic sulfur-containing heterocyclic group, a bicyclic nitrogen and oxygen-containing heterocyclic group, or a bicyclic nitrogen and sulfur-containing heterocyclic group.

The heterocyclic group means a monocyclic heterocyclic group or a bicyclic heterocyclic group.

The divalent cyclic hydrocarbon group means a group formed by removing any two hydrogen atoms from cyclic hydrocarbons such as cyclopropane-1,1-diyl, cyclobutane-1,1-diyl, cyclopentane-1,1-diyl, cyclohexane-1,1-diyl, cyclopropane-1,2-diyl, cyclobutane-1,3-diyl, cyclobutene-1,3-diyl, cyclopentane-1,3-diyl, cyclopentene-1,3-diyl, cyclopentadiene-1,3-diyl, cyclohexane-1,3-diyl, cyclohexane-1,4-diyl, cyclohexene-1,3-diyl, cyclohexene-1,4-diyl, cyclohexadiene-1,3-diyl, cyclohexadiene-1,4-diyl, cycloheptane-1,3-diyl, cycloheptene-1,4-diyl, cyclooctane-1,3-diyl, benzene-1,3-diyl, and benzene-1,4-diyl.

The divalent monocyclic saturated heterocyclic group is a divalent group formed by further removing any one hydrogen atom from the aforementioned monocyclic heterocyclic group not containing a multiple bond. For example, the divalent monocyclic saturated heterocyclic group means a group formed by further removing any one hydrogen atom from an aziridinyl, azetidinyl, pyrrolidinyl, piperidinyl, imidazolidinyl, pyrazolidinyl, piperazinyl, tetrahydrofuranyl, tetrahydropyranyl, or morpholinyl group, and the like.

The divalent heterocyclic group is a divalent group formed by further removing any one hydrogen atom from the aforementioned heterocyclic group. The divalent heterocyclic group includes a divalent monocyclic heterocyclic group and a divalent bicyclic heterocyclic group.

The divalent monocyclic heterocyclic group is a divalent group formed by further removing any one hydrogen atom from the aforementioned monocyclic heterocyclic group. The divalent monocyclic heterocyclic group includes a divalent monocyclic nitrogen-containing heterocyclic group, a divalent monocyclic oxygen-containing heterocyclic group, a divalent monocyclic sulfur-containing heterocyclic group, a divalent monocyclic nitrogen and oxygen-containing heterocyclic group, and a divalent monocyclic nitrogen and sulfur-containing heterocyclic group.

The divalent bicyclic heterocyclic group is a divalent group formed by further removing any one hydrogen atom from the aforementioned bicyclic heterocyclic group. The divalent bicyclic heterocyclic group includes a divalent bicyclic nitrogen-containing heterocyclic group, a divalent bicyclic oxygen-containing heterocyclic group, a divalent bicyclic sulfur-containing heterocyclic group, a divalent bicyclic nitrogen and oxygen-containing heterocyclic group, and a divalent bicyclic nitrogen and sulfur-containing heterocyclic group.

The divalent cyclic amino group is a divalent group formed by further removing any one hydrogen atom from the aforementioned cyclic amino group. Examples of the divalent cyclic amino group include a divalent group formed by removing any two hydrogen atoms from aziridine, azetidine, pyrrole, dihydropyrrole, pyrrolidine, tetrahydropyridine, piperidine, homopiperidine, pyrazolyl, pyrazoline, pyrazolidine, imidazole, imidazoline, imidazolidine, thiazoline, thiazolidine, dihydrothiadiazole, piperazine, homopiperazine, morpholine, homomorpholine, and thiomorpholine.

Examples of the leaving group include a halogen atom, a $C_{1-6}$ alkylsulfonyloxy group, an arylsulfonyloxy group, and an imidazole group. The $C_{1-6}$ alkylsulfonyloxy group, the arylsulfonyloxy group, or the imidazole group may have a substituent.

The hydroxyl protecting group includes all groups that can be used as a protecting group of general hydroxyl groups. Examples of the hydroxyl protecting group include the groups described in "Protective Groups in Organic Synthesis, W. Greene et al., 4th Edition, pp. 16-299, 2007, John Wiley & Sons, INC". Specifically, examples thereof include a $C_{1-6}$ alkyl group, a $C_{2-6}$ alkenyl group, an aryl $C_{1-6}$ alkyl group, a $C_{1-6}$ alkoxy $C_{1-6}$ alkyl group, an acyl group, a $C_{1-6}$ alkoxycarbonyl group, an aryl $C_{1-6}$ alkoxycarbonyl group, a $C_{1-6}$ alkylsulfonyl group, an arylsulfonyl group, a silyl group, a tetrahydrofuranyl group, and a tetrahydropyranyl group. These groups may be substituted with one or more groups selected from the substituent group A1.

The amino protecting group includes all groups that can be used as a protecting group of general amino groups. Examples of the amino protecting group include the groups described in "Protective Groups in Organic Synthesis, W. Greene et al., 4th Edition, pp. 696-926, 2007, John Wiley & Sons, INC". Specifically, examples thereof include an aryl $C_{1-6}$ alkyl group, a $C_{1-6}$ alkoxy $C_{1-6}$ alkyl group, an acyl group, a $C_{1-6}$ alkoxycarbonyl group, an aryl $C_{1-6}$ alkoxycarbonyl group, an aryloxycarbonyl group, a $C_{1-6}$ alkylsulfonyl group, an arylsulfonyl group, and a silyl group. These groups may be substituted with one or more groups selected from the substituent group A1.

The imino protecting group includes all groups that can be used as a protecting group of general imino groups. Examples of the imino protecting group include the groups described in "Protective Groups in Organic Synthesis, W. Greene et al., 4th Edition, pp. 696-868, 2007, John Wiley & Sons, INC". Specifically, examples thereof include an aryl $C_{1-6}$ alkyl group, a $C_{1-6}$ alkoxy $C_{1-6}$ alkyl group, an acyl group, a $C_{1-6}$ alkoxycarbonyl group, an aryl $C_{1-6}$ alkoxycarbonyl group, an aryloxycarbonyl group, a $C_{1-6}$ alkylsulfonyl group, an arylsulfonyl group, and a silyl group. These groups may be substituted with one or more groups selected from the substituent group A1.

The carboxyl protecting group includes all groups that can be used as a protecting group of general carboxyl groups. Examples of the carboxyl protecting group include the groups described in "Protective Groups in Organic Synthesis, W. Greene et al., 4th Edition, pp. 533-643, 2007, John Wiley & Sons, INC". Specifically, examples thereof include a $C_{1-6}$ alkyl group, a $C_{2-6}$ alkenyl group, an aryl $C_{1-6}$ alkyl group, a $C_{1-6}$ alkoxy $C_{1-6}$ alkyl group, and a silyl group. These groups may be substituted with one or more groups selected from the substituent group A1.

Examples of aliphatic hydrocarbons include pentane, hexane, cyclohexane, heptane, and decahydronaphthalene.

Examples of halogenated hydrocarbons include methylene chloride, chloroform, and dichloroethane.

Examples of alcohols include methanol, ethanol, propanol, 2-propanol, butanol, and 2-methyl-2-propanol.

Examples of ethers include diethyl ether, diisopropyl ether, dioxane, tetrahydrofuran, anisole, ethylene glycol dimethyl ether, diethylene glycol dimethyl ether, and diethylene glycol diethyl ether.

Examples of ketones include acetone, 2-butanone, and 4-methyl-2-pentanone.

Examples of esters include methyl acetate, ethyl acetate, propyl acetate, and butyl acetate.

Examples of amides include N,N-dimethylformamide, N,N-dimethylacetamide, and 1-methyl-2-pyrrolidone.

Examples of nitriles include acetonitrile and propionitrile.

Examples of aromatic hydrocarbons include benzene, toluene, and xylene.

In the present specification, the substituent group means the following.

Substituent group A1:
a hydrogen atom,
a halogen atom,
a cyano group,
a nitro group,
an oxo group,
a $C_{1-6}$ alkyl group which may be substituted with one or more groups selected from a substituent group B2,
a $C_{2-6}$ alkenyl group which may be substituted with one or more groups selected from the substituent group B2,
a $C_{2-6}$ alkynyl group which may be substituted with one or more groups selected from the substituent group B2,
a $C_{1-6}$ alkoxy group which may be substituted with one or more groups selected from the substituent group B2,
an aryloxy group which may be substituted with one or more groups selected from a substituent group B1,
an acyl group which may be substituted with one or more groups selected from the substituent group B1,
a $C_{1-6}$ alkylamino group which may be substituted with one or more groups selected from the substituent group B2,
a di($C_{1-6}$ alkyl)amino group which may be substituted with one or more groups selected from the substituent group B2,
an imino group which may be protected or substituted with one or more groups selected from the substituent group B1,
a $C_{1-6}$ alkylthio group which may be substituted with one or more groups selected from the substituent group B2,
an arylthio group which may be substituted with one or more groups selected from the substituent group B1,
a $C_{1-6}$ alkylsulfonyl group which may be substituted with one or more groups selected from the substituent group B2,
an arylsulfonyl group which may be substituted with one or more groups selected from the substituent group B1,
a $C_{3-8}$ cycloalkyl group which may be substituted with one or more groups selected from the substituent group B1,
an aryl group which may be substituted with one or more groups selected from the substituent group B1,
a heterocyclic group which may be substituted with one or more groups selected from the substituent group B1,
a carbamoyl group which may be substituted with one or more groups selected from the substituent group B1,
a sulfamoyl group which may be substituted with one or more groups selected from the substituent group B1,
a hydroxyl group which may be protected,
an amino group which may be protected, and
a carboxyl group which may be protected.
Substituent group A2:
a hydrogen atom,
a halogen atom,
a cyano group,
a nitro group,
an oxo group,
a $C_{1-6}$ alkoxy group which may be substituted with one or more groups selected from the substituent group B2,
an aryloxy group which may be substituted with one or more groups selected from a substituent group B1,
an acyl group which may be substituted with one or more groups selected from the substituent group B1,
a $C_{1-6}$ alkylamino group which may be substituted with one or more groups selected from the substituent group B2,
a di($C_{1-6}$ alkyl)amino group which may be substituted with one or more groups selected from the substituent group B2,
a $C_{1-6}$ alkylthio group which may be substituted with one or more groups selected from the substituent group B2,
an arylthio group which may be substituted with one or more groups selected from the substituent group B1,
a $C_{1-6}$ alkylsulfonyl group which may be substituted with one or more groups selected from the substituent group B2,
an arylsulfonyl group which may be substituted with one or more groups selected from the substituent group B1,
a $C_{3-8}$ cycloalkyl group which may be substituted with one or more groups selected from the substituent group B1,
an aryl group which may be substituted with one or more groups selected from the substituent group B1,
a heterocyclic group which may be substituted with one or more groups selected from the substituent group B1,
a carbamoyl group which may be substituted with one or more groups selected from the substituent group B1,
a sulfamoyl group which may be substituted with one or more groups selected from the substituent group B1,
a hydroxyl group which may be protected,
an amino group which may be protected, and
a carboxyl group which may be protected.
Substituent group B1:
a hydrogen atom,
a halogen atom,
a cyano group,
a nitro group,
an oxo group,
a $C_{1-6}$ alkyl group which may be substituted with one or more groups selected from a substituent group C,
a $C_{2-6}$ alkenyl group which may be substituted with one or more groups selected from the substituent group C,
a $C_{2-6}$ alkynyl group which may be substituted with one or more groups selected from the substituent group C,
a $C_{1-6}$ alkoxy group which may be substituted with one or more groups selected from the substituent group C,
an aryloxy group which may be substituted with one or more groups selected from the substituent group C,
an acyl group which may be substituted with one or more groups selected from the substituent group C,
a $C_{1-6}$ alkylamino group which may be substituted with one or more groups selected from the substituent group C,
a di($C_{1-6}$ alkyl)amino group which may be substituted with one or more groups selected from the substituent group C,
a $C_{1-6}$ alkylthio group which may be substituted with one or more groups selected from the substituent group C,
an arylthio group which may be substituted with one or more groups selected from the substituent group C,
a $C_{1-6}$ alkylsulfonyl group which may be substituted with one or more groups selected from the substituent group C,
an arylsulfonyl group which may be substituted with one or more groups selected from the substituent group C,
a $C_{3-8}$ cycloalkyl group which may be substituted with one or more groups selected from the substituent group C,
an aryl group which may be substituted with one or more groups selected from the substituent group C,
a heterocyclic group which may be substituted with one or more groups selected from the substituent group C, a carbamoyl group which may be substituted with one or more groups selected from the substituent group C,
a sulfamoyl group which may be substituted with one or more groups selected from the substituent group C,
a hydroxyl group which may be protected,
an amino group which may be protected, and
a carboxyl group which may be protected.
Substituent group B2:
a hydrogen atom,
a halogen atom,
a cyano group,
a nitro group,
an oxo group,
a $C_{1-6}$ alkoxy group which may be substituted with one or more groups selected from the substituent group C,
an aryloxy group which may be substituted with one or more groups selected from the substituent group C,
an acyl group which may be substituted with one or more groups selected from the substituent group C,
a $C_{1-6}$ alkylamino group which may be substituted with one or more groups selected from the substituent group C,
a di($C_{1-6}$ alkyl)amino group which may be substituted with one or more groups selected from the substituent group C,
a $C_{1-6}$ alkylthio group which may be substituted with one or more groups selected from the substituent group C,
an arylthio group which may be substituted with one or more groups selected from the substituent group C,
a $C_{1-6}$ alkylsulfonyl group which may be substituted with one or more groups selected from the substituent group C,
an arylsulfonyl group which may be substituted with one or more groups selected from the substituent group C,
a $C_{3-8}$ cycloalkyl group which may be substituted with one or more groups selected from the substituent group C,
an aryl group which may be substituted with one or more groups selected from the substituent group C,
a heterocyclic group which may be substituted with one or more groups selected from the substituent group C,
a carbamoyl group which may be substituted with one or more groups selected from the substituent group C,
a sulfamoyl group which may be substituted with one or more groups selected from the substituent group C,
a hydroxyl group which may be protected,
an amino group which may be protected, and
a carboxyl group which may be protected.
Substituent group C:
a halogen atom,
a cyano group,
a carbamoyl group,
a $C_{1-6}$ alkyl group,
a $C_{1-6}$ alkoxy group,
an amino group which may be protected, and
an imino group which may be protected,
a hydroxyl group which may be protected,
a carboxyl group which may be protected.

The $C_{1-6}$ alkylene group, the $C_{2-6}$ alkenylene group, and the $C_{2-6}$ alkynylene group represented by $X^1$, $Y^1$, and $Y^2$ may be substituted with one or more groups selected from the substituent group A2.

The $C_{1-6}$ alkyl group represented by $R^4$, $R^5$, $R^6$, $R^7$, $R^8$, $R^9$, and $R^{10}$ may be substituted with one or more groups selected from the substituent group A2.

The $C_{2-6}$ alkylene and $C_{2-6}$ alkenylene groups that $R^5$ and $R^6$ form in combination may be substituted with one or more groups selected from the substituent group A1.

The $C_{2-6}$ alkylene group that $R^{5a}$ and $R^{6a}$ form in combination may be substituted with one or more groups selected from the substituent group A1.

The $C_{1-6}$ alkoxy group, the $C_{1-6}$ alkylamino group, the di($C_{1-6}$ alkyl)amino group, and the amino group represented by $R^{10}$ may be substituted with one or more groups selected from the substituent group A2.

The $C_{1-6}$ alkoxy group represented by $R^{10a}$ may be substituted with one or more groups selected from the substituent group A2.

The cyclic amino group represented by $R^{10}$ may be substituted with one or more groups selected from the substituent group A1.

The carbamoyl group represented by $R^{10}$ and $R^{11}$ may be substituted with one or more groups selected from the substituent group A1.

The aryl group and the heterocyclic group represented by $R^2$ may be substituted with one or more groups selected from the substituent group A1.

The heterocyclic group represented by A may be substituted with one or more groups selected from the substituent group A1.

The divalent cyclic hydrocarbon group represented by $X^1$ may be substituted with one or more groups selected from the substituent group A1.

The divalent monocyclic saturated heterocyclic group represented by $X^1$ may be substituted with one or more groups selected from the substituent group A1.

The divalent heterocyclic group and the divalent cyclic amino group represented by $X^2$ and Q may be substituted with one or more groups selected from the substituent group A1.

As the compound according to the embodiment of the present invention, for example, the following compounds are preferable.

A compound in which $R^1$ represents a hydrogen atom is preferable.

A compound in which $R^2$ represents an aryl group that may be substituted is preferable, and a compound in which $R^2$ represents a phenyl group that may be substituted is more preferable.

As the substituent of the aryl group or the heterocyclic group represented by $R^2$, one or more groups selected from a halogen atom and a hydroxyl group which may be protected are preferable.

A compound in which $R^3$ represents a hydrogen atom is preferable.

$X^1$ is preferably a $C_{1-6}$ alkylene group which may be substituted or a divalent cyclic hydrocarbon group which may be substituted, and more preferably a $C_{1-3}$ alkylene group which may be substituted or a divalent cyclic hydrocarbon group which may be substituted.

A is preferably a compound that is a monocyclic heterocyclic group which may be substituted, more preferably a monocyclic nitrogen-containing heterocyclic group which may be substituted or a monocyclic nitrogen and sulfur-containing heterocyclic group which may be substituted, even more preferably a monocyclic nitrogen and sulfur-containing heterocyclic group, still more preferably 2-amino-5-chlorothiazol-4-yl, 5-amino-1,2,4-thiadiazole-3-yl, or 2-aminothiazol-4-yl, and particularly preferably 2-aminothiazol-4-yl.

Q is preferably a divalent heterocyclic group which may be substituted, more preferably a divalent monocyclic heterocyclic group which may be substituted, even more preferably a divalent imidazolidine group, a divalent piperazine group, a divalent pyrrolidine group, or a divalent oxazolidine group which may be substituted, and still more preferably a divalent imidazolidine group, a divalent piperazine group, or a divalent pyrrolidine group which may be substituted.

Q is preferably, for example, a 2-oxoimidazolidin-1-yl group, a 2,3-dioxopiperazin-1-yl group, a 2-oxopyrrolidin-1-yl group, or a 2-oxooxazolidin-3-yl group.

$Y^1$ is preferably a $C_{1-6}$ alkylene group which may be substituted, a group represented by Formula —N=CH—CH=N—, a group represented by Formula —N=CH—CH=N—O—, a group represented by —N=CH—CH$_2$—, a group represented by Formula —N=CHC(=O)—, a group represented by Formula —NHC(=O)—, a group represented by Formula —NHC(=O)CH$_2$, a group represented by Formula —NHC(=O)NH—, a group represented by Formula —NHC(=O)NH—O—, a group represented by Formula —NHC(=O)C(=O)NH—, a group represented by Formula —NHCH$_2$C(=O)—, a group represented by Formula —NHS(=O)$_2$NHC(=O)—, a group represented by Formula —NHC(=O)NHS(=O)$_2$—, or a bond, more preferably a $C_{1-6}$ alkylene group which may be substituted, a group represented by Formula —N=CH—CH=N—, a group represented by Formula —N=CH—CH$_2$—, a group represented by Formula —N=CHC(=O)—, a group represented by Formula —NHC(=O)—, a group represented by Formula —NHC(=O)CH$_2$—, a group represented by Formula —NHC(=O)NH—, a group represented by Formula —NHC(=O)NH—O—, a group represented by Formula —NHC(=O)C(=O)NH—, a group represented by Formula —NHCH$_2$C(=O)—, or a bond, and even more preferably a group represented by formula —NHC(=O)—, a group represented by formula —NHC(=O)C(=O)NH—, or a bond.

$X^2$ is preferably a group represented by General Formula —NR$^{4a}$— (where R$^{4a}$ represents a hydrogen atom or a carbamoyl group), a group represented by General Formula —N$^+$R$^{5a}$R$^{6a}$— (where R$^{5a}$ and R$^{6a}$ in combination represent a $C_{2-6}$ alkylene group which may be substituted), a group represented by General Formula —NR$^{7a}$—C(=O)—NR$^{8a}$— (where R$^{7a}$ and R$^{8a}$ each represent a hydrogen atom), a divalent cyclic amino group which may be substituted, a divalent heterocyclic group which may be substituted, or a bond, and more preferably a group represented by General Formula —NR$^{4b}$— (where R$^{4b}$ represents a hydrogen atom) or a bond.

$Y^2$ is preferably a $C_{1-6}$ alkylene group which may be substituted or a bond, and more preferably a $C_{1-3}$ alkylene group or a bond.

$X^3$ is preferably a group represented by General Formula —NR$^{9a}$— (where R$^{9a}$ represents a hydrogen atom) or a bond.

$Y^3$ is preferably a group represented by Formula —C(=O)—, a group represented by Formula —C(=O)—C(=O)—, a group represented by General Formula —C(=O)—C(=NR$^{10a}$)— (where R$^{10a}$ represents a $C_{1-6}$ alkoxy group which may be substituted, a hydroxyl group which may be protected, or a ureido group), or a group represented by Formula —N=CR$^{11a}$— (where R$^{11a}$ represents a carbamoyl group which may be substituted or a carboxyl group which may be protected), and more preferably a group represented by Formula —C(=O)— or a group represented by Formula —C(=O)—C(=O)—.

More specifically, the following compounds are preferable.

(3R,5R,6R)-6-((Z)-2-(2-aminothiazol-4-yl)-2-(((2-carboxypropan-2-yl)oxy)imino)acetamido)-3-(3-(2-chloro-3,4-dihydroxybenzamido)-2-oxoimidazolidin-1-yl)-7-oxo-4-thia-1-azabicyclo[3.2.0]heptane-3-carboxylate (compound of Example 2)

(3R,5R,6R)-6-((Z)-2-(2-aminothiazol-4-yl)-2-((1-carboxycyclopropoxy)imino)acetamido)-3-(3-(2-chloro-3,4-dihydroxybenzamido)-2-oxoimidazolidin-1-yl)-7-oxo-4-thia-1-azabicyclo[3.2.0]heptane-3-carboxylate (compound of Example 8)

(3R,5R,6R)-6-((Z)-2-(2-aminothiazol-4-yl)-2-((1-carboxycyclobutoxy)imino)acetamido)-3-(3-(2-(2-chloro-3,4-dihydroxyphenyl)-2-oxoacetamido)-2-oxoimidazolidin-1-yl)-7-oxo-4-thia-1-azabicyclo[3.2.0]heptane-3-carboxylate (compound of Example 19)

(3R,5R,6R)-6-((Z)-2-(2-aminothiazol-4-yl)-2-(((2-carboxypropan-2-yl)oxy)imino)acetamido)-3-(3-(2-(2-chloro-3,4-dihydroxyphenyl)-2-oxoacetamido)-2-oxoimidazolidin-1-yl)-7-oxo-4-thia-1-azabicyclo[3.2.0]heptane-3-carboxylate (compound of Example 20)

(3R,5R,6R)-6-((Z)-2-(2-aminothiazol-4-yl)-2-((1-carboxycyclopropoxy)imino)acetamido)-3-(3-(2-(2-chloro-3,4-dihydroxyphenyl)-2-oxoacetamido)-2-oxoimidazolidin-1-yl)-7-oxo-4-thia-1-azabicyclo[3.2.0]heptane-3-carboxylate (compound of Example 21)

(3R,5R,6R)-6-((Z)-2-(2-amino-5-chlorothiazol-4-yl)-2-(((2-carboxypropan-2-yl)oxy)imino)acetamido)-3-(3-(2(2-chloro-3,4-dihydroxyphenyl)-2-oxoacetamido)-2-oxoimidazolidin-1-yl)-7-oxo-4-thia-1-azabicyclo[3.2.0]heptane-3-carboxylate (compound of Example 22)

(3R,5R,6R)-6-((Z)-2-(5-amino-1,2,4-thiadiazol-3-yl)-2-(((2-carboxypropan-2-yl)oxy)imino)acetamido)-3-(3-(2-(2-chloro-3,4-dihydroxyphenyl)-2-oxoacetamido)-2-oxoimidazolidin-1-yl)-7-oxo-4-thia-1-azabicyclo[3.2.0]heptane-3-carboxylate (compound of Example 23)

(3R,5R,6R)-6-((Z)-2-(2-aminothiazol-4-yl)-2-(((2-carboxypropan-2-yl)oxy)imino)acetamido)-3-(4-(2-(2-chloro-3,4-dihydroxyphenyl)-2-oxoacetamido)-5-oxo-4,5-dihydro-1H-1,2,4-triazol-1-yl)-7-oxo-4-thia-1-azabicyclo[3.2.0]heptane-3-carboxylate (compound of Example 26)

(3R,5R,6R)-6-((Z)-2-(2-aminothiazol-4-yl)-2-(((2-carboxypropan-2-yl)oxy)imino)acetamido)-3-(3-(3-(2-chloro-3,4-dihydroxybenzamido)propanamido)-2-oxoimidazolidin-1-yl)-7-oxo-4-thia-1-azabicyclo[3.2.0]heptane-3-carboxylate (compound of Example 28)

(3R,5R,6R)-6-((Z)-2-(2-aminothiazol-4-yl)-2-(((2-carboxypropan-2-yl)oxy)imino)acetamido)-3-(3-2-(2-(2-chloro-3,4-dihydroxyphenyl)-2-oxoacetamido)acetamido)-2-oxoimidazolidin-1-yl)-7-oxo-4-thia-1-azabicyclo[3.2.0]heptane-3-carboxylate (compound of Example 29)

(3R,5R,6R)-6-((Z)-2-(2-aminothiazol-4-yl)-2-(((2-carboxypropan-2-yl)oxy)imino)acetamido)-3-(3-(3-(2-(2-chloro-3,4-dihydroxyphenyl)-2-oxoacetamido)propanamido)-2-oxoimidazolidin-1-yl)-7-oxo-4-thia-1-azabicyclo[3.2.0]heptane-3-carboxylate (compound of Example 30)

(3R,5R,6R)-6-((Z)-2-(2-aminothiazol-4-yl)-2-((1-carboxycyclopropoxy)imino)acetamido)-3-(3-(3-(2-(2-chloro-3,4-dihydroxyphenyl)-2-oxoacetamido)propanamido)-2-oxoimidazolidin-1-yl)-7-oxo-4-thia-1-azabicyclo[3.2.0]heptane-3-carboxylate (compound of Example 31)

(3R,5R,6R)-6-((Z)-2-(2-aminothiazol-4-yl)-2-(((2-carboxypropan-2-yl)oxy)imino)acetamido)-3-((S)-(3-(((E)-2-(2-chloro-3,4-dihydroxybenzamido)ethylidene)amino)-5-methyl-2-oxoimidazolidin-1-yl)-7-oxo-4-thia-1-azabicyclo[3.2.0]heptane-3-carboxylate (compound of Example 45)

- (3R,5R,6R)-6-((Z)-2-(2-aminothiazol-4-yl)-2-(((2-carboxypropan-2-yl)oxy)imino)acetamido)-3-((S)-(3-(((E)-2-(2-(2-chloro-3,4-dihydroxyphenyl)-2-oxoacetamido)ethylidene)amino)-5-methyl-2-oxoimidazolidin-1-yl)-7-oxo-4-thia-1-azabicyclo[3.2.0]heptane-3-carboxylate (compound of Example 47)
- (3R,5R,6R)-6-((Z)-2-(2-aminothiazol-4-yl)-2-(((2-carboxypropan-2-yl)oxy)imino)acetamido)-3-(3-(((1E,2E)-2-(2-((2-(2-chloro-3,4-dihydroxybenzamido)ethyl)carbamoyl)hydrazono)ethylidene)amino)-2-oxoimidazolidin-1-yl)-7-oxo-4-thia-1-azabicyclo[3.2.0]heptane-3-carboxylate (compound of Example 53)
- (3R,5R,6R)-6-((Z)-2-(2-aminothiazol-4-yl)-2-(((2-carboxypropan-2-yl)oxy)imino)acetamido)-3-(3-(2-((2-(2-chloro-3,4-dihydroxybenzamido)ethyl)amino)-2-oxoacetamido)-2-oxoimidazolidin-1-yl)-7-oxo-4-thia-1-azabicyclo[3.2.0]heptane-3-carboxylate (compound of Example 68)
- (3R,5R,6R)-6-((Z)-2-(2-aminothiazol-4-yl)-2-(((2-carboxypropan-2-yl)oxy)imino)acetamido)-3-(5-((2-chloro-3,4-dihydroxybenzamido)methyl)-2-oxooxazolidin-3-yl)-7-oxo-4-thia-1-azabicyclo[3.2.0]heptane-3-carboxylate (compound of Example 73)
- (3R,5R,6R)-6-((Z)-2-(2-aminothiazol-4-yl)-2-(((2-carboxypropan-2-yl)oxy)imino)acetamido)-3-(4-((2-chloro-3,4-dihydroxybenzamido)methyl)-1H-1,2,3-triazol-1-yl)-7-oxo-4-thia-1-azabicyclo[3.2.0]heptane-3-carboxylate (compound of Example 74)
- (3R,5R,6R)-6-((Z)-2-(2-amino-5-chlorothiazol-4-yl)-2-((1-carboxycyclopropoxy)imino)acetamido)-3-(3-(2-(2-chloro-3,4-dihydroxyphenyl)-2-oxoacetamido)-2-oxoimidazolidin-1-yl)-7-oxo-4-thia-1-azabicyclo[3.2.0]heptane-3-carboxylate (compound of Example 76)
- (3R,5R,6R)-6-((Z)-2-(2-amino-5-chlorothiazol-4-yl)-2-((1-carboxycyclobutoxy)imino)acetamido)-3-(3-(2-(2-chloro-3,4-dihydroxyphenyl)-2-oxoacetamido)-2-oxoimidazolidin-1-yl)-7-oxo-4-thia-1-azabicyclo[3.2.0]heptane-3-carboxylate (compound of Example 78)
- (3R,5R,6R)-6-((Z)-2-(2-aminothiazol-4-yl)-2-(((2-carboxypropan-2-yl)oxy)imino)acetamido)-3-(4-(2-(2-chloro-3,4-dihydroxyphenyl)-2-oxoacetamido)-2,5-dioxopiperazin-1-yl)-7-oxo-4-thia-1-azabicyclo[3.2.0]heptane-3-carboxylate (compound of Example 82)
- (3R,5R,6R)-6-((Z)-2-(2-aminothiazol-4-yl)-2-(((2-carboxypropan-2-yl)oxy)imino)acetamido)-3-(3-(2,5-dichloro-3,4-dihydroxybenzamido)-2-oxoimidazolidin-1-yl)-7-oxo-4-thia-1-azabicyclo[3.2.0]heptane-3-carboxylate (compound of Example 83)
- (3R,5R,6R)-6-((Z)-2-(2-aminothiazol-4-yl)-2-(((2-carboxypropan-2-yl)oxy)imino)acetamido)-3-((S)-3-(2-(2-chloro-3,4-dihydroxyphenyl)-2-oxoacetamido)-2-oxopyrrolidin-1-yl)-7-oxo-4-thia-1-azabicyclo[3.2.0]heptane-3-carboxylate (compound of Example 84)
- (3R,5R,6R)-6-((Z)-2-(2-aminothiazol-4-yl)-2-(((2-carboxypropan-2-yl)oxy)imino)acetamido)-3-((R)-3-(2-(2-chloro-3,4-dihydroxyphenyl)-2-oxoacetamido)-2-oxopyrrolidin-1-yl)-7-oxo-4-thia-1-azabicyclo[3.2.0]heptane-3-carboxylate (compound of Example 85)
- (3R,5R,6R)-6-((Z)-2-(2-aminothiazol-4-yl)-2-(((2-carboxypropan-2-yl)oxy)imino)acetamido)-3-(3-(-2-(2-chloro-3,4-dihydroxyphenyl)-2-oxoacetamido)-2-oxotetrahydropyrimidin-1(2H)-yl)-7-oxo-4-thia-1-azabicyclo[3.2.0]heptane-3-carboxylate (compound of Example 86)
- (3R,5R,6R)-6-((Z)-2-(2-aminothiazol-4-yl)-2-(((2-carboxypropan-2-yl)oxy)imino)acetamido)-3-(3-(2-(2-(2-chloro-3,4-dihydroxyphenyl)-2-oxoacetyl)hydradienyl)-2-oxoacetamido)-2-oxoimidazolidin-1-yl)-7-oxo-4-thia-1-azabicyclo[3.2.0]heptane-3-carboxylate (compound of Example 88)
- (3R,5R,6R)-6-((Z)-2-(2-aminothiazol-4-yl)-2-(((2-carboxypropan-2-yl)oxy)imino)acetamido)-3-(3-(2-((2-(2-chloro-3,4-dihydroxybenzamido)ethyl)(hydroxy)amino)-2-oxoacetamido)-2-oxoimidazolidin-1-yl)-7-oxo-4-thia-1-azabicyclo[3.2.0]heptane-3-carboxylate (compound of Example 104)
- (3R,5R,6R)-6-((Z)-2-(2-aminothiazol-4-yl)-2-(((S)-1-carboxypropoxy)imino)acetamido)-3-(3-(2-(2-chloro-3,4-dihydroxyphenyl)-2-oxoacetamido)-2-oxoimidazolidin-1-yl)-7-oxo-4-thia-1-azabicyclo[3.2.0]heptane-3-carboxylate (compound of Example 105)
- (3R,5R,6R)-6-((Z)-2-(2-amino-5-chlorothiazol-4-yl)-2-((1-carboxycyclopropoxy)imino)acetamido)-3-(3-(3-(2-(2-chloro-3,4-dihydroxyphenyl)-2-oxoacetamido)propanamido)-2-oxoimidazolidin-1-yl)-7-oxo-4-thia-1-azabicyclo[3.2.0]heptane-3-carboxylate (compound of Example 107)
- (3R,5R,6R)-6-((Z)-2-(2-aminothiazol-4-yl)-2-(((S)-1-carboxy-2-hydroxyethoxy)imino)acetamido)-3-(3-(2-(2-chloro-3,4-dihydroxyphenyl)-2-oxoacetamido)-2-oxoimidazolidin-1-yl)-7-oxo-4-thia-1-azabicyclo[3.2.0]heptane-3-carboxylate (compound of Example 113)
- (3R,5R,6R)-6-((Z)-2-(2-aminothiazol-4-yl)-2-(((S)-1-carboxy-2-methylpropoxy)imino)acetamido)-3-(3-(2-(2-chloro-3,4-dihydroxyphenyl)-2-oxoacetamido)-2-oxoimidazolidin-1-yl)-7-oxo-4-thia-1-azabicyclo[3.2.0]heptane-3-carboxylate (compound of Example 114)
- (3R,5R,6R)-6-((Z)-2-(2-aminothiazol-4-yl)-2-(((S)-1-carboxybutoxy)imino)acetamido)-3-(3-(2-(2-chloro-3,4-dihydroxyphenyl)-2-oxoacetamido)-2-oxoimidazolidin-1-yl)-7-oxo-4-thia-1-azabicyclo[3.2.0]heptane-3-carboxylate (compound of Example 115)
- (3R,5R,6R)-6-((Z)-2-(2-aminothiazol-4-yl)-2-(((2-carboxypropan-2-yl)oxy)imino)acetamido)-3-(3-((Z)-2-(2-chloro-3,4-dihydroxyphenyl)-2-(hydroxyimino)acetamido)-2-oxoimidazolidin-1-yl)-7-oxo-4-thia-1-azabicyclo[3.2.0]heptane-3-carboxylate (compound of Example 117)
- (3R,5R,6R)-6-((Z)-2-(2-aminothiazol-4-yl)-2-(((2-carboxypropan-2-yl)oxy)imino)acetamido)-3-(3-(2-((2-(2-chloro-3,4-dihydroxyphenyl)-2-oxoacetamide(ethyl)amino)-2-oxoacetamido)-2-oxoimidazolidin-1-yl)-7-oxo-4-thia-1-azabicyclo[3.2.0]heptane-3-carboxylate (compound of Example 121)
- (3R,5R,6R)-6-((Z)-2-(2-aminothiazol-4-yl)-2-(((2-carboxypropan-2-yl)oxy)imino)acetamido)-3-(3-(3-((Z)-2-(2-chloro-3,4-dihydroxyphenyl)-2-(hydroxyimino)acetamido)propanamido)-2-oxoimidazolidin-1-yl)-7-oxo-4-thia-1-azabicyclo[3.2.0]heptane-3-carboxylate (compound of Example 122)
- (3R,5R,6R)-6-((Z)-2-(2-aminothiazol-4-yl)-2-(((2-carboxypropan-2-yl)oxy)imino)acetamido)-3-(4-(2-(2-chloro-3,4-dihydroxyphenyl)-2-oxoacetamido)-2,3-dioxopiperazin-1-yl)-7-oxo-4-thia-1-azabicyclo[3.2.0]heptane-3-carboxylate (compound of Example 126)
- (3R,5R,6R)-6-((Z)-2-(2-aminothiazol-4-yl)-2-(((2-carboxypropan-2-yl)oxy)imino)acetamido)-3-(4-(2-chloro-3,4-dihydroxybenzamido)-2,3-dioxopiperazin-1-yl)-7-oxo-4-thia-1-azabicyclo[3.2.0]heptane-3-carboxylate (compound of Example 132)
- (3R,5R,6R)-6-((Z)-2-(2-amino-5-chlorothiazol-4-yl)-2-(((2-carboxypropan-2-yl)oxy)imino)acetamido)-3-(3-(2-(2-(2-chloro-3,4-dihydroxyphenyl)-2-oxoacetyl)hydradienyl)-2-oxoacetamido)-2-oxoimidazolidin-1-yl)-7-oxo-4-thiathia-1-azabicyclo[3.2.0]heptane-3-carboxylate (compound of Example 136)

(3R,5R,6R)-6-((Z)-2-(2-aminothiazol-4-yl)-2-(((2-carboxypropan-2-yl)oxy)imino)acetamido)-3-(3-((R)-2-(2-(2-chloro-3,4-dihydroxyphenyl)-2-oxoacetamido)-3-methoxypropanamido)-2-oxoimidazolidin-1-yl)-7-oxo-4-thia-1-azabicyclo[3.2.0]heptane-3-carboxylate (compound of Example 139)

(3R,5R,6R)-6-((Z)-2-(2-aminothiazol-4-yl)-2-(((2-carboxypropan-2-yl)oxy)imino)acetamido)-3-(5-((2-chloro-3,4-dihydroxybenzamido)methyl)-2H-tetrazol-2-yl)-7-oxo-4-thia-1-azabicyclo[3.2.0]heptane-3-carboxylate (compound of Example 141)

Examples of the salt of the compound represented by General Formula [1] include salts in a basic group such as a generally known amino group or in an acidic group such as a hydroxyl or carboxyl group.

Examples of the salts in the basic group include salts with mineral acids such as hydrochloric acid, hydrobromic acid, nitric acid, and sulfuric acid; salts with organic carboxylic acids such as formic acid, acetic acid, citric acid, oxalic acid, fumaric acid, maleic acid, succinic acid, malic acid, tartaric acid, aspartic acid, trichloroacetic acid, and trifluoroacetic acid; and salts with sulfonic acids such as methanesulfonic acid, benzenesulfonic acid, p-toluenesulfonic acid, mesitylenesulfonic acid, and naphthalenesulfonic acid.

Examples of the salts in the acidic group include salts with alkali metals such as sodium and potassium; salts with alkaline earth metals such as calcium and magnesium; ammonium salts; salts with nitrogen-containing organic bases such as trimethylamine, triethylamine, tributylamine, pyridine, N,N-dimethylaniline, N-methylpiperidine, N-methylmorpholine, diethylamine, dicyclohexylamine, procaine, dibenzylamine, N-benzyl-β-phenethylamine, 1-ephenamine, and N,N'-dibenzylethylenediamine, and the like.

Among the above salts, for example, pharmacologically acceptable salts are preferable.

In a case where the compound represented by General Formula [1] or a salt thereof has isomers (for example, an optical isomer, a geometric isomer, a tautomer, and the like), the present invention includes the isomers as well as solvates, hydrates, and various forms of crystals.

The compound or a salt thereof according to the embodiment of the present invention can be made into a pharmaceutical composition (pharmaceutical formulation) by being combined with one or two or more pharmaceutically acceptable carriers, excipients, or diluents.

The carriers, excipients, and diluents include, for example, water, lactose, dextrose, fructose, sucrose, sorbitol, mannitol, polyethylene glycol, propylene glycol, starch, gum, gelatin, alginate, calcium silicate, calcium phosphate, cellulose, aqueous syrup, methylcellulose, polyvinylpyrrolidone, alkyl parahydroxybenzosorbate, talc, magnesium stearate, stearic acid, glycerin, various oils such as sesame oil, olive oil, and soybean oil, and the like.

Furthermore, if necessary, by being mixed with the aforementioned carriers, excipients, and diluents as well as additives such as a bulking agent, a binder, a disintegrant, a pH adjuster, and a solubilizing agent that are generally used, the compound or a salt thereof can be made into oral or parenteral medicines such as tablets, pills, capsules, granules, powders, solutions, emulsions, suspensions, ointments, injections, or skin patches through commonly used formulation techniques.

The treatment using the compound or a salt thereof or the pharmaceutical composition according to the embodiment of the present invention include treatment and prevention.

The administration method, dosage, and number of doses of the compound according to the embodiment of the present invention or a salt thereof or the pharmaceutical composition according to the embodiment of the present invention can be appropriately selected according to the age, body weight, and symptom of the patient. Usually, for an adult, the compound according to the embodiment of the present invention may be orally or parenterally administered (for example, by means of injection, infusion, administration to the rectal site, and the like) at a dose of 0.01 to 1,000 mg/kg once a day or in divided portions a day.

The compound or a salt thereof or the pharmaceutical composition according to the embodiment of the present invention is preferably administered as an injection.

The pharmaceutical composition containing the compound or a salt thereof according to the embodiment of the present invention is preferably manufactured as a solution, a frozen solution, or a lyophilized formulation. The pharmaceutical composition is more preferably a lyophilized formulation.

Next, a method for manufacturing the compound according to the embodiment of the present invention will be described.

The compound according to the embodiment of the present invention is manufactured by combining known methods. For example, the compound can be manufactured according to a manufacturing method described below.

[Manufacturing Method 1]

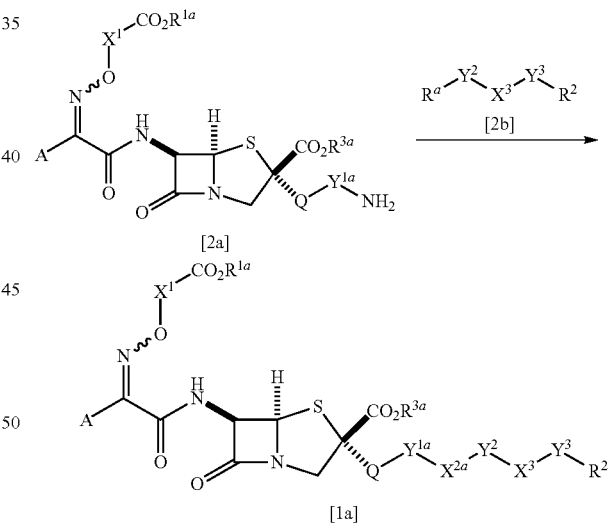

"In the formula, $R^a$ represents a halogen atom; $Y^{1a}$ represents a bond; $X^{2a}$ is a group represented by Formula —NH—; $R_{1a}$ and $R^{3a}$ each represent a carboxyl protecting group; and $R^2$, Q, $Y^2$, $Y^3$, $X^1$, $X^3$, and A have the same definitions as $R^2$, Q, $Y^2$, $Y^3$, $X^1$, $X^3$, and A described above."

The compound represented by General Formula [1a] can be manufactured by reacting the compound represented by General Formula [2a] with the compound represented by General Formula [2b] in the presence of a base.

Examples of the compound represented by General Formula [2b] include acid halides such as 2-chloro-3,4-bis((4-methoxybenzyl)oxy)benzoyl chloride and 2-(2-chloro-3,4- bis((4-methoxybenzyl)oxy)phenyl)-2-oxoacetyl chloride described in the present specification.

The amount of the compound represented by General Formula [2b] used is not particularly limited, but may be 0.9 to 10 times and preferably 0.9 to 2.0 times the molar amount of the compound represented by General Formula [2a].

The amount of the solvent used is not particularly limited, but may be 1 to 500 times (v/w) the amount of the compound represented by General Formula [2a].

The amount of the base used may be 1 to 50 times and preferably 1 to 10 times the molar amount of the compound represented by General Formula [2a].

This reaction may be carried out at −30° C. to 150° C. for 30 minutes to 72 hours, and preferably carried out at 0° C. to 40° C. for 1 to 4 hours.

The solvent used in this reaction is not particularly limited as long as it does not affect the reaction. Examples thereof include halogenated hydrocarbons, ethers, esters, amides, nitriles, sulfoxides, aromatic hydrocarbons, and water. These solvents may be used by being mixed together. As the solvent, for example, tetrahydrofuran, acetonitrile, and water are preferable. The solvent is more preferably a mixed solvent of tetrahydrofuran and water.

Examples of the base used in this reaction include an inorganic base and an organic base. As the base, for example, an inorganic base is preferable. The base is preferably sodium hydrogen carbonate.

[Manufacturing Method 2]

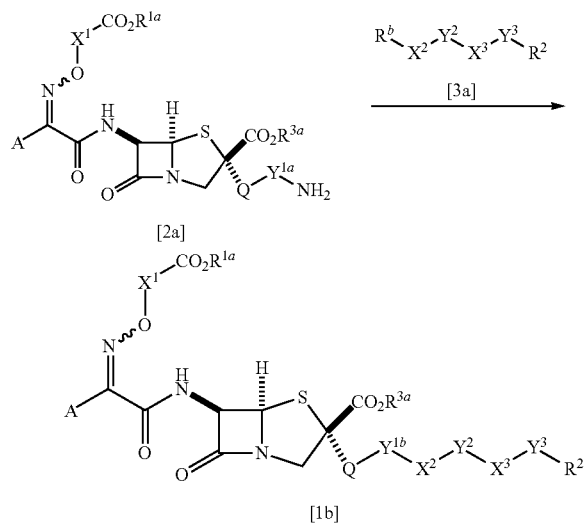

"In the formula, $R^b$ represents a hydroxyl group or a carboxyl group; $Y^{1b}$ is a group represented by —NHC (=O)—; and $R^{1a}$, $R^{3a}$, $R^2$, Q, $Y^{1a}$, $Y^2$, $Y^3$, $X^1$, $X^2$, $X^3$, and A have the same definitions as $R^{1a}$, $R^{3a}$, $R^2$, Q, $Y^{1a}$, $Y^2$, $Y^3$, $X^1$, $X^2$, $X^3$, and A described above."

The compound represented by General Formula [1b] can be manufactured by reacting the compound represented by General Formula [2a] with the compound represented by General Formula [3a] in the presence of a condensing agent or an acid halide or in the presence of a base.

The amount of the compound represented by General Formula [3a] used is not particularly limited, but may be 0.9 to 10 times and preferably 0.9 to 2.0 times the molar amount of the compound represented by General Formula [2a].

The amount of the solvent used is not particularly limited, but may be 1 to 500 times (v/w) the amount of the compound represented by General Formula [2a].

The amount of the base used may be 1 to 50 times and preferably 1 to 10 times the molar amount of the compound represented by General Formula [2a].

This reaction may be carried out at −30° C. to 150° C. for 30 minutes to 72 hours, and preferably carried out at 0° C. to 40° C. for 1 to 24 hours.

The solvent used in this reaction is not particularly limited as long as it does not affect the reaction. Examples thereof include halogenated hydrocarbons, ethers, esters, amides, nitriles, sulfoxides, aromatic hydrocarbons, and water. These solvents may be used by being mixed together.

In a case where a condensing agent is used, as the solvent, dimethylacetamide and DMF are preferable.

In a case where an acid halide is used, as the solvent, for example, tetrahydrofuran, acetonitrile, and water are preferable. As the solvent, a mixed solvent of tetrahydrofuran and water is more preferable.

Examples of the base used in this reaction include an inorganic base and an organic base.

In a case where a condensing agent is used, as the base, for example, an organic base is preferable. The condensing agent is more preferably N-methylmorpholine.

In a case where an acid halide is used, as the base, for example, an inorganic base is preferable. As the base, sodium hydrogen carbonate is preferable.

In a case where the condensing agent is used, examples of the condensing agent include carbodiimides such as N,N'-diisopropylcarbodiimide (DIC), N,N'-di-(tert-butyl)carbodiimide, N,N'-dicyclohexylcarbodiimide (DCC), N-(tert-butyl)-N'-ethylcarbodiimide (BEC), N-cyclohexyl-N'-(2-morpholinoethyl)carbodiimide (CMC), and 1-ethyl-3-(3-dimethylaminopropyl)carbodiimide (EDC); imidazoliums such as 1,1'-carbonyldiimidazole (CDI) and 1,1'-carbonyl di(1,2,4-triazole) (CDT); acid azides such as diphenylphosphoryl azide; acid cyanides such as diethylphosphoryl cyanide; 2-ethoxy-1-ethoxycarbonyl-1,2-dihydroquinoline; uroniums such as O-(benzotriazol-1-yl)-N,N,N',N'-tetramethyluronium hexafluorophosphate (HBTU), O-(7-azabenzotriazol-1-yl)-N,N,N',N'-tetramethyluronium hexafluorophosphate (HATU), 0-(benzotriazol-1-yl)-N,N,N',N'-bis(tetramethylene)uronium hexafluorophosphate (HBPyU), O-(benzotriazol-1-yl)-N,N,N',N'-bis(pentamethylene)uronium hexafluorophosphate (HBPipU), 0-(6-chlorobenzotriazol-1-yl)-N,N,N',N'-tetramethyluronium hexafluorophosphate (HCTU), O-(3,4-dihydro-4-oxo-1,2,3-benzotriazin-3-yl)-N,N,N',N'-tetramethyluronium hexafluorophosphate (HDBTU), 0-(2-oxo-1(2H)pyridyl)-N,N,N',N'-tetramethyluronium hexafluorophosphate (TPTU), O-((ethoxycarbonyl)cyanomethyleneamino)-N,N,N',N'-tetramethyluronium hexafluorophosphate (HOTU), O-((ethoxycarbonyl)cyanomethyleneamino)-N,N,N',N'-tetramethyluronium tetrafluoroborate (TOTU), N,N,N',N'-tetramethyl-O—(N-succinimidyl)uronium hexafluorophosphate (HSTU), N,N,N',N'-tetramethyl-O—(N-succinimidyl)uronium tetrafluoroborate (TSTU), dipyrrolidino(N-succinimidyloxy)carbenium hexafluorophosphate (HSPyU), and S-(1-oxide-2-pyridyl)-N,N,N',N'-tetramethylthiouronium tetrafluoroborate (TOTT); and triazines such as 4-(4,6-dimethoxy-1,3,5-triazin-2-yl)-4-methylmorpholinium chloride (DMT-MM).

As a condensing agent, for example, carbodiimides, uroniums, and triazines are preferable. The condensing agent is more preferably EDC, HATU, or DMT-MM.

In a case where a condensing agent is used, the amount of the condensing agent used may be 1 to 50 times and preferably 1 to 5 times the molar amount of the compound represented by General Formula [2a].

In a case where carbodiimides are used as a condensing agent, it is preferable to further add additives thereto.

Examples of the additives include 1-hydroxybenzotriazole (HOBT), 1-hydroxy-7-azabenzotriazole (HOAT), and ethyl(hydroxyimino)cyanoacetate. Among these, HOBT and ethyl(hydroxyimino)cyanoacetate are preferable.

The amount of the additives used may be 0.01 to 10 times and preferably 0.1 to 1 time the molar amount of the compound represented by General Formula [2a].

In a case where an acid halide is used, examples of the acid halide include oxalyl chloride; carboxylic acid halides such as acetyl chloride and trifluoroacetyl chloride; sulfonic acid halides such as methanesulfonyl chloride and tosyl chloride; chloroformic acid esters such as ethyl chloroformate and isobutyl chloroformate; halides of sulfites such as thionyl chloride and thionyl bromide; and halides of phosphate such as phosphorus oxychloride, phosphorus oxybromide, phosphorus trichloride, and phosphorus pentachloride. Among these, oxalyl chloride is preferable.

The amount of the acid halide used may be 0.9 to 3 times and preferably 0.9 to 1.5 times the molar amount of the compound represented by General Formula [3a].

[Manufacturing Method 3]

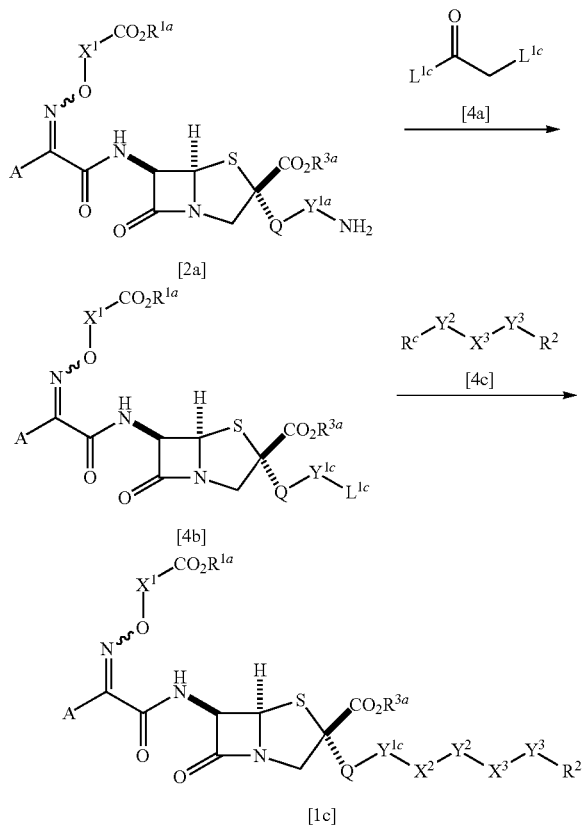

"In the formula, $L^{1c}$ represents a leaving group; $Y^1$ is a group represented by Formula —NHC(=O)CH$_2$—; $R^c$ represents a tertiary amino group or a heterocyclic group; $X^2$ is a group represented by General Formula —N$^+$R$^5$R$^6$— (where $R^5$ and $R^6$ have the same definitions as $R^5$ and $R^6$ described above); and $R^{1a}$, $R^{3a}$, $R^2$, Q, $Y^{1a}$, $Y^2$, $Y^3$, $X^1$, $X^3$, and A have the same definitions as $R^{1a}$, $R^{3a}$, $R^2$, Q, $Y^{1a}$, $Y^2$, $Y^3$, $X^1$, $X^3$, and A described above."

The compound represented by General Formula [1c] can be manufactured by the following method.

(3-1) Condensation

As the compound represented by General Formula [4a], for example, chloroacetyl chloride and the like are known.

The compound represented by General Formula [4b] can be manufactured by reacting the compound represented by General Formula [2a] with the compound represented by General Formula [4a] in the presence of a base.

The amount of the compound represented by General Formula [4a] used is not particularly limited, but may be 0.9 to 20 times and preferably 0.9 to 10 times the molar amount of the compound represented by General Formula [2a].

The amount of the solvent used is not particularly limited, but may be 1 to 500 times (v/w) the amount of the compound represented by General Formula [2a].

The amount of the base used may be 1 to 50 times and preferably 1 to 20 times the molar amount of the compound represented by General Formula [2a].

This reaction may be carried out at −30° C. to 150° C. for 30 minutes to 48 hours, and preferably carried out at 0° C. to 40° C. for 1 to 5 hours.

The solvent used in this reaction is not particularly limited as long as it does not affect the reaction. Examples thereof include halogenated hydrocarbons, ethers, esters, amides, nitriles, sulfoxides, aromatic hydrocarbons, and water. These solvents may be used by being mixed together.

Examples of the base used in this reaction include an inorganic base and an organic base. As the base, for example, an organic base is preferable. The base is more preferably pyridine.

(3-2) Alkylation

Examples of the compound represented by General Formula [4c] include 2-chloro-3,4-bis((4-methoxybenzyl)oxy)-N-(2-(pyrrolidin-1-yl)ethyl)benzamide described in the present specification and the like.

The compound represented by General Formula [1c] can be manufactured by reacting the compound represented by General Formula [4b] with the compound represented by General Formula [4c].

The amount of the compound represented by General Formula [4c] used is not particularly limited, but may be 1 to 20 times and preferably 1 to 5 times the molar amount of the compound represented by General Formula [4b].

The amount of the solvent used is not particularly limited, but may be 1 to 500 times (v/w) the amount of the compound represented by General Formula [4b].

This reaction may be carried out at −30° C. to 150° C. for 30 minutes to 72 hours, and preferably carried out at 0° C. to 50° C. for 1 to 24 hours.

The solvent used in this reaction is not particularly limited as long as it does not affect the reaction. Examples of the solvent include halogenated hydrocarbons, ethers, esters, amides, nitriles, sulfoxides, and aromatic hydrocarbons. These solvents may be used by being mixed together.

[Manufacturing Method 4]

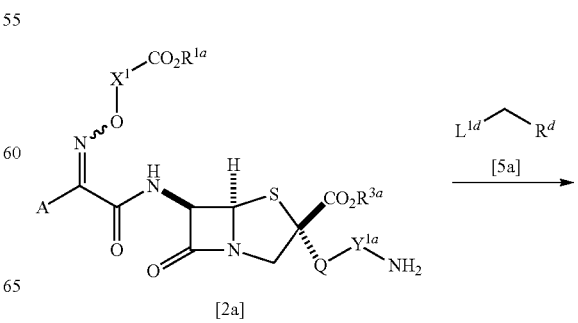

-continued

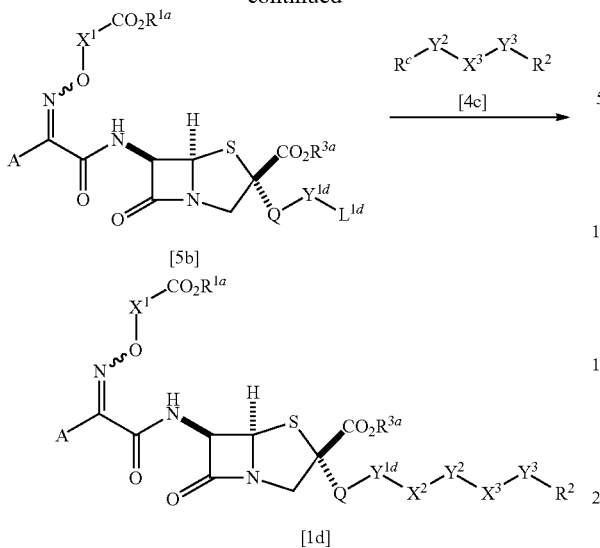

"In the formula, $L^{1d}$ represents a leaving group; $R^d$ represents an aldehyde group which may be protected; $Y^{1d}$ is a group represented by Formula —N═CH—CH$_2$—; and $R^{1a}$, $R^{3a}$, $R^2$, $R^c$, Q, $Y^{1a}$, $Y^2$, $Y^3$, $X^1$, $X^2$, $X^3$, and A have the same definitions as $R^{1a}$, $R^{3a}$, $R^2$, $R^c$, Q, $Y^{1a}$, $Y^2$, $Y^3$, $X^1$, $X^2$, $X^3$, and A described above."

The compound represented by General Formula [1d] can be manufactured by the following method.

(4-1) Alkylation

As the compound represented by General Formula [5a], for example, chloroacetaldehyde, acetal-protected chloroacetaldehyde, and the like are known.

The compound represented by General Formula [5b] can be manufactured by reacting the compound represented by General Formula [2a] with the compound represented by General Formula [5a].

The amount of the compound represented by General Formula [5a] used is not particularly limited, but may be 0.9 to 20 times and preferably 0.9 to 10 times the molar amount of the compound represented by General Formula [2a].

The amount of the solvent used is not particularly limited, but may be 1 to 500 times (v/w) the amount of the compound represented by General Formula [2a].

This reaction may be carried out at −30° C. to 150° C. for 30 minutes to 48 hours, and preferably carried out at 0° C. to 50° C. for 1 to 4 hours.

The solvent used in this reaction is not particularly limited as long as it does not affect the reaction. Examples of the solvent include halogenated hydrocarbons, ethers, esters, amides, nitriles, sulfoxides, and aromatic hydrocarbons. These solvents may be used by being mixed together.

In a case where acetal-protected halogenated acetaldehyde is used as the compound represented by General Formula [5a], it is desirable to further add an acid catalyst thereto. Examples of the acid catalyst include p-toluenesulfonic acid monohydrate, pyridinium p-toluenesulfonate, 10-camphorsulfonic acid, and the like. Among these, p-toluenesulfonic acid monohydrate is preferable.

The amount of the acid catalyst used may be 0.01 to 10 times and preferably 0.1 to 1 time the molar amount of the compound represented by General Formula [5a].

(4-2) Alkylation

Examples of the compound represented by General Formula [4c] include 2-chloro-3,4-bis((4-methoxybenzyl)oxy)-N-(2-(pyrrolidin-1-yl)ethyl)benzamide described in the present specification and the like.

The compound represented by General Formula [1d] can be manufactured by reacting the compound represented by General Formula [5b] with the compound represented by General Formula [4c].

The amount of the compound represented by General Formula [4c] used is not particularly limited, but may be 1 to 20 times and preferably 1 to 5 times the molar amount of the compound represented by General Formula [5b].

The amount of the solvent used is not particularly limited, but may be 1 to 500 times (v/w) the amount of the compound represented by General Formula [5b].

This reaction may be carried out at −30° C. to 150° C. for 30 minutes to 72 hours, and preferably carried out at 0° C. to 50° C. for 1 to 4 hours.

The solvent used in this reaction is not particularly limited as long as it does not affect the reaction. Examples of the solvent include halogenated hydrocarbons, ethers, esters, amides, nitriles, sulfoxides, and aromatic hydrocarbons. These solvents may be used by being mixed together.

[Manufacturing Method 5]

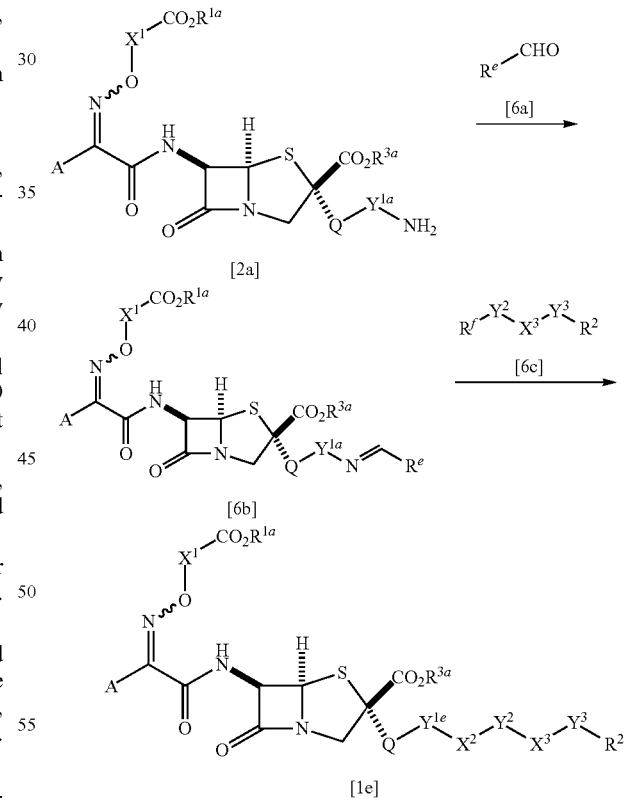

"In the formula, $R^e$ represents an aldehyde group and a carboxyl group; $R^f$ represents a substituted primary amino group; $Y^{1e}$ is a group represented by Formula —N═CH—CH═N—, a group represented by Formula —N═CH—CH═N—O—, or a group represented by Formula —N═CH—C(═O)—, $X^2$ is a group represented by Formula —NH—, a group represented by Formula —NHC(═O)NH—, or a bond; and $R^{1a}$, $R^{3a}$, $R^2$, Q, $Y^{1a}$, $Y^2$, $Y^3$, $X^1$, $X^3$, and A have the same definitions as $R^{1a}$, $R^{3a}$, $R^2$, Q, $Y^{1a}$, $Y^2$, $Y^3$, $X^1$, $X^3$, and A described above."

The compound represented by General Formula [1e] can be manufactured by the following method.

(5-1) Iminoization

As the compound represented by General Formula [6a], for example, glyoxal, glyoxylic acid, hydrates of these, and the like are known.

The compound represented by General Formula [6b] can be manufactured by reacting the compound represented by General Formula [2a] with the compound represented by General Formula [6a].

The amount of the compound represented by General Formula [6a] used is not particularly limited, but may be 1 to 50 times and preferably 1 to 20 times the molar amount of the compound represented by General Formula [2a].

The amount of the solvent used is not particularly limited, but may be 1 to 500 times (v/w) the amount of the compound represented by General Formula [2a].

This reaction may be carried out at −30° C. to 150° C. for 30 minutes to 48 hours, and preferably carried out at 0° C. to 40° C. for 1 to 12 hours.

The solvent used in this reaction is not particularly limited as long as it does not affect the reaction. Examples of the solvent include halogenated hydrocarbons, ethers, esters, amides, nitriles, sulfoxides, and aromatic hydrocarbons. These solvents may be used by being mixed together.

(5-2) Iminoization

Examples of the compound represented by General Formula [6c] include N-(2-aminoethyl)-2-chloro-3,4-bis((4-methoxybenzyl)oxy)benzamide described in the present specification and the like.

The compound represented by General Formula [1e] can be manufactured by reacting the compound represented by General Formula [6b] with the compound represented by General Formula [6c].

The amount of the compound represented by General Formula [6c] used is not particularly limited, but may be 1 to 20 times and preferably 1 to 10 times the molar amount of the compound represented by General Formula [6b].

The amount of the solvent used is not particularly limited, but may be 1 to 500 times (v/w) the amount of the compound represented by General Formula [6b].

This reaction may be carried out at −30° C. to 150° C. for 30 minutes to 72 hours, and preferably carried out at 0° C. to 40° C. for 1 to 12 hours.

The solvent used in this reaction is not particularly limited as long as it does not affect the reaction. Examples of the solvent include halogenated hydrocarbons, ethers, esters, amides, nitriles, sulfoxides, and aromatic hydrocarbons. These solvents may be used by being mixed together.

[Manufacturing Method 6]

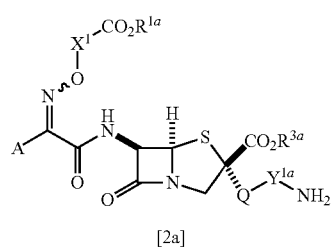

[2a]

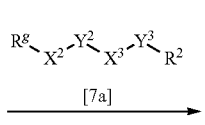

[7a]

-continued

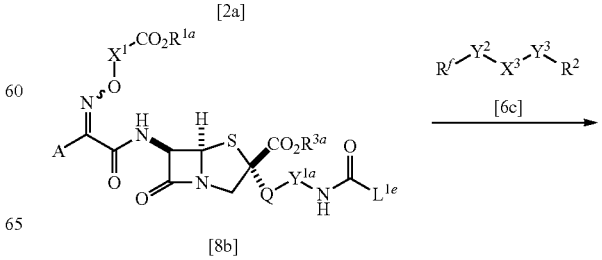

[1f]

"In the formula, $R^g$ represents an acetaldehyde group; $Y^{1f}$ is a group represented by Formula —N=CH—CH$_2$—; $X^2$ is a group represented by Formula —NH—; and $R^{1a}$, $R^{3a}$, $R^2$, Q, $Y^{1a}$, $Y^2$, $Y^3$, $X^1$, $X^3$, and A have the same definitions as $R^{1a}$, $R^{3a}$, $R^2$, Q, $Y^{1a}$, $Y^2$, $Y^3$, $X^1$, $X^3$, and A described above."

The compound represented by General Formula [1 f] can be manufactured by the following method.

Examples of the compound represented by General Formula [7a] include 2-chloro-3,4-bis((4-methoxybenzyl)oxy)-N-(2-oxoethyl)benzamide described in the present specification and the like.

The compound represented by General Formula [1f] can be manufactured by reacting the compound represented by General Formula [2a] with the compound represented by General Formula [7a].

The amount of the compound represented by General Formula [7a] used is not particularly limited, but may be 1 to 50 times and preferably 1 to 10 times the molar amount of the compound represented by General Formula [2a].

The amount of the solvent used is not particularly limited, but may be 1 to 500 times (v/w) the amount of the compound represented by General Formula [2a].

This reaction may be carried out at −30° C. to 150° C. for 30 minutes to 72 hours, and preferably carried out at 0° C. to 40° C. for 1 to 12 hours.

The solvent used in this reaction is not particularly limited as long as it does not affect the reaction. Examples of the solvent include halogenated hydrocarbons, ethers, esters, amides, nitriles, sulfoxides, and aromatic hydrocarbons. These solvents may be used by being mixed together.

[Manufacturing Method 7]

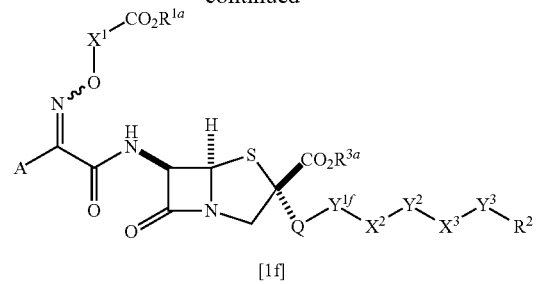

[2a]

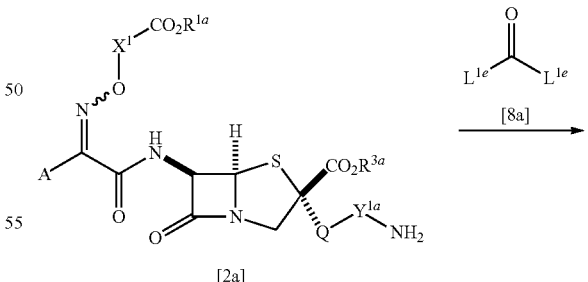

[8b]

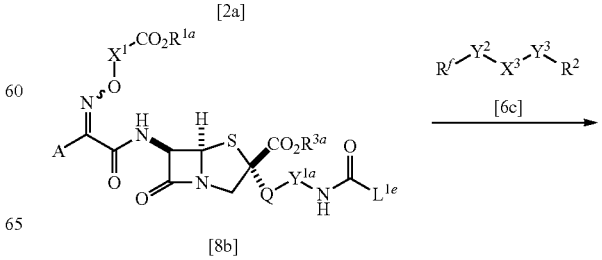

-continued

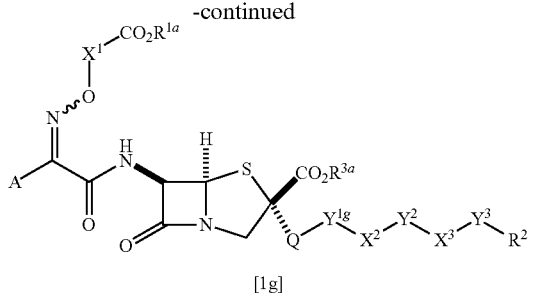

[1g]

"In the formula, $L^{1e}$ represents a leaving group; $R^f$ represents a primary amino group, a secondary amino group, and a secondary cyclic amino group; $Y^{1g}$ is a group represented by Formula —NHC(=O)—, a group represented by Formula —NHC(=O)NH—, or a group represented by Formula —NHC(=O)NH—O—, $X^2$ is a group represented by Formula —NH—, a group represented by Formula —NHC(=O)NH—, a heterocyclic group, or a bond; and $R^{1a}$, $R^{3a}$, $R^2$, Q, $Y^{1a}$, $Y^2$, $Y^3$, $X^1$, $X^3$, and A have the same definitions as $R^{1a}$, $R^{3a}$, $R^2$, Q, $Y^{1a}$, $Y^2$, $Y^3$, $X^1$, $X^3$, and A described above."

The compound represented by General Formula [1g] can be manufactured by the following method.

(7-1) Acyl Imidazolation

Examples of the compound represented by General Formula [8a] include phosgene, triphosgene, carbonyldiimidazole, and the like.

The compound represented by General Formula [8b] can be manufactured by reacting the compound represented by General Formula [2a] with the compound represented by General Formula [8a].

The amount of the compound represented by General Formula [8a] used is not particularly limited, but may be 1 to 20 times and preferably 1 to 10 times the molar amount of the compound represented by General Formula [2a].

The amount of the solvent used is not particularly limited, but may be 1 to 500 times (v/w) the amount of the compound represented by General Formula [2a].

This reaction may be carried out at −30° C. to 150° C. for 30 minutes to 48 hours, and preferably carried out at 0° C. to 80° C. for 1 to 24 hours.

The solvent used in this reaction is not particularly limited as long as it does not affect the reaction. Examples of the solvent include halogenated hydrocarbons, ethers, esters, amides, nitriles, sulfoxides, and aromatic hydrocarbons. These solvents may be used by being mixed together.

(7-2) Condensation

Examples of the compound represented by General Formula [6c] include N-(2-aminoethyl)-2-chloro-3,4-bis((4-methoxybenzyl)oxy)benzamide described in the present specification and the like.

The compound represented by General Formula [1g] can be manufactured by reacting the compound represented by General Formula [8b] with the compound represented by General Formula [6c] in the presence of a base.

The amount of the compound represented by General Formula [6c] used is not particularly limited, but may be 1 to 20 times and preferably 1 to 5 times the molar amount of the compound represented by General Formula [8b].

Examples of the base used in this reaction include an inorganic base and an organic base.

The amount of the base used may be 1 to 50 times and preferably 1 to 10 times the molar amount of the compound represented by General Formula [2a].

The amount of the solvent used is not particularly limited, but may be 1 to 500 times (v/w) the amount of the compound represented by General Formula [8b].

This reaction may be carried out at −30° C. to 150° C. for 30 minutes to 48 hours, and preferably carried out at 0° C. to 40° C. for 1 to 12 hours.

The solvent used in this reaction is not particularly limited as long as it does not affect the reaction. Examples thereof include halogenated hydrocarbons, ethers, esters, amides, nitriles, sulfoxides, aromatic hydrocarbons, and water. These solvents may be used by being mixed together.

Next, a method for manufacturing raw materials for manufacturing the compound according to the embodiment of the present invention will be described.

[Manufacturing Method 8] Deprotection

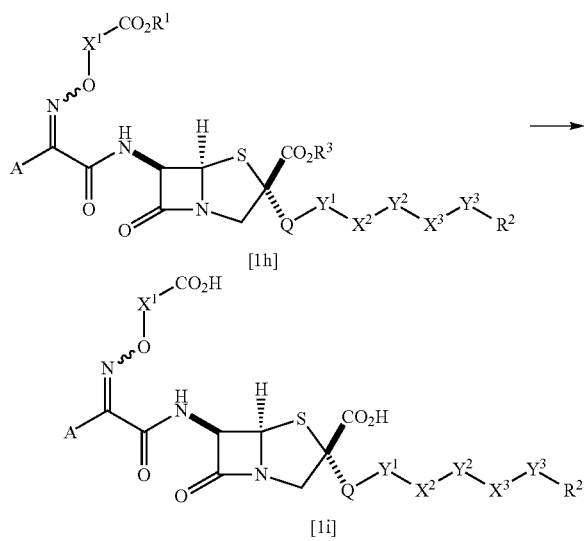

"In the formula, $R^1$, $R^2$, $R^3$, Q, $Y^1$, $Y^2$, $Y^3$, $X^1$, $X^2$, $X^3$, and A have the same definition as $R^1$, $R^2$, $R^3$, Q, $Y^1$, $Y^2$, $Y^3$, $X^1$, $X^2$, $X^3$, and A described above. Here, in General Formula [1h], at least one of $R^1$ or $R^3$ is a protecting group."

The compound represented by General Formula [1i] can be manufactured by performing deprotection by the method described, for example, in "Protective Groups in Organic Synthesis, W. Greene et al., 4th edition, pp. 533-643, 2007, John Wiley & Sons, INC." and the like.

[Manufacturing Method A]

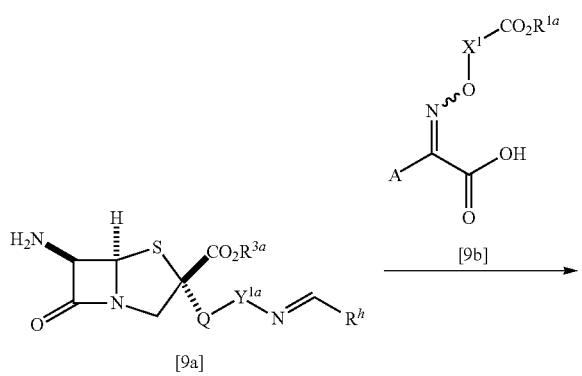

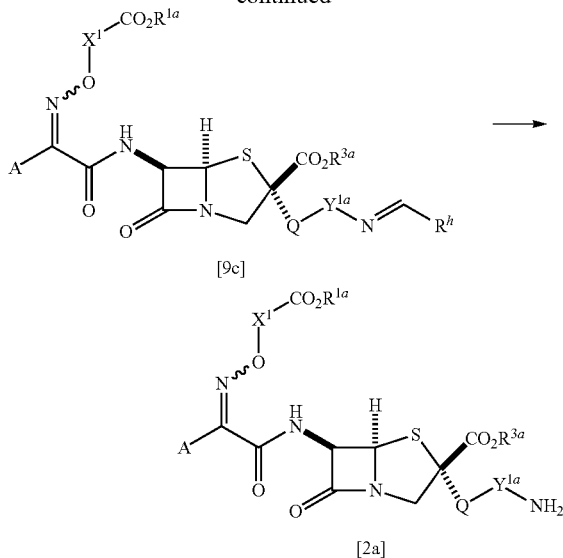

[9c]

[2a]

"In the formula, $R^h$ represents an aryl group; and $R^{1a}$, $R^{3a}$, Q, $X^1$, $Y^{1a}$, and A have the same definitions as $R^{1a}$, $R^{3a}$, Q, $X^1$, $Y^{1a}$, and A described above."

The compound represented by General Formula [2a] can be manufactured by the following method.

(A-1) Condensation

The compound represented by General Formula [9c] can be manufactured by reacting the compound represented by General Formula [9a] or a hydrochloride thereof with the compound represented by General Formula [9b] in the presence of a condensing agent or an acid halide or in the presence of a base.

Examples of the compound represented by General Formula [9a] include benzhydryl (3R,5R,6R)-6-amino-3-(3-(((E)-benzylidene)amino)-2-oxoimidazolidin-1-yl)-7-oxo-4-thia-1-azabicyclo[3.2.0]heptane-3-carboxylate hydrochloride described in the present specification.

The compound represented by General Formula [9a] can be manufactured based on the methods described, for example, on pp. 9-14 in JP1992-074182A (JP-H04-074182A), pp. 6-12 in JP1998-182654A (JP-H10-182654A), and pp. 8-20 in U.S. Pat. No. 5,185,330A, in addition to the method described in the present specification.

Examples of the compound represented by General Formula [9b] include (Z)-2-(2-aminothiazol-4-yl)-2-(((1-(tert-butoxy)-2-methyl-1-oxopropan-2-yl)oxy)imino)acetic acid described in the present specification and the like.

Furthermore, the compound represented by General Formula [9c] can also be manufactured by reacting the compound represented by General Formula [9a] with a benzothiazolyl ester as the compound represented by General Formula [9b].

The solvent used in this reaction is not particularly limited as long as it does not affect the reaction. Examples of the solvent include halogenated hydrocarbons, ethers, esters, amides, nitriles, sulfoxides, and aromatic hydrocarbons. These solvents may be used by being mixed together.

As the solvent, for example, halogenated hydrocarbons, ethers, esters, and amides are preferable. Among these, halogenated hydrocarbons and amides are more preferable.

The amount of the solvent is not particularly limited, but may be 1 to 500 times (v/w) the amount of the compound represented by General Formula [9a].

Examples of the base used in this reaction include an inorganic base and an organic base.

As the base, for example, an organic base is preferable. As the organic base, triethylamine, N,N-diisopropylethylamine, and 4-methylmorpholine are more preferable, and N,N-diisopropylethylamine and 4-methylmorpholine are even more preferable.

The amount of the base used may be 1 to 50 times and preferably 1 to 10 times the molar amount of the compound represented by General Formula [9a].

Examples of the condensing agent used in this reaction include the condensing agent described in Manufacturing Method 3.

As the condensing agent, for example, carbodiimides are preferable. As the condensing agent, EDC is more preferable.

The amount of the condensing agent used may be 1 to 50 times and preferably 1 to 5 times the molar amount of the compound represented by General Formula [9a].

In a case where carbodiimides are used as the condensing agent, it is preferable to add additives thereto.

Examples of the additives include 1-hydroxybenzotriazole (HOBT), 1-hydroxy-7-azabenzotriazole (HOAT), and ethyl(hydroxyimino)cyanoacetate. Among these, HOBT and ethyl(hydroxyimino)cyanoacetate are preferable.

The amount of the additives used may be 0.01 to 10 times and preferably 0.1 to 1 time the molar amount of the compound represented by General Formula [9a].

Examples of the acid halide used in this reaction include oxalyl chloride; carboxylic acid halides such as acetyl chloride and trifluoroacetyl chloride; sulfonic acid halides such as methanesulfonyl chloride and tosyl chloride; chloroformic acid esters such as ethyl chloroformate and isobutyl chloroformate; halides of sulfites such as thionyl chloride and thionyl bromide; and halides of phosphate such as phosphorus oxychloride, phosphorus oxybromide, phosphorus trichloride, and phosphorus pentachloride.

The amount of the acid halide used may be 0.9 to 3 times and preferably 0.9 to 1.5 times the molar amount of the compound represented by General Formula [9b].

The amount of the compound represented by General Formula [9b] used is not particularly limited, but may be 1 to 10 times and preferably 1 to 3 times the molar amount of the compound represented by General Formula [9a].

This reaction may be carried out at −30° C. to 150° C. for 30 minutes to 48 hours, and preferably carried out at 0° C. to 50° C. for 1 to 12 hours.

(A-2) Deprotection

The compound represented by General Formula [2a] can be manufactured by deprotecting the compound represented by General Formula [9c] by the method described, for example, in "Protective Groups in Organic Synthesis, W. Greene et al., 4th edition, pp. 533-643, 2007, John Wiley & Sons, INC." and the like.

EXAMPLES

Next, the present invention will be described based on examples and reference examples, but the present invention is not limited thereto.

Unless otherwise specified, silica gel column chromatography is flash column chromatography in which B. W. Silica gel, BW-300 manufactured by Fuji Silysia Chemical, Ltd. is used as a carrier.

In the medium-pressure reverse-phase silica gel column chromatography, Isolera SV or Isolera LSV manufactured by Biotage Japan Ltd. was used. Furthermore, as a carrier, SNAP Ultra C18 Cartridge manufactured by Biotage Japan Ltd. was used.

The mixing ratio in the eluent is a volume ratio.

The NMR spectrum was measured using AVANCE III HD400 (Bruker).

The NMR spectrum shows proton NMR, and the internal standard is as follows.

The δ value is expressed as ppm.

Deuterated chloroform (CDCl$_3$): tetramethylsilane (0.00 ppm)

Deuterated methanol (CD$_3$OD): methanol (CH$_3$OH) (3.30 ppm)

Deuterated dimethyl sulfoxide (CD$_3$SOCD$_3$): tetramethylsilane (0.00 ppm)

Heavy water (D$_2$O): water (4.65 ppm)

In the NMR spectrum, for example, the description of [1.45]1.46 (3H, s) means that the peak derived from each diastereomer in a diastereomer mixture, the peak derived from each isomer in a geometric isomer mixture, or the peak derived from the same protons observed separately in a pH-dependent manner is observed as a singlet at 1.45 and 1.46, and the total number of protons is 3.

Unless otherwise stated, the NMR spectra in reference examples were measured using CDCl$_3$, and the NMR spectra in examples were measured using D$_2$O.

The MS spectrum was measured by an electrospray ionization method (ESI) by using an ACQUITY SQD LC/MS System (Waters Corporation).

The abbreviation in each of the examples and reference examples has the following meaning.

Alloc: allyloxycarbonyl, BH: diphenylmethyl, Boc: tert-butoxycarbonyl, Cbz: benzyloxycarbonyl, DBU: 1,8-diazabicyclo[5.4.0]-7-undecene, DMAC: N,N-dimethylacetamide, DMAP: 4-(dimethylamino)pyridine, DMF: N,N-dimethylformamide, EDC: 1-ethyl-3-(3-dimethylaminopropyl)carbodiimide hydrochloride, ESI: electrospray ionization method, Et: ethyl, HOBt: 1-hydroxybenzotriazole monohydrate, HATU: 0-(7-azabenzotriazol-1-yl)-N,N,N',N'-tetramethyluronium hexafluorophosphate, IPE: diisopropyl ether, Me: methyl, Moz: 4-methoxybenzyloxycarbonyl, Ms: methanesulfonyl, MTBE: tert-butyl methyl ether, NMM: N-methylmorpholine, NMP: 1-methyl-2-pyrrolidone, PMB: 4-methoxybenzyl, PNZ: p-nitrobenzyloxycarbonyl, SEM: 2-(trimethylsilyl)ethoxymethyl, TBDPS: tert-butyldiphenylsilyl, TBS: tert-butyldimethylsilyl, t-Bu: tert-butyl, THF: tetrahydrofuran, THP: tetrahydro-2H-pyran-2-yl, Tr: triphenylmethyl, Ts: p-toluenesulfonyl, s: singlet, brs: broad singlet, d: doublet, dd: double doublet, dt: doublet triplet, m: multiplet, t: triplet Reference Example 1

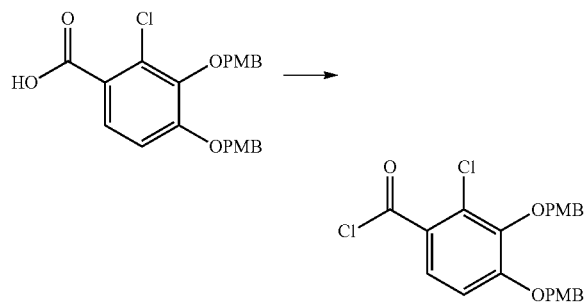

THF (400 mL) was added to 2-chloro-3,4-bis((4-methoxybenzyl)oxy)benzoic acid (40.0 g), and the mixture was stirred under ice cooling. At the same temperature, DMF (361 µL) was added to the reaction mixture, and then oxalyl dichloride (14.2 g) was added dropwise thereto. The reaction mixture was stirred at room temperature for 1 hour, and then oxalyl dichloride (14.2 g) was added dropwise thereto. The reaction mixture was stirred at room temperature overnight, and then IPE (400 mL) was added to the reaction mixture. Solids were collected by filtration and washed with IPE. The solids were dried, thereby obtaining 2-chloro-3,4-bis((4-methoxybenzyl)oxy)benzoyl chloride (30 g) as white solids.

NMR (DMSO-d$_6$): 3.74 (3H, s), 3.78 (3H, s), 4.88 (2H, s), 5.18 (2H, s), 6.82-6.89 (2H, m), 6.95-7.02 (2H, n), 7.23 (1H, d, J=9.2 Hz), 7.26-7.33 (2H, m), 7.41-7.49 (2H, m), 7.62 (1H, d, J=8.4 Hz)

Reference Example 2

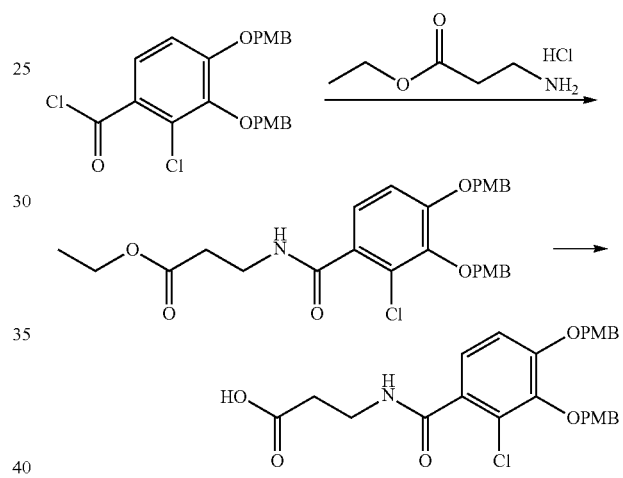

Reference Example 2 (1)

THF (20 mL), water (20 mL), sodium hydrogen carbonate (281 mg), and 2-chloro-3,4-bis((4-methoxybenzyl)oxy)benzoyl chloride (500 mg) were sequentially added to ethyl 3-aminopropanoate hydrochloride (257 mg). The reaction mixture was stirred at room temperature for 4 hours, ethyl acetate (50 mL) and water (50 mL) were then added to the reaction mixture, and the organic layer was separated. The organic layer was washed with a saturated aqueous sodium chloride solution and dehydrated and dried over anhydrous sodium sulfate. The solvent was distilled away under reduced pressure, thereby obtaining a target substance (600 mg) as yellow solids.

Reference Example 2 (2)

Methanol (5.8 mL), THF (5.8 mL), and a 2 mol/L aqueous sodium hydroxide solution (4.5 mL) were added to the compound (600 mg) obtained in Reference Example 2 (1), and the mixture was stirred at room temperature overnight. Ethyl acetate (20 mL) and water (20 mL) were added to the reaction mixture, 2 mol/L hydrochloric acid was added thereto such that the pH was adjusted to 1.8. The reaction mixture was stirred at room temperature for 30 minutes, and solids were collected by filtration. The solids were dried under reduced pressure, thereby obtaining 3-(2-chloro-3,4-bis((4-methoxybenzyl)oxy)benzamido)propionic acid (488 mg) as white solids.

NMR (DMSO-d$_6$): 2.48 (2H, t, J=6.8 Hz), 3.39 (2H, q, J=6.7 Hz), 3.75 (3H, s), 3.77 (3H, s), 4.87 (2H, s), 5.15 (2H, s), 6.87 (2H, dd, J=6.8, 2.0 Hz), 6.97 (2H, dd, J=6.6, 1.8 Hz), 7.11 (1H, d, J=8.8 Hz), 7.18 (1H, d, J=8.4 Hz), 7.31 (2H, dd, J=6.8, 2.0 Hz), 7.43 (2H, d, J=8.8 Hz), 8.33 (1H, t, J=5.4 Hz), 12.22 (1H, s)

Reference Example 3

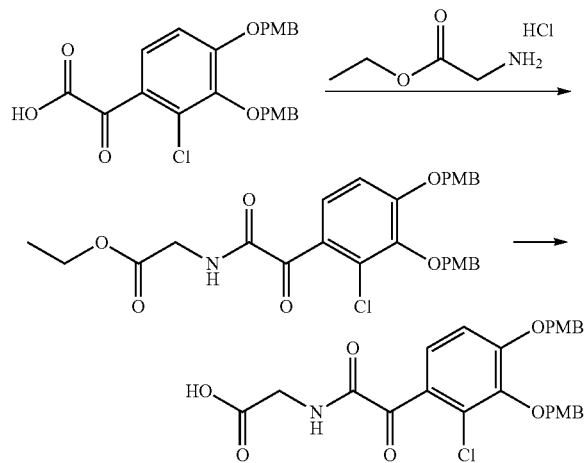

Reference Example 3 (1)

2-(2-Chloro-3,4-bis((4-methoxybenzyl)oxy)phenyl)-2-oxoacetic acid (1.64 g), HOBt (532 mg), EDC (755 mg), DMF (10 mL), and NMM (0.47 mL) were sequentially added to ethyl glycinate hydrochloride (500 mg). The reaction mixture was stirred at room temperature overnight. Ethyl acetate (30 mL) and water (30 mL) were added to the reaction mixture, and the organic layer was separated. The organic layer was washed with a saturated aqueous sodium chloride solution and dehydrated and dried over anhydrous sodium sulfate. The solvent was distilled away under reduced pressure, and the residue was purified by silica gel column chromatography [eluent; ethyl acetate:hexane=25:75→50:50], thereby obtaining a target substance (1.27 g) as light yellow solids.

Reference Example 3 (2)

Methanol (13 mL), THF (13 mL), and a 2 mol/L aqueous sodium hydroxide solution (4.7 mL) were added to the compound (1.27 g) obtained in Reference Example 3 (1), and the mixture was stirred at room temperature for 2 hours and 30 minutes. Hydrochloric acid (2 mol/L) was added to the reaction mixture such that the pH was adjusted to 1.9. Ethyl acetate (25 mL) and water (25 mL) were added to the reaction mixture, and the organic layer was separated. The organic layer was washed with a saturated aqueous sodium chloride solution and then dehydrated and dried over anhydrous sodium sulfate. The solvent was distilled away under reduced pressure, thereby obtaining (2-(2-chloro-3,4-bis((4-methoxybenzyl)oxy)phenyl)-2-oxoacetyl)glycine (1.19 g) as light yellow solids.

MS: 512.10 [M−H]$^−$

The compounds in Table 1 were obtained in the same manner as in Reference Example 3.

TABLE 1

| Reference Example No. | Structural Formula | Name |
|---|---|---|
| 4 | | 3-(2-(2-chloro-3,4-bis((4-methoxybenzyl)oxy)phenyl)-2-oxoacetamido)propionic acid |
| 5 | | 1-(2-chloro-3,4-bis((4-methoxybenzyl)oxy)benzoyl)azetidine-3-carboxylic acid |
| 6 | | 1-(2-(2-chloro-3,4-bis((4-methoxybenzyl)oxy)phenyl)-2-oxoacetyl)azetidine-3-carboxylic acid |

The measured values of NMR of the compounds in the table are as follows.

Reference Example 4

NMR (DMSO-d$_6$): 2.49-2.53 (2H, m), 3.41 (2H, q, J=6.5 Hz), 3.74 (3H, s), 3.78 (3H, s), 4.90 (2H, s), 5.22 (2H, s), 6.86 (2H, dd, J=6.8, 2.0 Hz), 6.99 (2H, dd, J=6.8, 2.0 Hz), 7.29 (2H, d, J=8.4 Hz), 7.31 (1H, d, J=8.8 Hz), 7.46 (2H, d, J=8.8 Hz), 7.52 (1H, d, J=8.8 Hz), 8.93 (1H, t, J=5.6 Hz), 12.31 (1H, s)

Reference Example 5

NMR (DMSO-d$_6$): 3.37-3.47 (1H, m), 3.73 (3H, s), 3.78 (3H, s), 3.81-4.06 (3H, m), 4.13-4.23 (1H, m), 4.92 (2H, s), 5.14 (2H, s), 6.80-6.88 (2H, m), 6.95-7.02 (2H, m), 7.11 (1H, d, J=8.4 Hz), 7.21 (1H, d, J=8.4 Hz), 7.23-7.30 (2H, m), 7.40-7.48 (2H, m), 12.75 (1H, s)

Reference Example 6

NMR (DMSO-d$_6$): 3.50-3.62 (1H, m), 3.74 (3H, s), 3.78 (3H, s), 4.05-4.13 (1H, m), 4.20-4.29 (2H, m), 4.34 (1H, m), 4.91 (2H, s), 5.23 (2H, s), 6.81-6.89 (2H, m), 6.96-7.03 (2H, m), 7.24-7.38 (3H, m), 7.42-7.50 (2H, m), 7.57 (1H, dd, J=14.4, 8.8 Hz), 12.85 (1H, s)

Reference Example 7

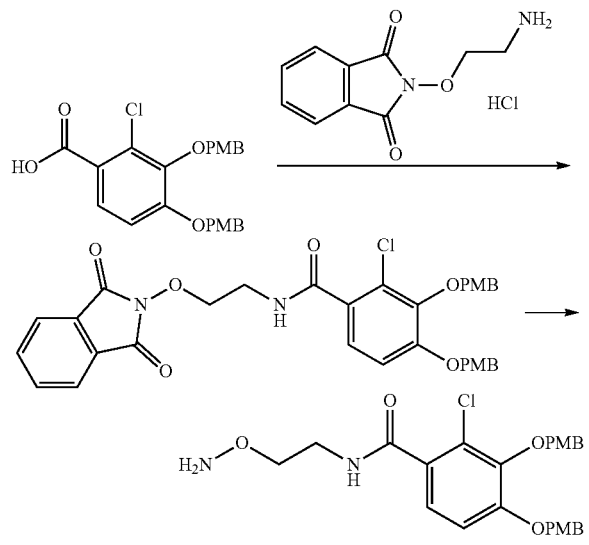

Reference Example 7 (1)

2-Chloro-3,4-bis((4-methoxybenzyl)oxy)benzoic acid (1.6 g), HOBt (555 mg), EDC (858 mg), DMAC (21 mL), and NMM (1.4 mL) were sequentially added to 2-(2-aminoethoxy)isoindoline-1,3-dioxohydrochloride (951 mg). The reaction mixture was stirred at room temperature for 3 hours and 30 minutes. Water (60 mL) was added to the reaction mixture, and solids were collected by filtration. The solids were dried, thereby obtaining a target substance (2.30 g) as light brown solids.

Reference Example 7 (2)

Dichloromethane (20 mL) and methylhydrazine (189 μL) were added to the compound (2.30 g) obtained in Reference Example 7 (1), and the mixture was stirred at room temperature for 2 hours. Then, solids were filtered, and the solvent was distilled away under reduced pressure, thereby obtaining N-(2-(aminooxy)ethyl)-2-chloro-3,4-bis((4-methoxybenzyl)oxy)benzamide (1.97 g) as brown solids.

NMR: 3.63-3.88 (10H, m), 4.94 (2H, s), 5.07 (2H, s), 6.72-6.97 (7H, m), 7.29-7.39 (4H, m), 7.44 (1H, d, J=8.8 Hz)

Reference Example 8

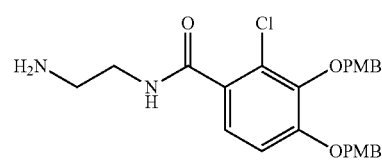

By using 2-(2-aminoethyl)isoindoline-1,3-dione hydrochloride instead of 2-(2-aminoethoxy)isoindoline-1,3-dione hydrochloride in Reference Example 7, N-(2-aminoethyl)-2-chloro-3,4-bis((4-methoxybenzyl)oxy)benzamide was obtained in the same manner as in Reference Example 7.

NMR: 1.40 (2H, s), 2.94 (2H, t, J=5.8 Hz), 3.46-3.55 (2H, m), 3.80 (3H, s), 3.83 (3H, s), 4.95 (2H, s), 5.08 (2H, s), 6.67 (1H, s), 6.80-6.97 (5H, m), 7.35 (4H, dd, J=8.6, 3.0 Hz), 7.45 (1H, d, J=8.8 Hz)

Reference Example 9

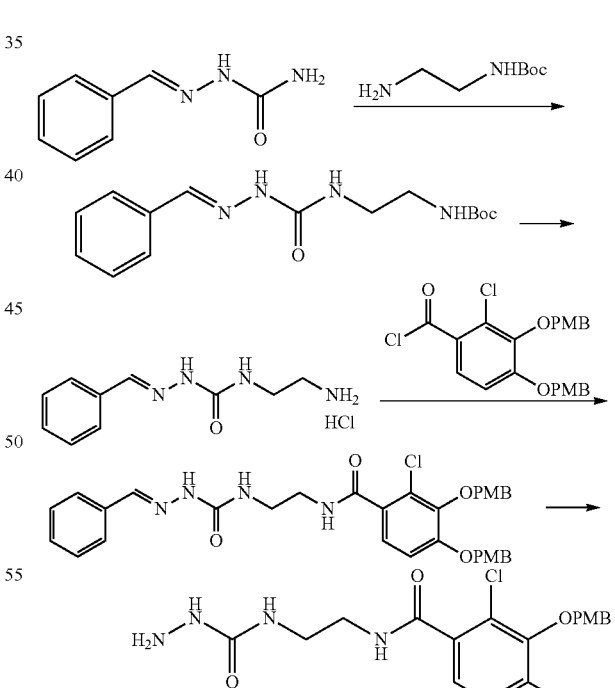

Reference Example 9 (1)

Chlorobenzene (30 mL) and tert-butyl (2-aminoethyl) carbamate (9.82 g) were sequentially added to (E)-2-benzylidenehydrazine-1-carboxamide (10.0 g), and the mixture was stirred. The reaction mixture was heated and stirred under reflux for 3 hours and 15 minutes. The reaction mixture was cooled to room temperature, and chlorobenzene (20 mL) and tert-butyl (2-aminoethyl)carbamate (2.95 g) were added thereto. The reaction mixture was heated and stirred under reflux for 2 hours 40 minutes. The reaction mixture was cooled to room temperature, IPE (200 mL) was added thereto, and the reaction mixture was stirred for 1 hour. Solids were collected by filtration and dried, thereby obtaining a target substance (18.0 g) as white solids.

Reference Example 9 (2)

Ethyl acetate (100 mL) and a 4 mol/L hydrochloric acid in an ethyl acetate solution (16.3 mL) were added to the compound (10.0 g) obtained in Reference Example 9 (1), and the mixture was stirred at room temperature for 1 hour. Methanol (1 mL) was added to the reaction mixture, and the reaction mixture was stirred at room temperature for 1 hour. 1,4-Dioxane (50 mL), 4 mol/L hydrochloric acid in a 1,4-dioxane solution (16.3 mL), and methanol (10 mL) were added to the reaction mixture, and the reaction mixture was stirred at room temperature for 2 hours and 30 minutes. IPE (150 mL) was added to the reaction mixture, and solids were collected by filtration. The solids were dried, thereby obtaining a target substance (5.0 g) as light brown solids.

Reference Example 9 (3)

THF (100 mL), water (39 mL), and sodium hydrogen carbonate (2.2 g) were added to the compound (1.3 g) obtained in Reference Example 9 (2), and the mixture was stirred under ice cooling. At the same temperature, water (39 mL), sodium hydrogen carbonate (2.2 g), and 2-chloro-3,4-bis((4-methoxybenzyl)oxy)benzoyl chloride (7.0 g) were sequentially added to the reaction mixture. At the same temperature, the reaction mixture was stirred for 2 hours and 30 minutes. THF (250 mL) and water (50 mL) were added to the reaction mixture, and the solvent was distilled away under reduced pressure. IPE was added to the residue, and solids were collected by filtration. The solids were dried, thereby obtaining a target substance (7.3 g) as white solids.

Reference Example 9 (4)

Dichloromethane (20 mL) and methanol (10 mL) were added to the compound (1.0 g) obtained in Reference Example 9 (3), and the mixture was stirred under ice cooling. At the same temperature, 2,4-dinitrophenylhydrazine (wetted with 50% water, 1.28 g) and p-toluenesulfonic acid monohydrate (308 mg) were sequentially added to the reaction mixture. The reaction mixture was stirred at room temperature for 2 hours and 30 minutes. Ethyl acetate (220 mL) and water (110 mL) were added to the reaction mixture. A saturated aqueous sodium hydrogen carbonate solution was added to the reaction mixture such that the pH was adjusted to 8.2. The organic layer was separated, washed with a saturated aqueous sodium chloride solution, and then dehydrated and dried over anhydrous sodium sulfate. The solvent was distilled away under reduced pressure, and the residue was purified by silica gel column chromatography [eluent; ethyl acetate:hexane=90:10→chloroform:methanol=90:10→80:20], thereby obtaining N-(2-(2-chloro-3,4-bis((4-methoxybenzyl)oxy)benzamido)ethyl)hydrazine carboxamide (250 mg) as light yellow solids.

NMR (DMSO-d$_6$): 3.17-3.27 (4H, m), 3.75 (3H, s), 3.77 (3H, s), 4.08 (2H, s), 4.88 (2H, s), 5.15 (2H, s), 6.57 (1H, s), 6.88 (2H, dd, J=6.4, 2.0 Hz), 6.98 (2H, dd, J=6.8, 2.0 Hz), 7.01 (1H, s), 7.17 (2H, dd, J=10.4, 8.8 Hz), 7.32 (2H, d, J=8.4 Hz), 7.58 (2H, d, J=8.4 Hz), 8.32 (1H, t, J=5.0 Hz)

Reference Example 10

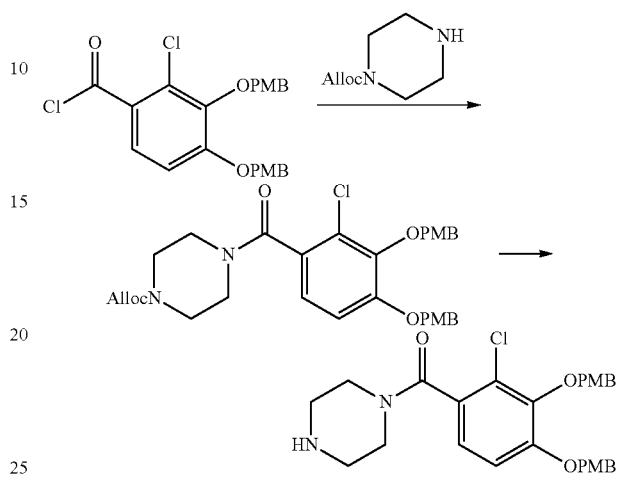

Reference Example 10 (1)

THF (100 mL) and water (75 mL) were added to allylpiperazine-1-carboxylate (2.5 g), and the mixture was stirred under ice cooling. Sodium hydrogen carbonate (1.5 g) and 2-chloro-3,4-bis((4-methoxybenzyl)oxy)benzoyl chloride (6.6 g) were sequentially added to the reaction mixture. The reaction mixture was stirred at room temperature overnight, ethyl acetate (100 mL) and water (50 mL) were then added to the reaction mixture, and the organic layer was separated. The organic layer was washed with a saturated aqueous sodium chloride solution and dehydrated and dried over anhydrous sodium sulfate. The solvent was distilled away under reduced pressure, thereby obtaining a target substance (9.17 g) as light yellow solids.

Reference Example 10 (2)

THF (170 mL), 1,3-dimethylbarbituric acid (2.5 g), and tetrakis(triphenylphosphine)palladium (0) (1.7 g) were sequentially added to the compound (8.5 g) obtained in Reference Example 10 (1), and the mixture was stirred at room temperature for 1 hour. Ethyl acetate (100 mL) and water (100 mL) were added to the reaction mixture, and the organic layer was separated. The organic layer was washed with a saturated aqueous sodium chloride solution and dehydrated and dried over anhydrous sodium sulfate. The solvent was distilled away under reduced pressure, and the residue was purified by silica gel column chromatography [carrier: silica gel NH-DM1020 (Fuji Silysia Chemical, Ltd.), eluent; chloroform], thereby obtaining 2-chloro-3,4-bis((4-methoxybenzyl)oxy)phenyl)(piperazin-1-yl)methanone (4.98 g) as a brown oily substance.

NMR: 2.65-2.74 (1H, m), 2.78-2.86 (1H, m), 2.86-2.99 (2H, m), 3.04-3.12 (1H, m), 3.12-3.21 (1H, m), 3.28 (1H, s), 3.66-3.75 (1H, m), 3.75-3.87 (1H, m), 3.79 (3H, s), 3.83 (3H, s), 4.93-5.06 (2H, m), 5.07 (2H, s), 6.78-6.85 (2H, m), 6.90-6.97 (4H, m), 7.29-7.39 (4H, m)

Reference Example 11

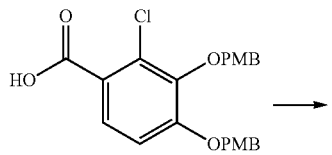

TABLE 2

| Reference Example No. | Structural Formula | Name |
|---|---|---|
| 12 | | 2-(2-chloro-3,4-bis((4-methoxybenzyl)oxy)phenyl)-N-(2-hydroxyethyl)-2-oxoacetamide |
| 13 | | (Z)-2-(2-chloro-3,4-bis((4-methoxybenzyl)oxy)phenyl)-N-(2-hydroxyethyl)-2-((trityloxy)imino)acetamide |
| 14 | | N-(2-(1H-imidazol-1-yl)ethyl)-2-chloro-3,4-bis((4-methoxybenzyl)oxy)benzamide |
| 15 | | 2-chloro-N-(1-hydroxy-3-methoxypropan-2-yl)-3,4-bis((4-methoxybenzyl)oxy)benzamide |

-continued

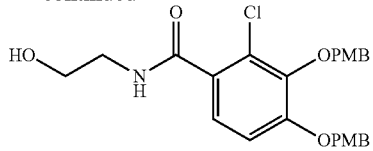

Reference Example 11

DMAC (16 mL), 2-chloro-3,4-bis((4-methoxybenzyl)oxy)benzoic acid (10.1 g), HOBt (3.89 g), EDC (6.03 g), and NMM (7.2 mL) were sequentially added to 2-aminoethanol (1.6 g). The reaction mixture was stirred at room temperature for 6 hours. Water (150 mL) and 1 mol/L hydrochloric acid were added to the reaction mixture such that the pH was adjusted to 4.9. The reaction mixture was stirred at room temperature for 1 hour, and solids were collected by filtration. The solids were dried, thereby obtaining 2-chloro-N-(2-hydroxyethyl)-3,4-bis((4-methoxybenzyl)oxy)benzamide (11.86 g) as gray solids.

NMR (DMSO-$d_6$): 3.21-3.30 (2H, m), 3.43-3.53 (2H, m), 3.75 (3H, s), 3.77 (3H, s), 4.69 (1H, t, J=5.6 Hz), 4.88 (2H, s), 5.15 (2H, s), 6.84-6.91 (2H, m), 6.94-7.01 (2H, m), 7.12-7.22 (2H, m), 7.28-7.35 (2H, m), 7.40-7.47 (2H, m), 8.22 (1H, t, J=5.6 Hz)

The compounds in Table 2 were obtained in the same manner as in Reference Example 11.

The measured values of NMR of the compounds in the table are as follows.

Reference Example 12

NMR (DMSO-$d_6$): 3.23-3.31 (2H, m), 3.46-3.54 (2H, m), 3.74 (3H, s), 3.78 (3H, s), 4.76 (1H, t, J=5.6 Hz), 4.90 (2H, s), 5.22 (2H, s), 6.81-6.89 (2H, m), 6.95-7.03 (2H, m), 7.24-7.35 (3H, m), 7.42-7.49 (2H, m), 7.52 (1H, d, J=8.4 Hz), 8.83 (1H, t, J=5.6 Hz)

Reference Example 13

NMR (DMSO-$d_6$): 3.10-3.20 (2H, m), 3.31-3.40 (2H, m), 3.66 (3H, s), 3.78 (3H, s), 4.69 (1H, t, J=5.2 Hz), 4.94 (2H, s), 5.20 (2H, s), 6.75-6.82 (2H, m), 6.96-7.03 (3H, m), 7.13-7.21 (7H, m), 7.25-7.34 (12H, m), 7.44-7.50 (2H, m)

Reference Example 14

NMR: 3.71-3.88 (2H, m), 3.80 (3H, s), 3.83 (3H, s), 4.23 (2H, t, J=5.8 Hz), 4.93 (2H, s), 5.08 (2H, s), 6.53 (1H, t, J=5.8 Hz), 6.83 (2H, d, J=8.4 Hz), 6.88-6.99 (4H, m), 7.07 (1H, s), 7.29-7.42 (5H, m), 7.51 (1H, s)

Reference Example 15

NMR: 3.40 (3H, s), 3.67 (1H, dd, J=9.6, 4.0 Hz), 3.71 (1H, dd, J=9.6, 3.6 Hz), 3.76-3.82 (1H, m), 3.81 (3H, s), 3.83 (3H, s), 3.94 (1H, dd, J=11.2, 4.0 Hz), 4.23-4.32 (1H, m), 4.95 (2H, s), 5.09 (2H, s), 6.84 (2H, dd, J=6.8, 2.0 Hz), 6.89-7.02 (4H, m), 7.35 (4H, dd, J=8.8, 1.2 Hz), 7.46 (1H, d, J=8.8 Hz)

Reference Example 16

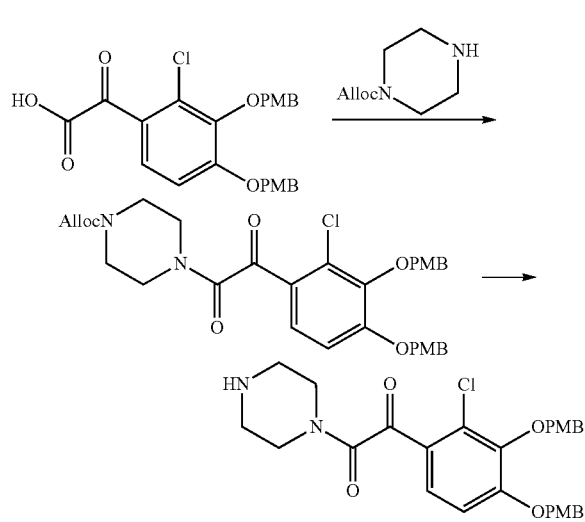

Reference Example 16 (1)

2-(2-Chloro-3,4-bis((4-methoxybenzyl)oxy)phenyl)-2-oxoacetic acid (6.7 g), HOBt (2.2 g), EDC (3.1 g), DMAC (25 mL), and NMM (1.9 mL) were sequentially added to allylpiperazine-1-carboxylate (2.5 g). The reaction mixture was stirred at room temperature overnight. Ethyl acetate (100 mL) and water (100 mL) were added to the reaction mixture, and the organic layer was separated. The organic layer was washed with a saturated aqueous sodium chloride solution and then dehydrated and dried over anhydrous sodium sulfate. The solvent was distilled away under reduced pressure, and the residue was purified by silica gel column chromatography [eluent; ethyl acetate:hexane=25:75→50:50], thereby obtaining a target substance (6.2 g) as light yellow solids.

Reference Example 16 (2)

THF (130 mL), 1,3-dimethylbarbituric acid (1.8 g), and tetrakis(triphenylphosphine)palladium (0) (1.2 g) were sequentially added to the compound (6.3 g) obtained in Reference Example 16 (1), and the mixture was stirred at room temperature for 1 hour. Ethyl acetate (100 mL) and water (100 mL) were added to the reaction mixture, and the organic layer was separated. The organic layer was washed with a saturated aqueous sodium chloride solution and dehydrated and dried over anhydrous sodium sulfate. The solvent was distilled away under reduced pressure, and the residue was purified by silica gel column chromatography [carrier: silica gel NH-DM1020 (Fuji Silysia Chemical, Ltd.), eluent; chloroform], thereby obtaining 1-(2-chloro-3,4-bis((4-methoxybenzyl)oxy)phenyl)-2-(piperazin-1-yl)ethane-1,2-dione (4.6 g) as a brown oily substance.

NMR: 2.90 (2H, t, J=5.0 Hz), 2.96 (2H, t, J=5.0 Hz), 3.28 (1H, s), 3.41 (2H, t, J=5.0 Hz), 3.68 (2H, t, J=5.0 Hz), 3.80 (3H, s), 3.83 (3H, s), 4.95 (2H, s), 5.13 (2H, s), 6.80-6.85 (2H, m), 6.90-6.95 (2H, m), 6.99 (1H, d, J=8.8 Hz), 7.30-7.35 (4H, m), 7.67-7.71 (1H, m)

Reference Example 17

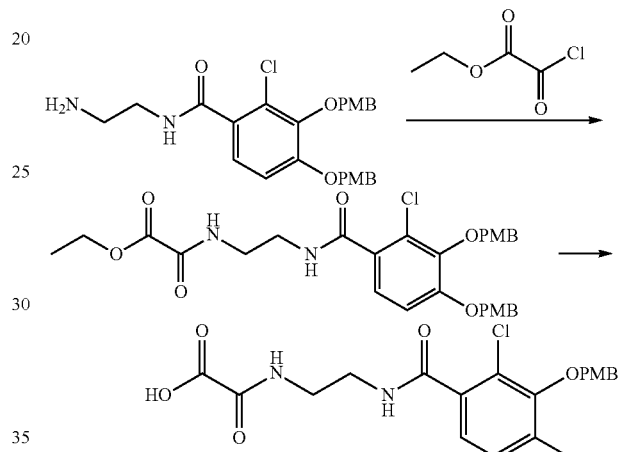

Reference Example 17 (1)

At room temperature, dichloromethane (40 mL), pyridine (310 μL), and ethyl chlorooxoacetate (430 μL) were sequentially added to N-(2-aminoethyl)-2-chloro-3,4-bis((4-methoxybenzyl)oxy)benzamide (1.2 g). The reaction mixture was stirred at a temperature of 40° C. to 50° C. for 2 hours. At the same temperature, pyridine (100 μL) and ethyl chlorooxoacetate (145 μL) were sequentially added to the reaction mixture. The reaction mixture was stirred at the same temperature for 3 hours. Chloroform and a saturated aqueous ammonium chloride solution were sequentially added to the reaction mixture, and the organic layer was separated. The organic layer was washed with a saturated aqueous sodium chloride solution and dehydrated and dried over anhydrous sodium sulfate. The solvent was distilled away under reduced pressure, and the residue was purified by silica gel column chromatography [eluent; ethyl acetate:hexane=0:100→100:0], thereby obtaining a target substance (0.61 g) as white solids.

Reference Example 17 (2)

THF (20 mL), water (10 mL), and lithium hydroxide (120 mg) were sequentially added to the compound obtained in Reference Example 17 (1), and the mixture was stirred at room temperature for 1 hour. Ethyl acetate and water were sequentially added to the reaction mixture, and the organic layer was separated. The organic layer was washed with a saturated aqueous sodium chloride solution and dehydrated and dried over anhydrous sodium sulfate. The solvent was distilled away under reduced pressure, IPE was added to the residue, and solids were collected by filtration. The solids were dried, thereby obtaining 2-((2-(2-chloro-3,4-bis((4-methoxybenzyl)oxy)benzamido)ethyl)amino)-2-oxoacetic acid (458 mg) as white solids.

NMR: 3.46-3.60 (4H, m), 3.80 (3H, s), 3.84 (3H, s), 4.95 (2H, s), 5.12 (2H, s), 6.83 (2H, d, J=8.8 Hz), 6.97 (2H, d, J=8.8 Hz), 7.13 (1H, d, J=8.4 Hz), 7.22 (1H, d, J=8.4 Hz), 7.31 (2H, d, J=8.4 Hz), 7.41 (2H, d, J=8.4 Hz)

Reference Example 18

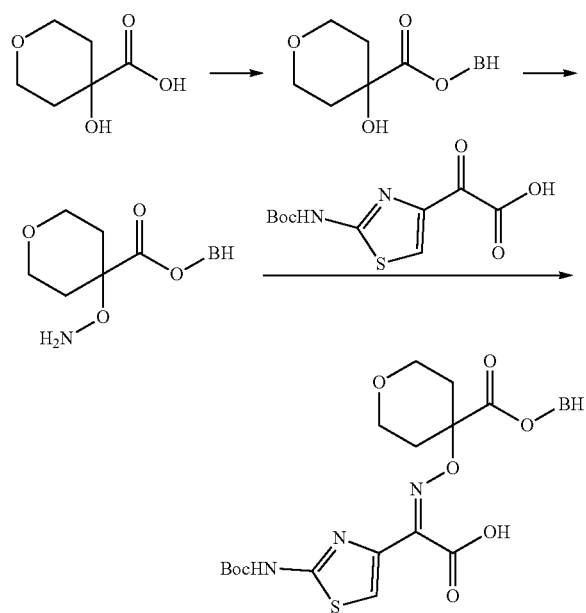

Reference Example 18 (1)

THF (16 mL) was added to 4-hydroxytetrahydro-2H-pyran-4-carboxylic acid (2.0 g), and the mixture was stirred under ice cooling. At the same temperature, 1 mol/L diphenyldiazomethane in a THF solution (16 mL) was added dropwise to the reaction mixture. The reaction mixture was stirred at room temperature overnight. The solvent was distilled away under reduced pressure, and the residue was purified by silica gel column chromatography [eluent; ethyl acetate:hexane=10:90→40:60], thereby obtaining a target substance (4.23 g) as white solids.

Reference Example 18 (2)

THF (40 mL) was added to the compound (4.32 g) obtained in Reference Example 18 (1), and the mixture was stirred under ice cooling. At the same temperature, 60% oily sodium hydride (664 mg) was added to the reaction mixture, and the reaction mixture was stirred for 20 minutes. At the same temperature, O-(mesitylsulfonyl)hydroxylamine (3.87 g) in a THF solution (40 mL) was added dropwise to the reaction mixture. At the same temperature, the reaction mixture was stirred for 3 hours. Ethyl acetate and water were added to the reaction mixture, and the organic layer was separated. The organic layer was washed with a saturated aqueous sodium chloride solution and dehydrated and dried over anhydrous sodium sulfate. The solvent was distilled away under reduced pressure, and the residue was purified by silica gel column chromatography [eluent; ethyl acetate:hexane=10:90→80:20], thereby obtaining benzhydryl 4-(aminooxy)tetrahydro-2H-pyran-4-carboxylate (3.85 g) as white solids.

NMR: 1.93-2.03 (2H, m), 2.07-2.19 (2H, m), 3.65-3.90 (4H, m), 5.29 (2H, s), 6.95 (1H, s), 7.24-7.42 (10H, m)

Reference Example 18 (3)

Methanol (40 mL) was added to benzhydryl 4-(aminooxy)tetrahydro-2H-pyran-4-carboxylate (2.73 g), and the mixture was stirred under ice cooling. At the same temperature, 2-(2-((tert-butoxycarbonyl)amino)thiazol-4-yl)-2-oxoacetic acid (2.07 g) was added to the reaction mixture, and the reaction mixture was stirred at room temperature for 3 hours. The solvent was distilled away under reduced pressure, ethyl acetate (100 mL), 1 mol/L hydrochloric acid (50 mL), and a saturated aqueous sodium chloride solution were added to the residue, and the organic layer was separated. The aqueous layer was extracted using ethyl acetate, and the organic layers were combined, washed with a saturated aqueous sodium chloride solution, and then dehydrated and dried over anhydrous sodium sulfate. The solvent was distilled away under reduced pressure, IPE (20 mL) and hexane (100 mL) were added to the residue, and solids were collected by filtration. The solids were dried, thereby obtaining (Z)-2-(((4-((benzhydryloxy)carbonyl)tetrahydro-2H-pyran-4-yl)oxy)imino)-2-(2-((tert-butoxycarbonyl)amino)thiazol-4-yl)acetic acid (3.88 g) as white solids.

NMR (DMSO-d$_6$): 1.47 (9H, s), 1.88-2.15 (4H, m), 3.50-3.76 (4H, m), 6.84 (1H, s), 7.19-7.47 (11H, m), 11.81 (1H, s), 14.17-14.22 (1H, brs)

Reference Example 19

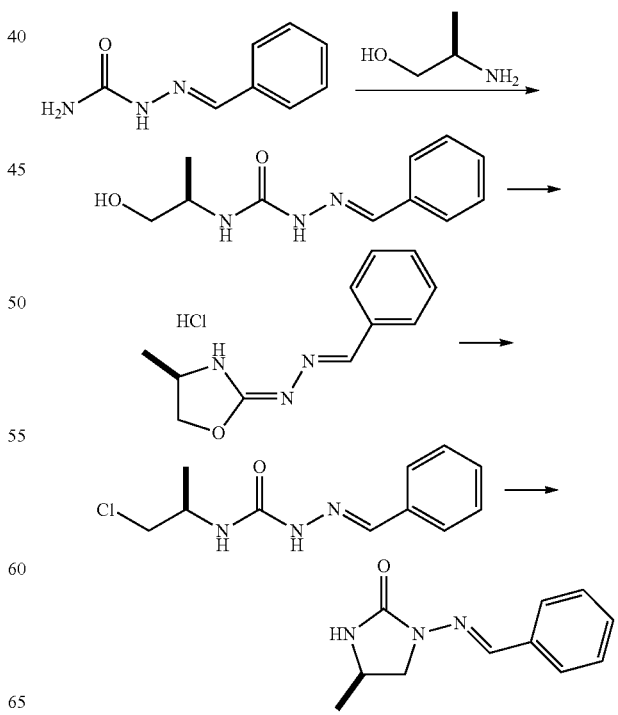

Reference Example 19 (1)

Chlorobenzene (20 mL) and D-alaninol (3.8 mL) were sequentially added to (E)-2-benzylidenehydrazine-1-carboxamide (8.00 g), and the mixture was stirred. The reaction mixture was heated and stirred under reflux for 4 hours and 20 minutes. At the same temperature, the solvent (14 mL) was distilled away. The reaction mixture was cooled to room temperature, thereby obtaining a target substance as a mixture of chlorobenzene.

Reference Example 19 (2)

Benzene (10 mL) was added to the compound obtained in Reference Example 19 (1). Thionyl chloride (5.4 mL) was added to the reaction mixture at room temperature, and the mixture was stirred for 2 hours and 30 minutes. The solvent was distilled away under reduced pressure, diethyl ether was added to the residue, and solids were collected by filtration. The solids were dried, thereby obtaining a target substance (10.93 g) as light yellow solids.

Reference Example 19 (3)

Benzene (120 mL) and toluene (40 mL) were added to the compound (10.93 g) obtained in Reference Example 19 (2), and the mixture was stirred. The reaction mixture was heated and stirred under reflux for 1 hour and 40 minutes. The reaction mixture was cooled to room temperature, and the solvent was distilled away under reduced pressure, thereby obtaining a target substance as light yellow solids.

Reference Example 19 (4)

DMF (80 mL) was added to the compound obtained in Reference Example 19 (3), and the mixture was stirred under ice cooling. At the same temperature, 60% oily sodium hydride (1.76 g) was added to the reaction mixture by being divided into three portions. The reaction mixture was stirred at room temperature for 1 hour. Ethyl acetate, water, and 1 mol/L hydrochloric acid were added to the reaction mixture. Solids were filtered, and the organic layer was separated from the filtrate. The aqueous layer was extracted twice by using ethyl acetate, and the organic layers were combined and washed with a 5% aqueous sodium chloride solution. The organic layer was dehydrated and dried over anhydrous sodium sulfate, and the solvent was distilled away under reduced pressure. IPE was added to the residue, and solids were collected by filtration. The solids were dried, thereby obtaining (R,E)-1-(benzylideneamino)-4-methylimidazolidin-2-one (6.01 g) as light yellow solids.

NMR (DMSO-$d_6$): 1.21 (3H, d, J=6.0 Hz), 3.21-3.29 (1H, m), 3.78-3.95 (2H, m), 7.29 (1H, s), 7.31-7.45 (3H, m), 7.59 (1H, s), 7.62-7.69 (2H, m)

The compounds in Table 3 were obtained in the same manner as in Reference Example 19.

TABLE 3

| Reference Example No. | Structural Formula | Name |
|---|---|---|
| 20 | | (R,E)-1(benzylideneamino)-5-methylimidazolidin-2-one |
| 21 | | (S,E)-1(benzylideneamino)-5-methylimidazolidin-2-one |

The measured values of NMR of the compounds in the table are as follows.

Reference Example 20

NMR (DMSO-$d_6$): 1.26 (3H, d, J=6.0 Hz), 2.95-3.02 (1H, m), 3.51-3.58 (1H, m), 4.23-4.35 (1H, m), 7.07 (1H, s), 7.32-7.45 (3H, m), 7.64-7.70 (2H, m), 8.20 (1H, s)

Reference Example 21

NMR: 1.26 (3H, d, J=6.0 Hz), 2.94-3.04 (1H, m), 3.55 (1H, t, J=8.6 Hz), 4.23-4.25 (1H, m), 7.08 (1H, s), 7.32-7.47 (3H, m), 7.67 (2H, d, J=6.8 Hz), 8.20 (1H, s)

Reference Example 22

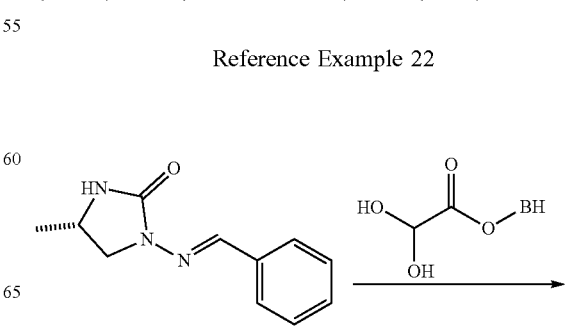

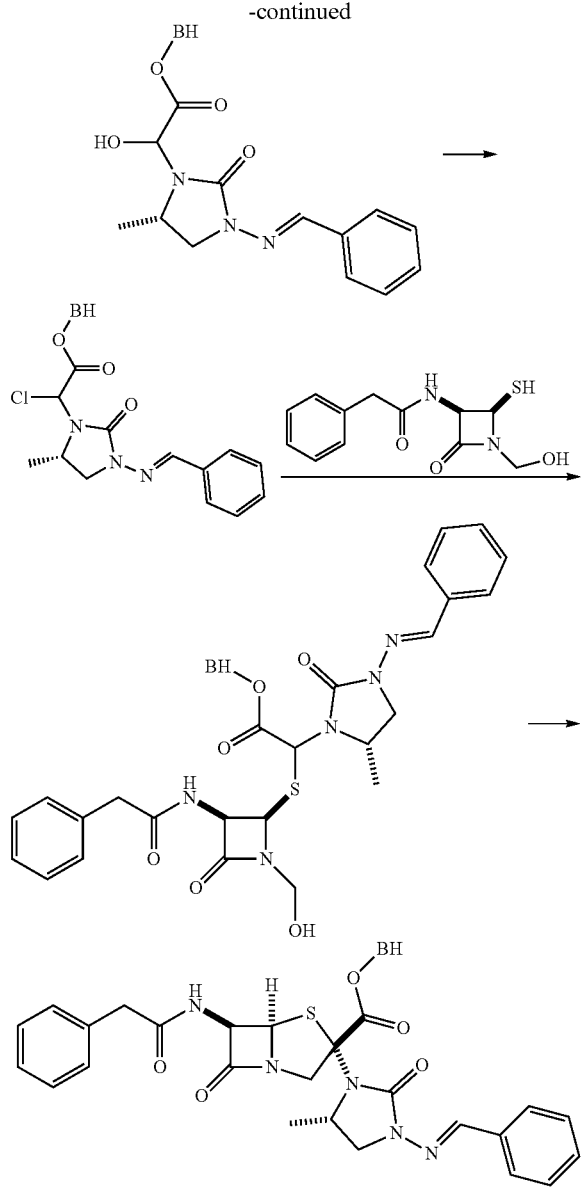

Reference Example 22 (1)

Benzhydryl 2,2-dihydroxyacetate (8.14 g) and dichloromethane (61 mL) were added to (S,E)-1-(benzylideneamino)-4-methylimidazolidin-2-one (6.10 g), and the mixture was stirred under ice cooling. At the same temperature, DBU (226 μL) was added to the reaction mixture, and then the reaction mixture was stirred at room temperature for 5 hours and 30 minutes. At room temperature, benzhydryl 2,2-dihydroxyacetate (1.16 g) was added to the reaction mixture, and the reaction mixture was stirred for 30 minutes. The solvent was distilled away under reduced pressure, thereby obtaining a target substance (13.3 g) as a yellow oily substance.

Reference Example 22 (2)

THF (130 mL) was added to the compound (13.3 g) obtained in Reference Example 22 (1), and the mixture was stirred under ice cooling. At the same temperature, 2,6-lutidine (3.8 mL) and thionyl chloride (2.4 mL) were sequentially added to the reaction mixture. The reaction mixture was stirred at room temperature for 2 hours. The reaction mixture was ice-cooled, 2,6-lutidine (3.1 mL) and thionyl chloride (2.0 mL) were sequentially added thereto, and the reaction mixture was stirred at room temperature for 30 minutes. Insoluble matters were filtered, thereby obtaining a mixture containing a target substance.

Reference Example 22 (3)

DMF (130 mL) was added to the mixture obtained in Reference Example 22 (2), and the mixture was stirred under ice cooling. At the same temperature, N-((2R,3R)-1-(hydroxymethyl)-2-mercapto-4-oxoazetidin-3-yl)-2-phenylacetamide (8.8 g) and triethylamine (4.6 mL) were sequentially added to the reaction mixture. The reaction mixture was stirred at room temperature for 1 hour. Ethyl acetate (300 mL), water (300 mL), and 1 mol/L hydrochloric acid (20 mL) were added to the reaction mixture. The organic layer was separated and sequentially washed with water and a saturated aqueous sodium chloride solution. After the organic layer was dehydrated and dried over anhydrous sodium sulfate, the solvent was distilled away under reduced pressure. IPE was added to the residue, and solids were collected by filtration. The solids were dried, thereby obtaining a target substance (20.1 g) as light yellow solids.

Reference Example 22 (4)

THF (15 mL) was added to the compound (1.5 g) obtained in Reference Example 22 (3), and the mixture was stirred under ice cooling. At the same temperature, 2,6-lutidine (280 μL) and thionyl chloride (170 μL) were sequentially added to the reaction mixture. The reaction mixture was stirred at room temperature for 1 hour. The reaction mixture was ice-cooled, 2,6-lutidine (76 μL) and thionyl chloride (47 μL) were sequentially added thereto, and the reaction mixture was stirred at room temperature for 50 minutes. Insoluble matters were filtered, and the solvent was distilled away under reduced pressure. DMF (15 mL) was added to the residue, and the mixture was stirred under ice cooling. At the same temperature, DBU (326 μL) was added to the reaction mixture, and the reaction mixture was stirred for 1 hour. Ethyl acetate (50 mL), water (50 mL), and 1 mol/L hydrochloric acid (4 mL) were added to the reaction mixture, and the organic layer was separated. The organic layer was sequentially washed with water and a 5% aqueous sodium chloride solution. After the organic layer was dehydrated and dried over anhydrous sodium sulfate, the solvent was distilled away under reduced pressure. The residue was purified by silica gel column chromatography [eluent; ethyl acetate:hexane=30:70→75:25], thereby obtaining benzhydryl (3R,5R,6R)-3-((S)-3-(((E))-benzylidene)amino)-5-methyl-2-oxoimidazolidin-1-yl)-7-oxo-6-(2-phenylacetamido)-4-thia-1-azabicyclo[3.2.0]heptane-3-carboxylate (660 mg) as yellow solids.

NMR: 1.27 (3H, d, J=7.2 Hz), 3.28-3.41 (3H, m), 3.44-3.52 (1H, m), 3.76-3.85 (1H, m), 4.17-4.28 (1H, m), 5.17 (1H, d, J=13.6 Hz), 5.48-5.56 (2H, m), 6.31 (1H, d, J=8.4 Hz), 6.89 (1H, s), 7.13-7.19 (2H, m), 7.20-7.45 (16H, m), 7.67 (1H, s), 7.70-7.77 (2H, m)

The compounds in Table 4 were obtained in the same manner as in Reference Example 22.

TABLE 4

| Reference Example No. | Structural Formula | Name |
|---|---|---|
| 23 | | Benzhydryl (3R,5R,6R)-3-((S)-3-(((E)-benzylidene)amino)-4-methyl-2-oxoimidazolidin-1-yl)-7-oxo-6-(2-phenylacetamido)-4-thia-1-azabicyclo[3.2.0]heptane-3-carboxylate |
| 24 | | Benzhydryl (3R,5R,6R)-3-((R)-3-(((E)-benzylidene)amino)-4-methyl-2-oxoimidazolidin-1-yl)-7-oxo-6-(2-phenylacetamido)-4-thia-1-azabicyclo[3.2.0]heptane-3-carboxylate |
| 25 | | Benzhydryl (3R,5R,6R)-3-((R)-3-(((E)-benzylidene)amino)-5-methyl-2-oxoimidazolidin-1-yl)-7-oxo-6-(2-phenylacetamido)-4-thia-1-azabicyclo[3.2.0]heptane-3-carboxylate |

The measured values of NMR of the compounds in the table are as follows.

Reference Example 23

NMR: 1.37 (3H, d, J=6.0 Hz), 3.26 (1H, dd, J=7.8, 5.4 Hz), 3.36 (1H, dd, J=13.2, 0.8 Hz), 3.39-3.41 (2H, m), 3.73 (1H, t, J=8.0 Hz), 4.10-4.22 (1H, m), 4.85 (1H, d, J=13.2 Hz), 5.50 (1H, d, J=4.0 Hz), 5.61 (1H, ddd, J=8.9, 3.9, 0.7 Hz), 6.56 (1H, d, J=9.2 Hz), 6.88 (1H, s), 7.15-7.43 (17H, m), 7.63-7.72 (3H, m), 8.61 (1H, s)

Reference Example 24

NMR: 1.35 (3H, d, J=6.0 Hz), 3.19 (1H, t, J=8.0 Hz), 3.35 (1H, d, J=13.2 Hz), 3.40 (2H, s), 3.80 (1H, t, J=8.0 Hz), 4.12-4.18 (1H, m), 4.93 (1H, d, J=13.2 Hz), 5.50 (1H, d, J=4.0 Hz), 5.57 (1H, dd, J=8.8, 3.6 Hz), 6.48 (1H, d, J=8.4 Hz), 6.90 (1H, s), 7.18 (2H, d, J=8.0 Hz), 7.21-7.43 (16H, m), 7.65-7.70 (2H, m), 8.73 (1H, s)

Reference Example 25

NMR: 1.45 (3H, d, J=6.4 Hz), 3.27 (2H, s), 3.34 (1H, dd, J=13.4, 1.0 Hz), 3.79 (1H, t, J=8.8 Hz), 4.03-4.11 (2H, m), 5.23 (1H, d, J=13.2 Hz), 5.45-5.53 (2H, m), 6.05 (1H, d, J=3.6 Hz), 6.88 (1H, s), 7.15-7.43 (17H, m), 7.54 (1H, s), 7.68-7.77 (2H, m)

Reference Example 26

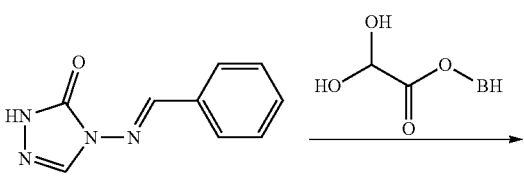

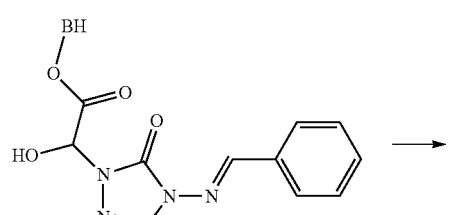

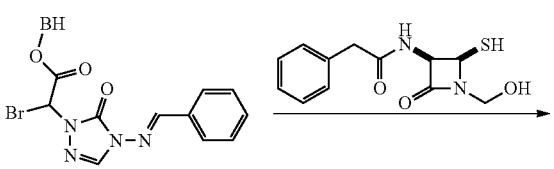

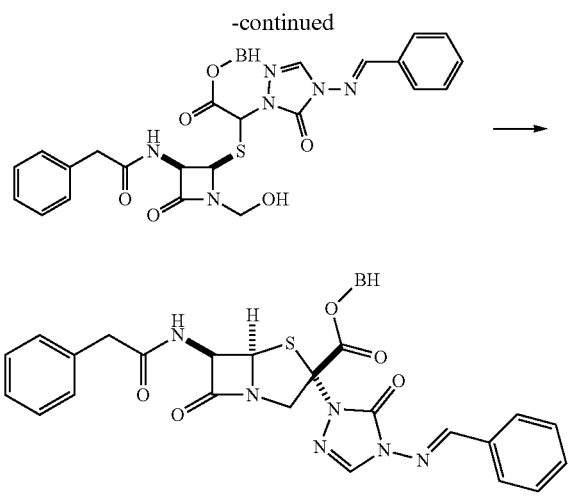

Reference Example 26 (1)

Benzhydryl 2,2-dihydroxyacetate (2.88 g) and dichloromethane (30 mL) were added to (E)-4-(benzylideneamino)-2,4-dihydro-3H-1,2,4-triazol-3-one (2.00 g), and the mixture was stirred under ice cooling. At the same temperature, DBU (79 µL) was added to the reaction mixture, and then the reaction mixture was stirred at room temperature for 1 hour and 15 minutes. Ethyl acetate (30 mL) was added to the reaction mixture, and solids were collected by filtration. The solids were washed with ethyl acetate. The solids were dried under reduced pressure, thereby obtaining a target substance (3.87 g) as white solids.

Reference Example 26 (2)

DMF (19 mL) was added to the compound (1.89 g) obtained in Reference Example 26 (1), and the mixture was stirred under ice cooling. At the same temperature, triphenylphosphine (1.5 g) and bromine (272 µL) were sequentially added to the reaction mixture. The reaction mixture was stirred at room temperature for 1 hour and 30 minutes. The reaction mixture was added to a mixture of ethyl acetate (50 mL) and water (50 mL). The organic layer was separated and sequentially washed with water and a saturated aqueous sodium chloride solution. The organic layer was dehydrated and dried over anhydrous sodium sulfate, and then the solvent was distilled away under reduced pressure. The residue was purified by silica gel column chromatography [eluent; ethyl acetate:hexane=15:85→20:80], thereby obtaining a target substance (2.02 g) as yellow solids.

Reference Example 26 (3)

DMF (40 mL) was added to the compound (2.02 g) obtained in Reference Example 26 (2), and the mixture was stirred under ice cooling. At the same temperature, N-((2R,3R)-1-(hydroxymethyl)-2-mercapto-4-oxoazetidin-3-yl)-2-phenylacetamide (1.2 g) and triethylamine (630 µL) were sequentially added to the reaction mixture. At the same temperature, the reaction mixture was stirred for 35 minutes. Ethyl acetate (78 mL) and water (62 mL) were added to the reaction mixture. The organic layer was separated and sequentially washed with water and a saturated aqueous sodium chloride solution. The organic layer was dehydrated and dried over anhydrous sodium sulfate, and the solvent was distilled away under reduced pressure. The residue was purified by silica gel column chromatography [eluent; ethyl acetate:hexane=75:25→80:20], thereby obtaining a target substance (2.81 g) as white solids.

Reference Example 26 (4)

THF (56 mL) was added to the compound (2.81 g) obtained in Reference Example 26 (3), and the mixture was stirred under ice cooling. At the same temperature, 2,6-lutidine (773 µL) and thionyl chloride (484 µL) were sequentially added to the reaction mixture. The reaction mixture was stirred at room temperature for 1 hour. Insoluble matters were filtered, and the solvent was distilled away under reduced pressure. DMF (28 mL) was added to the residue, and the mixture was stirred under ice cooling. DBU (749 µL) was added to the reaction mixture, and the reaction mixture was stirred at the same temperature for 1 hour and 30 minutes. Then, at the same temperature, DBU (62 µL) was added to the reaction mixture, and the reaction mixture was stirred for 20 minutes. The reaction mixture was added to a mixture of ethyl acetate (82 mL), water (82 mL), and 1 mol/L hydrochloric acid (5 mL), and the organic layer was separated. The aqueous layer was extracted three times by using ethyl acetate (100 mL), and the organic layers were combined and sequentially washed with water and a saturated aqueous sodium chloride solution. After the organic layer was dehydrated and dried over anhydrous sodium sulfate, the solvent was distilled away under reduced pressure. Ethyl acetate (15 mL) was added to the residue, and solids were collected by filtration. The solids were dried, thereby obtaining benzhydryl (3R,5R,6R)-3-(4-(((E)-benzylidene)amino)-5-oxo-4,5-dihydro-1H-1,2,4-triazol-1-yl)-7-oxo-6-(2-phenylacetamido)-4-thia-1-azabicyclo[3.2.0]heptane-3-carboxylate (1.97 g) as white solids.

NMR: 3.47 (2H, s), 3.93 (1H, dd, J=13.4, 0.6 Hz), 4.75 (1H, d, J=13.6 Hz), 5.58 (1H, d, J=4.0 Hz), 5.73 (1H, dd, J=9.2, 3.6 Hz), 6.75 (1H, d, J=9.6 Hz), 6.78 (1H, s), 7.16-7.35 (14H, m), 7.44-7.56 (4H, m), 7.75 (2H, dd, J=8.2, 1.4 Hz), 7.80 (1H, s), 9.54 (1H, s)

Reference Example 27

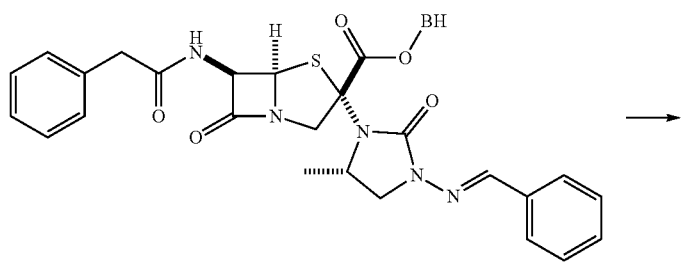

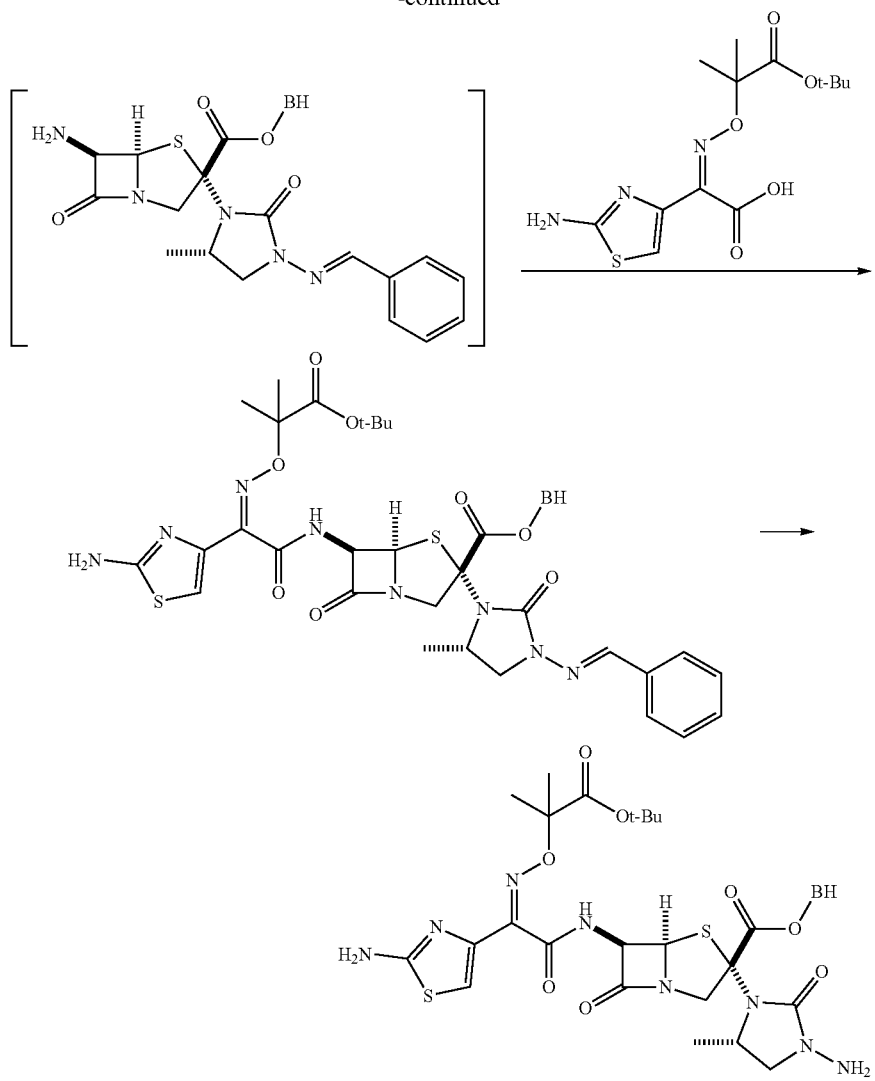

Reference Example 27 (1)

Dichloromethane (6.6 mL) was added to benzhydryl (3R,5R,6R)-3-((S)-3-(((E)-benzylidene)amino)-5-methyl-2-oxoimidazolidin-1-yl)-7-oxo-6-(2-phenylacetamido)-4-thia-1-azabicyclo[3.2.0]heptane-3-carboxylate (660 mg), and the reaction mixture was cooled to a temperature equal to or lower than −30° C. At the same temperature, N,N-dimethylaniline (435 μL) and phosphorus pentachloride (306 mg) were sequentially added to the reaction mixture, and the reaction mixture was stirred at −30° C. for 1 hour. Then, at the same temperature, methanol (600 μL) was added to the reaction mixture, and the reaction mixture was stirred for 30 minutes under ice cooling. Dichloromethane (20 mL) and an aqueous sodium hydrogen carbonate solution (1.07 g of sodium hydrogen carbonate/20 mL of water) were added to the reaction mixture, and the organic layer was separated. The organic layer was dehydrated and dried over anhydrous sodium sulfate, and solids were filtered. (Z)-2-(2-aminothiazol-4-yl)-2-(((1-(tert-butoxy)-2-methyl-1-oxopropan-2-yl)oxy)imino)acetic acid (355 mg), HATU (410 mg), 2,6-lutidine (251 μL), and DMF (6.6 mL) were added to the filtrate. The reaction mixture was stirred at room temperature under reduced pressure until the reaction mixture became a solution. Water (20 mL) and ethyl acetate (20 mL) were added to the reaction mixture, and the organic layer was separated. The organic layer was washed three times with a 5% aqueous sodium chloride solution. The organic layer was dehydrated and dried over anhydrous sodium sulfate, and then the solvent was distilled away under reduced pressure. The residue was purified by silica gel column chromatography [eluent; ethyl acetate:hexane=60:40→100:0], thereby obtaining a target substance (180 mg) as a yellow oily substance.

Reference Example 27 (2)

Dichloromethane (3.6 mL) and methanol (1.8 mL) were added to the compound (180 mg) obtained in Reference Example 27 (1), and the mixture was stirred under ice cooling. At the same temperature, 2,4-dinitrophenylhydrazine (wetted with 50% water, 165 mg) and p-toluenesulfonic acid monohydrate (40 mg) were sequentially added to the reaction mixture. The reaction mixture was stirred at room temperature for 5 hours. Ethyl acetate (20 mL) and water (10 mL) were added to the reaction mixture. A saturated aqueous sodium hydrogen carbonate solution was added to the reaction mixture such that the pH was adjusted to 7.7. The organic layer was separated, washed with a 5% aqueous sodium chloride solution, and then dehydrated and dried over anhydrous sodium sulfate. The solvent was distilled away under reduced pressure, and the residue was purified by silica gel column chromatography [eluent; ethyl acetate:hexane=70:30→100:0→chloroform:2-propanol=100:0→80:20], thereby obtaining benzhydryl (3R,5R,6R)-3-((S)-3-amino-5-methyl-2-oxoimidazolidinon-1-yl)-6-((Z)-2-(2-aminothiazol-4-yl)-2-(((1-(tert-butoxy)-2-methyl-1-oxopropan-2-yl)oxy)imino)acetamido)-7-oxo-4-thia-1-azabicyclo[3.2.0]heptane-3-carboxylate (90 mg) as a yellow oily substance.

NMR: 1.16-1.23 (3H, m), 1.41 (9H, s), 1.49 (3H, s), 1.51 (3H, s), 3.17 (1H, dd, J=8.4, 2.0 Hz), 3.36 (1H, d, J=13.2 Hz), 3.45-3.54 (1H, m), 3.81 (2H, s), 3.92-4.03 (1H, m), 5.07 (1H, d, J=13.2 Hz), 5.59 (1H, d, J=4.0 Hz), 5.80 (1H, dd, J=8.8, 4.0 Hz), 6.48 (2H, s), 6.79 (1H, s), 6.88 (1H, s), 6.92-7.01 (1H, m), 7.21-7.42 (10H, m)

The compounds in Table 5 were obtained in the same manner as in Reference Example 27.

TABLE 5

| Reference Example No. | Structural Formula | Name |
|---|---|---|
| 28 |  | Benzhydryl (3R,5R,6R)-3-(3-amino-2-oxoimidazolidin-1-yl)-6-((Z)-2-(2-aminothiazol-4-yl)-2-(((1-(tert-butoxy)-2-methyl-1-oxopropan-2-yl)oxy)imino)acetamido)-7-oxo-4-thia-1-azabicyclo[3.2.0]heptane-3-carboxylate |
| 29 |  | Benzhydryl (3R,5R,6R)-3-((S)-3-amino-5-methyl-2-oxoimidazolidin-1-yl)-6-((Z)-2-(((1-(tert-butoxy)-2-methyl-1-oxopropan-2-yl)oxy)imino)-2-(2-((tert-butoxycarbonyl)amino)thiazol-4-yl)acetamido)-7-oxo-4-thia-1-azabicyclo[3.2.0]heptane-3-carboxylate |
| 30 |  | Benzhydryl (3R,5R,6R)-3-((S)-3-amino-4-methyl-2-oxoimidazolidin-1-yl)-6-((Z)-2-(((1-(tert-butoxy)-2-methyl-1-oxopropan-2-yl)oxy)imino)-2-(2-((tert-butoxycarbonyl)amino)thiazol-4-yl)acetamido)-7-oxo-4-thia-1-azabicyclo[3.2.0]heptane-3-carboxylate |

TABLE 5-continued

| Reference Example No. | Structural Formula | Name |
|---|---|---|
| 31 | | Benzhydryl (3R,5R,6R)-3-((R)-3-amino-4-methyl-2-oxoimidazolidin-1-yl)-6-((Z)-2-(2-aminothiazol-4-yl)-2-(((1-(tert-butoxy)-2-methyl-1-oxopropan-2-yl)oxy)imino)acetamido)-7-oxo-4-thia-1-azabicyclo[3.2.0]heptane-3-carboxylate |
| 32 | | Benzhydryl (3R,5R,6R)-3-((R)-3-amino-5-methyl-2-oxoimidazolidin-1-yl)-6-((Z)-2-(2-aminothiazol-4-yl)-2-(((1-(tert-butoxy)-2-methyl-1-oxopropan-2-yl)oxy)imino)acetamido)-7-oxo-4-thia-1-azabicyclo[3.2.0]heptane-3-carboxylate |
| 33 | | Benzhydryl (3R,5R,6R)-3-((R)-3-amino-5-methyl-2-oxoimidazolidin-1-yl)-6-((Z)-2-((1-((benzhydryloxy)carbonyl)cyclobutoxy)imino)-2-(2-((tert-butoxy)amino)thiazol-4-yl)acetamido)-7-oxo-4-thia-1-azabicyclo[3.2.0]heptane-3-carboxylate |
| 34 | | Benzhydryl (3R,5R,6R)-3-((4-amino-5-oxo-4,5-dihydro-1H-1,2,4-triazol-1-yl))-6-((Z)-2-(((1-(tert-butoxy)-2-methyl-1-oxopropan-2-yl)oxy)imino)-2-(2-((tert-butoxycarbonyl)amino)thiazol-4-yl)acetamido)-7-oxo-4-thia-1-azabicyclo[3.2.0]heptane-3-carboxylate |

The measured values of NMR of the compounds in the table are as follows.

Reference Example 28

NMR: 1.39 (9H, s), 1.48 (3H, s), 1.50 (3H, s), 3.40-3.55 (5H, m), 3.83 (2H, s), 4.95 (1H, d, J=13.2 Hz), 5.57 (1H, d, J=4.0 Hz), 5.79 (1H, dd, J=8.4, 3.6 Hz), 6.40 (2H, s), 6.79 (1H, s), 6.87 (1H, s), 7.06 (1H, d, J=8.8 Hz), 7.16-7.40 (10H, m)

Reference Example 29

NMR: 1.19 (3H, d, J=6.4 Hz), 1.41 (9H, s), 1.49-1.57 (15H, m), 3.17 (1H, dd, J=8.0, 1.6 Hz), 3.35 (1H, dd, J=13.2, 0.8 Hz), 3.45-3.54 (1H, m), 3.81 (2H, s), 3.93-4.04 (1H, m), 5.09 (1H, d, J=13.2 Hz), 5.60 (1H, d, J=4.0 Hz), 5.78 (1H, dd, J=8.0, 4.0 Hz), 6.88 (1H, s), 7.09-7.17 (1H, m), 7.19-7.43 (11H, m), 8.15 (1H, s)

Reference Example 30

NMR: 1.23 (3H, d, J=6.0 Hz), 1.39 (9H, s), 1.50 (3H, s), 1.52 (3H, s), 1.54 (9H, s), 3.01 (1H, t, J=6.8 Hz), 3.43-3.57 (3H, m), 3.67 (2H, s), 4.83 (1H, d, J=12.8 Hz), 5.58 (1H, d, J=4.0 Hz), 5.82 (1H, dd, J=8.4, 3.6 Hz), 6.86 (1H, s), 7.14-7.44 (11H, m), 7.54 (1H, d, J=8.8 Hz), 8.19 (1H, s)

Reference Example 31

NMR: 1.22 (3H, d, J=6.0 Hz), 1.39 (9H, s), 1.50 (3H, s), 1.52 (3H, s), 3.01 (1H, t, J=8.4 Hz), 3.46-3.58 (2H, m), 3.60-3.73 (3H, m), 4.99 (1H, d, J=13.2 Hz), 5.57 (1H, d, J=4.0 Hz), 5.75-5.81 (1H, m), 6.84 (1H, s), 6.85 (1H, s), 7.15-7.38 (13H, m)

Reference Example 32

NMR: 1.35 (3H, d, J=6.4 Hz), 1.39 (9H, s), 1.48 (3H, s), 1.49 (3H, s), 3.14 (1H, dd, J=8.2, 3.0 Hz), 3.36 (1H, dd, J=13.2, 0.8 Hz), 3.54 (1H, t, J=8.6 Hz), 3.69 (2H, s), 3.83-3.94 (1H, m), 5.15 (1H, d, J=13.2 Hz), 5.58 (1H, d, J=4.0 Hz), 5.74 (1H, dd, J=7.8, 3.4 Hz), 6.50 (2H, s), 6.77 (1H, s), 6.88 (1H, s), 6.95 (1H, d, J=8.4 Hz), 7.14-7.42 (10H, m)

Reference Example 33

NMR: 1.32 (3H, d, J=6.4 Hz), 1.55 (9H, s), 1.92-2.03 (2H, m), 2.38-2.51 (2H, m), 2.55-2.69 (2H, m), 3.12 (1H, dd, J=8.0, 2.8 Hz), 3.35 (1H, dd, J=13.0, 1.0 Hz), 3.49 (1H, t, J=8.4 Hz), 3.66 (2H, s), 3.77-3.87 (1H, m), 5.17 (1H, d, J=13.6 Hz), 5.55 (1H, d, J=3.6 Hz), 5.75 (1H, dd, J=8.0, 3.6 Hz), 6.86 (1H, s), 6.91 (1H, s), 7.03 (1H, s), 7.11-7.42 (21H, m), 8.16 (1H, s)

Reference Example 34

NMR: 1.38 (9H, s), 1.51 (3H, s), 1.53 (9H, s), 1.54 (3H, s), 4.00 (1H, d, J=13.6 Hz), 4.24 (2H, s), 4.70 (1H, d, J=13.6 Hz), 5.64 (1H, d, J=4.0 Hz), 5.93 (1H, dd, J=9.2, 4.0 Hz), 6.81 (1H, s), 7.17-7.40 (11H, m), 7.56 (1H, s), 7.63 (1H, d, J=9.2 Hz), 8.20 (1H, s)

Reference Example 35

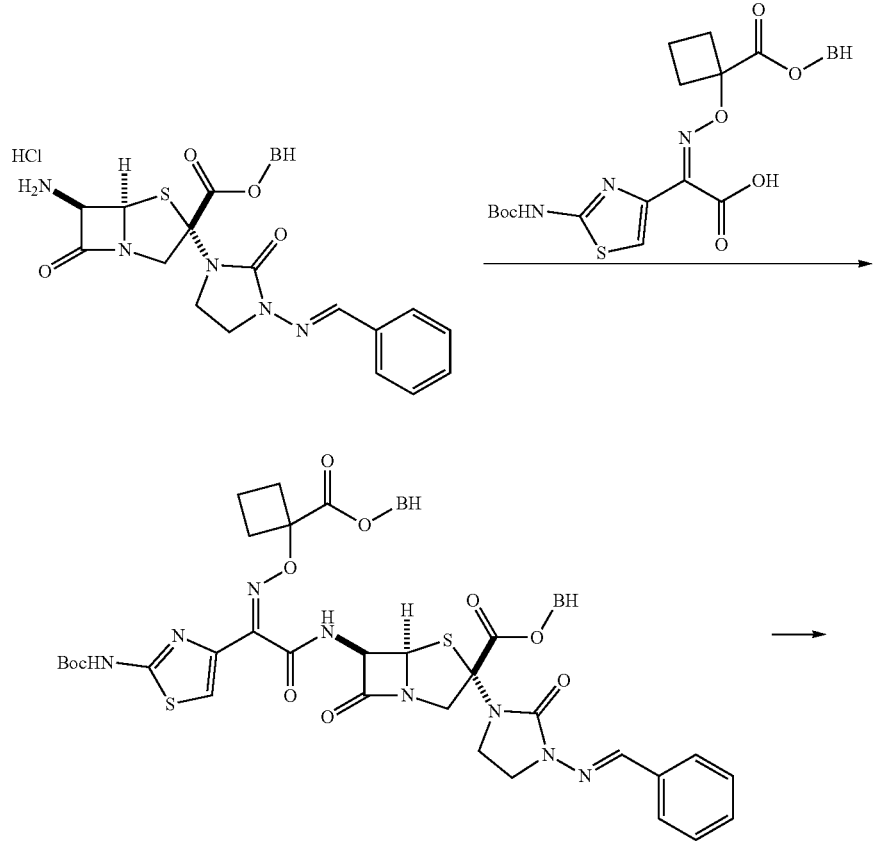

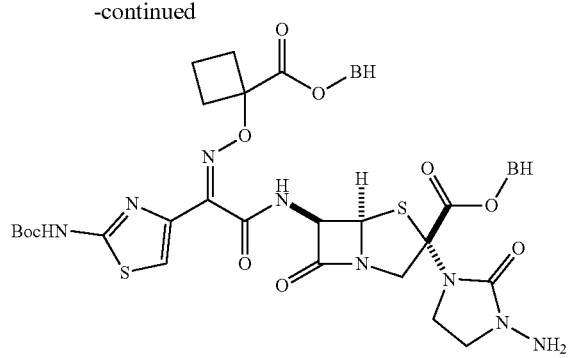

Reference Example 35 (1)

(Z)-2-((1-((benzhydryloxy)carbonyl)cyclobutoxy)imino)-2-(2-((tert-butoxycarbonyl)amino)thiazol-4-yl)acetic acid (191 mg), HOBt (51 mg), EDC (73 mg), NMM (84 μL), and DMF (2 mL) were sequentially added to benzhydryl (3R,5R,6R)-6-amino-3-(3-(((E)-benzylidene)amino)-2-oxoimidazolidin-1-yl)-7-oxo-4-thia-1-azabicyclo[3.2.0]heptane-3-carboxylate hydrochloride (200 mg). The reaction mixture was stirred at room temperature overnight. Ethyl acetate (10 mL) and water (10 mL) were added to the reaction mixture, and the organic layer was separated. The organic layer was washed with a saturated aqueous sodium chloride solution and dehydrated and dried over anhydrous sodium sulfate. The solvent was distilled away under reduced pressure, and the residue was purified by silica gel column chromatography [eluent; ethyl acetate:hexane=40:60→80:20], thereby obtaining a target substance (159 mg) as light yellow solids.

Reference Example 35 (2)

Dichloromethane (3.2 mL) and methanol (1.6 mL) were added to the compound (159 mg) obtained in Reference Example 35 (1), and the mixture was stirred under ice cooling. At the same temperature, 2,4-dinitrophenylhydrazine (wetted with 50% water, 59 mg) and p-toluenesulfonic acid monohydrate (28 mg) were sequentially added to the reaction mixture. The reaction mixture was stirred at room temperature for 3 hours. Ethyl acetate (20 mL) and water (20 mL) were added to the reaction mixture. A saturated aqueous sodium hydrogen carbonate solution was added to the reaction mixture such that the pH was adjusted to 6.4. The organic layer was separated, washed with a saturated aqueous sodium chloride solution, and then dehydrated and dried over anhydrous sodium sulfate. The solvent was distilled away under reduced pressure, and the residue was purified by silica gel column chromatography [eluent; ethyl acetate:hexane=70:30→100:0], thereby obtaining benzhydryl (3R,5R,6R)-3-(3-amino-2-oxoimidazolidin-1-yl)-6-((Z)-2-((1-((benzhydryloxy)carbonyl)cyclobutoxy)imino)-2-(2-((tert-butoxycarbonyl)amino)thiazol-4-yl)acetamido)-7-oxo-4-thia-1-azabicyclo[3.2.0]heptane-3-carboxylate (104 mg) as light yellow solids.

NMR: 1.54 (9H, s), 1.92-2.02 (2H, m), 2.36-2.53 (2H, m), 2.56-2.67 (2H, m), 3.31-3.49 (4H, m), 3.52 (1H, d, J=13.2 Hz), 3.81 (2H, s), 4.95 (1H, d, J=13.2 Hz), 5.55 (1H, d, J=4.0 Hz), 5.79 (1H, dd, J=8.8, 3.6 Hz), 6.84 (1H, s), 6.90 (1H, s), 7.06 (1H, s), 7.09-7.15 (1H, m), 7.17-7.39 (20H, m), 8.13 (1H, s)

The compounds in Table 6 were obtained in the same manner as in Reference Example 35.

TALBE 6

| Reference Example No. | Structural Formula | Name |
|---|---|---|
| 36 | | Benzhydryl (3R,5R,6R)-3-(3-amino-2-oxoimidazolidin-1-yl)-6-((Z)-2-(((1-(tert-butoxy)-2-methyl-1-oxopropan-2-yl)oxy)imino)-2-(2-((tert-butoxycarbonyl)amino)thiazol-4-yl)acetamido)-7-oxo-4-thia-1-azabicyclo[3.2.0]heptane-3-carboxylate |

TABLE 6-continued

| | | |
|---|---|---|
| 37 | 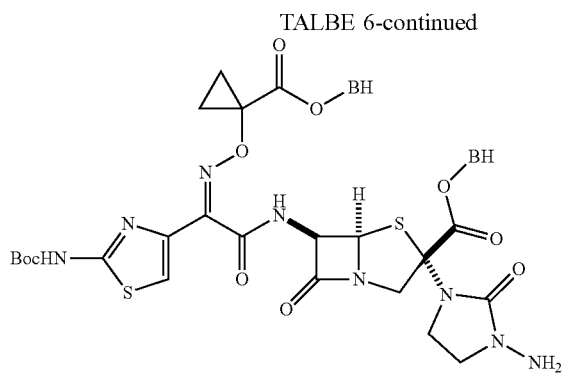 | Benzhydryl (3R,5R,6R)-3-(3-amino-2-oxoimidazolidin-1-yl)-6-((Z)-2-((1-((benzhydryloxy)carbonyl)cyclopropoxy)imino)-2-(2-(((tert-butoxycarbonyl)amino)thiazol-4-yl)acetamido)-7-oxo-4-thia-1-azabicyclo[3.2.0]heptane-3-carboxylate |
| 38 | 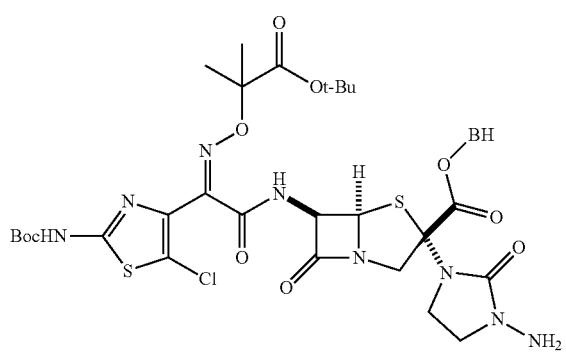 | Benzhydryl (3R,5R,6R)-3-(3-amino-2-oxoimidazolidin-1-yl)-6-((Z)-2-(((1-(tert-butoxy)-2-methyl-1-oxopropan-2-yl)oxy)imino)-2-(2-((tert-butoxycarbonyl)amino)-5-chlorothiazol-4-yl)acetamido)-7-oxo-4-thia-1-azabicyclo[3.2.0]heptane-3-carboxylate |
| 39 | 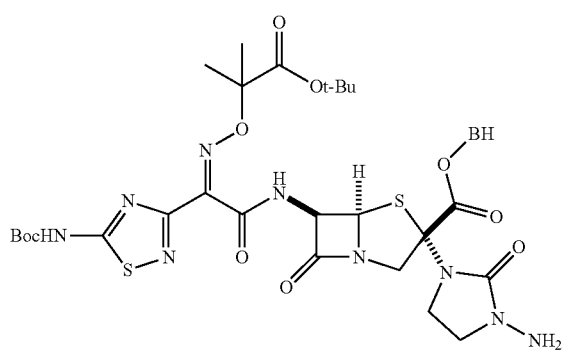 | Benzhydryl (3R,5R,6R)-3-(3-amino-2-oxoimidazolidin-1-yl)-6-((Z)-2-(((1-(tert-butoxy)-2-methyl-1-oxopropan-2-yl)oxy)imino)-2-(5-((tert-butoxycarbonyl)amino)-1,2,4-thiadiazol-3-yl)acetamido)-7-oxo-4-thia-1-azabicyclo[3.2.0]heptanne-3-carboxylate |
| 40 | 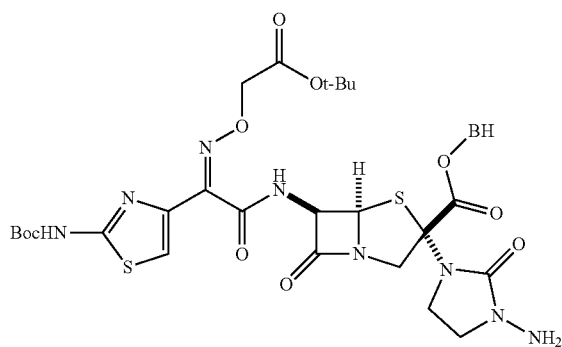 | Benzhydryl (3R,5R,6R)-3-(3-amino-2-oxoimidazolidin-1-yl)-6-((Z)-2-((2-((tert-butoxy)-2-oxoethoxy)imino)-2-(2-(((tert-butoxycarbonyl)amino)thiazol-4-yl)acetamido)-7-oxo-4-thia-1-azabicyclo[3.2.0]heptane-3-carboxylate |

TABLE 6-continued

| 41 | 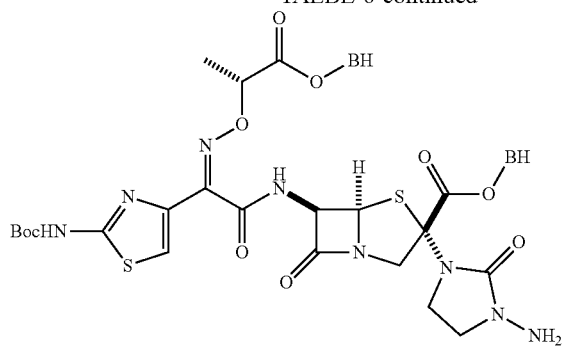 | Benzhydryl (3R,5R,6R)-3-(3-amino-2-oxoimidazolidin-1-yl)-6-((Z)-2-((((R)-1-(benzydryloxy)-1-oxopropan-2-yl)oxy)imino)-2-(2-((tert-butoxycarbonyl)amino)thiazol-4-yl)acetamido)-7-oxo-4-thia-1-azabicyclo[3.2.0]heptane-3-carboxylate |
| --- | --- | --- |
| 42 | 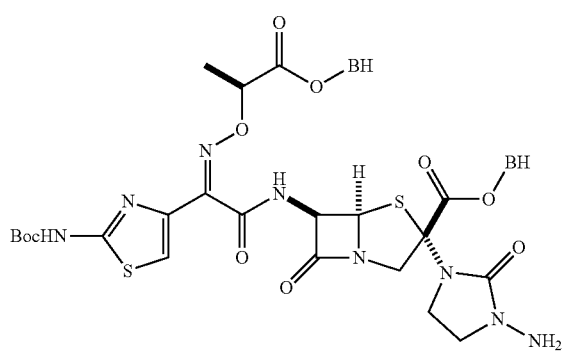 | Benzhydryl (3R,5R,6R)-3-(3-amino-2-oxoimidazolidin-1-yl)-6-((Z)-2-((((S)-1-(benzhydryloxy)-1-oxopropan-2-yl)oxy)imino)-2-(2-((tert-butoxycarbonyl)amino)thiazol-4-yl)acetamido)-7-oxo-4-thia-1-azabicyclo[3.2.0]heptane-3-carboxylate |
| 43 | 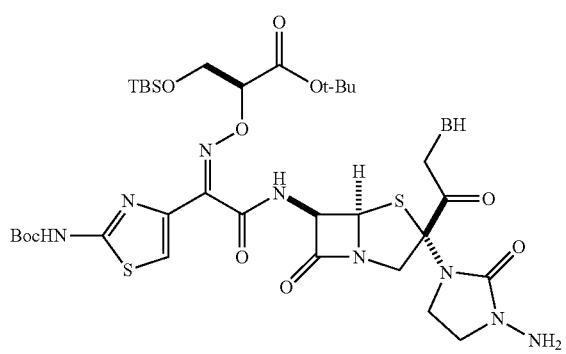 | Benzhydryl (3R,5R,6R)-3-(3-amino-2-oxoimidazolidin-1-yl)-6-((S,Z)-5-(tert-butoxycarbonyl)-2-(2-((tert-butoxycarbonyl)amino)thiazol-4-yl)-8,8,9,9-tetramethyl-4,7-dioxa-3-aza-8-siladec-2-enamido)-7-oxo-4-thia-1-azabicyclo[3.2.0]heptane-3-carboxylate |
| 44 | 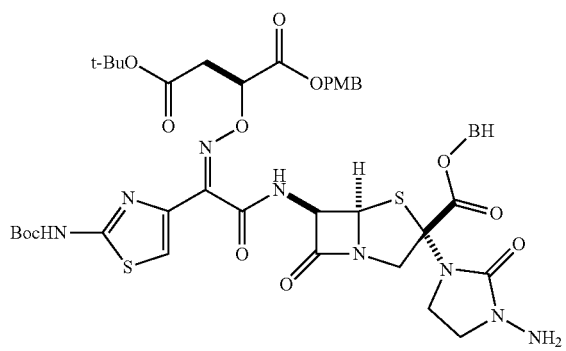 | 4-(tert-butyl)1-(4-methoxybenzyl) (S)-2-((((Z)-2-(((3R,5R,6R)-3-(3-amino-2-oxoimidazolidin-1-yl)-3-((benzhydryloxy)carbonyl)-7-oxo-4-thia-1-azabicyclo[3.2.0]heptan-6-yl)amino)-1-(2-((tert-butoxycarbonyl)amino)thiazol-4-yl)-2-oxoethylidene)amino)oxy)succinic acid |

TABLE 6-continued

| | | |
|---|---|---|
| 45 | 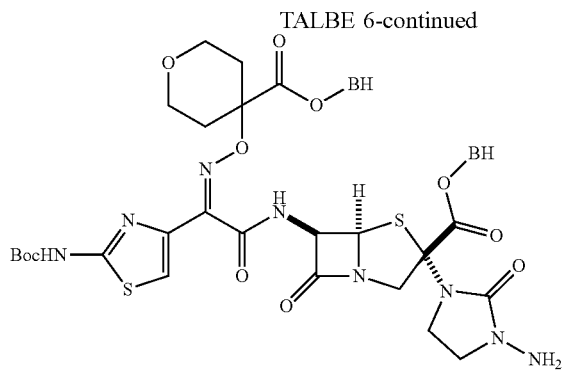 | Benzhydryl (3R,5R,6R)-3-(3-amino-2-oxoimidazolidin-1-yl)-6-((Z)-2-(((4-((benzhydryloxy)carbonyl)tetrahydro-2H-pyran-4-yl)oxy)imino)-2-(2-((tert-butoxycarbonyl)amino)thiazol-4-yl)acetamido)-7-oxo-4-thia-1-azabicyclo[3.2.0]heptane-3-carboxylate |
| 46 | 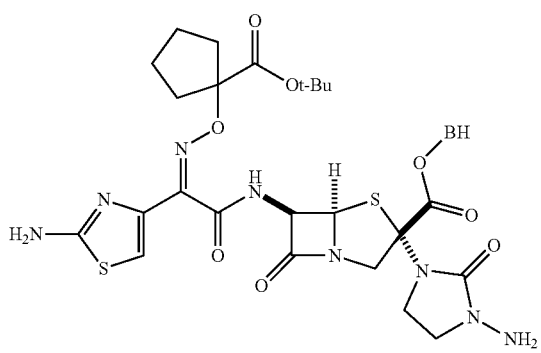 | Benzhydryl (3R,5R,6R)-3-(3-amino-2-oxoimidazolidin-1-yl)-6-((Z)-2-(2-aminothiazol-4-yl)-2-(((1-(tert-butoxycarbonyl)cyclopentyl)oxy)imino)acetamido)-7-oxo-4-thia-1-azabicyclo[3.2.0]heptane-3-carboxylate |

The measured values of NMR of the compounds in the table are as follows.

Reference Example 36

NMR: 1.39 (9H, s), 1.48-1.56 (15H, m), 3.37-3.57 (5H, m), 3.81 (2H, s), 4.95 (1H, d, J=13.2 Hz), 5.58 (1H, d, J=4.0 Hz), 5.79 (1H, dd, J=8.0, 4.0 Hz), 6.87 (1H, s), 7.12-7.20 (1H, m), 7.21-7.41 (10H, m), 7.47 (1H, d, J=8.0 Hz), 8.12 (1H, s)

Reference Example 37

NMR: 1.46-1.61 (4H, m), 1.54 (9H, s), 3.31-3.48 (4H, m), 3.50 (1H, d, J=13.2 Hz), 3.82 (2H, s), 4.94 (1H, d, J=13.2 Hz), 5.56 (1H, d, J=3.6 Hz), 5.74 (1H, dd, J=8.4, 3.6 Hz), 6.83 (1H, s), 6.88 (1H, s), 7.08-7.15 (1H, m), 7.16-7.43 (21H, m), 8.18 (1H, s)

Reference Example 38

NMR: 1.40 (9H, s), 1.50 (3H, s), 1.52 (3H, s), 1.52 (9H, s), 3.38-3.56 (5H, m), 3.81 (2H, s), 4.95 (1H, d, J=13.2 Hz), 5.56 (1H, d, J=4.0 Hz), 5.79 (1H, dd, J=8.8, 3.2 Hz), 6.88 (1H, s), 7.18-7.39 (11H, m), 8.05 (1H, s)

Reference Example 39

NMR: 1.39 (9H, s), 1.55 (3H, s), 1.57 (3H, s), 1.57 (9H, s), 3.38-3.56 (5H, m), 3.83 (2H, s), 4.92 (1H, d, J=13.2 Hz), 5.57 (1H, d, J=3.6 Hz), 5.83 (1H, dd, J=8.8, 3.6 Hz), 6.87 (1H, s), 7.12-7.18 (1H, m), 7.22-7.43 (10H, m), 8.58 (1H, s)

Reference Example 40

NMR: 1.41 (9H, s), 1.55 (9H, s), 3.37-3.58 (5H, m), 3.80 (2H, s), 4.57 (1H, d, J=16.4 Hz), 4.63 (1H, d, J=16.4 Hz), 5.00 (1H, d, J=13.2 Hz), 5.60 (1H, d, J=4.0 Hz), 5.66 (1H, dd, J=7.2, 3.4 Hz), 6.87 (1H, s), 7.10-7.18 (1H, m), 7.20-7.41 (10H, m), 7.90 (1H, d, J=7.2 Hz), 8.13 (1H, s)

Reference Example 41

NMR: 1.53 (3H, d, J=7.2 Hz), 1.54 (9H, s), 3.25-3.49 (4H, m), 3.53 (1H, d, J=13.2 Hz), 3.80 (2H, s), 4.96 (1H, d, J=13.2 Hz), 5.02 (1H, dd, J=14.0, 7.2 Hz), 5.55 (1H, d, J=4.0 Hz), 5.78 (1H, dd, J=9.2, 3.6 Hz), 6.82 (1H, s), 6.89 (1H, s), 7.05-7.12 (1H, m), 7.12-7.42 (21H, m), 8.12 (1H, s)

Reference Example 42

NMR: 1.51 (3H, d, J=7.2 Hz), 1.55 (9H, s), 3.37-3.53 (5H, m), 3.83 (2H, s), 4.97-5.06 (2H, m), 5.53 (1H, d, J=4.0 Hz), 5.69 (1H, dd, J=7.6, 3.6 Hz), 6.86 (1H, s), 6.89 (1H, s), 7.06-7.12 (1H, m), 7.15-7.44 (21H, m), 8.08 (1H, s)

Reference Example 43

NMR: −0.01 (3H, s), 0.00 (3H, s), 0.82 (9H, s), 1.57 (9H, s), 3.25-3.60 (5H, m), 3.84 (2H, s), 4.06-4.18 (3H, m), 5.04-5.11 (2H, m), 5.46-5.53 (1H, m), 5.59 (1H, d, J=4.0 Hz), 6.85 (1H, s), 6.92 (1H, s), 6.98-7.40 (20H, m), 7.72 (1H, d, J=5.6 Hz), 8.10 (1H, s)

Reference Example 44

NMR: 1.40 (9H, s), 1.55 (9H, s), 2.83 (21H, d, J=6.8 Hz), 3.34-3.59 (5H, m), 3.76 (3H, s), 3.81 (2H, s), 4.97 (1H, d, J=12.0 Hz), 5.02 (1H, d, J=13.2 Hz), 5.03 (1H, d, J=12.0 Hz), 5.26 (1H, t, J=6.4 Hz), 5.58 (1H, d, J=3.6 Hz), 5.64 (1H, dd, J=6.8, 3.6 Hz), 6.78 (1H, d, J=8.8 Hz), 6.86 (1H, s), 7.12-7.40 (14H, m), 7.70 (1H, d, J=7.2 Hz), 8.13 (1H, s)

71
Reference Example 45
NMR: 1.54 (9H, s), 2.09-2.29 (4H, m), 3.32-3.49 (4H, m), 3.52 (1H, dd, J=13.2, 0.8 Hz), 3.67-3.85 (6H, m), 4.85 (1H, d, J=13.2 Hz), 5.57 (1H, d, J=4.0 Hz), 5.86 (1H, dd, J=9.2, 3.6 Hz), 6.85 (1H, s), 6.90-6.93 (2H, m), 7.13-7.45 (21H, m), 8.15 (1H, s)
72
Reference Example 46
NMR: 1.38 (9H, s), 1.64-1.79 (4H, m), 2.02-2.25 (4H, m), 3.38-3.59 (5H, m), 3.82 (2H, s), 4.97 (1H, d, J=13.2 Hz), 5.57 (1H, d, J=3.6 Hz), 5.77 (1H, dd, J=8.0, 3.6 Hz), 6.82 (1H, s), 6.87 (1H, s), 7.13-7.40 (11H, m)
Reference Example 47
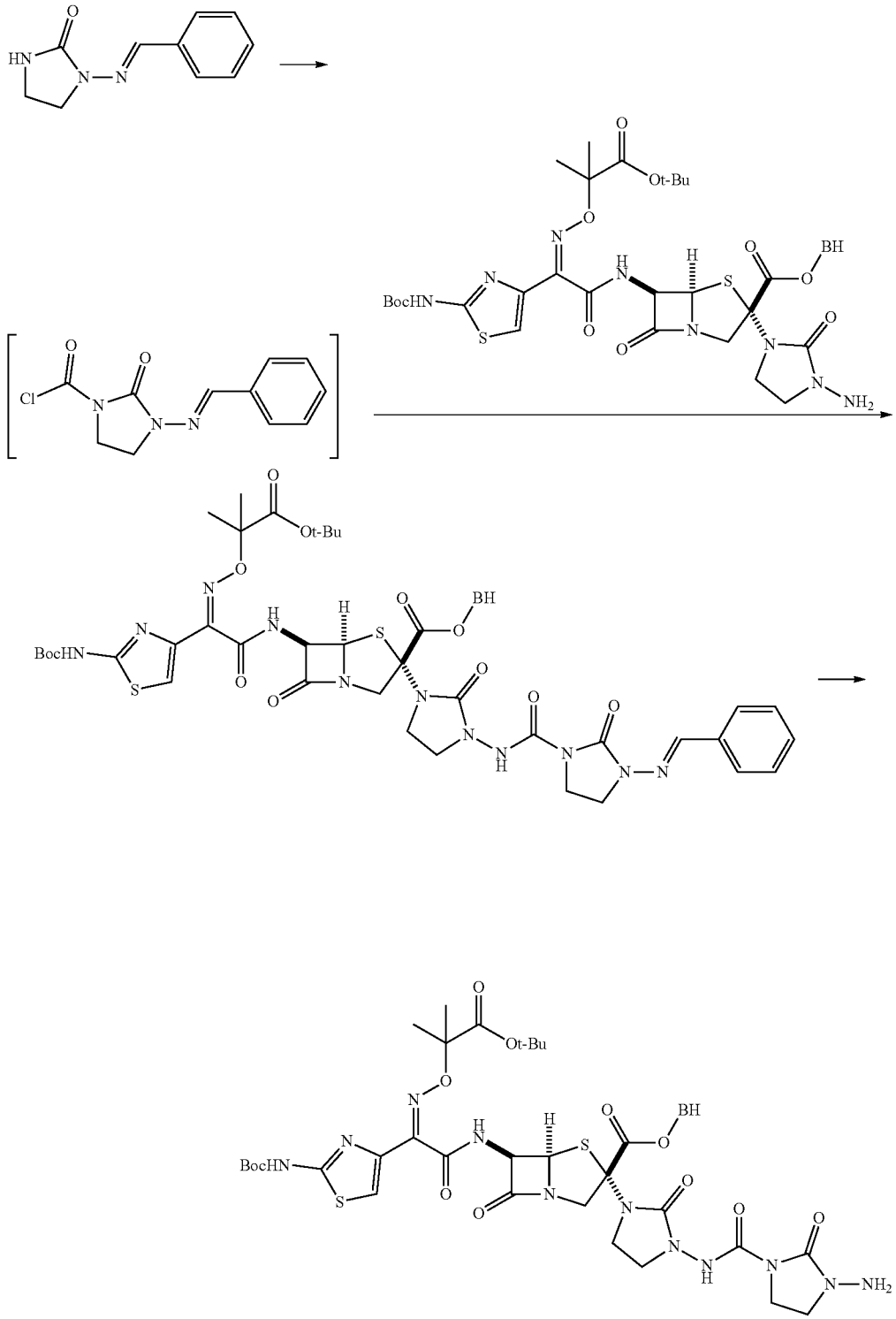

Reference Example 47 (1)

THF (2.3 mL) was added to (E)-1-(benzylideneamino) imidazolidin-2-one (230 mg), and the mixture was stirred under ice cooling. At the same temperature, triphosgene (180 mg) was added to the reaction mixture, and the reaction mixture was stirred at room temperature for 1 hour. Then, the reaction mixture was stirred at 60° C. for 2 hours, thereby obtaining a THF mixture of (E)-3-(benzylideneamino)-2-oxoimidazolidine-1-carbonyl chloride.

THF (3 mL) and water (6 mL) were added to benzhydryl (3R,5R,6R)-3-(3-amino-2-oxoimidazolidin-1-yl)-6-((Z)-2-(((1-(tert-butoxy)-2-methyl-1-oxopropan-2-yl)oxy)imino)-2-(2-((tert-butoxycarbonyl)amino)thiazol-4-yl)acetamido)-7-oxo-4-thia-1-azabicyclo[3.2.0]heptane-3-carboxylate (300 mg), and the mixture was stirred under ice cooling. At the same temperature, sodium hydrogen carbonate (146 mg) and the prepared THF mixture of (E)-3-(benzylideneamino)-2-oxoimidazolidine-1-carbonyl chloride were sequentially added to the reaction mixture, and the reaction mixture was stirred for 1 hour. Ethyl acetate (15 mL) and water (15 mL) were added to the reaction mixture, and the organic layer was separated. The organic layer was washed with a 5% aqueous sodium chloride solution and then dehydrated and dried over anhydrous sodium sulfate. The solvent was distilled away under reduced pressure, and the residue was purified by silica gel column chromatography [eluent; chloroform:2-propanol=100:0→90:10], thereby obtaining a target substance (66 mg) as a yellow oily substance.

Reference Example 47 (2)

By using the compound (66 mg) obtained in Reference Example 47 (1), benzhydryl (3R,5R,6R)-3-(3-(3-amino-2-oxoimidazolidine-1-carboxamido)-2-oxoimidazolidin-1-yl)-6-((Z)-2-(((1-(tert-butoxy)-2-methyl-1-oxopropan-2-yl)oxy)imino)-2-(2-((tert-butoxycarbonyl)amino)thiazol-4-yl)acetamido)-7-oxo-4-thia-1-azabicyclo[3.2.0]heptane-3-carboxylate (20 mg) was obtained in the same manner as in Reference Example 27 (2) as a brown oily substance.

NMR: 1.39 (9H, s), 1.47-1.56 (15H, m), 3.48-3.63 (4H, m), 3.66-3.84 (7H, m), 5.03 (1H, d, J=13.2 Hz), 5.59 (1H, d, J=3.6 Hz), 5.78 (1H, dd, J=8.8, 3.6 Hz), 6.86 (1H, s), 7.08-7.44 (11H, m), 9.43 (1H, s)

Reference Example 48

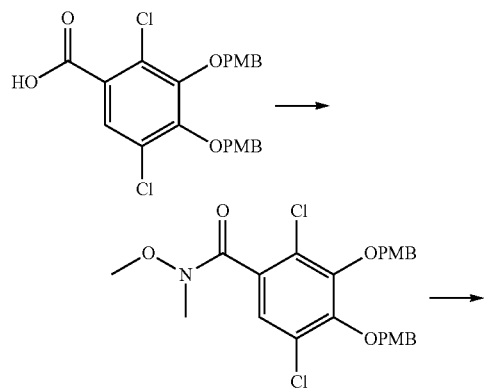

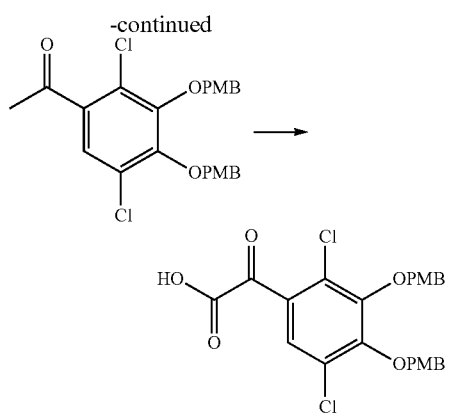

Reference Example 48 (1)

Dichloromethane (48 mL), N,O-dimethylhydroxylamine hydrochloride (1.64 g), and EDC (3.23 g) were sequentially added to 2,5-dichloro-3,4-bis((4-methoxybenzyl)oxy)benzoic acid (6.0 g). The reaction mixture was stirred at room temperature for 4 hours. Water (20 mL) was added to the reaction mixture, and the organic layer was separated. The organic layer was sequentially washed with water (20 mL), a 2% aqueous sodium chloride solution (20 mL), and a 10% aqueous sodium chloride solution (20 mL). The organic layer was dehydrated and dried over anhydrous magnesium sulfate, and then the solvent was distilled away under reduced pressure, thereby obtaining a target substance (3.7 g) as a yellow oily substance.

Reference Example 48 (2)

THF (40 mL) was added to the compound (3.7 g) obtained in Reference Example 48 (1), and the mixture was stirred under ice cooling. At the same temperature, a 3 mol/L methyl magnesium bromide/diethyl ether solution (5.5 mL) was added to the reaction mixture, and the reaction mixture was stirred at room temperature for 2 hours and 30 minutes. At the same temperature, a 3 mol/L methyl magnesium bromide/diethyl ether solution (2.7 mL) was added to the reaction mixture, and the reaction mixture was stirred at room temperature for 2 hours. A 3 mol/L methyl magnesium bromide/diethyl ether solution (2.7 mL) was added to the reaction mixture, and the reaction mixture was stirred at room temperature for 1 hour. A saturated aqueous ammonium chloride solution, ethyl acetate, and 6 mol/L hydrochloric acid were sequentially added to the reaction mixture such that the pH was adjusted to 5.0. The organic layer was separated and washed with a saturated aqueous sodium chloride solution. The organic layer was dehydrated and dried over anhydrous magnesium sulfate, and then the solvent was distilled away under reduced pressure, thereby obtaining a target substance (1.62 g) as light yellow solids.

Reference Example 48 (3)

Pyridine (16 mL) and selenium dioxide (0.98 g) were sequentially added to the compound (1.62 g) obtained in Reference Example 48(2). The reaction mixture was stirred at a temperature of 90° C. to 100° C. for 5 hours and 30 minutes. The reaction mixture was filtered through celite, and the residue was sequentially washed with water and ethyl acetate. The organic layer was separated, 6 mol/L hydrochloric acid was added to the aqueous layer such that the pH was adjusted to a value lower than 2, and extraction was performed using ethyl acetate. The organic layers were combined and dehydrated and dried over anhydrous magnesium sulfate, and the solvent was distilled away under reduced pressure. The residue was purified by silica gel column chromatography [eluent; methanol:chloroform=0:100→30:70]. The fraction containing a target substance was concentrated under reduced pressure, and ethyl acetate and IPE were added to the residue. Solids were collected by filtration, thereby obtaining 2-(2,5-dichloro-3,4-bis((4-methoxybenzyl)oxy)phenyl)-2-oxoacetic acid (200 mg) as light brown solids.

NMR (DMSO-$d_6$): 3.77 (3H, s), 3.78 (3H, s), 4.98 (2H, s), 5.07 (2H, s), 6.91-6.99 (5H, m), 7.34-7.43 (4H, m), 7.60 (1H, s)

Reference Example 49

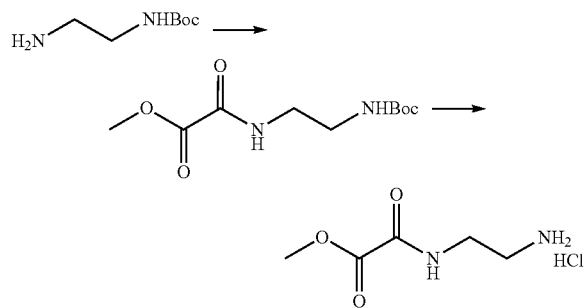

Reference Example 49 (1)

Dichloromethane (150 mL) and triethylamine (4.48 mL) were added to tert-butyl(2-aminoethyl)carbamate (5.0 g), and the mixture was stirred under ice cooling. At the same temperature, methyl chloroglyoxylate (2.95 mL) was added to the reaction mixture, and the reaction mixture was stirred at room temperature for 6 hours and 30 minutes. Water (100 mL) was added to the reaction mixture, and 1 mol/L hydrochloric acid was added thereto such that the pH was adjusted to 2.6. The organic layer was separated, and the aqueous layer was extracted twice by using dichloromethane (50 mL). The organic layers were combined and sequentially washed with water and a saturated aqueous sodium chloride solution. The organic layer was dehydrated and dried over anhydrous sodium sulfate, and then the solvent was distilled away under reduced pressure, thereby obtaining a target substance (7.1 g) as white solids.

Reference Example 49 (2)

Ethyl acetate (210 mL) was added to the compound (7.1 g) obtained in Reference Example 49 (1), and the mixture was stirred under ice cooling. At the same temperature, a 4 mol/L hydrochloric acid/ethyl acetate solution (71 mL) was added to the reaction mixture, and the reaction mixture was stirred at room temperature for 8 hours. Solids were collected by filtration and washed with ethyl acetate. The solids were dried, thereby obtaining methyl 2-((2-aminoethyl)amino)-2-oxoacetate hydrochloride (6.42 g) as white solids.

NMR ($D_2O$): 3.23 (2H, t, J=6.0 Hz), 3.64 (2H, t, J=6.0 Hz), 3.91 (3H, s)

The compounds in Table 7 were obtained in the same manner as in Reference Example 49.

TABLE 7

| Reference Example No. | Structural Formula | Name |
|---|---|---|
| 50 | ![structure] | Methyl 2((3-aminopropyl)amino)-2-oxoacetate hydrochloride |
| 51 | ![structure] | Methyl 2((4-aminobutyl)amino)-2-oxoacetate hydrochloride |

The measured values of NMR of the compounds in the table are as follows.

Reference Example 50

NMR ($D_2O$): 1.96 (2H, quintet, J=7.2 Hz), 3.04 (2H, t, J=7.8 Hz), 3.42 (2H, t, J=6.8 Hz), 3.91 (3H, s)

Reference Example 51

NMR ($D_2O$): 1.61-1.77 (4H, m), 3.03 (2H, t, J=7.2 Hz), 3.35 (2H, t, J=6.4 Hz), 3.90 (3H, s)

Reference Example 52

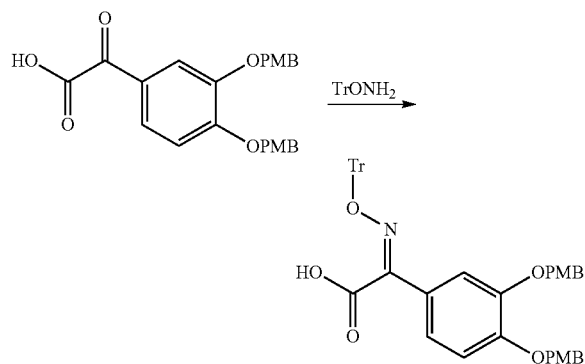

Methanol (25 mL) and O-tritylhydroxylamine (3.58 g) were added to 2-(3,4-bis((4-methoxybenzyl)oxy)phenyl)-2-oxoacetic acid (5.00 g), and the mixture was stirred at room temperature for 1 hour and 30 minutes. Water (125 mL) was added to the reaction mixture, the reaction mixture was stirred at room temperature for 30 minutes, and solids were collected by filtration. The solids were dried, thereby obtaining (Z)-2-(3,4-bis((4-methoxybenzyl)oxy)phenyl)-2-((trityloxy)imino)acetic acid (7.84 g) as yellow solids.

NMR (DMSO-$d_6$): 3.72 [3.74](3H, s), 3.74 [3.76](3H, s), 4.90 [4.92](2H, s), 5.04 [5.11] (2H, s), 6.81-6.99 (5H, m), 7.05-7.11 (1H, m), 7.15-7.44 (20H, m)

The compounds in Table 8 were obtained in the same manner as in Reference Example 52.

TABLE 8

| Reference Example No. | Structural Formula | Name |
|---|---|---|
| 53 | | (Z)-2-(2-(tert-butoxycarbonyl)hydradienylidene)-2-(2-chloro-3,4-bis((4-methoxybenzyl)oxy)phenyl) acetic acid |
| 54 | | (Z)-2-(2-(1-(tert-butoxycarbonyl)piperidine-4-carbonyl)hydradienylidene)-2-(2-chloro-3,4-bis((4-methoxybenzyl)oxy)phenyl) acetic acid |

The measured values of NMR of the compounds in the table are as follows.

Reference Example 53

NMR (DMSO-d$_6$): 1.44 [1.47](9H, s), 3.75 [3.75](3H, s), 3.78 [3.78](3H, s), 4.89 (2H, s), 5.15 (2H, s), 6.83-6.91 (2H, m), 6.93-7.04 (2H, m), 7.07-7.25 (2H, m), 7.27-7.37 (2H, m), 7.40-7.49 (2H, m), 9.90 (1H, s), 12.40-12.44 (1H, brs)

Reference Example 54

NMR (DMSO-d$_6$): 1.16-1.46 (2H, m), 1.39 (9H, s), 1.47-1.74 (2H, m), 2.70-2.90 (1H, m), 3.72-4.05 (4H, m), 3.75 (3H, s), 3.78 (3H, s), 4.89 (2H, s), 5.16 (2H, s), 6.83-6.91 (2H, m), 6.95-7.09 (3H, m), 7.14-7.36 (3H, m), 7.40-7.50 (2H, m), 10.33-10.60 (1H, brs)

The compounds in Table 9 were obtained in the same manner as in Reference Example 3.

The measured values of NMR of the compounds in the table are as follows.

Reference Example 55

NMR (DMSO-d$_6$): 1.44 [1.46](9H, s), 2.37-2.49 (2H, m), 3.25-3.35 (1H, m), 3.35-3.43 (1H, m), 3.75 [3.75](3H, s), 3.78 (3H, s), 4.81-4.98 (2H, m), 5.15 [5.16](2H, s), 6.84-6.93 (3H, m), 6.95-7.04 (2H, m), 7.15-7.37 (3H, m), 7.40-7.49 (2H, m), 7.83-7.93 (1H, m), 9.91 (1H, s), 12.26 [12.48](1H, s)

Reference Example 56

NMR (DMSO-d$_6$): 1.97 [2.20](2H, t, J=6.2 Hz), 3.12-3.21 (2H4, m), 3.66 [3.74](3H, s), 3.76 [3.78](3H, s), 4.81 [4.93](2H, s), 5.10 [5.20](2H, s), 6.76-6.88 (2H, m), 6.93-7.03 (2H, m), 7.10-7.18 (4H, m), 7.18-7.37 (15H, m), 7.37-7.51 (2H, m), 8.03 (1H, t, J=5.4 Hz)

TABLE 9

| Reference Example No. | Structural Formula | Name |
| --- | --- | --- |
| 55 | | (Z)-3-(2-(2-(tert-butoxycarbonyl)hydradienylidene)-2-(2-chloro-3,4-bis((4-methoxybenzyl)oxy)phenyl)acetamido)propionic acid |
| 56 | | (Z)-3-(2-(2-chloro-3,4-bis((4-methoxybenzyl)oxy)phenyl)-2-((trityloxy)imino)acetamido)propionic acid |
| 57 | | 2-((2-(2-(2-chloro-3,4-bis((4-methoxybenzyl)oxy)phenyl)-2-oxoacetamido)ethyl)amino)-2-oxoacetic acid |
| 58 | | 2-((3-(2-(2-chloro-3,4-bis((4-methoxybenzyl)oxy)phenyl)-2-oxoacetamido)propyl)amino)-2-oxoacetic acid |
| 59 | | 2-((4-(2-(2-chloro-3,4-bis((4-methoxybenzyl)oxy)phenyl)-2-oxoacetamido)butyl)amino)-2-oxoacetic acid |
| 60 | | N-(2-(2-chloro-3,4-bis((4-methoxybenzyl)oxy)phenyl)-2-oxoacetyl)-O-methyl-D-serine |

Reference Example 57

NMR: 3.58-3.65 (4H, m), 3.79 (3H, s), 3.83 (3H, s), 4.94 (2H, s), 5.09 (2H, s), 6.78-6.84 (2H, m), 6.89-6.97 (3H, m), 7.29-7.37 (5H, m), 7.41 (1H, s), 7.60 (1H, d, J=8.8 Hz), 7.86 (1H, s)

Reference Example 58

NMR: 1.83-1.91 (2H, m), 3.42-3.51 (4H, m), 3.80 (3H, s), 3.84 (3H, s), 5.00 (2H, s), 5.12 (2H, s), 6.80-6.86 (2H, m), 6.88-7.00 (3H, m), 7.22-7.39 (6H, m), 7.62 (1H, d, J=8.8 Hz), 7.90 (1H, s)

Reference Example 59

NMR: 1.65-1.73 (4H, m), 3.40-3.47 (4H, m), 3.80 (3H, s), 3.84 (3H, s), 4.96 (2H, s), 5.12 (2H, s), 6.81-6.85 (2H, m), 6.90-6.97 (3H, m), 7.03-7.10 (1H, m), 7.23-7.39 (6H, m), 7.62 (1H, d, J=8.4 Hz)

Reference Example 60

NMR: 3.42 (3H, s), 3.72 (1H, dd, J=9.4, 3.8 Hz), 3.80 (3H, s), 3.83 (3H, s), 3.98 (1H, dd, J=9.6, 3.2 Hz), 4.80 (1H, dt, J=8.0, 3.6 Hz), 4.96 (2H, s), 5.11 (2H, s), 6.80-6.85 (2H, m), 6.90-6.97 (3H, m), 7.31-7.37 (5H, m), 7.61 (1H, d, J=8.8 Hz), 7.68 (1H, d, J=8.0 Hz)

Reference Example 61

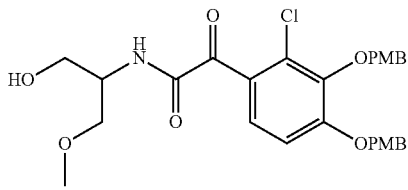

In the same manner as in Reference Example 3 (1), 2-(2-chloro-3,4-bis((4-methoxybenzyl)oxy)phenyl)-N-(1-hydroxy-3-methoxypropan-2-yl)-2-oxoacetamide was obtained as a light yellow oily substance.

NMR: 3.41 (3H, s), 3.63 (1H, dd, J=9.6, 4.4 Hz), 3.70 (1H, dd, J=9.6, 4.0 Hz), 3.76-3.83 (11H, m), 3.80 (3H, s), 3.84 (3H, s), 3.93 (1H, dd, J=11.6, 4.0 Hz), 4.09-4.18 (1H, m), 4.96 (2H, s), 5.11 (2H, s), 6.80-6.86 (2H, m), 6.90-6.98 (3H, m), 7.31-7.38 (4H, m), 7.51 (1H, d, J=8.4 Hz), 7.60 (1H, d, J=8.4 Hz)

Reference Example 62

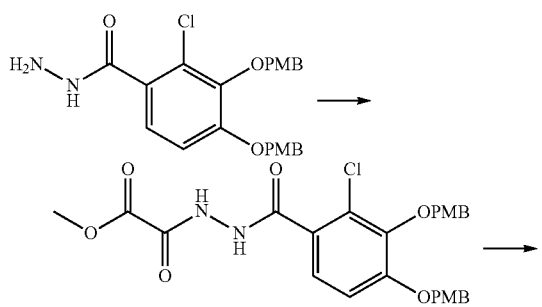

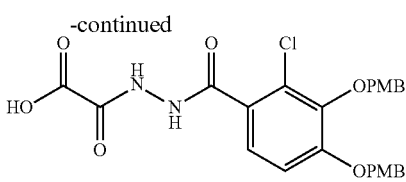

Reference Example 62 (1)

Dichloromethane (45 mL) and triethylamine (991 μL) were added to 2-chloro-3,4-bis ((4-methoxybenzyl)oxy) benzohydrazide (3.0 g), and the mixture was stirred under ice cooling. At the same temperature, methyl chloroglyoxylate (654 μL) was added to the reaction mixture, and the reaction mixture was stirred at room temperature overnight. Water (60 mL) was added to the reaction mixture, and solids were collected by filtration. The solids were washed twice with dichloromethane (5 mL), thereby obtaining a target substance (3.42 g) as white solids.

Reference Example 62 (2)

THF (68 mL), water (34 mL), and lithium hydroxide monohydrate (1.36 g) were sequentially added to the compound (3.42 g) obtained in Reference Example 62 (1), and the mixture was stirred at room temperature for 1 hour. Water (250 mL) and 2 mol/L hydrochloric acid were added to the reaction mixture under ice cooling such that the pH was adjusted to 1.9. Solids were collected by filtration, thereby obtaining 2-((2-(2-chloro-3,4-bis((4-methoxybenzyl)oxy)benzoyl)hydradienyl)-2-oxoacetic acid (1.43 g) as white solids.

NMR (DMSO-$d_6$): 3.75 (3H, s), 3.78 (3H, s), 4.90 (2H, s), 5.17 (2H, s), 6.85-6.90 (2H, m), 6.96-7.01 (2H, m), 7.20-7.28 (2H, m), 7.29-7.34 (2H, m), 7.42-7.47 (2H, m), 10.31 (1H, s), 10.78 (1H, s), 13.67-14.62 (1H, brs)

Reference Example 63

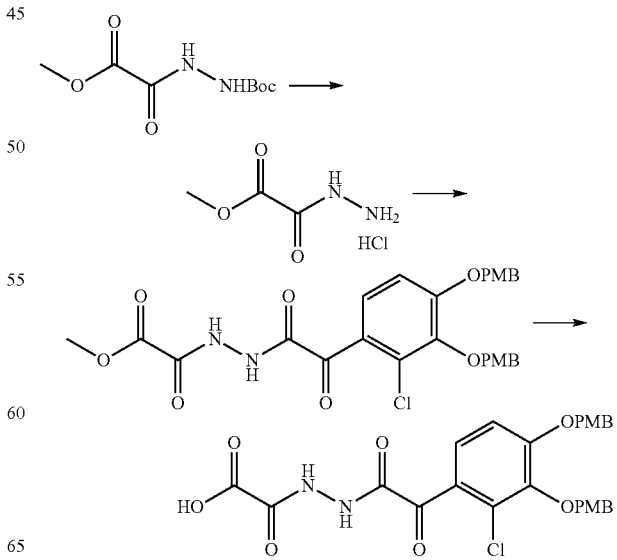

Reference Example 63 (1)

Ethyl acetate (64 mL) was added to tert-butyl 2-(2-methoxy-2-oxoacetyl)hydrazine-1-carboxylate (4.23 g), and the mixture was stirred under ice cooling. At the same temperature, a 4 mol/L hydrochloric acid/ethyl acetate solution (42 mL) was added to the reaction mixture, and the reaction mixture was stirred at room temperature for 6 hours. Solids were collected by filtration and washed with ethyl acetate. The solids were dried, thereby obtaining a target substance (2.65 g) as white solids.

Reference Example 63 (2)

2-(2-Chloro-3,4-bis((4-methoxybenzyl)oxy)phenyl)-2-oxoacetic acid (4.0 g), HOBt (1.42 g), EDC (2.01 g), DMAC (80 mL), and NMM (4.4 mL) were sequentially added to the compound (1.35 g) obtained in Reference Example 63 (1). The reaction mixture was stirred at room temperature overnight. Ethyl acetate (160 mL) and water (160 mL) were added to the reaction mixture. Hydrochloric acid (1 mol/L) was added to the reaction mixture such that the pH was adjusted to 3.5. The organic layer was separated, washed twice with water (100 mL), and sequentially washed with a saturated aqueous sodium hydrogen carbonate solution (100 mL) and a saturated aqueous sodium chloride solution (100 mL). The organic layer was dehydrated and dried over anhydrous sodium sulfate, and the solvent was distilled away under reduced pressure. Dichloromethane (15 mL) and hexane (15 mL) were added to the residue, and solids were collected by filtration, thereby obtaining a target substance (1.60 g) as white solids.

Reference Example 63 (3)

By using the compound (1.60 g) obtained in Reference Example 63 (2), 2-(2-(2-(2-chloro-3,4-bis((4-methoxybenzyl)oxy)phenyl)-2-oxoacetyl)hydradienyl)-2-oxoacetic acid (1.43 g) was obtained as white solids in the same manner as in Reference Example 62 (2).

NMR (DMSO-$d_6$): 3.74 (3H, s), 3.78 (3H, s), 4.91 (2H, s), 5.26 (2H, s), 6.83-6.88 (2H, m), 6.97-7.02 (2H, m), 7.26-7.32 (2H, m), 7.37 (1H, d, J=8.8 Hz), 7.43-7.50 (3H, m), 7.74 (1H, d, J=8.8 Hz), 10.70-10.92 (1H, brs), 10.95 (1H, s)

Reference Example 64

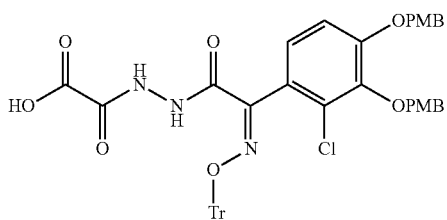

In the same manner as in Reference Example 63, (Z)-2-(2-(2-(2-chloro-3,4-bis((4-methoxybenzyl)oxy)phenyl)-2-((trityloxy)imino)acetyl)hydradienyl)-2-oxoacetic acid was obtained as white solids.

NMR: 3.73 (3H, s), 3.84 (3H, s), 5.01 (2H, s), 5.11 (2H, s), 6.76-6.81 (2H, m), 6.90-7.05 (4H, m), 7.20-7.41 (20H, m), 8.47 (1H, s), 9.26-9.48 (1H, brs)

Reference Example 65

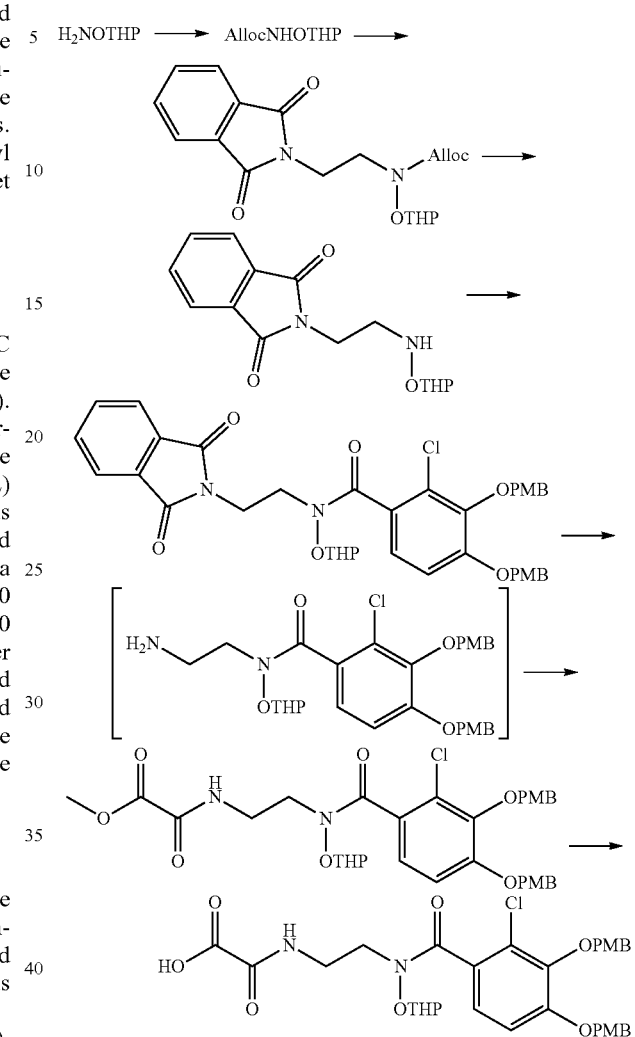

Reference Example 65 (1)

THF (70 mL), water (70 mL), and sodium hydrogen carbonate (9.8 g) were sequentially added to O-(tetrahydro-2H-pyran-2-yl)hydroxylamine (7.5 g), and the mixture was stirred under ice cooling. At the same temperature, allyl chloroformate (6.2 mL) was added to the reaction mixture, and the reaction mixture was stirred at room temperature for 1 hour. Ethyl acetate (50 mL) and water (50 mL) were added to the reaction mixture. Hydrochloric acid (2 mol/L) was added to the reaction mixture such that the pH was adjusted to 2.3. The organic layer was separated and washed with a saturated aqueous sodium chloride solution. The organic layer was dehydrated and dried over anhydrous sodium sulfate. The solvent was distilled away under reduced pressure, thereby obtaining a target substance (12.4 g) as a colorless oily substance.

Reference Example 65 (2)

2-(2-Hydroxyethyl)isoindoline-1,3-dione (3.2 g), triphenylphosphine (5.35 g), and toluene (30 mL) were added to the compound (3.0 g) obtained in Reference Example 65 (1), and the mixture was stirred under ice cooling. At the same temperature, a 40% diisopropyl azodicarboxylate/toluene solution (9.1 mL) was added dropwise to the reaction mixture, and the reaction mixture was stirred at room temperature overnight. Magnesium chloride (3.54 g) was added to the reaction mixture, and the reaction mixture was stirred at 60° C. for 1 hour. At the same temperature, hexane (30 mL) was added to the reaction mixture, and the reaction mixture was stirred for 1 hour at the same temperature. The reaction mixture was cooled to room temperature, and insoluble matters were filtered. The residue was washed with toluene (20 mL), and the solvent was distilled away under reduced pressure. The residue was purified by silica gel column chromatography [eluent; ethyl acetate:hexane=10: 90→40:60], and the fraction containing a target substance was concentrated under reduced pressure. The residue was purified by silica gel column chromatography [eluent; chloroform], thereby obtaining a target substance (4.02 g) as a colorless oily substance.

Reference Example 65 (3)

By using the compound (1.5 g) obtained in Reference Example 65 (2), a target substance (592 mg) was obtained as a colorless oily substance in the same manner as in Reference Example 10 (2).

Reference Example 65 (4)

By using the compound (592 mg) obtained in Reference Example 65 (3), a target substance (1.41 g) was obtained as white solids in the same manner as in Reference Example 2 (1).

Reference Example 65 (5)

THF (7 mL), methanol (7 mL), and hydrazine hydrate (485 μL) were added to the compound (700 mg) obtained in Reference Example 65 (4), and the mixture was stirred at 70° C. for 1 hour. The reaction mixture was cooled to room temperature. The reaction mixture was filtered, and the residue was washed with dichloromethane (20 mL). Water was added to the filtrate, and the organic layer was separated. The aqueous layer was extracted twice by using dichloromethane (10 mL). The organic layers were combined and sequentially washed with water and a saturated aqueous sodium chloride solution. The organic layer was dehydrated and dried over anhydrous sodium sulfate, and the solvent was distilled away under reduced pressure until the amount of the solvent became about 50 mL. Triethylamine (143 μL) and methyl chloroglyoxylate (92 μL) were added to the reaction mixture under ice cooling, and the reaction mixture was stirred at room temperature overnight. Water (30 mL) was added to the reaction mixture, and the organic layer was separated. The aqueous layer was extracted twice by using dichloromethane (10 mL). The organic layers were combined and sequentially washed with water and a saturated aqueous sodium chloride solution. The organic layer was dehydrated and dried over anhydrous sodium sulfate, and the solvent was distilled away under reduced pressure. The residue was purified by silica gel column chromatography [eluent; ethyl acetate:hexane=40: 60→60:40], thereby obtaining a target substance (280 mg) as white solids.

Reference Example 65 (6)

By using the compound (280 mg) obtained in Reference Example 65 (5), 2-((2-(2-chloro-3,4-bis((4-methoxybenzyl) oxy)-N-((tetrahydro-2H-pyran-2-yl)oxy)benzamido)ethyl) amino)-2-oxoacetic acid (276 mg) was obtained as white solids in the same manner as in Reference Example 62 (2).

NMR: 1.30-1.88 (6H, m), 3.52-3.78 (3H, m), 3.80 (3H, s), 3.83 (3H, s), 3.85-4.21 (3H, m), 4.60-4.90 (1H, m), 4.96 (2H, s), 5.08 (2H, s), 6.81-6.86 (2H, m), 6.87-6.94 (3H, m), 6.95-7.01 (1H, m), 7.32-7.37 (5H, m), 8.20 (1H, s)

Reference Example 66

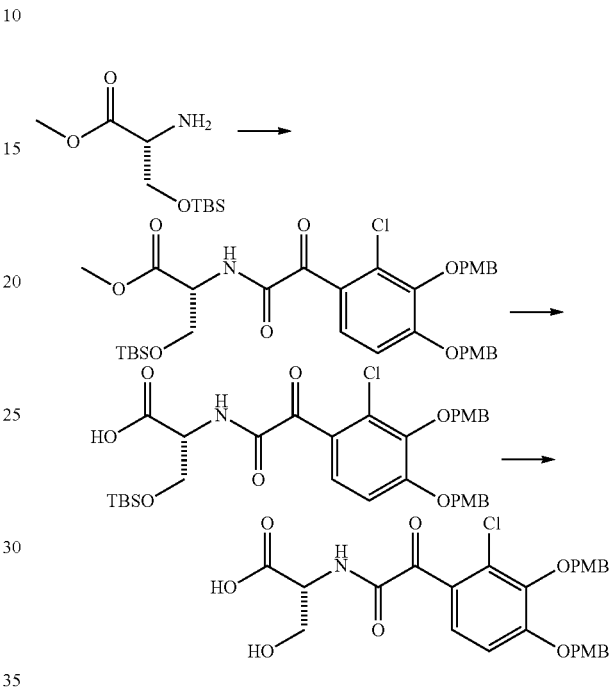

Reference Example 66 (1)

By using methyl O-(tert-butyldimethylsilyl)-D-serinate (2.3 g), a target substance (2.16 g) was obtained as a light yellow oily substance in the same manner as in reference Example 11.

Reference Example 66 (2)

By using the compound (2.16 g) obtained in Reference Example 66 (1), a target substance (1.92 g) was obtained as green solids in the same manner as in Reference Example 62 (2).

Reference Example 66 (3)

THF (8 mL) was added to the compound (400 mg) obtained in Reference Example 66 (2), and the mixture was stirred under ice cooling. At the same temperature, a 1 mol/L tetra-n-butylammonium fluoride/THF solution (912 μL) was added to the reaction mixture, and the reaction mixture was stirred at room temperature overnight. Ethyl acetate (10 mL) and water (10 mL) were added to the reaction mixture, and the organic layer was separated. The aqueous layer was extracted twice by using ethyl acetate (10 mL). The organic layer was washed with a saturated aqueous sodium chloride solution and dehydrated and dried over anhydrous sodium sulfate. The solvent was distilled away under reduced pressure, thereby obtaining (2-(2-chloro-3,4-bis((4-methoxybenzyl)oxy)phenyl)-2-oxoacetyl)-D-serine (313 mg) as green solids.

NMR: 3.74 (3H, s), 3.79 (3H, s), 3.83 (1H, s), 3.89-3.97 (1H, m), 4.17 (1H, dd, J=11.6, 3.6 Hz), 4.60-4.66 (1H, m), 4.84 (2H, s), 4.96 (2H, s), 6.75 (2H, d, J=8.8 Hz), 6.81-6.88 (3H, m), 7.20-7.38 (5H, m), 7.56 (1H, d, J=8.4 Hz), 8.15 (1H, d, J=7.2 Hz)

Reference Example 67

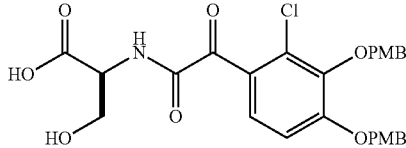

(2-(2-Chloro-3,4-bis((4-methoxybenzyl)oxy)phenyl)-2-oxoacetyl)-L-serine was obtained in the same manner as in Reference Example 66.

NMR: 3.75 (3H, s), 3.80 (3H, s), 3.83 (1H, s), 3.92-4.00 (1H, m), 4.15-4.22 (1H, m), 4.65-4.71 (1H, m), 4.86 (2H, s), 4.98 (2H, s), 6.74-6.78 (3H, m), 6.83-6.90 (4H, m), 7.22-7.38 (3H, m), 7.56 (1H, d, J=8.8 Hz), 8.06 (1H, d, J=6.8 Hz)

Reference Example 68

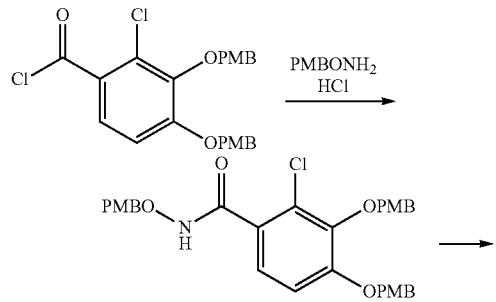

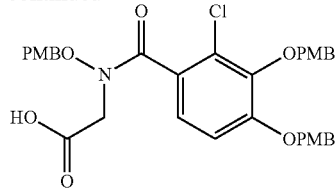

Reference Example 68 (1)

By using O-(4-methoxybenzyl)hydroxylamine hydrochloride (500 mg), a target substance (1.38 g) was obtained as white solids in the same manner as in Reference Example 2 (1).

Reference Example 68 (2)

Potassium carbonate (686 mg), acetone (3.5 mL), and 2-bromoacetic acid (345 mg) were sequentially added to the compound (700 mg) obtained in Reference Example 68 (1), and the mixture was stirred at room temperature overnight. DMF (7 mL), potassium carbonate (686 mg), and 2-bromoacetic acid (345 mg) were added to the reaction mixture, and the reaction mixture was stirred at room temperature for 2 days. Ethyl acetate (30 mL), water (30 mL), and 1 mol/L hydrochloric acid were added to the reaction mixture such that the pH was adjusted to 2.3. The organic layer was separated and washed with water and a saturated aqueous sodium chloride solution. The organic layer was dehydrated and dried over anhydrous sodium sulfate, and the solvent was distilled away under reduced pressure. The residue was purified by silica gel column chromatography [eluent; ethyl acetate:hexane=34:66→66:34], thereby obtaining N-(2-chloro-3,4-bis((4-methoxybenzyl)oxy)benzoyl)-N-((4-methoxybenzyl)oxy)glycine (114 mg) as a colorless oily substance.

NMR: 3.78-3.82 (6H, m), 3.83 (3H, s), 4.91-5.00 (4H, m), 5.02-5.12 (4H, m), 6.88-7.00 (11H, m), 7.21-7.40 (4H, m)

Reference Example 69

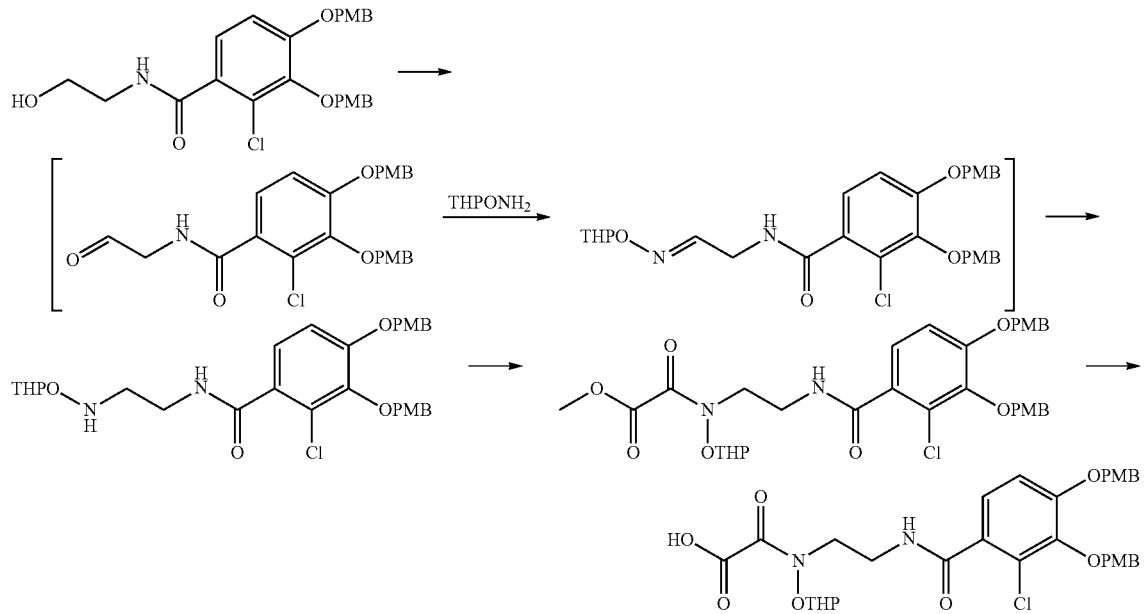

Reference Example 69 (1)

By using 2-chloro-N-(2-hydroxyethyl)-3,4-bis((4-methoxybenzyl)oxy)benzamide (2.0 g), a target substance (642 mg) was obtained as light yellow solids in the same manner as in Example 65 (1).

Reference Example 69 (2)

By using the compound (500 mg) obtained in Reference Example 69 (1), a target substance (607 mg) was obtained as light yellow solids in the same manner as in Reference Example 49 (1).

Reference Example 69 (3)

By using the compound (500 mg) obtained in Reference Example 69 (2), 2-((2-(2-chloro-3,4-bis((4-methoxybenzyl)oxy)benzamido)ethyl)((tetrahydro-2H-pyran-2-yl)oxy)amino)-2-oxoacetic acid (496 mg) was obtained as yellow solids in the same manner as in Reference Example 62 (2).

NMR: 1.45-1.57 (4H, m), 1.65-1.82 (2H, m), 3.15-3.21 (2H, m), 3.48-3.57 (1H, m), 3.63-3.70 (2H, m), 3.80 (3H, s), 3.83 (3H, s), 3.85-3.93 (1H, m), 4.73-4.78 (1H, m), 4.94 (2H, s), 5.08 (21H, s), 6.81-6.86 (2H, m), 6.89-6.94 (3H, m), 6.94-7.00 (1H, m), 7.30-7.38 (5H, m), 7.42 (1H, d, J=8.8 Hz)

Reference Example 70

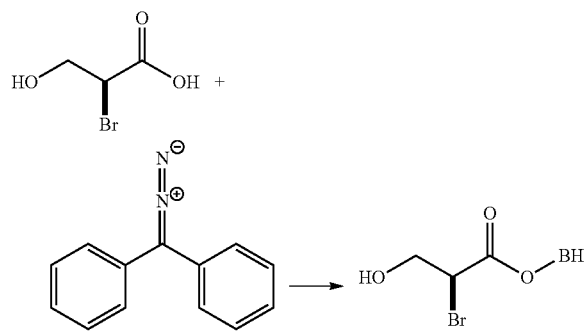

THF (14 mL) was added to (S)-2-bromo-3-hydroxypropionic acid (4.4 g), and the mixture was stirred under ice cooling. At the same temperature, diphenylmethyldiazomethane (4.6 g) in a THF (24 mL) solution was added dropwise to the reaction mixture for 40 minutes. The reaction mixture was stirred at room temperature overnight. Ethyl acetate (22 mL) and water (11 mL) were added to the reaction mixture. A saturated aqueous sodium hydrogen carbonate solution (11 mL) was added to the reaction mixture, and the organic layer was separated. The organic layer was washed with a saturated aqueous sodium chloride solution and dehydrated and dried over anhydrous sodium sulfate. The solvent was distilled away under reduced pressure, thereby obtaining benzhydryl (S)-2-bromo-3-hydroxypropanoate (7.52 g) as a light yellow oily substance.

NMR: 2.35 (1H, t, J=7.2 Hz), 3.92-4.01 (1H, m), 4.02-4.11 (1H, m), 4.43-4.49 (1H, m), 6.91 (1H, s), 7.28-7.40 (10H, m)

Reference Example 71

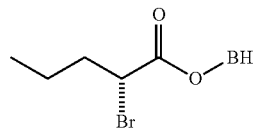

Benzhydryl (R)-2-bromopentanoate was obtained in the same manner as in Reference Example 70.

NMR: 0.91 (3H, t, J=7.4 Hz), 1.22-1.52 (2H, m), 1.93-2.12 (21H, m), 4.33 (1H, dd, J=8.0, 6.8 Hz), 6.89 (1H, s), 7.26-7.40 (10H, m)

Reference Example 72

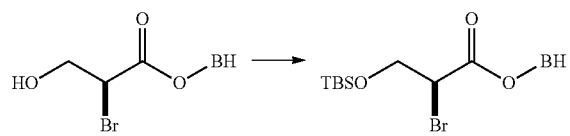

THF (75 mL) was added to benzhydryl (S)-2-bromo-3-hydroxypropanoate (7.52 g), and the mixture was stirred under ice cooling. At the same temperature, Imidazole (1.68 g), tert-butyl dimethylchlorosilane (3.83 g), and DMF (7.5 mL) were sequentially added to the reaction mixture, and the reaction mixture was stirred at room temperature overnight. Ethyl acetate (180 mL) and water (90 mL) were added to the reaction mixture, and the organic layer was separated. The organic layer was sequentially washed with water and a saturated aqueous sodium chloride solution and dehydrated and dried over anhydrous magnesium sulfate. The solvent was distilled away under reduced pressure. The residue was purified by silica gel column chromatography [eluent; ethyl acetate:hexane=0:100→20:80], thereby obtaining benzhydryl (S)-2-bromo-3-((tert-butyldimethylsilyl)oxy)propanoate (7.0 g) as a light yellow oily substance.

NMR: −0.01 (3H, s), 0.03 (3H, s), 0.81 (9H, s), 3.88-3.96 (1H, m), 4.08-4.16 (1H, m), 4.28-4.35 (1H, m), 6.91 (1H, s), 7.27-7.38 (10H, m)

Reference Example 73

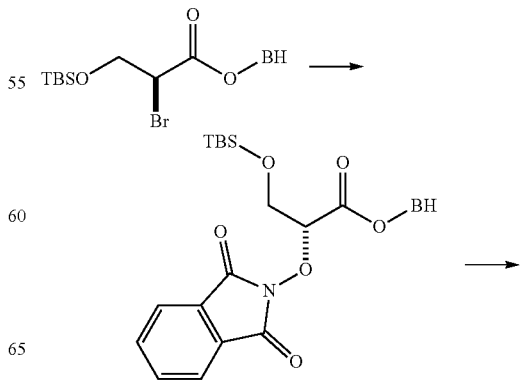

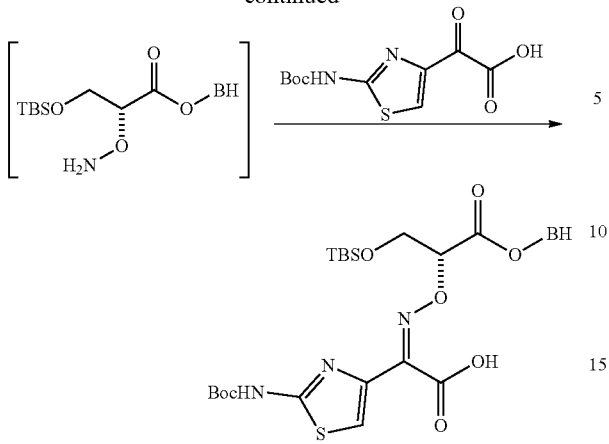

Reference Example 73 (1)

At room temperature, DMF (46 mL), N-hydroxyphthalimide (4.73 g), and triethylamine (3.24 mL) were sequentially added to benzhydryl (S)-2-bromo-3-((tert-butyldimethylsilyl)oxy)propanoate (6.52 g). The reaction mixture was stirred at the same temperature for 4 hours. Ethyl acetate (150 mL) and water (50 mL) were sequentially added to the reaction mixture, and the organic layer was separated. The organic layer was washed three times with a saturated aqueous sodium hydrogen carbonate solution and then washed with a saturated aqueous sodium chloride solution. The organic layer was dehydrated and dried over anhydrous sodium sulfate. The solvent was distilled away under reduced pressure, thereby obtaining a target substance (7.82 g) as a light yellow oily substance.

Reference Example 73 (2)

Dichloromethane (24 mL) was added to the compound (7.82 g) obtained in Reference Example 73 (1), and the mixture was stirred under ice cooling. At the same temperature, methylhydrazine (780 µL) was added to the reaction mixture, and the reaction mixture was stirred for 2 hours and 30 minutes at the same temperature. The reaction mixture was filtered, and the solvent was distilled away under reduced pressure. Methanol (47 mL) was added to the residue, and the mixture was stirred under ice cooling. At the same temperature, 2-(2-((tert-butoxycarbonyl)amino)thiazol-4-yl)-2-oxoacetic acid (4.0 g) was added to the reaction mixture, and the reaction mixture was stirred at room temperature for 2 hours and 30 minutes. Ethyl acetate (80 mL), water (50 mL), and 1 mol/L hydrochloric acid were added to the reaction mixture such that the pH was adjusted to 2.1, and the organic layer was separated. The organic layer was washed with a saturated aqueous sodium chloride solution and dehydrated and dried over anhydrous sodium sulfate. The solvent was distilled away under reduced pressure, hexane (200 mL) was added to the residue, and solids were collected by filtration. The solids were dried, thereby obtaining (R,Z)-5-((benzhydryloxy)carbonyl)-2-(2-((tert-butoxycarbonyl)amino)thiazol-4-yl)-8,8,9,9-tetramethyl-4,7-dioxa-3-aza-8-siladec-2-enoic acid (8.73 g) as light yellow solids.

NMR: −0.02 (3H, s), 0.02 (3H, s), 0.81 (9H, s), 0.88 (9H, s), 4.09-4.18 (1H, m), 4.19-4.26 (1H, m), 5.11-5.15 (1H, m), 6.97 (1H, s), 7.27-7.34 (11H, m), 7.41 (1H, s), 8.22 (1H, s)

Reference Example 74

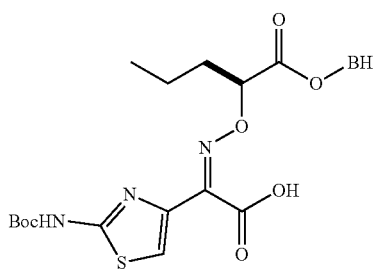

In the same manner as in Reference Example 73, (S,Z)-2-(((1-(benzhydryloxy)-1-oxopentan-2-yl)oxy)imino)-2-(2-((tert-butoxycarbonyl)amino)thiazol-4-yl)acetic acid was obtained.

NMR: 0.90 (3H, t, J=7.4 Hz), 1.32-1.51 (2H, m), 1.53 (9H, s), 1.81-1.99 (2H, m), 5.09 (1H, dd, J=8.0, 4.4 Hz), 6.93 (1H, s), 7.27-7.36 (11H, m), 7.37 (1H, s)

Reference Example 75

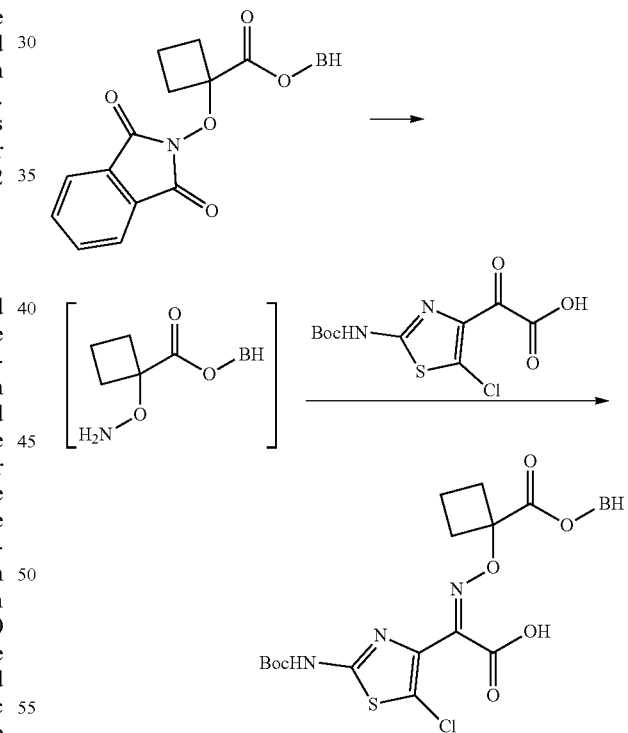

By using benzhydryl 1-((1,3-dioxoisoindoline-2-yl)oxy)cyclobutane-1-carboxylate, (Z)-2-((1-((benzhydryloxy)carbonyl)cyclobutoxy)imino)-2-(2-((tert-butoxycarbonyl)amino)-5-chlorothiazol-4-yl)acetic acid was obtained in the same manner as in Reference Example 73 (2).

NMR: 1.52 (9H, s), 2.07-2.19 (2H, m), 2.55-2.70 (4H, m), 6.94 (1H, s), 7.27-7.38 (12H, m)

The compounds in Table 10 were obtained in the same manner as in Reference Example 75.

TABLE 10

| Reference Example No. | Structural Formula | Name |
|---|---|---|
| 76 | | (Z)-2-(((1-(tert-butoxy)-2-methyl-1-oxopropan-2-yl)oxy)imino)-2-(2-((tert-butoxycarbonyl)amino)-5-methylanisol-4-yl) acetic acid |
| 77 | | (Z)-2-((1-((benzhydryloxy)carbonyl)cyclobutoxy)imino)-2-(5-((tert-butoxycarbonyl)amino)-1,2,4-thiadiazol-3-yl) acetic acid |

The measured values of NMR of the compounds in the table are as follows.

Reference Example 76

NMR (DMSO-d$_6$): 1.39 (9H, s), 1.42 (9H, s), 1.42 (3H, s), 1.46 (3H, s), 2.42 (3H, s), 11.54 (1H, s)

Reference Example 77

NMR: 1.57 (9H, s), 1.93-2.14 (2H, m), 2.42-2.72 (4H, m), 6.90 (1H, s), 7.20-7.40 (11H, m), 8.95-9.22 (11H, brs)

Reference Example 78

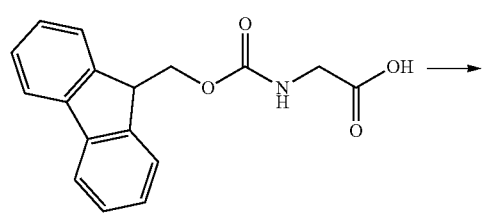

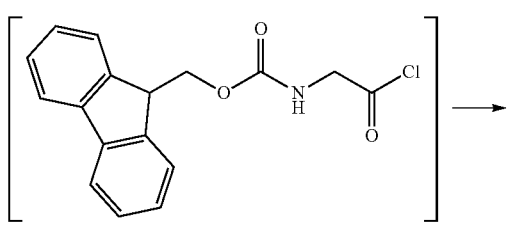

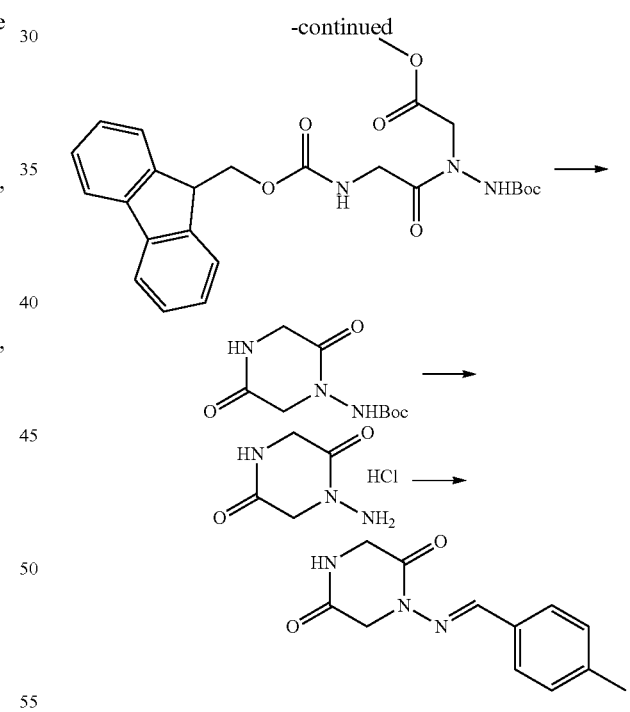

Reference Example 78 (1)

Dichloromethane (120 mL) was added to (((9H-fluoren-9-yl)methoxy)carbonyl)glycine (6.96 g), and the mixture was stirred under ice cooling. Oxalyl chloride (2.4 mL) and DMF (91 µL) were sequentially added to the reaction mixture. The reaction mixture was stirred at room temperature for 2 hours, and the solvent was distilled away under reduced pressure. Dichloromethane (50 mL) was added to the residue, thereby obtaining an acid chloride in a dichloromethane solution.

At room temperature, dichloromethane (25 mL), sodium hydrogen carbonate (5.90 g), and water (70 mL) were added to tert-butyl 2-(2-methoxy-2-oxoethyl)hydrazine-1-carboxylate (4.78 g). At the same temperature, the acid chloride in a dichloromethane solution was added dropwise to the reaction mixture. The reaction mixture was stirred at room temperature for 1 hour, and the organic layer was separated. The aqueous layer was extracted by using dichloromethane (20 mL), and the organic layer was dehydrated and dried over anhydrous sodium sulfate. The solvent was distilled away under reduced pressure. The residue was purified by silica gel column chromatography [eluent; ethyl acetate: hexane=10:90→35:65], thereby obtaining a target substance (9.36 g) as white solids.

Reference Example 78 (2)

Dichloromethane (100 mL) was added to the compound (9.36 g) obtained in Reference Example 78 (1), and the mixture was stirred under ice cooling. At the same temperature, piperidine (5.7 mL) was added to the reaction mixture, and the reaction mixture was stirred at room temperature for 6 hours. The solvent was distilled away under reduced pressure, diethyl ether (20 mL) was added to the residue, and solids were collected by filtration. The residue was purified by silica gel column chromatography [eluent; methanol: chloroform=0:100→10:90], thereby obtaining a target substance (3.03 g) as white solids.

Reference Example 78 (3)

Dichloromethane (65 mL) was added to the compound (3.0 g) obtained in Reference Example 78 (2), and the mixture was stirred under ice cooling. At the same temperature, a 4 mol/L hydrochloric acid/1,4-dioxane solution (33 mL) was added to the reaction mixture, and the reaction mixture was stirred at room temperature for 1 hour and 30 minutes. The solvent was distilled away under reduced pressure, thereby obtaining a target substance (2.2 g) as white solids.

Reference Example 78 (4)

Ethanol (22 mL) and p-tolualdehyde (1.6 mL) were added to the compound (2.2 g) obtained in Reference Example 78 (3), and the mixture was stirred at room temperature overnight. Solids were collected by filtration and washed with ethanol (10 mL). The solids were dried, thereby obtaining (E)-1-((4-methylbenzylidene)amino)piperazine-2,5-dione (2.72 g) as white solids.

NMR (DMSO-$d_6$): 2.35 (3H, s), 3.98 (2H, s), 4.32 (2H, s), 7.28 (2H, d, J=8.0 Hz), 7.67 (2H, d, J=8.0 Hz), 8.24 (1H, s), 8.31 (1H, s)

Reference Example 79

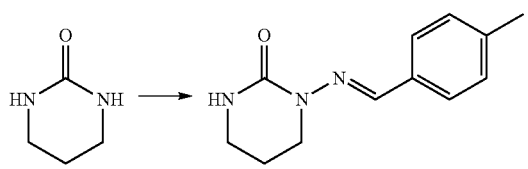 [SMILES: O=C1NCCCN1 ; Cc1ccc(/C=N/N2CCCNC2=O)cc1]

Concentrated sulfuric acid (69.1 g) was added dropwise to ice water (650 mL) under ice cooling. At the same temperature, tetrahydropyrimidin-2(1H)-one (25.0 g) was added to the reaction mixture. At the same temperature, a 34% aqueous sodium nitrite solution (50 mL) was added dropwise to the reaction mixture. At the same temperature, the reaction mixture was stirred for 1 hour. At the same temperature, zinc dust (37.5 g) was added to the reaction mixture by being divided into 5 portions. The reaction mixture was stirred at 20° C. for 2 hours. Celpure (5 g) was added to the reaction mixture, and the reaction mixture was filtered. The residue was washed with water (50 mL). At room temperature, ethanol (100 mL) and p-tolualdehyde (27.0 g) were sequentially added to the filtrate, and the mixture was stirred for 3 hours at the same temperature. Solids were collected by filtration and sequentially washed with water (250 mL) and ethanol (25 mL). The solids were blast-dried at 40° C., thereby obtaining (E)-1-((4-methylbenzylidene)amino)tetrahydropyrimidin-2(1H)-one (7.3 g) as white solids.

Reference Example 80

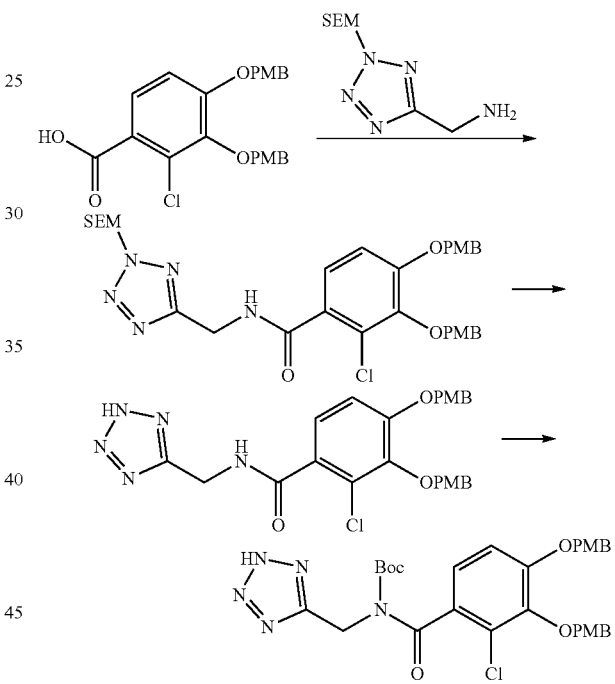

Reference Example 80 (1)

In the same manner as in Reference Example 3 (1), a target substance (10.8 g) was obtained as white solids from (2-((2-(trimethylsilyl)ethoxy)methyl)-2H-tetrazol-5-yl) methanamine (4.5 g).

Reference Example 80 (2)

In the same manner as in Reference Example 66 (3), a target substance (5.75 g) was obtained as white solids from the compound (10.8 g) obtained in Reference Example 80 (1).

Reference Example 80 (3)

THF (115 mL) was added to the compound (5.75 g) obtained in Reference Example 80 (2), and the mixture was stirred under ice cooling. At the same temperature, N,O-bis(trimethylsilyl)acetamide (2.78 mL) and 4-dimethylaminopyridine (1.38 g) were sequentially added to the reaction mixture, and the reaction mixture was stirred at room temperature for 1 hour. At the same temperature, di-tert-butyl dicarbonate (5.1 mL) was added dropwise to the reaction mixture, and the reaction mixture was stirred at room temperature for 1 hour. Ethyl acetate (200 mL) and water (200 mL) were added to the reaction mixture, and 1 mol/L hydrochloric acid was added thereto such that the pH was adjusted to 3.1. The organic layer was separated and washed with a saturated aqueous sodium chloride solution. The organic layer was dehydrated and dried over anhydrous magnesium sulfate, and the solvent was distilled away under reduced pressure. The residue was purified by silica gel column chromatography [eluent; methanol:chloroform=0:100→10:90], thereby obtaining tert-butyl((2H-tetrazol-5-yl)methyl)(2-chloro-3,4-bis((4-methoxybenzyl)oxy)benzoyl)carbamate (5.56 g) as white solids.

NMR (DMSO-$d_6$): 1.08 (9H, s), 3.75 (3H, s), 3.77 (3H, s), 4.89 (2H, s), 5.17-5.25 (4H, m), 6.84-6.91 (2H, m), 6.94-7.01 (2H, m), 7.20-7.35 (4H, m), 7.41-7.48 (2H, m)

The compounds in Table 11 were obtained in the same manner as in Reference Example 22.

The measured values of NMR of the compounds in the table are as follows.

Reference Example 81

NMR: 1.13 (9H, s), 3.45-3.56 (3H, s), 3.80 (3H, s), 3.82-3.84 (5H, m), 4.95 (2H, s), 5.07 (1H, d, J=13.6 Hz), 5.11 (2H, s), 5.66-5.72 (2H, m), 6.82-6.88 (4H, m), 6.88-6.96 (5H, m), 7.07-7.42 (18H, m)

Reference Example 82

NMR: 3.30-3.64 (6H, m), 3.74-3.89 (1H, m), 4.56-4.69 (1H, m), 4.90 [5.01](1H, d, J=13.4 Hz), 5.10-5.19 (2H, m), 6.15-6.31 (1H, m), 6.86 [6.87](1H, s), 7.12-7.17 (2H, m), 7.20-7.44 (13H, m)

Reference Example 83

NMR: 1.46 (9H, s), 3.65 (2H, d, J=2.4 Hz), 4.12 (1H, dd, J=13.4, 1.0 Hz), 4.38 (2H, d, J=5.6 Hz), 4.83 (1H, d, J=13.2 Hz), 4.94-5.00 (1H, brs), 5.13 (1H, d, J=13.2 Hz), 5.19 (1H,

TABLE 11

| Reference Example No. | Structural Formula | Name |
|---|---|---|
| 81 | | Benzhydryl (3R,5R,6R)-3-(5-((N-(tert-butoxycarbonyl)-2-chloro-3,4-bis((4-methoxybenzyl)oxy)benzamido)methyl)-2H-tetrazol-2-yl)-7-oxo-6-(2-phenylacetamido)-4-thia-1-azabicyclo[3.2.0]heptane-3-carboxylate |
| 82 | | Benzhydryl (3R,5R,6R)-3-(5-(azidomethyl)-2-oxooxazolidin-3-yl)-7-oxo-6-(2-phenylacetamido)-4-thia-1-azabicyclo[3.2.0]heptane-3-carboxylate |
| 83 | | 4-Nitrobenzyl (3R,5R,6R)-3-(4-(((tert-butoxycarbonyl)amino)methyl)-1H-1,2,3-triazol-1-yl)-7-oxo-6-(2-phenylacetamido)-4-thia-1-azabicyclo[3.2.0]heptane-3-carboxylate | d, J=13.6 Hz), 5.64 (1H, d, J=4.0 Hz), 5.82 (1H, ddd, J=9.3, 3.9, 0.9 Hz), 6.71 (1H, d, J=9.6 Hz), 7.22-7.37 (7H, m), 7.65 (1H, s), 8.19-8.27 (2H, m)

Reference Example 84 reaction mixture was stirred overnight. IPE (110 mL) was added to the reaction mixture, and solids were collected by filtration and washed with IPE (50 mL). The solids were dried, thereby obtaining a target substance (21.4 g) as white solids.

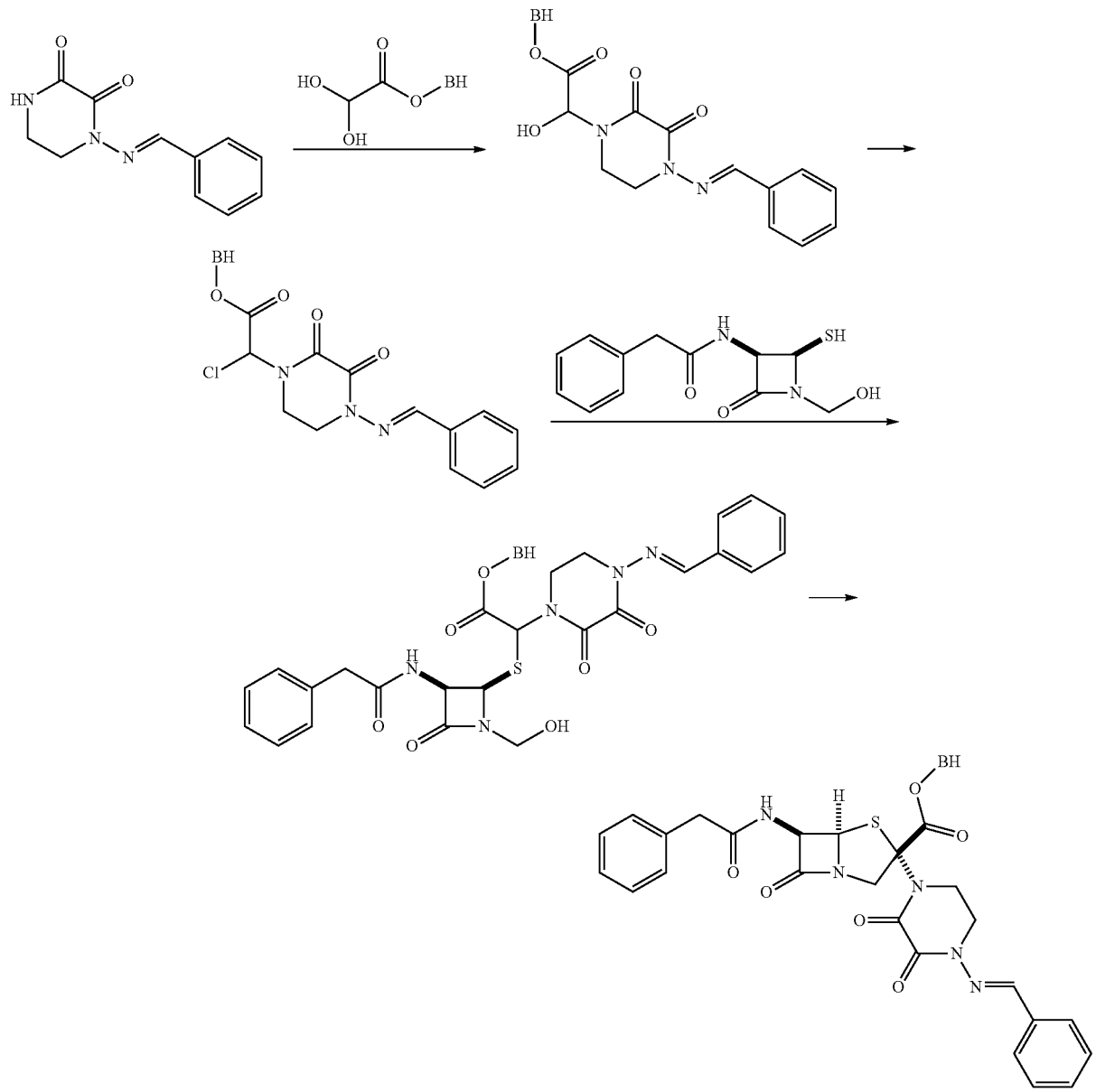

Reference Example 84 (1)

Dichloromethane (220 mL) and benzhydryl 2,2-dihydroxyacetate (13.7 g) were sequentially added to (E)-1-(benzylideneamino)piperazine-2,3-dione (11.0 g), and the mixture was stirred under ice cooling. At the same temperature, DBU (0.38 mL) was added to the reaction mixture, and the reaction mixture was stirred at room temperature for 3 hours. At the same temperature, benzhydryl 2,2-dihydroxyacetate (6.85 g) was added to the reaction mixture, and the Reference Example 84 (2)

THF (420 mL) was added to the compound (21.0 g) obtained in Reference Example 84 (1), and the mixture was stirred under ice cooling. At the same temperature, 2,6-lutidine (9.1 mL) and thionyl chloride (5.4 mL) were sequentially added to the reaction mixture. The reaction mixture was stirred at room temperature for 2 hours and 30 minutes, and insoluble matters were filtered. The solvent was distilled away under reduced pressure, thereby obtaining a mixture containing a target substance.

Reference Example 84 (3)

Dichloromethane (420 mL) and N-((2R,3R)-1-(hydroxymethyl)-2-mercapto-4-oxoazetidin-3-yl)-2-phenylacetamide (13.4 g) were sequentially added to the mixture obtained in Reference Example 84 (2), and the mixture was stirred under ice cooling. At the same temperature, triethylamine (7.0 mL) was added to the reaction mixture, and the reaction mixture was stirred for 2 hours. Water (420 mL) and 6 mol/L hydrochloric acid were added to the reaction mixture such that the pH was adjusted to 2.0. The organic layer was separated and sequentially washed with water and a saturated aqueous sodium chloride solution. The organic layer was dehydrated and dried over anhydrous sodium sulfate, and the solvent was distilled away under reduced pressure. The residue was purified by silica gel column chromatography [eluent; ethyl acetate:hexane=50:50→100:0], thereby obtaining a target substance (16.1 g) as white solids.

Reference Example 84 (4)

THF (370 mL) was added to the compound (18.5 g) obtained in Reference Example 84 (3), and the mixture was stirred under ice cooling. At the same temperature, 2,6-lutidine (4.1 mL) and thionyl chloride (2.48 mL) were sequentially added to the reaction mixture. The reaction mixture was stirred at room temperature for 1 hour and 30 minutes. Insoluble matters were filtered, and the solvent was distilled away under reduced pressure. At room temperature, THF (370 mL) and N,O-bis(trimethylsilyl)acetamide (7.8 mL) were sequentially added to the residue, and the mixture was stirred for 30 minutes. At the same temperature, hexamethylphosphoric triamide (23 mL) was added to the reaction mixture, and the reaction mixture was cooled to −60° C. At the same temperature, a 1.3 mol/L lithium bis(trimethylsilyl)amide/tetrahydrofuran solution (24 mL) was added dropwise to the reaction mixture. The reaction mixture was stirred at −10° C. for 1 hour. The reaction mixture was added to a mixture of ethyl acetate (750 mL), water (370 mL), and 1 mol/L hydrochloric acid (52 mL) under ice cooling, and the organic layer was separated. The organic layer was sequentially washed with water and a saturated aqueous sodium chloride solution. The organic layer was dehydrated and dried over anhydrous magnesium sulfate, and the solvent was distilled away under reduced pressure. The residue was purified by silica gel column chromatography [eluent; ethyl acetate:hexane=40:60→80:20], thereby obtaining benzhydryl (3R,5R,6R)-3-(4-(((E)-benzylidene)amino)-2,3-dioxopiperazin-1-yl)-7-oxo-6-(2-phenylacetamido)-4-thia-1-azabicyclo[3.2.0]heptane-3-carboxylate (6.0 g) as light yellow solids.

NMR: 3.12 (1H, d, J=13.6 Hz), 3.24 (1H, d, J=15.2 Hz), 3.29 (1H, d, J=14.8 Hz), 3.97-4.17 (4H, m), 5.39 (1H, d, J=13.6 Hz), 5.42-5.49 (2H, m), 5.93 (1H, d, J=6.8 Hz), 6.92 (1H, s), 7.06-7.14 (2H, m), 7.22-7.49 (16H, m), 7.69-7.78 (2H, m), 9.22 (1H, s)

The compounds in Table 12 were obtained in the same manner as in Reference Example 84.

TABLE 12

| Reference Example No. | Structural Formula | Name |
|---|---|---|
| 85 | | Benzhydryl (3R,5R,6R)-3-(4-(((E)-4-methylbenzylidene)amino)-2,5-dioxopiperazin-1-yl)-7-oxo-6-(2-phenylacetamido)-4-thia-1-azabicyclo[3.2.0]heptane-3-carboxylate |
| 86 | | Benzhydryl (3R,5R,6R)-3-((S)-3-((tert-butoxycarbonyl)amino)-2-oxopyrrolidin-1-yl)-7-oxo-6-(2-phenylacetamido)-4-thia-1-azabicyclo[3.2.0]heptane-3-carboxylate |

TABLE 12-continued

| Reference Example No. | Structural Formula | Name |
|---|---|---|
| 87 | | Benzhydryl (3R,5R,6R)-3-((R)-3-((tert-butoxycarbonyl)amino)-2-oxopyrrolidin-1-yl)-7-oxo-6-(2-phenylacetamido)-4-thia-1-azabicyclo[3.2.0]heptane-3-carboxylate |
| 88 | | Benzhydryl (3R,5R,6R)-3-(3-(((E)-4-methylbenzylidene)amino-2-oxotetrahydropyrimidin-1(2H)-yl)-7-oxo-6-(2-phenylacetamido)-4-thia-1-azabicyclo[3.2.0]heptane-3-carboxylate |

The measured values of NMR of the compounds in the table are as follows.

Reference Example 85

NMR: 2.40 (3H, s), 3.10 (1H, dd, J=13.4, 1.0 Hz), 3.30 (2H, s), 4.19-4.41 (2H, m), 4.42-4.60 (2H, m), 5.29 (1H, d, J=13.2 Hz), 5.46 (1H, d, J=3.6 Hz), 5.52 (1H, dd, J=8.0, 2.8 Hz), 6.05 (1H, d, J=8.0 Hz), 6.92 (1H, s), 7.08-7.14 (2H, m), 7.20-7.43 (14H, m), 7.60-7.68 (3H, m), 8.59 (1H, s)

Reference Example 86

NMR: 1.45 (9H, s), 1.86-2.01 (1H, m), 2.53-2.66 (1H, m), 3.25 (1H, dd, J=13.4, 1.0 Hz), 3.34 (2H, s), 3.46-3.56 (1H, m), 3.59-3.69 (1H, m), 3.97-4.09 (1H, m), 4.79-4.93 (1H, m), 5.01 (1H, d, J=13.2 Hz), 5.44 (1H, d, J=4.0 Hz), 5.54 (1H, dd, J=8.6, 3.0 Hz), 6.29 (1H, d, J=8.4 Hz), 6.85 (1H, s), 7.11-7.18 (2H, m), 7.19-7.43 (13H, m)

Reference Example 87

NMR: 1.46 (9H, s), 1.74-1.89 (1H, m), 2.55-2.72 (1H, m), 3.18 (1H, dd, J=13.2, 0.8 Hz), 3.33 (2H, s), 3.50-3.63 (2H, m), 4.16-4.33 (1H, m), 4.63-4.78 (1H, m), 5.02 (1H, d, J=13.2 Hz), 5.46 (1H, d, J=3.6 Hz), 5.52 (1H, dd, J=8.2, 3.4 Hz), 6.28 (1H, d, J=8.4 Hz), 6.85 (1H, s), 7.10-7.16 (2H, m), 7.18-7.43 (13H, m)

Reference Example 88

NMR: 2.15-2.26 (2H, m), 2.38 (3H, s), 3.18 (1H, dd, J=13.4, 1.0 Hz), 3.29 (2H, s), 3.53-3.77 (4H, m), 5.19 (1H, d, J=13.6 Hz), 5.41 (1H, d, J=3.6 Hz), 5.49 (1H, ddd, J=8.4, 3.8, 0.8 Hz), 6.28 (1H, d, J=8.4 Hz), 6.91 (1H, s), 7.11-7.42 (17H, m), 7.62 (2H, d, J=8.4 Hz), 7.94 (1H, s)

The compounds in Table 13 were obtained in the same manner as in Reference Example 27.

TABLE 13

| Reference Example No. | Structural Formula | Name |
|---|---|---|
| 89 | | Benzhydryl (3R,5R,6R)-3-(4-amino-2,3-dioxopiperazin-1-yl)-6-((Z)-2-(2-aminothiazol-4-yl)-2-(((1-(tert-butoxy)-2-methyl-1-oxopropan-2-yl)oxy)imino)acetamido)-7-oxo-4-thia-1-azabicyclo[3.2.0]heptane-3-carboxylate |

TABLE 13-continued

| Reference Example No. | Structural Formula | Name |
|---|---|---|
| 90 | | Benzhydryl (3R,5R,6R)-3-(4-amino-2,3-dioxopiperazin-1-yl)-6-((Z)-2-(((1-(tert-butoxy)-2-methyl-1-oxopropan-2-yl)oxy)imino)-2-((tert-butoxycarbonyl)amino)thiazol-4-yl)acetamido)-7-oxo-4-thia-1-azabicyclo[3.2.0]heptane-3-carboxylate |
| 91 | | Benzhydryl (3R,5R,6R)-3-(4-amino-2,5-dioxopiperazin-1-yl)-6-((Z)-((2-aminothiazol-4-yl)-2-(((1-(tert-butoxy)-2-methyl-1-oxopropan-2-yl)oxy)imino)acetamido)-7-oxo-4-thia-1-azabicyclo[3.2.0]heptane-3-carboxylate |
| 92 | | Benzhydryl (3R,5R,6R)-3-(3-amino-2-oxotetrahydropyrimidin-1(2H)-yl)-6-((Z)-2-(2-aminothiazol-4-yl)-2-(((1-(tert-butoxy)-2-methyl-1-oxopropan-2-yl)oxy)imino)acetamido)-7-oxo-4-thia-1-azabicyclo[3.2.0]heptane-3-carboxylate |
| 93 | | Benzhydryl (3R,5R,6R)-3-(4-amino-2,3-dioxopiperazin-1-yl)-6-((Z)-2-(5-bromo-2-((tert-butoxycarbonyl)amino)thiazol-4-yl)-2-(((1-(tert-butoxy)-2-methyl-1-oxopropan-2-yl)oxy)imino)acetamido)-7-oxo-4-thia-1-azabicyclo[3.2.0]heptane-3-carboxylate |

TABLE 13-continued

| Reference Example No. | Structural Formula | Name |
|---|---|---|
| 94 | | Benzhydryl (3R,5R,6R)-3-(4-amino-2,3-dioxopiperazin-1-yl)-6-((Z)-2-(((1-(tert-butoxy)-2-methyl-1-oxopropan-2-yl)oxy)imino)-2-(5-((tert-butoxycarbonyl)amino)-1,2,4-thiadiazol-3-yl)acetamido)-7-oxo-4-thia-1-azabicyclo[3.2.0]heptane-3-carboxylate |
| 95 | | Benzhydryl (3R,5R,6R)-3-(4-amino-2,3-dioxopiperazin-1-yl)-6-((Z)-2-(((1-(tert-butoxy)-2-methyl-1-oxopropan-2-yl)oxy)imino)-2-(2-((tert-butoxycarbonyl)amino)-5-chlorothiazol-4-yl)acetamido)-7-oxo-4-thia-1-azabicyclo[3.2.0]heptane-3-carboxylate |

The measured values of NMR of the compounds in the table are as follows.

Reference Example 89

NMR: 1.40 (91H, s), 1.50 (6H, s), 3.12 (1H, d, J=13.6 Hz), 3.71-3.85 (2H, m), 3.97-4.07 (2H, m), 5.42 (1H, d, J=13.6 Hz), 5.53 (1H, d, J=3.6 Hz), 5.66 (1H, dd, J=7.2, 3.2 Hz), 6.10 (21H, s), 6.78 (1H, s), 6.84-6.92 (2H, m), 7.06-7.12 (1H, m), 7.15-7.44 (11H, m)

Reference Example 90

NMR: 1.40 (9H, s), 1.52 (3H, s), 1.52 (3H, s), 1.55 (9H, s), 3.11 (1H, dd, J=13.6, 0.8 Hz), 3.69-3.86 (2H, m), 3.92-4.12 (2H, m), 4.59 (2H, s), 5.47 (1H, d, J=13.6 Hz), 5.54 (1H, d, J=3.6 Hz), 5.65 (1H, dd, J=6.8, 3.6 Hz), 6.86 (1H, s), 7.00-7.08 (1H, m), 7.13-7.45 (11H, m), 8.14 (1H, s)

Reference Example 91

NMR: 1.40 (9H, s), 1.50 (3H, s), 1.51 (3H, s), 3.10 (1H, d, J=13.6 Hz), 3.92-4.17 (2H, m), 4.30-4.46 (4H, m), 5.40 (1H, d, J=13.6 Hz), 5.50 (1H, d, J=3.6 Hz), 5.76 (1H, dd, J=7.8, 3.4 Hz), 6.07 (2H, s), 6.80 (1H, s), 6.88 (1H, s), 7.14-7.33 (11H, m)

Reference Example 92

NMR: 1.39 (9H, s), 1.46 (3H, s), 1.48 (3H, s), 2.01-2.12 (2H, m), 3.17 (1H, dd, J=13.4, 1.0 Hz), 3.36-3.48 (2H, m), 3.63 (2H, t, J=6.0 Hz), 3.84-3.99 (2H, brs), 5.16 (1H, d, J=13.6 Hz), 5.47 (1H, d, J=4.0 Hz), 5.75 (1H, ddd, J=8.6, 3.8, 0.8 Hz), 6.63 (2H, s), 6.77 (1H, s), 6.89 (1H, s), 7.01 (1H, d, J=8.4 Hz), 7.14-7.43 (10H, m)

Reference Example 93

NMR: 1.42 (9H, s), 1.51-1.56 (15H, m), 3.08 (1H, dd, J=13.8, 1.0 Hz), 3.70-3.86 (2H, m), 3.99-4.07 (2H, m), 4.58 (2H, s), 5.49 (1H, d, J=13.6 Hz), 5.53 (1H, d, J=3.6 Hz), 5.64 (1H, dd, J=7.2, 3.6 Hz), 6.86 (1H, s), 6.93-7.44 (11H, m), 8.07 (1H, s)

Reference Example 94

NMR: 1.41 (9H, s), 1.55 (9H, s), 1.56 (3H, s), 1.58 (3H, s), 3.10 (1H, d, J=12.8 Hz), 3.72-3.86 (2H, m), 4.00-4.09 (2H, m), 4.59 (2H, s), 5.47 (1H, d, J=13.6 Hz), 5.54 (1H, d, J=3.6 Hz), 5.66 (1H, d, J=7.8, 3.0 Hz), 6.82 (1H, d, J=7.2 Hz), 6.87 (1H, s), 6.98-7.06 (1H, m), 7.08-7.45 (9H, m), 8.41 (1H, s)

Reference Example 95

NMR: 1.42 (9H, s), 1.53 (9H, s), 1.54 (6H, s), 3.08 (1H, d, J=12.4 Hz), 3.70-3.85 (2H, m), 3.97-4.08 (2H, m), 4.58 (2H, s), 5.49 (1H, d, J=14.0 Hz), 5.53 (1H, d, J=4.0 Hz), 5.64 (1H, d, J=7.2, 3.2 Hz), 6.87 (1H, s), 6.97-7.01 (1H, m), 7.07-7.14 (1H, m), 7.17-7.43 (9H, m), 7.95 (1H, s)

The compounds in Table 14 were obtained in the same manner as in Reference Example 27(1).

TABLE 14

| Reference Example No. | Structural Formula | Name |
|---|---|---|
| 96 | | Benzhydryl (3R,5R,6R)-6-((Z)-2-(2-aminothiazol-4-yl)-2-(((1-(tert-butoxy)-2-methyl-1-oxopropan-2-yl)oxy)imino) acetamido)-3-(5-((N-(tert-butoxycarbonyl)-2-chloro-3,4-bis((4-methoxybenzyl) oxy)benzamido)methyl)-2H-tetrazol-2-yl)-7-oxo-4-thia-1-azabicyclo[3.2.0] heptane-3-carboxylate |
| 97 | | Benzhydryl (3R,5R,6R)-3-(5-(azidomethyl)-2-oxooxazolidin-3-yl)-6-((Z)-2-(((1-(tert-butoxy)-2-methyl-1-oxopropan-2-yl)oxy)imino)-2-(2-((tert-butoxycarbonyl)amino) thiazol-4-yl)acetamido)-7-oxo-4-thia-1-azabicyclo [3.2.0]heptane-3-carboxylate |
| 98 | | 4-Nitrobenzyl (3R,5R,6R)-6-((Z)-2-(2-aminothiazol-4-yl)-2-(((1-(tert-butoxy)-2-methyl-1-oxopropan-2-yl)oxy)imino) acetamido)-3-(4-(((tert-butoxycarbonyl)amino) methyl)-1H-1,2,3-triazol-1-yl)-7-oxo-4-thia-1-azabicyclo[3.2.0] heptane-3-carboxylate |
| 99 | | Benzhydryl (3R,5R,6R)-6-((Z)-2-(2-aminothiazol-4-yl)-2-(((1-(tert-butoxy)-2-methyl-1-oxopropan-2-yl)oxy)imino)acetamido)-3-((S)-3-((tert-butoxycarbonyl)amino)-2-oxopyrrolidin-1-yl)-7-oxo-4-thia-1-azabicyclo [3.2.0]heptane-3-carboxylate |

TABLE 14-continued

| Reference Example No. | Structural Formula | Name |
|---|---|---|
| 100 | | Benzhydryl (3R,5R,6R)-6-((Z)-2-(2-aminothiazol-4-yl)-2-(((1-(tert-butoxy)-2-methyl-1-oxopropan-2-yl)oxy)imino)acetamido)-3-((R)-3-((tert-butoxycarbonyl)amino)-2-oxopyrrolidin-1-yl)-7-oxo-4-thia-1-azabicyclo[3.2.0]heptane-3-carboxylate |

The measured values of NMR of the compounds in the table are as follows.

Reference Example 96

NMR: 1.09-1.19 (9H, m), 1.36-1.60 (15H, m), 3.78-3.85 (6H, m), 4.94 (2H, s), 5.06-5.15 (3H, m), 5.30-5.38 (1H, m), 5.55-5.65 (1H, m), 5.72-5.76 (1H, m), 5.88-6.00 (1H, m), 6.81-6.87 (2H, m), 6.88-6.95 (4H, m), 7.10-7.40 (15H, m)

Reference Example 97

NMR: 1.39 (9H, s), 1.51 (3H, s), 1.53 (3H, s), 1.54 (9H, s), 3.33 (1H, d, J=5.2 Hz), 3.43-3.66 (3H, m), 3.82 [3.91] (1H, t, J=8.4 Hz), 4.58-4.70 (1H, m), 5.00 [5.06](1H, d, J=13.2 Hz), 5.61-5.66 (1H, m), 5.74-5.85 (1H, m), 6.87 (1H, s), 7.13-7.21 (1H, m), 7.22-7.56 (11H, m), 8.09 (1H, s)

Reference Example 98

NMR: 1.42 (9H, s), 1.46 (3H, s), 1.46 (3H, s), 1.46 (9H, s), 4.08 (1H, d, J=13.6 Hz), 4.39 (2H, d, J=5.6 Hz), 4.92 (1H, d, J=13.2 Hz), 5.18-5.38 (2H, m), 5.75 (1H, d, J=4.0 Hz), 5.95 (1H, dd, J=8.4, 4.4 Hz), 6.27 (2H, s), 6.88 (1H, s), 6.94-7.01 (1H, m), 7.38-7.45 (2H, m), 7.61-7.73 (2H, m), 8.13-8.19 (2H, m)

Reference Example 99

NMR: 1.40 (9H, s), 1.44 (9H, s), 1.48 (3H, s), 1.50 (3H, s), 1.89-2.03 (1H, m), 2.50-2.68 (1H, m), 3.34 (1H, d, J=13.2 Hz), 3.49-3.59 (1H, m), 3.68 (1H, t, J=8.6 Hz), 3.99-4.09 (1H, m), 4.84-4.97 (1H, m), 5.09 (1H, d, J=13.6 Hz), 5.54 (1H, d, J=4.0 Hz), 5.78 (1H, dd, J=8.6, 3.8 Hz), 6.66-6.76 (2H, brs), 6.76 (1H, s), 6.85 (1H, s), 6.86-6.94 (1H, m), 7.12-7.45 (10H, m)

Reference Example 100

NMR: 1.39 (9H, s), 1.44 (9H, s), 1.48 (3H, s), 1.49 (3H, s), 1.78-1.91 (1H, m), 2.51-2.71 (1H, m), 3.28 (1H, d, J=13.2 Hz), 3.48-3.65 (2H, m), 4.17-4.35 (1H, m), 4.69-4.80 (1H, m), 5.10 (1H, d, J=13.6 Hz), 5.57 (1H, d, J=3.6 Hz), 5.78 (1H, dd, J=8.2, 3.8 Hz), 6.39-6.67 (2H, brs), 6.79 (1H, s), 6.86 (1H, s), 7.05-7.14 (1H, m), 7.18-7.43 (10H, m)

Reference Example 101

Reference Example 101 (1)

Ethyl acetate (3 mL) and 10% palladium-carbon (300 mg) were added to 4-nitrobenzyl(3R,5R,6R)-6-((Z)-2-(2-aminothiazol-4-yl)-2-(((1-(tert-butoxy)-2-methyl-1-oxopropan-2-yl)oxy)imino)acetamido)-3-(4-(((tert-butoxycarbonyl)amino)methyl)-1H-1,2,3-triazol-1-yl)-7-oxo-4-thia-1-azabicyclo[3.2.0]heptane-3-carboxylate (300 mg), and the mixture was stirred at room temperature for 3 hours in a hydrogen atmosphere. The reaction mixture was filtered through celite, and the residue was washed with ethyl acetate. The solvent was distilled away under reduced pressure, thereby obtaining a target substance (233 mg) as yellow solids.

Reference Example 101 (2)

Dichloromethane (3.5 mL) and nitromethane (1.2 mL) were added to the compound (230 mg) obtained in Reference Example 101 (1), and the mixture was stirred at −20° C. At the same temperature, anisole (1.4 mL) and aluminum chloride (353 mg) were sequentially added to the reaction mixture. The reaction mixture was stirred at a temperature equal to or lower than −20° C. for 1 hour and 30 minutes. At the same temperature, trifluoroacetic acid (0.13 mL) was added to the reaction mixture, and the reaction mixture was stirred at a temperature equal to or lower than −10° C. for 1 hour 30 minutes. The reaction mixture was added to a mixture of acetonitrile (10 mL), water (10 mL), and trisodium citrate dihydrate (1.17 g) under ice cooling. A saturated aqueous sodium hydrogen carbonate solution was added to the reaction mixture such that the pH was adjusted to 5.1, and the aqueous layer was separated. The aqueous layer was concentrated under reduced pressure, and the residue was purified by medium-pressure reverse-phase silica gel column chromatography [eluent; water:acetonitrile=100: 0→85:15]. The aqueous solution containing a target substance was concentrated under reduced pressure and lyophilized, thereby obtaining (3R,5R,6R)-3-(4-(aminomethyl)-1H-1,2,3-triazol-1-yl)-6-((Z)-2-(2-aminothiazol-4-yl)-2-(((2-carboxypropan-2-yl)oxy)imino)acetamido)-7-oxo-4-thia-1-azabicyclo[3.2.0]heptane-3-carboxylate (40 mg) as white solids.

NMR (D$_2$O): 1.50 (3H, s), 1.52 (3H, s), 4.08 (1H, dd, J=13.2, 1.2 Hz), 4.36 (2H, s), 4.74 (1H, d, J=13.2 Hz), 5.64 (1H, d, J=3.6 Hz), 5.81 (1H, dd, J=3.6, 1.2 Hz), 7.04 (1H, s), 7.92 (1H, s)

Reference Example 102

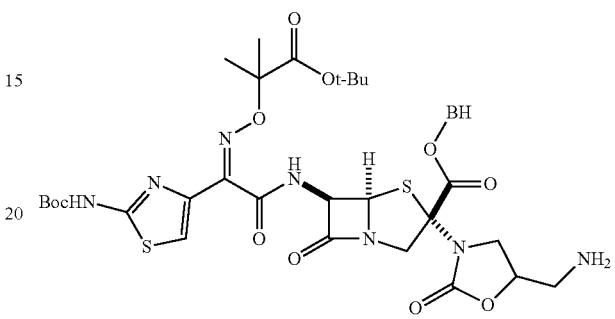

In the same manner as in Reference Example 101(1), benzhydryl(3R,5R,6R)-3-(5-(aminomethyl)-2-oxooxazolidin-3-yl)-6-((Z)-2-(((1-(tert-Butoxy)-2-methyl-1-oxopropan-2-yl)oxy)imino)-2-(2-((tert-butoxycarbonyl)amino)thiazol-4-yl)acetamido)-7-Oxo-4-thia-1-azabicyclo[3.2.0]heptane-3-carboxylate was obtained.

NMR: 1.39 [1.39](9H, s), 1.50 (3H, s), 1.52 (3H, s), 1.54 (9H, s), 2.73 [2.76](1H, d, J=5.8 Hz), 2.92-3.01 (1H, m), 3.55-3.63 (2H, m), 3.76 [3.86](1H, t, J=7.9 Hz), 4.54-4.61 (1H, m), 4.95 [5.05](1H, d, J=13.2 Hz), 5.61 [5.62](1H, d, J=3.8 Hz), 5.72-5.84 (1H, m), 6.88 (1H, s), 7.13-7.53 (15H, m)

The compounds of Table 15 were obtained in the same manner as in Reference Example 101 (2).

TABLE 15

| Reference Example No. | Structural Formula | Name |
| --- | --- | --- |
| 103 | | (3R,5R,6R)-3-((S)-3-amino-2-oxopyrrolidin-1-yl)-6-((Z)-2-(2-aminothiazol-4-yl)-2-(((2-carboxypropan-2-yl)oxy)imino)acetamido)-7-oxo-4-thia-1-azabicyclo[3.2.0]heptane-3-carboxylate |

TABLE 15-continued

| Reference Example No. | Structural Formula | Name |
|---|---|---|
| 104 | | (3R,5R,6R)-3-((R)-3-amino-2-oxopyrrolidin-1-yl)-6-((Z)-2-(2-aminothiazol-4-yl)-2-(((2-carboxypropan-2-yl)oxy)imino)acetamido)-7-oxo-4-thia-1-azabicyclo[3.2.0]heptane-3-carboxylate |

The measured values of NMR of the compounds in the table are as follows.

Reference Example 103

NMR (D$_2$O): 1.49 (3H, s), 1.51 (3H, s), 2.10-2.24 (1H, m), 2.59-2.72 (1H, m), 3.38 (1H, dd, J=12.8, 1.2 Hz), 3.72-3.82 (1H, m), 3.86 (1H, t, J=9.2 Hz), 4.25 (1H, dd, J=10.4, 9.2 Hz), 4.82 (1H, d, J=12.8 Hz), 5.68 (1H, d, J=3.6 Hz), 5.72 (1H, dd, J=3.6, 1.2 Hz), 7.05 (1H, s)

Reference Example 104

NMR (D$_2$O): 1.50 (3H, s), 1.51 (3H, s), 2.12-2.26 (1H, m), 2.61-2.73 (1H, m), 3.36 (1H, dd, J=12.8, 1.2 Hz), 3.67-3.80 (1H, m), 3.80-3.93 (1H, m), 4.23 (1H, dd, J=10.0, 9.2 Hz), 4.82 (1H, d, J=12.8 Hz), 5.68 (1H, d, J=3.6 Hz), 5.72 (1H, dd, J=3.6, 1.2 Hz), 7.06 (1H, s)

The compounds in Table 16 were obtained in the same manner as in Reference Example 35.

TABLE 16

| Reference Example No. | Structural Formula | Name |
|---|---|---|
| 105 | | Benzhydryl (3R,5R,6R)-3-(3-amino-2-oxoimidazolidin-1-yl)-6-((Z)-2-((((S)-1-(benzhydryloxy)-1-oxobutan-2-yl)oxy)imino)-2-(2-((tert-butoxycarbonyl)amino)thiazol-4-yl)acetamido)-7-oxo-4-thia-1-azabicyclo[3.2.0]heptane-3-carboxylate |
| 106 | | Benzhydryl (3R,5R,6R)-3-(3-amino-2-oxoimidazolidin-1-yl)-6-((Z)-2-((1-((benzhydryloxy)carbonyl)cyclopropoxy)imino)-2-(5-((tert-butoxycarbonyl)amino)-1,2,4-thiadiazol-3-yl)acetamido)-7-oxo-4-thia-1-azabicyclo[3.2.0]heptane-3-carboxylate |

TABLE 16-continued

| Reference Example No. | Structural Formula | Name |
|---|---|---|
| 107 | | Benzhydryl (3R,5R,6R)-3-(3-amino-2-oxoimidazolidin-1-yl)-6-((Z)-2-((1-((benzhydryloxy)carbonyl)cyclopropoxy)imino)-2-(2-((tert-butoxycarbonyl)amino)-5-chlorothiazol-4-yl)acetamido)-7-oxo-4-thia-1-azabicyclo[3.2.0]heptane-3-carboxylate |
| 108 | | Benzhydryl (3R,5R,6R)-3-(3-amino-2-oxoimidazolidin-1-yl)-6-((Z)-2-((1-((benzhydryloxy)carbonyl)cyclobutoxy)imino)-2-(2-((tert-butoxycarbonyl)amino)-5-chlorothiazol-4-yl)acetamido)-7-oxo-4-thia-1-azabicyclo[3.2.0]heptane-3-carboxylate |
| 109 | | Benzhydryl (3R,5R,6R)-3-(3-amino-2-oxoimidazolidin-1-yl)-6-((Z)-2-((1-((benzhydryloxy)carbonyl)cyclobutoxy)imino)-2-(5-((tert-butoxycarbonyl)amino)-1,2,4-thiadiazol-3-yl)acetamido)-7-oxo-4-thia-1-azabicyclo[3.2.0]heptane-3-carboxylate |
| 110 | | Benzhydryl (3R,5R,6R)-3-(3-amino-2-oxoimidazolidin-1-yl)-6-((Z)-2-(((1-(tert-butoxy)-2-methyl-1-oxopropan-2-yl)oxy)imino)-2-(2-((tert-butoxycarbonyl)amino)-5-methylthiazol-4-yl)acetamido)-7-oxo-4-thia-1-azabicyclo[3.2.0]heptane-3-carboxylate |

TABLE 16-continued

| Reference Example No. | Structural Formula | Name |
|---|---|---|
| 111 | | Benzhydryl (3R,5R,6R)-3-(3-amino-2-oxoimidazolidin-1-yl)-6-((Z)-2-(5-bromo-2-((tert-butoxycarbonyl)amino)thiazol-4-yl)-2-(((1-(tert-butoxy)-2-methyl-1-oxopropan-2-yl)oxy)imino)acetamido)-7-oxo-4-thia-1-azabicyclo[3.2.0]heptane-3-carboxylate |
| 112 | | Benzhydryl (3R,5R,6R)-3-(3-amino-2-oxoimidazolidin-1-yl)-6-((Z)-2-((((S)-1-(benzhydryloxy)-3-methyl-1-oxobutan-2-yl)oxy)imino)-2-(2-((tert-butoxycarbonyl)amino)thiazol-4-yl)acetamido)-7-oxo-4-thia-1-azabicyclo[3.2.0]heptane-3-carboxylate |
| 113 | | Benzhydryl (3R,5R,6R)-3-(3-amino-2-oxoimidazolidin-1-yl)-6-((Z)-2-((((S)-1-benzhydryloxy)-1-oxopentan-2-yl)oxy)imino)-2(2-((tert-butoxycarbonyl)amino)thizaol-4-yl)acetamido)-7-oxo-4-thia-1-azabicyclo[3.2.0]heptane-3-carboxylate |
| 114 | | Benzhydryl (3R,5R,6R)-3-(3-amino-2-oxoimidazolidin-1-yl)-6-((R,Z)-5-(benzhydryloxy)carbonyl-2-(2-((tert-butoxycarbonyl)amino)thiazol-4-yl)-8,8,9,9-tetramethyl-4,7-dioxa-3-aza-8-siladec-2-enamido)-7-oxo-4-thia-1-azabicyclo[3.2.0]heptane-3-carboxylate |

The measured values of NMR of the compounds in the table are as follows.

Reference Example 105

NMR: 0.94 (3H, t, J=7.4 Hz), 1.55 (9H, s), 1.85-2.02 (2H, m), 3.30-3.57 (5H, m), 3.84 (2H, s), 4.91 (1H, dd, J=7.8, 5.2 Hz), 5.03 (1H, d, J=13.2 Hz), 5.56 (1H, d, J=3.6 Hz), 5.64 (1H, dd, J=6.6, 3.4 Hz), 6.86 (1H, s), 6.90 (1H, s), 7.01-7.09 (1H, m), 7.12-7.40 (20H, m), 7.58 (1H, d, J=6.8 Hz), 8.11 (1H, s)

Reference Example 106

NMR: 1.51-1.64 (4H, m), 1.58 (9H, s), 3.33-3.55 (5H, m), 3.82 (2H, s), 4.91 (1H, d, J=13.6 Hz), 5.56 (1H, d, J=4.0 Hz), 5.78 (1H, dd, J=8.6, 3.4 Hz), 6.83 (1H, s), 6.87 (1H, s), 7.07-7.14 (2H, m), 7.16-7.42 (19H, m), 8.60 (1H, s)

Reference Example 107

NMR: 1.46-1.59 (4H, m), 1.53 (9H, s), 3.32-3.54 (5H, m), 3.81 (2H, s), 4.92 (1H, d, J=13.2 Hz), 5.53 (1H, d, J=4.0 Hz), 5.75 (1H, dd, J=8.6, 3.8 Hz), 6.82 (1H, s), 6.89 (1H, s), 7.14-7.43 (21H, m), 8.08 (1H, s)

Reference Example 108

NMR: 1.52 (9H, s), 1.90-2.02 (2H, m), 2.37-2.66 (4H, m), 3.35-3.51 (5H, m), 3.82 (2H, s), 4.95 (1H, d, J=13.2 Hz), 5.52 (1H, d, J=3.6 Hz), 5.77 (1H, dd, J=9.4, 3.4 Hz), 6.83 (1H, s), 6.89 (1H, s), 7.13-7.42 (22H, m), 8.11 (1H, s)

Reference Example 109

NMR: 1.57 (9H, s), 1.97-2.09 (2H, m), 2.45-2.59 (2H, m), 2.60-2.71 (2H, m), 3.31-3.47 (4H, m), 3.50 (1H, dd, J=13.2, 0.8 Hz), 3.83 (2H, s), 4.93 (1H, d, J=13.2 Hz), 5.54 (1H, d, J=3.6 Hz), 5.80 (1H, dd, J=8.6, 3.4 Hz), 6.83 (1H, s), 6.88 (1H, s), 7.02-7.13 (2H, m), 7.16-7.43 (19H, m), 8.63 (1H, s)

Reference Example 110

NMR: 1.39 (9H, s), 1.47-1.55 (15H, m), 2.48 (3H, s), 3.37-3.56 (5H, m), 3.82 (2H, s), 4.96 (1H, d, J=13.2 Hz), 5.56 (1H, d, J=4.0 Hz), 5.83 (1H, dd, J=9.2, 4.0 Hz), 6.88 (1H, s), 7.13-7.21 (2H, m), 7.22-7.39 (9H, m), 7.94 (1H, s)

Reference Example 111

NMR: 1.40 (9H, s), 1.50-1.56 (15H, m), 3.40-3.56 (5H, m), 3.82 (2H, s), 4.95 (1H, d, J=13.2 Hz), 5.56 (1H, d, J=4.0 Hz), 5.79 (1H, dd, J=8.4, 3.8 Hz), 6.88 (1H, s), 7.17-7.42 (11H, m), 8.14 (1H, s)

Reference Example 112

NMR: 0.90 (3H, d, J=6.8 Hz), 1.00 (3H, d, J=7.2 Hz), 1.55 (9H, s), 2.25-2.38 (1H, m), 3.39-3.58 (5H, m), 3.85 (2H, s), 4.84 (1H, d, J=4.8 Hz), 5.06 (1H, d, J=13.2 Hz), 5.52-5.57 (1H, m), 5.59 (1H, d, J=3.6 Hz), 6.86 (1H, s), 6.91 (1H, s), 6.99-7.05 (1H, m), 7.09-7.41 (20H, m), 7.81 (1H, d, J=5.6 Hz), 8.13 (1H, s)

Reference Example 113

NMR: 0.88 (3H, t, J=7.4 Hz), 1.34-1.46 (2H, m), 1.55 (9H, s), 1.82-1.92 (2H, m), 3.48-3.56 (5H, m), 3.86 (2H, s), 4.97 (1H, t, J=6.8 Hz), 5.05 (1H, d, J=13.2 Hz), 5.57 (1H, d, J=4.0 Hz), 5.64 (1H, dd, J=6.6, 3.4 Hz), 6.86 (1H, s), 6.89 (1H, s), 7.01-7.08 (1H, m), 7.11-7.41 (20H, m), 7.53 (1H, d, J=7.2 Hz), 8.12 (1H, s)

Reference Example 114

NMR: −0.04 (6H, s), 0.82 (9H, s), 1.55 (9H, s), 3.24-3.41 (4H, m), 3.50 (1H, d, J=12.8 Hz), 3.82 (2H, s), 4.09-4.16 (2H, m), 5.01 (1H, d, J=13.2 Hz), 5.05 (1H, t, J=4.6 Hz), 5.50 (1H, d, J=4.0 Hz), 5.77 (1H, dd, J=8.8, 3.6 Hz), 6.83 (1H, s), 6.90 (1H, s), 6.99-7.08 (1H, m), 7.09-7.43 (21H, m), 8.15 (1H, s)

Reference Example 115

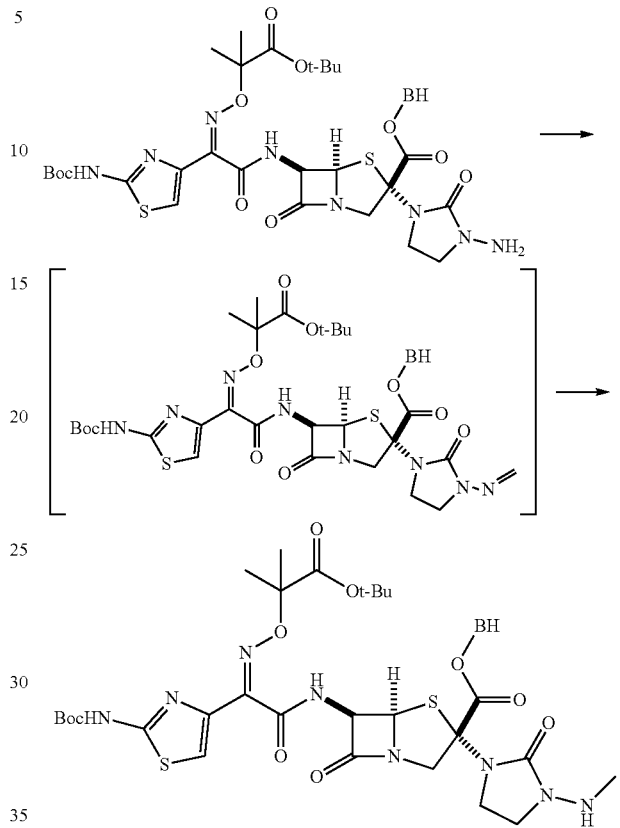

Paraformaldehyde (123 mg) and NMP (1 mL) were added to benzhydryl (3R,5R,6R)-3-(3-amino-2-oxoimidazolidin-1-yl)-6-((Z)-2-(((1-(tert-butoxy)-2-methyl 1-oxopropan-2-yl)oxy)imino)-2-(2-((tert-butoxycarbonyl)amino)thiazol-4-yl)acetamido)-7-oxo-4-thia-1-azabicyclo[3.2.0]heptane-3-carboxylate (100 mg), and the mixture was stirred at room temperature overnight. Acetic acid (14 µL) was added to the reaction mixture, and the mixture was stirred at room temperature for 8 hours. The reaction mixture was stirred at 50° C. for 10 hours. The reaction mixture was cooled to room temperature, ethyl acetate (5 mL) and water (5 mL) were added to the reaction mixture, and the organic layer was separated. The organic layer was washed twice with a 5% aqueous sodium chloride solution. The organic layer was dehydrated and dried over anhydrous sodium sulfate, and the solvent was distilled away under reduced pressure. Dichloromethane (1 mL) was added to the residue, and a 85% borane-2-picoline complex (18 mg) and p-toluenesulfonic acid monohydrate (31 mg) were sequentially added thereto under ice cooling, and the reaction mixture was stirred at room temperature for 1 hour. At room temperature, ethyl acetate (5 mL) and water (5 mL) were added to the reaction mixture, and the organic layer was separated. The organic layer was washed twice with a 5% aqueous sodium chloride solution and then dehydrated and dried over anhydrous sodium sulfate. The solvent was distilled away under reduced pressure. The residue was purified by silica gel column chromatography [eluent; ethyl acetate:hexane=70:30→100:0], thereby obtaining benzhydryl (3R,5R,6R)-6-((Z)-2-(((1-(tert-butoxy)-2-methyl-1-oxopropan-2-yl)oxy)

imino)-2-(2-((tert-butoxycarbonyl)amino)thiazol-4-yl)
acetamido)-3-(3-methylamino)-2-oxoimidazolidin-1-yl)-7-
oxo-4-thia-1-azabicyclo[3.2.0]heptane-3-carboxylate (52
mg) as a yellow oily substance.

NMR: 1.39 (9H, s), 1.51 (3H, s), 1.53 (3H, s), 1.54 (9H, s), 2.57 (3H, s), 3.39-3.57 (6H, m), 4.91 (1H, d, J=13.2 Hz), 5.58 (1H, d, J=4.0 Hz), 5.81 (1H, dd, J=8.6, 3.4 Hz), 6.87 (1H, s), 7.15-7.41 (13H, m)

Example 1

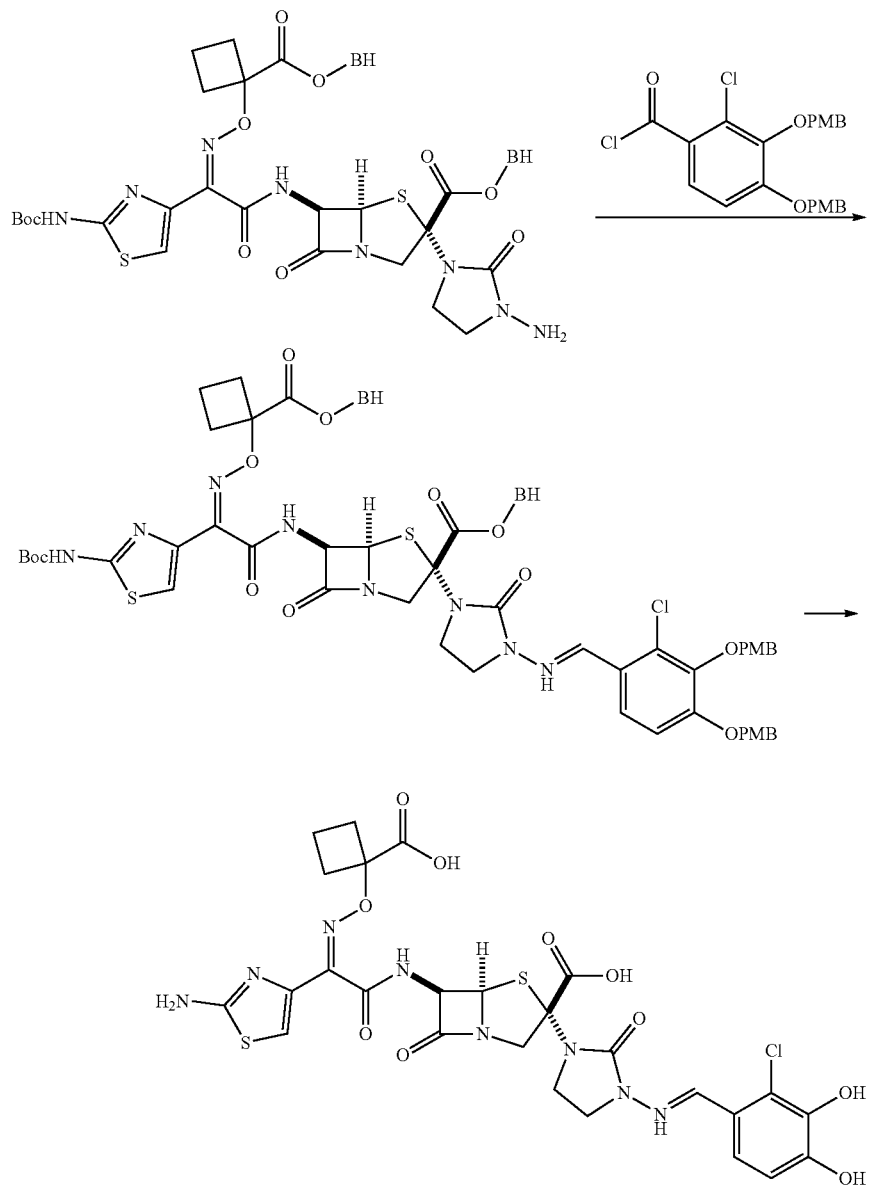

Example 1 (1)

THF (4.2 mL) and water (4.2 mL) were added to benzhydryl (3R,5R,6R)-3-(3-amino-2-oxoimidazolidin-1-yl)-6-((Z)-2-((1-((benzhydryloxy)carbonyl)cyclobutoxy)imino)-2-(2-((tert-butoxycarbonyl)amino)thiazol-4-yl)acetamido)-7-oxo-4-thia-1-azabicyclo[3.2.0]heptane-3-carboxylate (104 mg), and the mixture was stirred under ice cooling. At the same temperature, sodium hydrogen carbonate (11 mg) was added to the reaction mixture, and then 2-chloro-3,4-bis((4-methoxybenzyl)oxy)benzoyl chloride (52 mg) obtained in Reference Example 1 was sequentially added thereto. The reaction mixture was stirred at room temperature for 4 hours, ethyl acetate (15 mL) and water (15 mL) were then added thereto, and the organic layer was separated. The organic layer was washed with a saturated aqueous sodium chloride solution and dehydrated and dried over anhydrous sodium sulfate. The solvent was distilled away under reduced pressure, thereby obtaining a target substance (126 mg) as light yellow solids.

Example 1 (2)

Dichloromethane (1.9 mL) was added to the compound (126 mg) obtained in Example 1 (1), and the mixture was cooled to −20° C. At the same temperature, anisole (0.59 mL) and aluminum chloride (180 mg) were sequentially added to the reaction mixture, and the reaction mixture was stirred at the same temperature for 30 minutes. The reaction mixture was added to a mixture of acetonitrile (5 mL), water (5 mL), and trisodium citrate dihydrate (596 mg) under ice cooling. A saturated aqueous sodium hydrogen carbonate solution was added to the reaction mixture such that the pH was adjusted to 5.1, and the aqueous layer was separated. The aqeuous layer was concentrated under reduced pressure, and the residue was purified by medium-pressure reverse-phase silica gel column chromatography [eluent; water: acetonitrile=100:0→85:15]. The aqueous solution containing a target substance was lyophilized, thereby obtaining (3R,5R,6R)-6-((Z)-2-(2-aminothiazol-4-yl)-2-(((1-carboxy-cyclobutoxy)imino)acetamido)-3-(3-(2-chloro-3,4-dihydroxybenzamido)-2-oxoimidazolidin-1-yl)-7-oxo-4-thia-1-azabicyclo[3.2.0]heptane-3-carboxylate (15 mg) as white solids.

NMR: 1.80-2.09 (2H, m), 2.24-2.40 (2H, m), 2.40-2.62 (2H, m), 3.64 (1H, d, J=12.4 Hz), 3.69-3.80 (4H, m), 4.69 (1H, d, J=12.4 Hz), 5.73 (1H, d, J=4.0 Hz), 5.79 (1H, d, J=2.8 Hz), 6.94 (1H, d, J=8.0 Hz), 7.07 (1H, s), 7.10 (1H, d, J=8.4 Hz) MS: 725.00 [M+H]+, 722.95 [M−H]−

The compounds shown in Table 17 were obtained in the same manner as in Example 1.

TABLE 17

| Example No | Structural Formula | Name |
|---|---|---|
| 2 |  | (3R,5R,6R)-6-((Z)-2-(2-aminothiazol-4-yl)-2-(((2-carboxypropan-2-yl)oxy)imino)acetamido)-3-(3-(2-chloro-3,4-dihydroxybenzamido)-2-oxoimidazolidin-1-yl)-7-oxo-4-thia-1-azabicyclo[3.2.0]heptane-3-carboxylate |
| 3 |  | (3R,5R,6R)-6-((Z)-2-(2-aminothiazol-4-yl)-2-(((2-carboxypropan-2-yl)oxy)imino)acetamido)-3-((S)-3-(2-chloro-3,4-dihydroxybenzamido)-5-methyl-2-oxoimidazolidin-1-yl)-7-oxo-4-thia-1-azabicyclo[3.2.0]heptane-3-carboxylate |
| 4 |  | (3R,5R,6R)-6-((Z)-2-(2-aminothiazol-4-yl)-2-(((2-carboxypropan-2-yl)oxy)imino)acetamido)-3-((S)-3-(2-chloro-3,4-dihydroxybenzamido)-4-methyl-2-oxoimidazolidin-1-yl)-7-oxo-4-thia-1-azabicyclo[3.2.0]heptane-3-carboxylate |

TABLE 17-continued

| Example No | Structural Formula | Name |
|---|---|---|
| 5 | | (3R,5R,6R)-6-((Z)-2-(2-aminothiazol-4-yl)-2-(((2-carboxypropan-2-yl)oxy)imino)acetamido)-3-((R)-3-(2-chloro-3,4-dihydroxybenzamido)-4-methyl-2-oxoimidazolidin-1-yl)-7-oxo-4-thia-1-azabicyclo[3.2.0]heptane-3-carboxylate |
| 6 | | (3R,5R,6R)-6-((Z)-2-(2-aminothiazol-4-yl)-2-(((2-carboxypropan-2-yl)oxy)imino)acetamido)-3-((R)-3-(2-chloro-3,4-dihydroxybenzamido)-5-methyl-2-oxoimidazolidin-1-yl)-7-oxo-4-thia-1-azabicyclo[3.2.0]heptane-3-carboxylate |
| 7 | | (3R,5R,6R)-6-((Z)-2-(2-aminothiazol-4-yl)-2-((1-carboxycyclobutoxy)imino)acetamido)-3-((R)-3-(2-chloro-3,4-dihydroxybenzamido)-5-methyl-2-oxoimidazolidin-1-yl)-7-oxo-4-thia-1-azabicyclo[3.2.0]heptane-3-carboxylate |
| 8 | | (3R,5R,6R)-6-((Z)-2-(2-aminothiazol-4-yl)-2-((1-carboxycyclopropoxy)imino)acetamido)-3-(3-(2-chloro-3,4-dihydroxybenzamido)-2-oxoimidazolidin-1-yl)-7-oxo-4-thia-1-azabicyclo[3.2.0]heptane-3-carboxylate |

TABLE 17-continued

| Example No | Structural Formula | Name |
|---|---|---|
| 9 | | (3R,5R,6R)-6-((Z)-2-(2-amino-5-chlorothiazol-4-yl)-2-(((2-carboxypropan-2-yl)oxy)imino)acetamido)-3-(3-(2-chloro-3,4-dihydroxybenzamido)-2-oxoimidazolidin-1-yl)-7-oxo-4-thia-1-azabicyclo[3.2.0]heptane-3-carboxylate |
| 10 | | (3R,5R,6R)-6-((Z)-2-(5-amino-1,2,4-thiadiazol-3-yl)-2-(((2-carboxypropan-2-yl)oxy)imino)acetamido)-3-(3-(2-chloro-3,4-dihydroxybenzamido)-2-oxoimidazolidin-1-yl)-7-oxo-4-thia-1-azabicyclo[3.2.0]heptane-3-carboxylate |
| 11 | | (3R,5R,6R)-6-((Z)-2-(2-aminothiazol-4-yl)-2-((carboxymethoxy)imino)acetamido)-3-(3-(2-chloro-3,4-dihydroxybenzamido)-2-oxoimidazolidin-1-yl)-7-oxo-4-thia-1-azabicyclo[3.2.0]heptane-3-carboxylate |
| 12 | | (3R,5R,6R)-6-((Z)-2-(2-aminothiazol-4-yl)-2-(((R)-1-carboxyethoxy)imino)acetamido)-3-(3-(2-chloro-3,4-dihydroxybenzamido)-2-oxoimidazolidin-1-yl)-7-oxo-4-thia-1-azabicyclo[3.2.0]heptane-3-carboxylate |

TABLE 17-continued

| Example No | Structural Formula | Name |
|---|---|---|
| 13 | | (3R,5R,6R)-6-((Z)-2-(2-aminothiazol-4-yl)-2-(((S)-1-carboxyethoxy)imino)acetamido)-3-(3-(2-chloro-3,4-dihydroxybenzamido)-2-oxoimidazolidin-1-yl)-7-oxo-4-thia-1-azabicyclo[3.2.0]heptane-3-carboxylate |
| 14 | | (3R,5R,6R)-6-((Z)-2-(2-aminothiazol-4-yl)-2-(((S)-1-carboxy-2-hydroxyethoxy)imino)acetamido)-3-(3-(2-chloro-3,4-dihydroxybenzamido)-2-oxoimidazolidin-1-yl)-7-oxo-4-thia-1-azabicyclo[3.2.0]heptane-3-carboxylate |
| 15 | | (S)-2-((((Z)-1-(2-aminothiazol-4-yl)-2-(((3R,5R,6R)-3-carboxy-3-(2-chloro-3,4-dihydroxybenzamido)-2-oxoimidazolidin-1-yl)-7-oxo-4-thia-1-azabicyclo[3.2.0]heptan-6-yl)amino)-2-oxoethylidene)amino)oxy)succinic acid |
| 16 | | (3R,5R,6R)-6-((Z)-2-(2-aminothiazol-4-yl)-2-(((4-carboxytetrahydro-2H-pyran-4-yl)oxy)imino)acetamido)-3-(3-(2-chloro-3,4-dihydroxybenzamido)-2-oxoimidazolidin-1-yl)-7-oxo-4-thia-1-azabicyclo[3.2.0]heptane-3-carboxylate |

TABLE 17-continued

| Example No | Structural Formula | Name |
|---|---|---|
| 17 | | (3R,5R,6R)-6-((Z)-2-(2-aminothiazol-4-yl)-2-(((1-carboxycyclopentyl)oxy)imino)acetamido)-3-(3-(2-chloro-3,4-dihydroxybenzamido)-2-oxoimidazolidin-1-yl)-7-oxo-4-thia-1-azabicyclo[3.2.0]heptane-3-carboxylate |
| 18 | | (3R,5R,6R)-6-((Z)-2-(2-aminothiazol-4-yl)-2-(((2-carboxypropan-2-yl)oxy)imino)acetamido)-3-(4-(2-chloro-3,4-dihydroxybenzamido)-5-oxo-4,5-dihydro-1H-1,2,4-triazol-1-yl)-7-oxo-4-thia-1-azabicyclo[3.2.0]heptane-3-carboxylate |

The measured values of NMR and MS of the compounds in the table are as follows.

Example 2

NMR: 1.49 (3H, s), 1.51 (3H, s), 3.64 (1H, d, J=12.4 Hz), 3.70-3.80 (4H, m), 4.68 (1H, d, J=12.4 Hz), 5.71 (1H, d, J=3.6 Hz), 5.76 (1H, d, J=2.8 Hz), 6.94 (1H, d, J=8.4 Hz), 7.04 (1H, s), 7.10 (1H, d, J=8.4 Hz)
MS: 713.00 [M+H]+, 710.90 [M−H]−

Example 3

NMR: 1.28 (3H, d, J=6.0 Hz), 1.42 (3H, s), 1.44 (3H, s), 3.28-3.40 (2H, m), 3.76-3.84 (1H, m), 4.21-4.31 (1H, m), 5.66 (2H, s), 6.87 (1H, d, J=8.4 Hz), 6.97 (1H, s), 7.04 (1H, d, J=8.4 Hz)
MS: 727.05 [M+H]+, 725.00 [M−H]−

Example 4

NMR: 1.28 (3H, d, J=6.0 Hz), 1.40 (3H, s), 1.42 (3H, s), 3.17 (1H, t, J=9.4 Hz), 3.57 (1H, d, J=13.2 Hz), 3.73-3.81 (1H, m), 3.85-3.97 (1H, m), 4.54 (1H, d, J=12.4 Hz), 5.60 (1H, d, J=3.6 Hz), 5.67 (1H, d, J=2.8 Hz), 6.85 (1H, d, J=8.4 Hz), 6.95 (1H, s), 7.02 (1H, d, J=8.4 Hz)
MS: 727.05 [M+H]+, 725.10 [M−H]−

Example 5

NMR: 1.37 (3H, d, J=5.6 Hz), 1.49 (3H, s), 1.51 (3H, s), 3.35 (1H, t, J=8.0 Hz), 3.61 (1H, dd, J=12.6, 1.0 Hz), 3.94-4.08 (2H, m), 4.71 (1H, d, J=12.8 Hz), 5.72 (1H, d, J=3.6 Hz), 5.77 (1H, dd, J=3.8, 0.8 Hz), 6.94 (1H, d, J=8.4 Hz), 7.03 (1H, s), 7.10 (1H, d, J=8.4 Hz), 7.43 (1H, s)
MS: 727.10 [M+H]+, 725.00 [M−H]−

Example 6

NMR: 1.47 (3H, d, J=6.4 Hz), 1.49 (3H, s), 1.51 (3H, s), 3.41 (1H, dd, J=8.0, 2.0 Hz), 3.50 (1H, dd, J=12.6, 1.4 Hz), 3.89 (1H, t, J=8.2 Hz), 4.22-4.33 (1H, m), 4.83 (1H, d, J=13.6 Hz), 5.75 (1H, dd, J=3.8, 1.0 Hz), 5.78 (1H, d, J=3.6 Hz), 6.93 (1H, d, J=8.4 Hz), 7.04 (1H, s), 7.09 (1H, d, J=8.4 Hz)
MS: 727.05 [M+H]+, 725.05 [M−H]−

Example 7

NMR: 1.47 (3H, d, J=6.4 Hz), 1.80-2.09 (2H, m), 2.26-2.79 (4H, m), 3.41 (1H, dd, J=8.0, 2.4 Hz), 3.52 (1H, dd, J=12.8, 1.2 Hz), 3.89 (1H, t, J=8.2 Hz), 4.23-4.32 (1H, m), 4.83 (1H, d, J=12.8 Hz), 5.78 (1H, d, J=3.6 Hz), 5.81 (1H, d, J=3.6 Hz), 6.94 (1H, d, J=8.4 Hz), 7.08 (1H, s), 7.10 (1H, d, J=8.4 Hz)
MS: 739.05 [M+H]+, 737.05 [M−H]−

Example 8

NMR: 1.22-1.43 (4H, m), 3.63 (1H, d, J=12.4 Hz), 3.68-3.80 (4H, m), 4.67 (1H, d, J=12.8 Hz), 5.69 (1H, d,

J=3.6 Hz), 5.74 (1H, d, J=3.2 Hz), 6.93 (1H, d, J=8.4 Hz), 7.10 (1H, d, J=7.2 Hz), 7.11 (1H, s)
MS: 711.00 [M+H]+, 708.95 [M−H]−

Example 9

NMR: 1.51 (3H, s), 1.52 (3H, s), 3.67 (1H, d, J=12.8 Hz), 3.70-3.79 (4H, m), 4.67 (1H, d, J=12.8 Hz), 5.69 (1H, d, J=4.0 Hz), 5.80 (1H, d, J=2.8 Hz), 6.93 (1H, d, J=8.4 Hz), 7.10 (1H, d, J=8.4 Hz)
MS: 747.00 [M+H]+, 744.90 [M−H]−

Example 10

NMR: 1.53 (3H, s), 1.55 (3H, s), 3.65 (1H, d, J=12.8 Hz), 3.70-3.80 (4H, m), 4.67 (1H, d, J=12.8 Hz), 5.70 (1H, d, J=3.6 Hz), 5.82 (1H, d, J=4.0 Hz), 6.93 (1H, d, J=8.4 Hz), 7.10 (1H, d, J=8.4 Hz)
MS: 714.00 [M+H]+, 711.95 [M−H]−

Example 11

NMR: 3.62 (1H, d, J=12.8 Hz), 3.69-3.80 (4H, m), 4.57 (2H, s), 4.68 (1H, d, J=12.8 Hz), 5.70 (1H, d, J=3.6 Hz), 5.77 (1H, d, J=3.6 Hz), 6.94 (1H, d, J=8.4 Hz), 7.10 (1H, s), 7.10 (1H, d, J=8.4 Hz)
MS: 685.00 [M+H]+, 682.95 [M−H]−

Example 12

NMR: 1.46 (3H, d, J=7.2 Hz), 3.63 (1H, d, J=12.8 Hz), 3.68-3.80 (4H, m), 4.63 (1H, d, J=6.8 Hz), 4.68 (1H, d, J=12.4 Hz), 5.71 (1H, d, J=3.6 Hz), 5.76 (1H, d, J=2.8 Hz), 6.94 (1H, d, J=8.4 Hz), 7.07 (1H, s), 7.10 (1H, d, J=8.4 Hz)
MS: 699.05 [M+H]+, 697.05 [M−H]−

Example 13

NMR: 1.47 (3H, d, J=7.2 Hz), 3.63 (1H, d, J=12.8 Hz), 3.69-3.80 (4H, m), 4.63-4.69 (1H, m), 4.68 (1H, d, J=13.2 Hz), 5.72 (1H, d, J=3.6 Hz), 5.78 (1H, d, J=2.8 Hz), 6.94 (1H, d, J=8.4 Hz), 7.08 (1H, s), 7.10 (1H, d, J=8.4 Hz)
MS: 699.05 [M+H]+, 696.95 [M−H]−

Example 14

NMR: 3.63 (1H, d, J=12.8 Hz), 3.69-3.80 (4H, m), 3.95 (1H, dd, J=12.6, 7.0 Hz), 4.02 (1H, dd, J=12.6, 3.0 Hz), 4.68 (1H, d, J=12.8 Hz), 4.71 (1H, dd, J=6.8, 3.2 Hz), 5.72 (1H, d, J=3.6 Hz), 5.80 (1H, d, J=3.6 Hz), 6.94 (1H, d, J=8.4 Hz), 7.10 (1H, s), 7.10 (1H, d, J=8.4 Hz)
MS: 715.00 [M+H]+, 712.85 [M−H]−

Example 15

NMR: 2.65 (1H, dd, J=16.0, 10.0 Hz), 2.78 (1H, dd, J=15.8, 3.8 Hz), 3.62 (1H, d, J=12.8 Hz), 3.68-3.81 (4H, m), 4.68 (1H, d, J=12.8 Hz), 4.92 (1H, dd, J=10.0, 3.6 Hz), 5.70 (1H, d, J=4.0 Hz), 5.73 (1H, d, J=2.8 Hz), 6.94 (1H, d, J=8.4 Hz), 7.09 (1H, s), 7.11 (1H, d, J=9.2 Hz)
MS: 743.00 [M+H]+, 741.00 [M−H]−

Example 16

NMR: 1.97-2.20 (4H, m), 3.62-3.93 (9H, m), 4.67 (1H, d, J=12.8 Hz), 5.73 (1H, d, J=4.0 Hz), 5.81 (1H, d, J=3.6 Hz), 6.94 (1H, d, J=8.4 Hz), 7.07 (1H, s), 7.10 (1H, d, J=8.4 Hz)
MS: 755.10 [M+H]+, 753.10 [M−H]−

Example 17

NMR: 1.65-1.80 (4H, m), 1.97-2.17 (4H, m), 3.65 (1H, d, J=12.4 Hz), 3.69-3.79 (4H, m), 4.68 (1H, d, J=12.4 Hz), 5.71 (1H, d, J=3.6 Hz), 5.75 (1H, d, J=3.6 Hz), 6.93 (1H, d, J=8.4 Hz), 7.03 (1H, s), 7.09 (1H, d, J=8.4 Hz)
MS: 739.00 [M+H]+, 736.90 [M−H]−

Example 18

NMR: 1.49 (3H, s), 1.52 (3H, s), 4.00 (1H, d, J=13.6 Hz), 4.57 (1H, d, J=12.8 Hz), 5.68 (1H, d, J=4.0 Hz), 5.83 (1H, d, J=3.6 Hz), 6.81 (1H, d, J=8.4 Hz), 7.03 (1H, s), 7.22 (1H, d, J=8.4 Hz), 8.15 (1H, s)
MS: 711.90 [M+H]+, 710.00 [M−H]−

Example 19

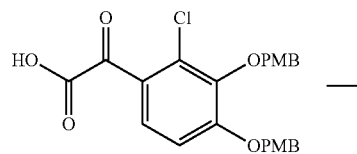

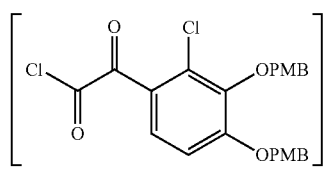

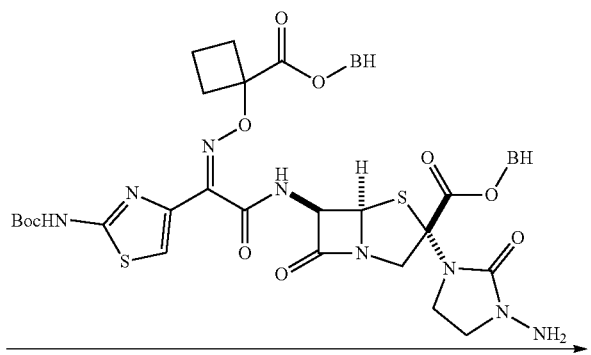

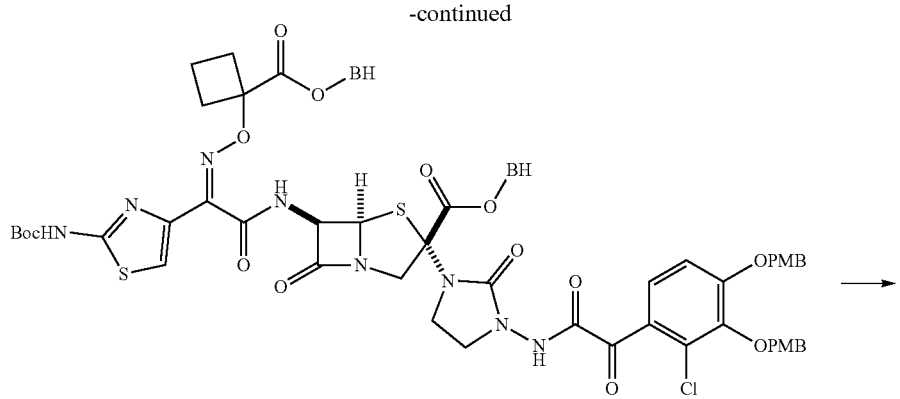

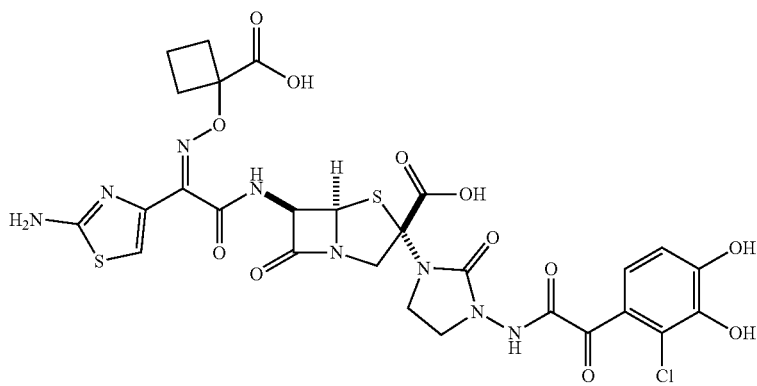

Example 19 (1)

Dichloromethane (1.0 mL) was added to 2-(2-chloro-3,4-bis((4-methoxybenzyl)oxy)phenyl)-2-oxoacetic acid (100 mg), and then oxalyl chloride (23 μL) and DMF (2 μL) were sequentially added thereto under ice cooling. The reaction mixture was stirred at room temperature for 1 hour, thereby obtaining 2-(2-chloro-3,4-bis((4-methoxybenzyl)oxy)phenyl)-2-oxoacetyl chloride in a dichloromethane solution.

Example 19 (2)

THF (2 mL) and water (2 mL) were added to benzhydryl (3R,5R,6R)-3-(3-amino-2-oxoimidazolidin-1-yl)-6-((Z)-2-((1-((benzhydryloxy)carbonyl)cyclobutoxy)imino)-2-(2-((tert-butoxycarbonyl)amino)thiazol-4-yl)acetamido)-7-oxo-4-thia-1-azabicyclo[3.2.0]heptane-3-carboxylate (216 mg), and the mixture was stirred under ice cooling. At the same temperature, sodium hydrogen carbonate (55 mg) was added to the reaction mixture, and then 2-(2-chloro-3,4-bis((4-methoxybenzyl)oxy)phenyl)-2-oxoacetyl chloride obtained in Example 19 (1) in a dichloromethane solution was sequentially added thereto. The reaction mixture was stirred at room temperature for 1 hour, ethyl acetate (10 mL) and water (10 mL) were then added thereto, and the organic layer was separated. The organic layer was washed with a 5% aqueous sodium chloride solution and then dehydrated and dried over anhydrous sodium sulfate. The solvent was distilled away under reduced pressure, thereby obtaining a target substance (340 mg) as a yellow oily substance.

Example 19 (3)

Dichloromethane (6.2 mL) was added to the compound (312 mg) obtained in Example 19 (2), and the mixture was cooled to −20° C. At the same temperature, anisole (1.4 mL) and aluminum chloride (438 mg) were sequentially added to the reaction mixture. The reaction mixture was stirred at the same temperature for 1 hour. The reaction mixture was added to a mixture of acetonitrile (20 mL), water (10 mL), and trisodium citrate dihydrate (1.45 g) under ice cooling. A saturated aqueous sodium hydrogen carbonate solution was added to the reaction mixture such that the pH was adjusted to 5.2, and the aqueous layer was separated. The aqueous layer was concentrated under reduced pressure, and the residue was purified by medium-pressure reverse-phase silica gel column chromatography [eluent; water:acetonitrile=100:0→85:15]. The aqueous solution containing a target substance was lyophilized, thereby obtaining (3R,5R,6R)-6-((Z)-2-(2-aminothiazol-4-yl)-2-((-1-carboxycyclobutoxy)imino)acetamido)-3-(3-(2-(2-chloro-3,4-dihydroxyphenyl)-2-oxoacetamido)-2-oxoimidazolidin-1-yl)-7-oxo-4-thia-1-azabicyclo[3.2.0]heptane-3-carboxylate (33.5 mg) as yellow solids.

NMR: 1.80-2.10 (2H, m), 2.25-2.60 (4H, m), 3.62 (1H, d, J=12.2 Hz), 3.67-3.82 (4H, mi), 4.69 (1H, d, J=12.2 Hz), 5.70-5.82 (2H, m), 6.87-6.97 (1H, m), 7.07 (1H, s), 7.41-7.48 (1H, m)

MS: 753.05 [M+H]$^+$, 751.05 [M−H]$^−$

The compounds shown in Table 18 were obtained in the same manner as in Example 19.

TABLE 18

| Example No | Structural Formula | Name |
|---|---|---|
| 20 | | (3R,5R,6R)-6-((Z)-2-(2-aminothiazol-4-yl)-2-(((2-carboxypropan-2-yl)oxy)imino)acetamido)-3-(3-(2-(2-chloro-3,4-dihydroxyphenyl)-2-oxoacetamido)-2-oxoimidazolidin-1-yl)-7-oxo-4-thia-1-azabicyclo[3.2.0]heptane-3-carboxylate |
| 21 | | (3R,5R,6R)-6-((Z)-2-(2-aminothiazol-4-yl)-2-((1-carboxycyclopropoxy)imino)acetamido)-3-(3-(2-(2-chloro-3,4-diydroxyphenyl)-2-oxoacetamido)-2-oxoimidazolidin-1-yl)-7-oxo-4-thia-1-azabicyclo[3.2.0]heptane-3-carboxylate |
| 22 | | (3R,5R,6R)-6-((Z)-2-(2-amino-5-chlorothiazol-4-yl)-2-(((2-carboxypropan-2-yl)oxy)imino)acetamido)-3-(3-(2-(2-chloro-3,4-dihydroxyphenyl)-2-oxoacetamido)-2-oxoimidazolidin-1-yl)-7-oxo-4-thia-1-azabicyclo[3.2.0]heptane-3-carboxylate |
| 23 | | (3R,5R,6R)-6-((Z)-2-(5-amino-1,2,4-thiadiazol-3-yl)-2-(((2-carboxypropan-2-yl)oxy)imino)acetamido)-3-(3-(2-(2-chloro-3,4-dihydroxyphenyl)-2-oxoacetamido)-2-oxoimidazolidin-1-yl)-7-oxo-4-thia-1-azabicyclo[3.2.0]heptane-3-carboxylate |

TABLE 18-continued

| Example No | Structural Formula | Name |
|---|---|---|
| 24 | | (3R,5R,6R)-6-((Z)-2-(2-aminothiazol-4-yl)-2-(((4-carboxytetrahydro-2H-pyran-4-yl)oxy)imino)acetamido)-3-(3-(2-(2-chloro-3,4-dihydroxyphenyl)-2-oxoacetamido)-2-oxoimidazolidin-1-yl)-7-oxo-4-thia-1-azabicyclo[3.2.0]heptane-3-carboxylate |
| 25 | | (3R,5R,6R)-6-((Z)-2-(2-aminothiazol-4-yl)-2-(((2-carboxypropan-2-yl)oxy)imino)acetamido)-3-(3-(3-(2-(2-chloro-4-dihydroxyphenyl)-2-oxoacetamido)-2-oxoimidazolidin-1-carboxamido)-2-oxoimidazolidin-1-yl)-7-oxo-4-thia-1-azabicyclo[3.2.0]heptane-3-carboxylate |
| 26 | | (3R,5R,6R)-6-((Z)-2-(2-aminothiazol-4-yl)-2-(((2-carboxypropan-2-yl)oxy)imino)acetamido)-3-(4-(2-(2-chloro-3,4-dihydroxyphenyl)-2-oxoacetamido)-5-oxo-4,5-dihydro-1H-1,2,4-triazol-1-yl)-7-oxo-4-thia-1-azabicyclo[3.2.0]heptane-3-carboxylate |

The measured values of NMR and MS of the compounds in the table are as follows.

Example 20

NMR: 1.45-1.53 (6H, m), 3.62 (1H, d, J=12.8 Hz), 3.66-3.82 (4H, m), 4.68 (1H, d, J=12.8 Hz), 5.67-5.78 (2H, m), 6.89-6.98 (1H, m), 7.03 (1H, s), 7.41-7.48 (1H, m)
MS: 741.00 [M+H]+, 739.00 [M−H]−

Example 21

NMR: 1.22-1.43 (4H, m), 3.61 (1H, dd, J=12.6, 1.0 Hz), 3.68-3.81 (4H, m), 4.29 (1H, d, J=12.4 Hz), 5.69 (1H, d, J=3.6 Hz), 5.73 (1H, d, J=4.4 Hz), 6.87[6.91](1H, d, J=8.6 Hz), 7.10 [7.03](1H, s), 7.33 [7.44](1H, d, J=8.8 Hz)
MS: 739.00 [M+H]+, 736.90 [M−H]−

Example 22

NMR: 1.46-1.55 (6H, m), 3.38-3.49 (1H, m), 3.55-3.81 (4H, m), 4.67 (1H, d, J=12.4 Hz), 5.64-5.83 (2H, m), 6.88-6.97 (1H, m), 7.41-7.48 (1H, m)
MS: 774.95 [M+H]+, 773.00 [M−H]−

Example 23

NMR: 1.52 [1.53](3H, s), 1.53 [1.55](3H, s), 3.63 (1H, d, J=13.2 Hz), 3.68-3.81 (4H, m), 4.31 [4.67](1H, d, J=12.6 Hz), 5.68 [5.70](1H, d, J=3.8 Hz), 5.77 [5.81](1H, d, J=3.4 Hz), 6.89 [6.93](1H, d, J=8.8 Hz), 7.44 (1H, d, J=8.4 Hz)
MS: 742.00 [M+H]+, 740.00 [M−H]−

Example 24

NMR: 1.96-2.19 (4H, m), 3.35-3.50 (1H, m), 3.57-3.92 (8H, m), 4.27 [4.67](1H, d, J=12.6 Hz), 5.72 (1H, d, J=3.6 Hz), 5.76 [5.81](1H, d, J=3.4 Hz), 6.91 [6.95](1H, d, J=8.8 Hz), 7.06 (1H, s), 7.44 [7.46](1H, d, J=8.4 Hz)
MS: 783.05 [M+H]+, 780.90 [M−H]−

Example 25

NMR: 1.49 (3H, s), 1.51 (3H, s), 3.58-3.76 (2H, m), 3.80-3.88 (2H, m), 3.94-4.02 (5H, m), 4.66 (1H, d, J=12.4

Hz), 5.69 (1H, d, J=3.6 Hz), 5.75 (1H, d, J=3.6 Hz), 6.73 (1H, d, J=8.8 Hz), 7.03 (1H, s), 7.45 (1H, d, J=8.8 Hz)

MS: 868.00 [M+H]⁺, 865.95 [M−H]⁻

Example 26

NMR: 1.49 (3H, s), 1.52 (3H, s), 3.85 (1H, d, J=12.8 Hz), 4.56 (1H, d, J=12.4 Hz), 5.66 (1H, d, J=4.0 Hz), 5.82 (1H, d, J=3.6 Hz), 6.97 (1H, d, J=8.8 Hz), 7.03 (1H, s), 7.49 (1H, d, J=8.4 Hz), 8.09 (1H, s)

MS: 739.95 [M+H]⁺, 737.90 [M−H]⁻

Example 27 perature overnight. Ethyl acetate (10 mL) and water (10 mL) were added to the reaction mixture, and the organic layer was separated. The organic layer was washed with a saturated aqueous sodium chloride solution and dehydrated and dried over anhydrous sodium sulfate. The solvent was distilled away under reduced pressure, and the residue was purified by silica gel column chromatography [eluent; ethyl acetate:hexane=40:60→100:0], thereby obtaining a target substance (188 mg) as light yellow solids.

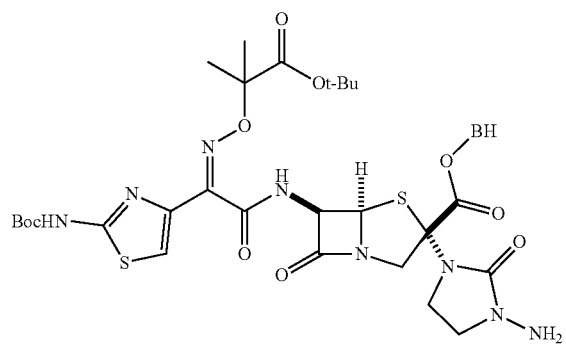

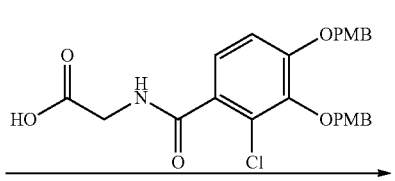

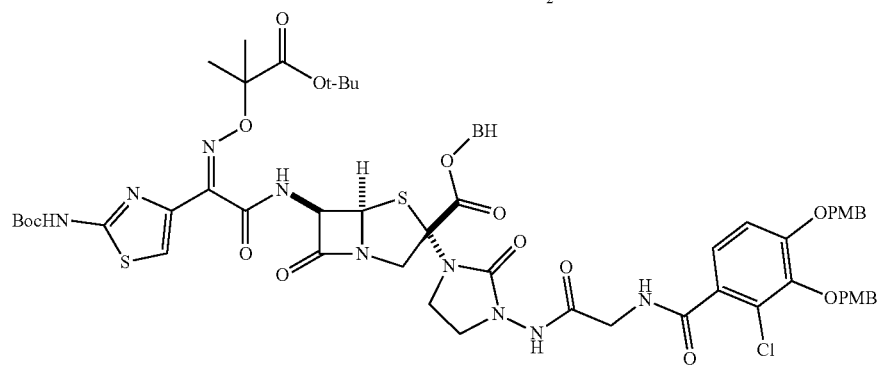

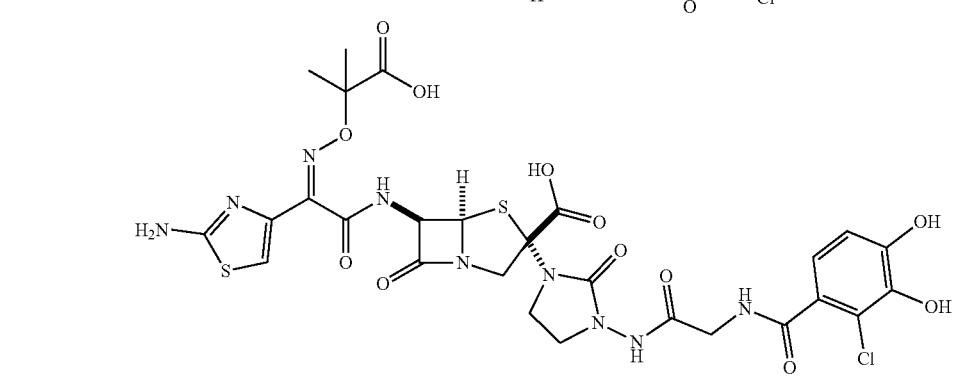

Example 27 (1)

Example 27 (2)

(2-Chloro-3,4-bis((4-methoxybenzyl)oxy)benzoyl)glycine (112 mg), HoBt (34 mg), EDC (49 mg), DMF (2 mL), and NMM (31 μL) were sequentially added to benzhydryl (3R,5R,6R)-3-(3-amino-2-oxoimidazolidin-1-yl)-6-((Z)-2-(((1-(tert-butoxy)-2-methyl-1-oxopropan-2-yl)oxy)imino)-2-(2-((tert-butoxycarbonyl)amino)thiazol-4-yl)acetamido)-7-oxo-4-thia-1-azabicyclo[3.2.0]heptane-3-carboxylate (200 mg). The reaction mixture was stirred at room tem- Dichloromethane (2.8 mL) was added to the compound (188 mg) obtained in Example 27 (1), and the mixture was stirred at −20° C. At the same temperature, anisole (0.92 mL) and aluminum chloride (282 mg) were sequentially added to the reaction mixture. The reaction mixture was stirred at a temperature equal to or lower than −20° C. for 30 minutes. The reaction mixture was added to a mixture of acetonitrile (5 mL), water (5 mL), and trisodium citrate dihydrate (933 mg) under ice cooling. A saturated aqueous sodium hydrogen carbonate solution was added to the reaction mixture such that the pH was adjusted to 5.1, and the aqueous layer was separated. The aqueous layer was concentrated under reduced pressure, and the residue was purified by medium-pressure reverse-phase silica gel column chromatography [eluent; water:acetonitrile=100:0→85:15]. The aqueous solution containing a target substance was lyophilized, thereby obtaining (3R,5R,6R)-6-((Z)-2-(2-aminothiazol-4-yl)-2-(((2-carboxypropan-2-yl)oxy)imino)acetamido)-3-(3-(2-(2-chloro-3,4-dihydroxybenzamide)acetamido)-2-oxoimidazolidin-1-yl)-7-oxo-4-thia-1-azabicyclo[3.2.0]heptane-3-carboxylate (42 mg) as light yellow solids.

NMR: 1.48 (3H, s), 1.50 (3H, s), 3.50-3.87 (5H, m), 4.17 (2H, s), 4.65 (1H, d, J=12.8 Hz), 5.69 (1H, d, J=4.0 Hz), 5.75 (1H, d, J=3.6 Hz), 6.91 (1H, d, J=8.4 Hz), 7.03 (1H, s), 7.07 (1H, d, J=8.4 Hz)

MS: 777.00 [M+H]$^+$, 768.00 [M−H]$^−$

The compounds shown in Table 19 were obtained in the same manner as in Example 27.

TABLE 19

| Example No | Structural Formula | Name |
|---|---|---|
| 28 | | (3R,5R,6R)-6-((Z)-2-(2-aminothiazol-4-yl)-2-(((2-carboxypropan-2-yl)oxy)imino)acetamido)-3-(3-(3-(2-chloro-3,4-dihydroxybenzamido)propanamido)-2-oxoimidazolidin-1-yl)-7-oxo-4-thia-1-azabicyclo[3.2.0]heptane-3-carboxylate |
| 29 | | (3R,5R,6R)-6-((Z)-2-(2-aminothiazol-4-yl)-2-(((2-carboxypropan-2-yl)oxy)imino)acetamido)-3-(3-(2-(2-(2-chloro-3,4-dihydroxyphenyl)-2-oxoacetamido)acetamido)-2-oxoimidazolidin-1-yl)-7-oxo-4-thia-1-azabicyclo[3.2.0]heptane-3-carboxylate |
| 30 | | (3R,5R,6R)-6-((Z)-2-(2-aminothiazol-4-yl)-2-(((2-carboxypropan-2-yl)oxy)imino)acetamido)-3-(3-(3-(2-(2-chloro-3,4-dihydroxyphenyl)-2-oxoacetamido)propanamido)-2-oxoimidazolidin-1-yl)-7-oxo-4-thia-1-azabicyclo[3.2.0]heptane-3-carboxylate |

TABLE 19-continued

| Example No | Structural Formula | Name |
|---|---|---|
| 31 | | (3R,5R,6R)-6-((Z)-2-(2-aminothiazol-4-yl)-2-((1-carboxycyclopropoxy)imino)acetamido)-3-(3-(3-(2-(2-chloro-3,4-dihydroxyphenyl)-2-oxoacetamido)propanamido)-2-oxoimidazolidin-1-yl)-7-oxo-4-thia-1-azabicyclo[3.2.0]heptane-3-carboxylate |
| 32 | | (3R,5R,6R)-6-((Z)-2-(2-aminothiazol-4-yl)-2-(((4-carboxytetrahydro-2H-pyran-4-yl)oxy)imino)acetamido)-3-(3-(3-(2-(2-chloro-3,4-dihydroxyphenyl)-2-oxoacetamido)propanamido)-2-oxoimidazolidin-1-yl)-7-oxo-4-thia-1-azabicyclo[3.2.0]heptane-3-carboxylate |
| 33 | | (3R,5R,6R)-6-((Z)-2-(2-aminothiazol-4-yl)-2-(((2-carboxypropan-2-yl)oxy)imino)acetamido)-3-(3-(1-(2-chloro-3,4-dihydroxybenzoyl)azetidine)-3-carboxamido)-2-oxoimidazolidin-1-yl)-7-oxo-4-thia-1-azabicyclo[3.2.0]heptane-3-carboxylate |
| 34 | | (3R,5R,6R)-6-((Z)-2-(2-aminothiazol-4-yl)-2-(((2-carboxypropan-2-yl)oxy)imino)acetamido)-3-(3-(1-(2-(2-chloro-3,4-dihydroxyphenyl)-2-oxoacetyl)azetidine-3-carboxamido)-2-oxoimidazolidin-1-yl)-7-oxo-4-thia-1-azabicyclo[3.2.0]heptane-3-carboxylate |

The measured values of NMR and MS of the compounds in the table are as follows.

Example 28

NMR: 1.48 (3H, s), 1.50 (3H, s), 2.65 (2H, t, J=6.2 Hz), 3.54-3.72 (7H, m), 4.63 (1H, d, J=12.8 Hz), 5.66 (1H, d, J=3.6 Hz), 5.74 (1H, d, J=3.2 Hz), 6.89 (1H, d, J=8.4 Hz), 6.95 (1H, d, J=8.4 Hz), 7.03 (1H, s)
MS: 784.05 [M+H]$^+$, 781.95 [M−H]$^-$.

Example 29

NMR: 1.49 (3H, s), 1.51 (3H, s), 3.50-3.77 (5H, m), 4.19 (2H, s), 4.66 (1H, d, J=12.8 Hz), 5.69 (1H, d, J=3.6 Hz), 5.75 (1H, d, J=3.2 Hz), 6.93 (1H, d, J=8.4 Hz), 7.03 (1H, s), 7.41 (1H, d, J=8.4 Hz)
MS: 798.00 [M+H]$^+$, 796.10 [M−H]$^-$

Example 30

NMR: 1.48 (3H, s), 1.50 (3H, s), 2.66 (2H, t, J=6.2 Hz), 3.50-3.74 (7H, m), 4.61 (1H, d, J=12.4 Hz), 5.64 (1H, d, J=3.6 Hz), 5.72 (1H, d, J=3.2 Hz), 6.94 (1H, d, J=8.8 Hz), 7.03 (1H, s), 7.34 (1H, d, J=8.8 Hz)
MS: 812.05 [M+H]$^+$, 810.15 [M−H]$^-$

Example 31

NMR: 1.21-1.43 (4H, m), 2.66 (2H, t, J=6.0 Hz), 3.46-3.74 (7H, m), 4.60 (1H, d, J=12.8 Hz), 5.62 (1H, d, J=4.0 Hz), 5.70 (1H, d, J=4.0 Hz), 6.92 (1H, d, J=8.4 Hz), 7.10 (1H, s), 7.34 (1H, d, J=8.8 Hz)
MS: 810.05 [M+H]$^+$, 807.90 [M−H]$^-$

Example 32

NMR: 1.95-2.18 (4H, m), 2.66 (2H, t, J=6.2 Hz), 3.49-3.76 (9H, m), 3.77-3.90 (2H, m), 4.59 (1H, d, J=12.4 Hz), 5.65 (1H, d, J=3.6 Hz), 5.77 (1H, d, J=3.2 Hz), 6.94 (1H, d, J=8.8 Hz), 7.06 (1H, s), 7.34 (1H, d, J=8.4 Hz)
MS: 854.10 [M+H]$^+$, 851.95 [M−H]$^-$

Example 33

NMR: 1.48 (3H, s), 1.50 (3H, s), 3.54-3.75 (6H, m), 4.13-4.34 (3H, m), 4.36-4.46 (1H, m), 4.65 (1H, dd, J=12.4, 1.2 Hz), 5.69 (1H, d, J=3.6 Hz), 5.75 (1H, d, J=3.6 Hz), 6.87-6.97 (2H, m), 7.03 (1H, s)
MS: 796.05 [M+H]$^+$, 794.05 [M−H]$^-$

Example 34

NMR: 1.48 (3H, s), 1.50 (3H, s), 3.55-3.75 (6H, m), 4.30-4.53 (4H, m), 4.65 (1H, d, J=12.4 Hz), 5.69 (1H, d, J=3.6 Hz), 5.75 (1H, d, J=3.6 Hz), 6.88 (1H, d, J=8.8 Hz), 7.03 (1H, s), 7.40 (1H, d, J=8.8 Hz)
MS: 824.05 [M+H]$^+$, 822.10 [M−H]$^-$

Example 35

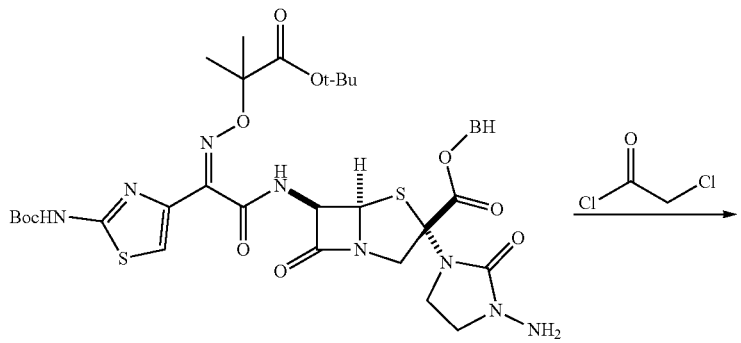

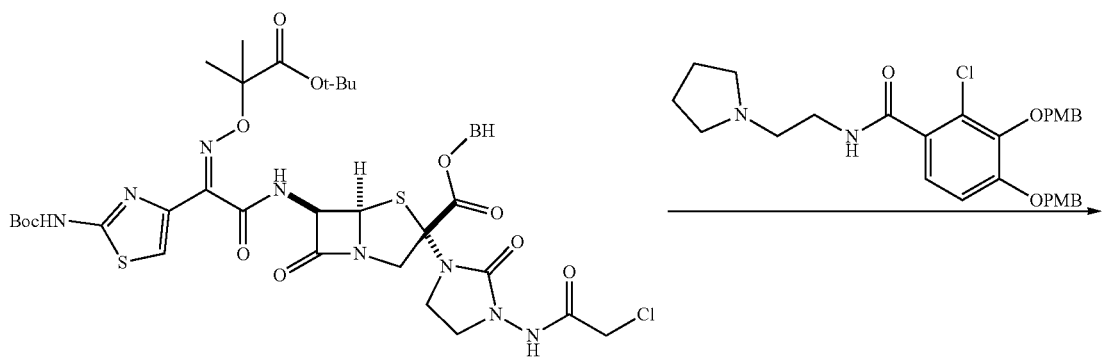

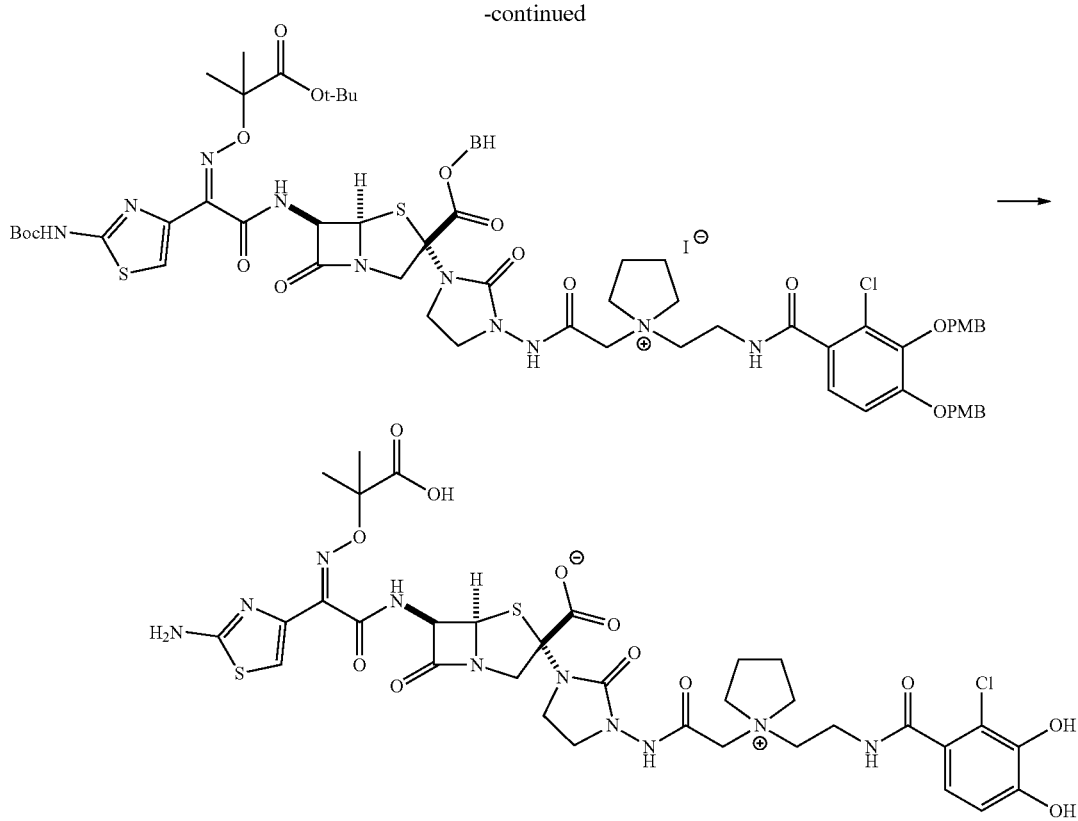

Example 35 (1)

Dichloromethane (3.9 mL) and pyridine (38 μL) were added to benzhydryl (3R,5R,6R)-3-(3-amino-2-oxoimidazo-lidin-1-yl)-6-((Z)-2-(((1-(tert-butoxy)-2-methyl-1-oxopropan-2-yl)oxy)imino)-2-(2-((tert-butoxycarbonyl)amino)thiazol-4-yl)acetamido)-7-oxo-4-thia-1-azabicyclo[3.2.0]heptane-3-carboxylate (390 mg), and the mixture was stirred under ice cooling. At the same temperature, chloroacetyl chloride (38 L1) was added to the reaction mixture, and the reaction mixture was stirred at room temperature for 2 hours. Water (10 mL) and 1 mol/L hydrochloric acid (2 mL) were added to the reaction mixture, and the organic layer was separated. The organic layer was dehydrated and dried over anhydrous sodium sulfate, and the solvent was distilled away under reduced pressure, thereby obtaining a target substance (424 mg) as a yellow oily substance.

Example 35 (2)

DMF (4.3 mL), 2-chloro-3,4-bis((4-methoxybenzyl)oxy)-N-(2-(pyrrolidin-1-yl)ethyl)benzamide (473 mg), and sodium iodide (68 mg) were sequentially added to the compound (424 mg) obtained in Example 35 (1), and the mixture was stirred at 40° C. for 11 hours. Ethyl acetate (15 mL) and water (15 mL) were added to the reaction mixture. Hydrochloric acid (1 mol/L) was added to the reaction mixture such that the pH was adjusted to 2.5. The organic layer was separated, washed twice with a 5% aqueous sodium chloride solution, and then dehydrated and dried over anhydrous sodium sulfate. The solvent was distilled away under reduced pressure, thereby obtaining a target substance (702 mg) as a brown oily substance.

Example 35 (3)

Dichloromethane (15.0 mL) was added to the compound (702 mg) obtained in Example 35 (2), and the mixture was stirred at a temperature equal to or lower than −20° C. At the same temperature, anisole (3.0 mL) and aluminum chloride (1.50 g) were sequentially added to the reaction mixture. The reaction mixture was stirred at a temperature equal to or lower than −20° C. for 1 hour. At a temperature equal to or lower than −20° C., aluminum chloride (421 mg) was added to the reaction mixture, and the reaction mixture was stirred at a temperature equal to or lower than −20° C. for 1 hour. The reaction mixture was added to a mixture of acetonitrile (25 mL), water (15 mL), and trisodium citrate dihydrate (6.37 g) under ice cooling. A saturated aqueous sodium hydrogen carbonate solution was added to the reaction mixture such that the pH was adjusted to 5.1, and the aqueous layer was separated. The aqueous layer was concentrated under reduced pressure, and the residue was purified by medium-pressure reverse-phase silica gel column chromatography [eluent; water:acetonitrile=100:0→85:15]. The aqueous solution containing a target substance was lyophilized, thereby obtaining (3R,5R,6R)-6-((Z)-2-(2-aminothiazol-4-yl)-2-(((2-carboxypropan-2-yl)oxy)imino)acetamido)-3-(3-(2-(1-(2-(2-chloro-3,4-dihydroxybenzamido)ethyl)pyrrolidin-1-ium-1-yl)acetamido)-2-oxoimidazolidin-1-yl)-7-oxo-4-thia-1-azabicyclo[3.2.0]heptane-3-carboxylate (33.5 mg) as white solids.

NMR: 1.48 (3H, s), 1.50 (3H, s), 2.17-2.34 (4H, m), 3.42-3.58 (4H, m), 3.61-3.71 (2H, m), 3.73-3.95 (9H, m), 4.59 (1H, d, J=12.8 Hz), 5.62 (1H, d, J=4.0 Hz), 5.72 (1H, d, J=4.0 Hz), 6.87-6.94 (1H, m), 6.96-7.04 (2H, m)

MS: 867.10 [M+H]$^+$, 865.05 [M−H]$^−$

Example 36

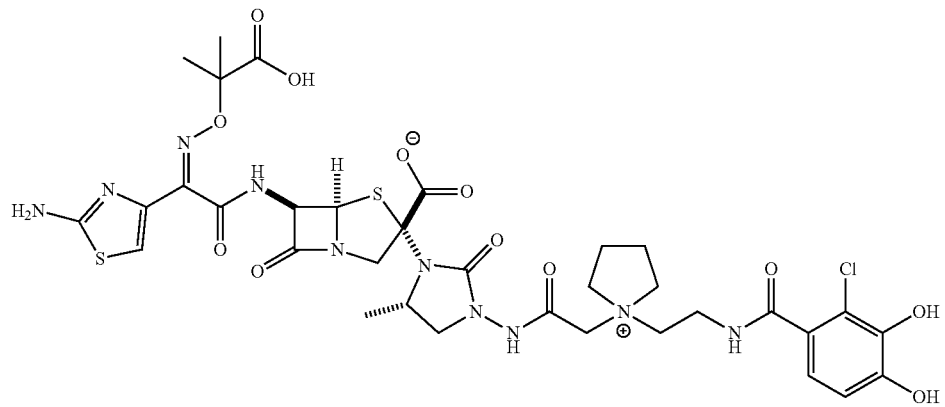

By using the compound obtained in Reference Example 29, (3R,5R,6R)-6-((Z)-2-(2-aminothiazol-4-yl)-2-(((2-carboxypropan-2-yl)oxy)imino)acetamido)-3-(S)-3-(2-(1-(2-(2-chloro-3,4-dihydroxybenzamido)ethyl)pyrrolidin-1-ium-1-yl)acetamido)-5-methyl-2-oxoimidazolidin-1-yl)-7-oxo-4-thia-1-azabicyclo[3.2.0]heptane-3-carboxylate was obtained in the same manner as in Example 35.

NMR: 1.26 (3H, d, J=4.8 Hz), 1.47 (3H, s), 1.50 (3H, s), 2.20-2.33 (4H, m), 3.06 (1H, dd, J=4.0, 2.0 Hz), 3.26 (1H, d, J=12.8 Hz), 3.58-3.67 (1H, m), 3.79-3.96 (9H, m), 4.17-4.27 (1H, m), 4.73 (1H, d, J=12.8 Hz), 5.55 (1H, d, J=3.6 Hz), 5.67 (1H, d, J=3.6 Hz), 6.91 (1H, d, J=8.4 Hz), 7.00 (1H, d, J=8.4 Hz), 7.01 (1H, s)

MS: 881.15 [M+H]$^+$, 879.15 [M−H]$^−$

Example 37

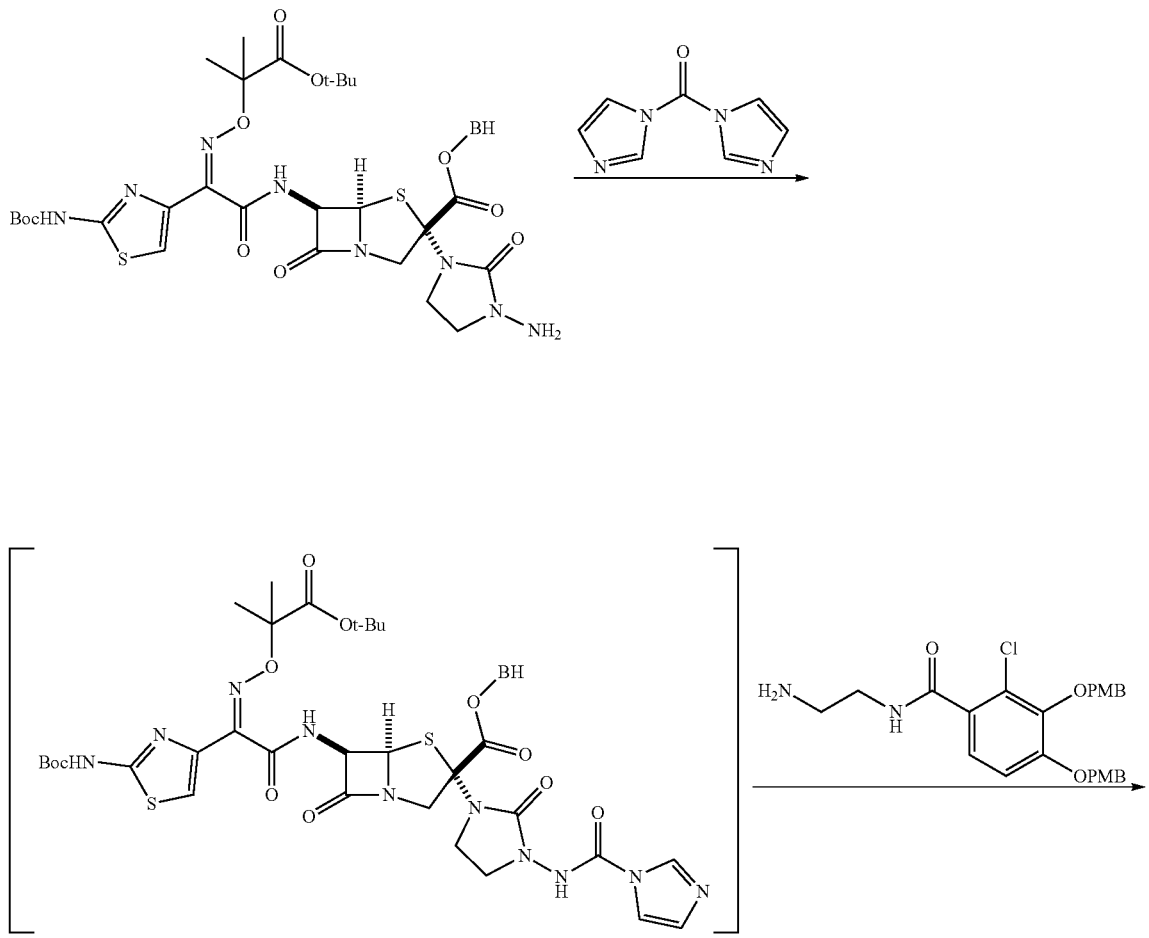

-continued

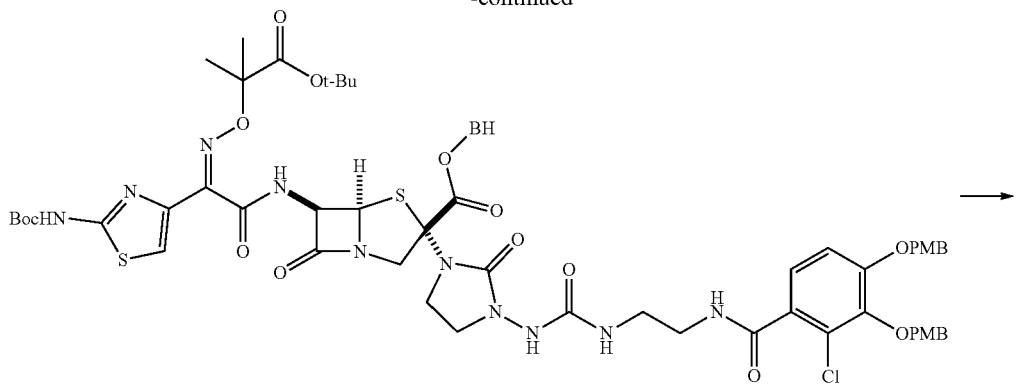

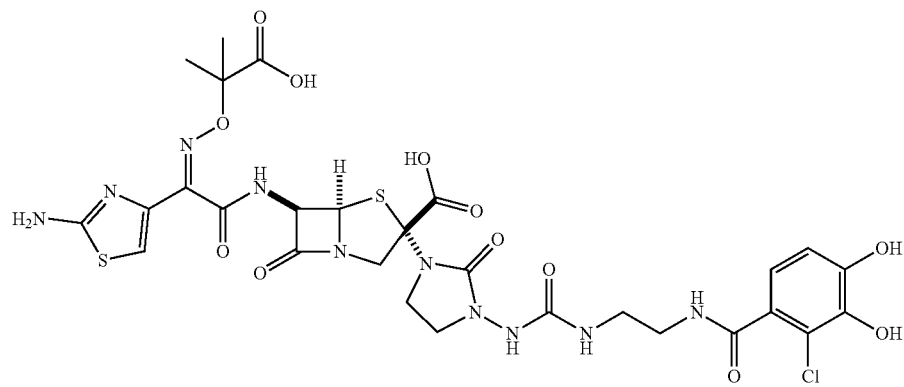

Example 37 (1)

Dichloromethane (7.0 mL) and 1,1'-carbonylimidazole (131 mg) were added to benzhydryl (3R,5R,6R)-3-(3-amino-2-oxoimidazolidin-1-yl)-6-(((Z)-2-(((1-(tert-butoxy)-2-methyl-1-oxopropan-2-yl)oxy)imino)-2-(2-((tert-butoxycarbonyl)amino)thiazol-4-yl)acetamido)-7-oxo-4-thia-1-azabicyclo[3.2.0]heptane-3-carboxylate (350 mg), and the mixture was stirred at room temperature for 4 hours. At the same temperature, N-(2-aminoethyl)-2-chloro-3,4-bis((4-methoxybenzyl)oxy)benzamide (381 mg)was added to the reaction mixture, and the reaction mixture was stirred at room temperature for 1 hour. The reaction mixture was added to a mixture of dichloromethane (35 mL) and water (35 mL) under ice cooling. Hydrochloric acid (1 mol/L) was added to the reaction mixture such that the pH was adjusted to 2.5. The organic layer was separated and sequentially washed with water and a saturated aqueous sodium chloride solution. The organic layer was dehydrated and dried over anhydrous sodium sulfate, and the solvent was distilled away under reduced pressure. The residue was purified by silica gel column chromatography [eluent; chloroform: 2-propanol=0: 100→93:7], thereby obtaining a target substance (310 mg) as yellow solids.

Example 37 (2)

Dichloromethane (6.2 mL) was added to the compound (310 mg) obtained in Example 37 (1), and the mixture was stirred at a temperature equal to or lower than −20° C. At the same temperature, anisole (1.49 mL) and aluminum chloride (455 mg) were sequentially added to the reaction mixture. The reaction mixture was stirred at a temperature equal to or lower than −20° C. for 30 minutes. The reaction mixture was added to a mixture of acetonitrile (20 mL), water (20 mL), and trisodium citrate dihydrate (1.51 g) under ice cooling. A saturated aqueous sodium hydrogen carbonate solution was added to the reaction mixture such that the pH was adjusted to 5.1, and the aqueous layer was separated. The aqueous layer was concentrated under reduced pressure, and the residue was purified by medium-pressure reverse-phase silica gel column chromatography [eluent; water:acetonitrile=100:0→84:16]. The aqueous solution containing a target substance was lyophilized, thereby obtaining (3R,5R,6R)-6-(((Z)-2-(2-aminothiazol-4-yl)-2-(((2-carboxypropan-2-yl)oxy)imino)acetamido)-3-(3-(3-(2-(2-chloro-3,4-dihydroxybenzamide)ethyl)ureido)-2-oxoimidazolidin-1-yl)-7-oxo-4-thia-1-azabicyclo[3.2.0]heptane-3-carboxylate (50 mg) as white solids.

NMR: 1.48 (3H, s), 1.50 (3H, s), 3.39-3.45 (2H, m), 3.48-3.56 (5H, m), 3.60-3.71 (2H, m), 4.59 (1H, d, J=12.4 Hz), 5.63 (1H, d, J=3.6 Hz), 5.72 (1H, d, J=3.2 Hz), 6.90 (1H, d, J=8.4 Hz), 6.97 (1H, d, J=8.4 Hz), 7.03 (1H, s)

MS: 799.05 [M+H]$^+$, 797.15 [M−H]$^-$

The compounds shown in Table 20 were obtained in the same manner as in Example 37.

TABLE 20

| Example No | Structural Formula | Name |
|---|---|---|
| 38 | | (3R,5R,6R)-6-((Z)-2-(2-aminothiazol-4-yl)-2-(((2-carboxypropan-2-yl)oxy)imino)acetamido)-3-(3-(2-(2-chloro-3,4-dihydroxybenzoyl)hydrazine-1-carboxamido)-2-oxoimidazolidin-1-yl)-7-oxo-4-thia-1-azabicyclo[3.2.0]heptane-3-carboxylate |
| 39 | | (3R,5R,6R)-6-((Z)-2-(2-aminothiazol-4-yl)-2-(((2-carboxypropan-2-yl)oxy)imino)acetamido)-3-(3-(3-(2-(2-chloro-3,4-dihydroxybenzamido)ethoxy)ureido)-2-oxoimidazolidin-1-yl)-7-oxo-4-thia-1-azabicyclo[3.2.0]heptane-3-carboxylate |
| 40 | | (3R,5R,6R)-6-((Z)-2-(2-aminothiazol-4-yl)-2-(((2-carboxypropan-2-yl)oxy)imino)acetamido)-3-(3-(2-((2-(2-chloro-3,4-dihydroxybenzamido)ethyl)carbamoyl)hydrazine-1-carboxamido)-2-oxoimidazolidin-1-yl)-7-oxo-4-thia-1-azabicyclo[3.2.0]heptane-3-carboxylate |
| 41 | | (3R,5R,6R)-6-((Z)-2-(2-aminothiazol-4-yl)-2-(((2-carboxypropan-2-yl)oxy)imino)acetamido)-3-(3-(3-((1,5-dihydroxy-4-oxo-1,4-dihydropyridin-2-yl)methyl)ureido)-2-oxoimidazolidin-1-yl)-7-oxo-4-thia-1-azabicyclo[3.2.0]heptane-3-carboxylate |

| Example No | Structural Formula | Name |
|---|---|---|
| 42 | | (3R,5R,6R)-6-((Z)-2-(2-aminothiazol-4-yl)-2-(((2-carboxypropan-2-yl)oxy)imino)acetamido)-3-(3-(4-(2-chloro-3,4-dihydroxybenzoyl)piperazine-1-carboxamido)-2-oxoimidazolidin-1-yl)-7-oxo-4-thia-1-azabicyclo[3.2.0]heptane-3-carboxylate |
| 43 | | (3R,5R,6R)-6-((Z)-2-(2-aminothiazol-4-yl)-2-(((2-carboxypropan-2-yl)oxy)imino)acetamido)-3-(3-(4-(2-(2-chloro-3,4-dihydroxyphenyl)-2-oxoacetyl)piperazine-1-carboxamido)-2-oxoimidazolidin-1-yl)-7-oxo-4-thia-1-azabicyclo[3.2.0]heptane-3-carboxylate |

The measured values of NMR and MS of the compounds in the table are as follows.

Example 38

NMR: 1.49 (3H, s), 1.51 (3H, s), 3.52-3.80 (5H, m), 5.70 (1H, d, J=3.6 Hz), 5.75 (1H, d, J=3.6 Hz), 6.93 (1H, d, J=8.4 Hz), 7.03 (1H, s), 7.11 (1H, d, J=8.4 Hz)
MS: 771.00 [M+H]$^+$, 769.00 [M−H]$^-$

Example 39

NMR: 1.48 (3H, s), 1.50 (3H, s), 3.43-3.73 (7H, m), 4.06-4.13 (2H, m), 4.69 (1H, d, J=12.8 Hz), 5.61 (1H, d, J=3.6 Hz), 5.74 (1H, d, J=3.6 Hz), 6.91 (1H, d, J=8.4 Hz), 6.99 (1H, d, J=8.4 Hz), 7.02 (1H, s)
MS: 815.10 [M+H]$^+$, 812.95 [M−H]$^-$

Example 40

NMR: 1.48 (3H, s), 1.50 (3H, s), 3.36-3.69 (9H, m), 4.60 (1H, d, J=12.0 Hz), 5.62 (1H, d, J=3.6 Hz), 5.73 (1H, d, J=3.6 Hz), 6.87-7.00 (2H, m), 7.02 (1H, s)
MS: 857.10 [M+H]$^+$, 854.90 [M−H]$^-$

Example 41

NMR: 1.47 (3H, s), 1.50 (3H, s), 3.50-3.80 (7H, m), 4.40-4.45 (1H, m), 5.70 (1H, d, J=4.0 Hz), 5.75 (1H, d, J=4.0 Hz), 6.72 (1H, s), 7.03 (1H, s), 7.44 (1H, s)
MS: 725.10 [M+H]$^+$, 723.05 [M−H]$^-$

Example 42

NMR: 1.48 (3H, s), 1.50 (3H, s), 3.40-3.50 (4H, m), 3.54-3.70 (6H, m), 3.66 (1H, d, J=7.2 Hz), 3.72-3.82 (1H, m), 3.82-3.90 (1H, m), 4.63 (1H, d, J=12.8 Hz), 5.68 (1H, d, J=3.6 Hz), 5.75 (1H, dd, J=4.0, 1.0 Hz), 6.82 (1H, d, J=8.4 Hz), 6.95 (1H, d, J=8.0 Hz), 7.02 (1H, s)
MS: 825.30 [M+H]$^+$, 823.20 [M−H]$^-$

Example 43

NMR: 1.48 (3H, s), 1.50 (3H, s), 3.58-3.70 (11H, m), 3.73-3.80 (2H, m), 4.63 (1H, d, J=12.4 Hz), 5.68 (1H, d, J=3.6 Hz), 5.74 (1H, d, J=3.6 Hz), 6.90 (1H, d, J=8.8 Hz), 7.03 (1H, s), 7.51 (1H, d, J=8.8 Hz)
MS: 853.05 [M+H]$^+$, 851.15 [M−H]$^-$

Example 44

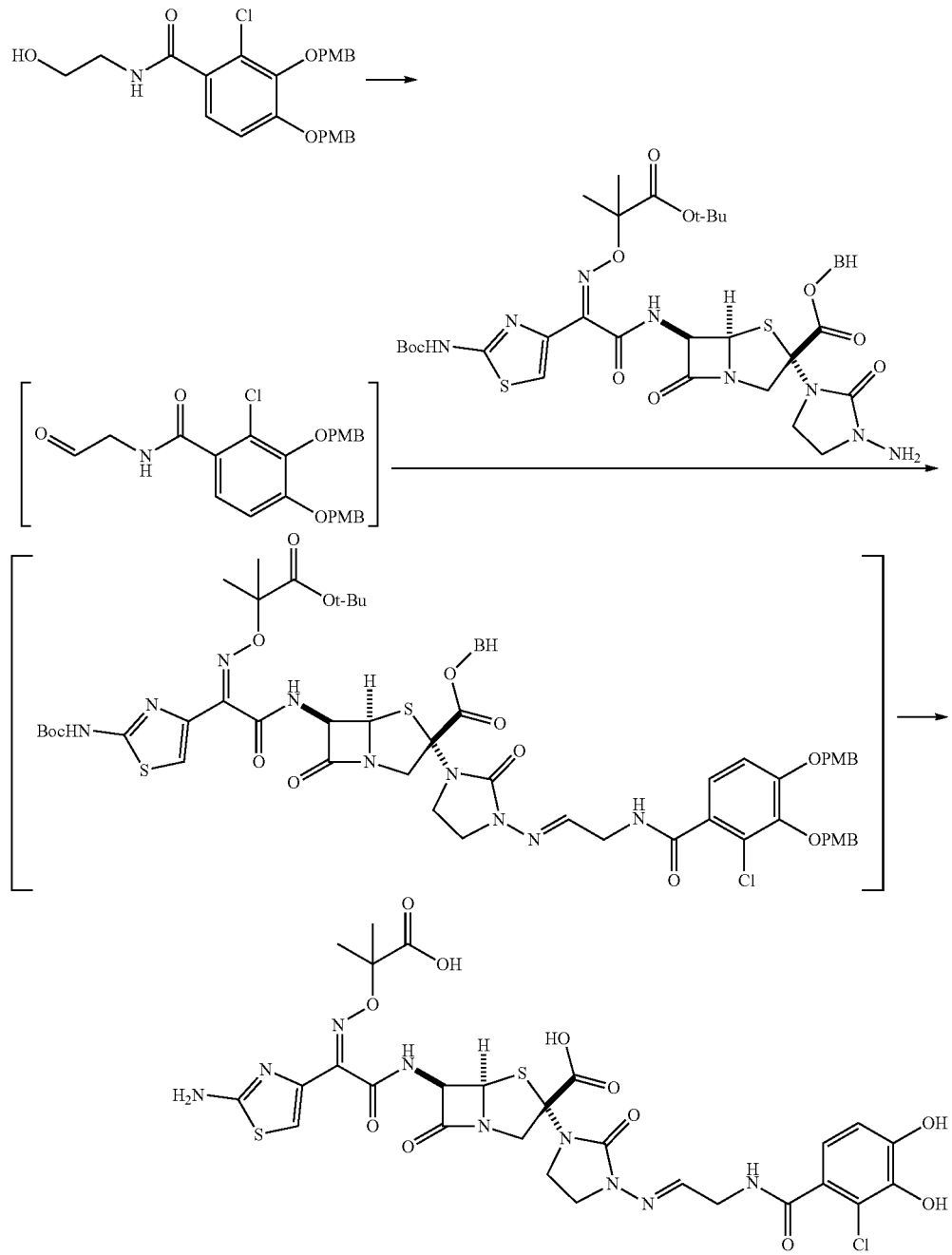

Dichloromethane (4.3 mL) was added to 2-chloro-N-(2-hydroxyethyl)-3,4-bis ((4-methoxybenzyl)oxy)benzamide (430 mg), and the mixture was stirred under ice cooling. Dess-Martin periodinane (773 mg) was added to the reaction mixture, and the reaction mixture was stirred at room temperature for 3 hours. Dichloromethane (10 mL), water (5 mL), and a 1 mol/L aqueous sodium thiosulfate solution (5 mL) were sequentially added to the reaction mixture, and the organic layer was separated. The organic layer was washed with a saturated aqueous sodium chloride solution and dehydrated and dried over anhydrous sodium sulfate. The solvent was distilled away under reduced pressure, dichloromethane (5 mL) benzhydryl (3R,5R,6R)-3-(3-amino-2-oxoimidazolidin-1-yl)-6-((Z)-2-(((1-(tert-butoxy)-2-methyl-1-oxopropan-2-yl)oxy)imino)-2-(2-((tert-butoxycarbonyl)amino)thiazol-4-yl)acetamido)-7-oxo-4-thia-1-azabicyclo [3.2.0]heptane-3-carboxylate (500 mg) were added to the residue, and the mixture was stirred at room temperature for 2 hours. Dichloromethane (15.2 mL) was added to the reaction mixture, and the reaction mixture was stirred at a temperature equal to or lower than −20° C. At the same temperature, anisole (3.8 mL) and aluminum chloride (1.16 g) were sequentially added to the reaction mixture. The reaction mixture was stirred at a temperature equal to or lower than −20° C. for 30 minutes. The reaction mixture was added to a mixture of acetonitrile (15 mL), water (15 mL), and trisodium citrate dihydrate (3.83 g) under ice cooling. A saturated aqueous sodium hydrogen carbonate solution was added to the reaction mixture such that the pH was adjusted to 5.1, and the aqueous layer was separated. The aqueous layer was concentrated under reduced pressure, and the residue was purified by medium-pressure reverse-phase silica gel column chromatography [eluent; water:acetonitrile=100:0→85:15]. The aqueous solution containing a target substance was lyophilized, thereby obtaining (3R,5R,6R)-6-((Z)-2-(2-aminothiazol-4-yl)-2-(((2-carboxypropan-2-yl)oxy)imino)acetamido)-3-(3-(((E)-2-(2-chloro-3,4-dihydroxybenzamido)ethylidene)amino)-2-oxoimidazolidin-1-yl)-7-oxo-4-thia-1-azabicyclo[3.2.0]heptane-3-carboxylate (22.7 mg) as white solids.

NMR: 1.40 (3H, s), 1.42 (3H, s), 3.49 (1H, d, J=12.8 Hz), 3.59-3.78 (4H, m), 4.16 (2H, d, J=4.0 Hz), 5.61 (1H, d, J=3.6 Hz), 5.66 (1H, d, J=3.6 Hz), 6.83 (1H, d, J=8.4 Hz), 6.95 (1H, s), 6.96 (1H, d, J=8.4 Hz), 6.99 (1H, t, J=4.0 Hz)

MS: 754.05 [M+H]$^+$, 752.10 [M−H]$^-$

Example 45

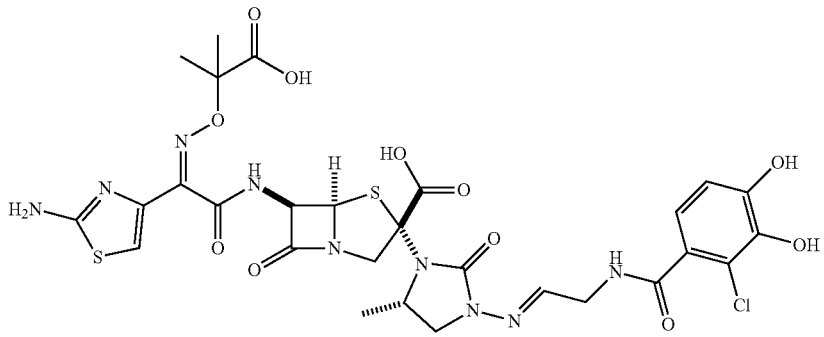

By using the compound obtained in Reference Example 29, (3R,5R,6R)-6-((Z)-2-(2-aminothiazol-4-yl)-2-(((2-carboxypropan-2-yl)oxy)imino)acetamido)-3-((S)-(3-(((E)-2-(2-chloro-3,4-dihydroxybenzamido)ethylidene)amino)-5-methyl-2-oxoimidazolidin-1-yl)-7-oxo-4-thia-1-azabicyclo[3.2.0]heptane-3-carboxylate was obtained in the same manner as in Example 44.

NMR: 1.21 (3H, d, J=4.8 Hz), 1.39 (3H, s), 1.41 (3H, s), 3.29-3.41 (2H, m), 3.63-3.72 (1H, m), 4.15 (2H, d, J=4.4 Hz), 4.24-4.35 (1H, m), 5.62-5.68 (2H, m), 6.82 (1H, d, J=8.4 Hz), 6.92-6.99 (3H, m)

MS: 768.05 [M+H]$^+$, 766.10 [M−H]$^-$.

Example 46

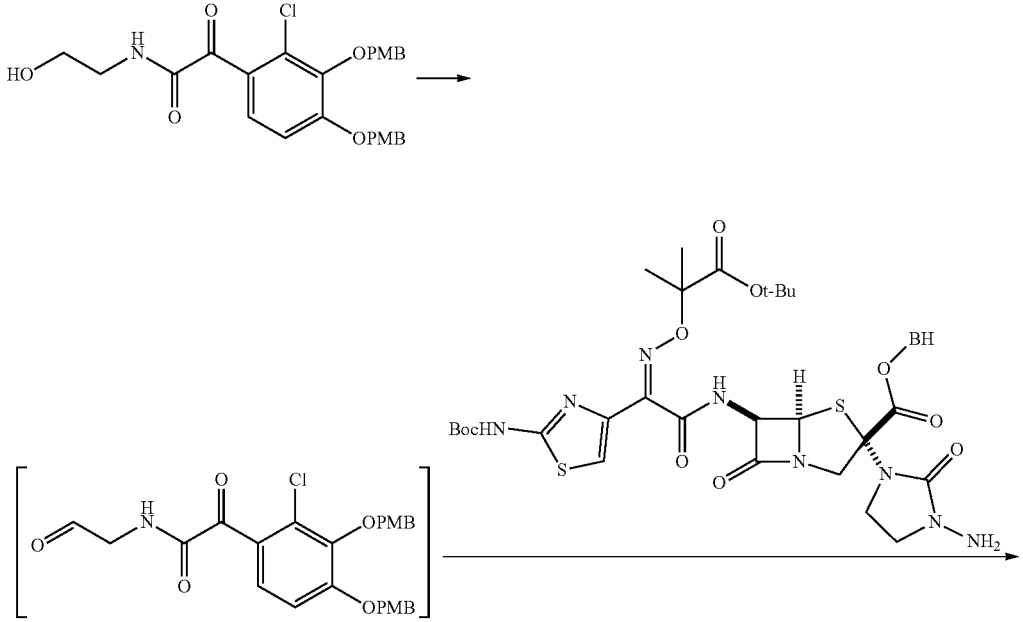

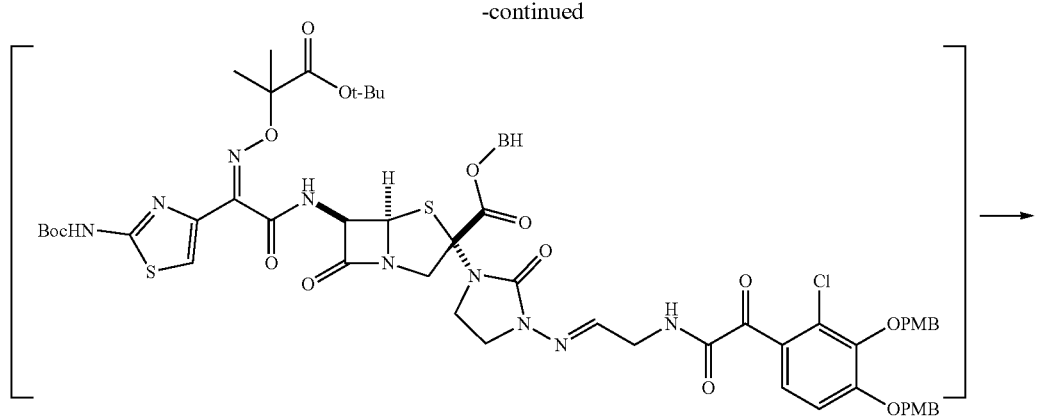

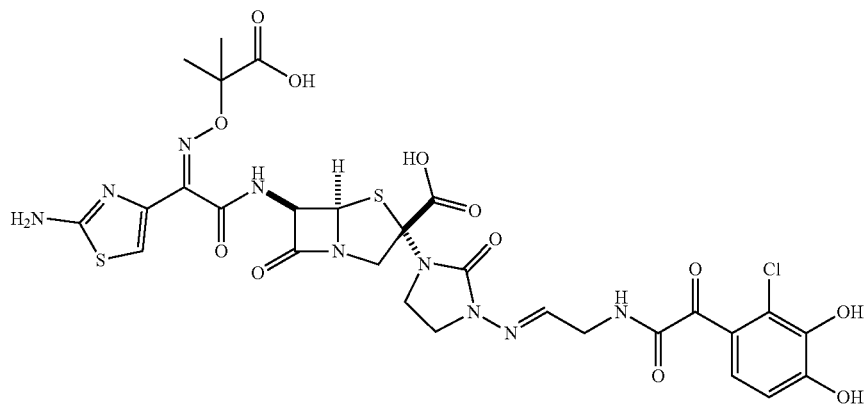

Dichloromethane (4.5 mL) was added to 2-(2-chloro-3,4-bis((4-methoxybenzyl)oxy)phenyl)-N-(2-hydroxyethyl)-2-oxoacetamide (450 mg), and the mixture was stirred under ice cooling. Dess-Martin periodinane (764 mg) was added to the reaction mixture, and the reaction mixture was stirred at room temperature for 3 hours. Dichloromethane (10 mL), water (5 mL), and a 1 mol/L aqueous sodium thiosulfate solution (5 mL) were sequentially added to the reaction mixture, and the organic layer was separated. The organic layer was washed with a saturated aqueous sodium chloride solution and dehydrated and dried over anhydrous sodium sulfate. The solvent was distilled away under reduced pressure, dichloromethane (5 mL) and benzhydryl (3R,5R,6R)-3-(3-amino-2-oxoimidazolidin-1-yl)-6-((Z)-2-(((1-(tert-butoxy)-2-methyl-1-oxopropan-2-yl)oxy)imino)-2-(2-((tert-butoxycarbonyl)amino)thiazol-4-yl)acetamido)-7-oxo-4-thia-1-azabicyclo[3.2.0]heptane-3-carboxylate (500 mg) were added to the residue under ice cooling, and the mixture was stirred at room temperature for 2 hours. Dichloromethane (15.6 mL) was added to the reaction mixture, and the reaction mixture was stirred at a temperature equal to or lower than −20° C. At the same temperature, anisole (3.8 mL) and aluminum chloride (1.16 g) were sequentially added to the reaction mixture. The reaction mixture was stirred at a temperature equal to or lower than −20° C. for 30 minutes. The reaction mixture was added to a mixture of acetonitrile (20 mL), water (20 mL), and trisodium citrate dihydrate (3.83 g) under ice cooling. A saturated aqueous sodium hydrogen carbonate solution was added to the reaction mixture such that the pH was adjusted to 5.1, and the aqueous layer was separated. The aqueous layer was concentrated under reduced pressure, and the residue was purified by medium-pressure reverse-phase silica gel column chromatography [eluent; water:acetonitrile=100:0→85:15]. The aqueous solution containing a target substance was lyophilized, thereby obtaining (3R,5R,6R)-6-((Z)-2-(2-aminothiazol-4-yl)-2-(((2-carboxypropan-2-yl)oxy)imino)acetamido)-3-(3-(((E)-2-(2-(2-chloro-3,4-dihydroxyphenyl)-2-oxoacetamido)ethylidene)amino)-2-oxoimidazolidin-1-yl)-7-oxo-4-thia-1-azabicyclo[3.2.0]heptane-3-carboxylate (43.5 mg) as light yellow solids.

NMR: 1.40 (3H, s), 1.42 (3H, s), 3.49 (1H, d, J=12.4 Hz), 3.58-3.80 (4H, m), 4.16 (2H, d, J=4.0 Hz), 5.62 (1H, d, J=3.6 Hz), 5.67 (1H, d, J=3.6 Hz), 6.86 (1H, d, J=8.8 Hz), 6.95 (1H, s), 6.97 (1H, t, J=4.0 Hz), 7.34 (1H, d, J=8.8 Hz)

MS: 782.05 [M+H]$^+$, 780.00 [M−H]$^−$

Example 47

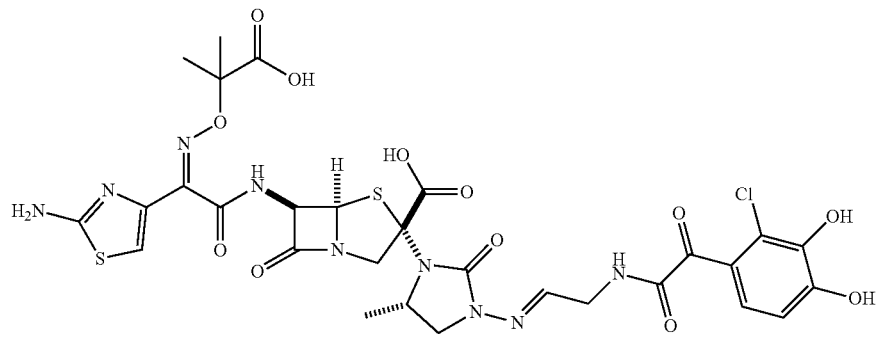

In the same manner as in Example 46, (3R,5R,6R)-6-((Z)-2-(2-aminothiazol-4-yl)-2-(((2-carboxypropan-2-yl)oxy)imino)acetamido)-3-((S)-3-(((E)-2-(2-(2-chloro-3,4-dihydroxyphenyl)-2-oxoacetamido)ethylidene)amino)-5-methyl-2-oxoimidazolidin-1-yl)-7-oxo-4-thia-1-azabicyclo[3.2.0]heptane-3-carboxylate was obtained.

NMR: 1.24 (3H, d, J=4.5 Hz), 1.40 (3H, s), 1.43 (3H, s), 3.28-3.43 (2H, m), 3.64-3.73 (1H, m), 4.17 (2H, d, J=4.4 Hz), 4.25-4.35 (1H, m), 5.60-5.71 (2H, m), 6.89 (1H, d, J=8.4 Hz), 6.93-7.01 (2H, m), 7.35 (1H, d, J=8.4 Hz)

MS: 796.05 [M+H]$^+$, 793.90 [M−H]$^−$

Example 48

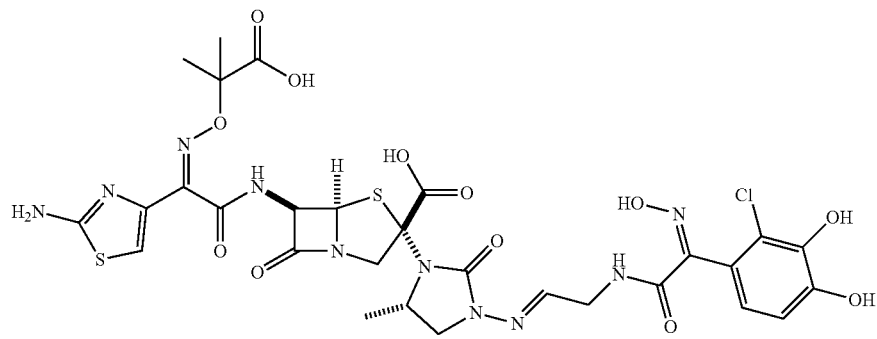

In the same manner as in Example 46, (3R,5R,6R)-6-((Z)-2-(2-aminothiazol-4-yl)-2-(((2-carboxypropan-2-yl)oxy)imino)acetamido)-3-(S)-(3-(((E)-2-((Z)-2-(2-chloro-3,4-dihydroxyphenyl)-2-(hydroxyimino)acetamido)ethylidene)amino)-5-methyl-2-oxoimidazolidin-1-yl)-7-oxo-4-thia-1-azabicyclo[3.2.0]heptane-3-carboxylate was obtained.

NMR: 1.22 (3H, d, J=4.8 Hz), 1.40 (3H, s), 1.42 (3H, s), 3.30-3.38 (2H, m), 3.62-3.70 (1H, m), 4.08-4.13 (2H, m), 4.25-4.33 (1H, m), 5.61-5.70 (2H, m), 6.77 (1H, d, J=8.4 Hz), 6.87-6.93 (2H, m), 6.96 (1H, s)

MS: 811.05 [M+H]$^+$, 809.00 [M−H]$^−$

Example 49

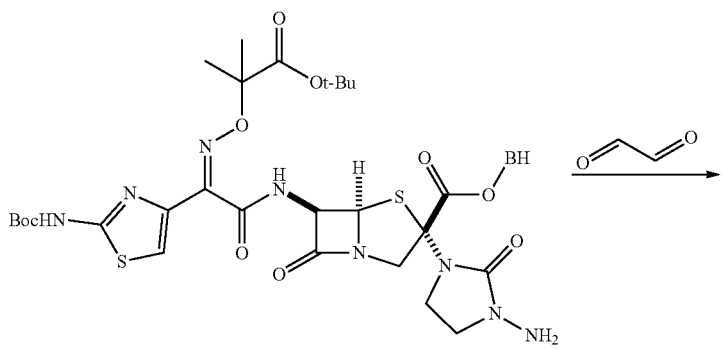

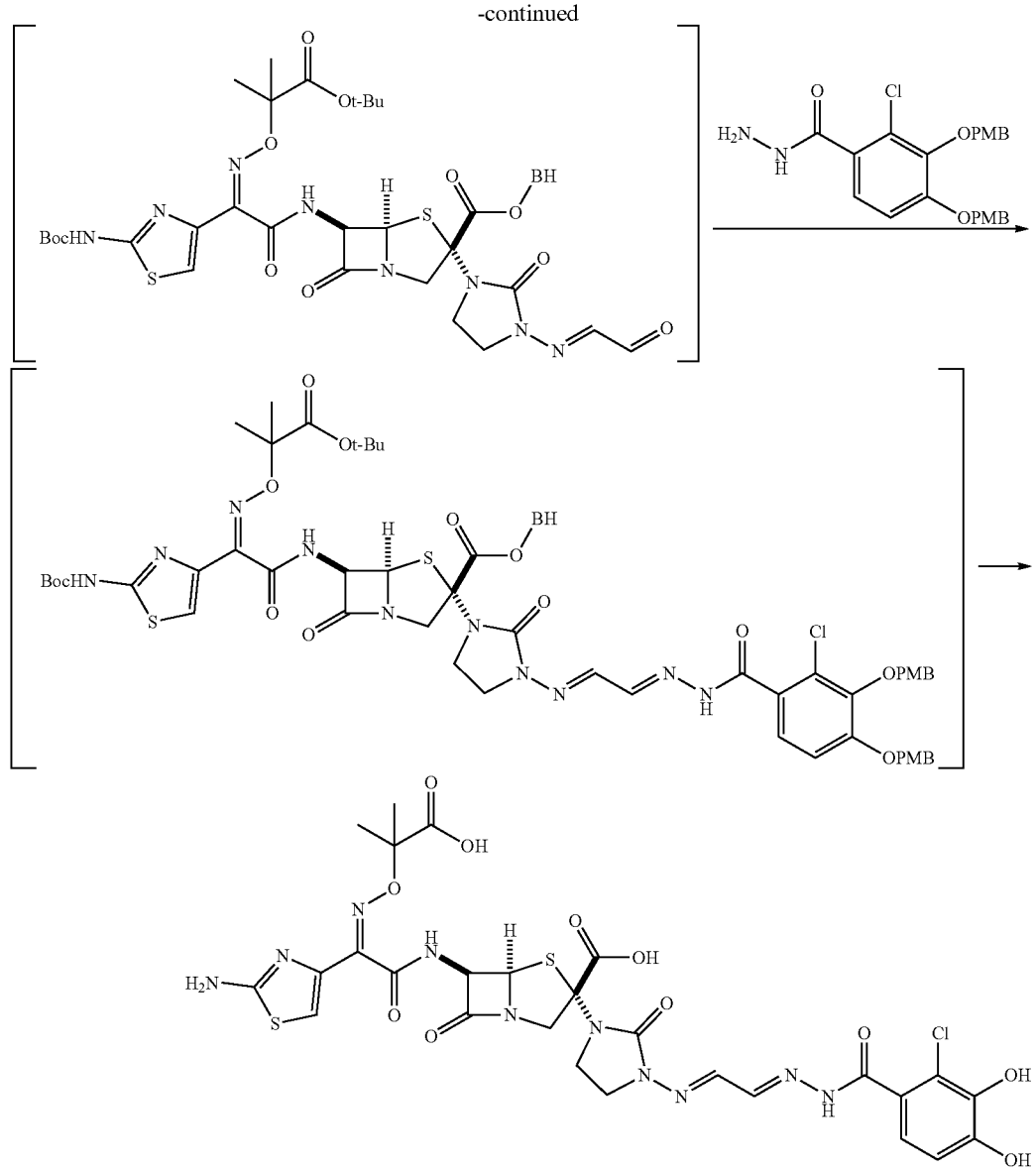

Example 49

THF (5 mL) was added to a 40% aqueous glyoxal solution (1.3 mL), and the mixture was stirred under ice cooling. Benzhydryl (3R,5R,6R)-3-(3-amino-2-oxoimidazolidin-1-yl)-6-(((Z)-2-(((1-(tert-butoxy)-2-methyl-1-oxopropan-2-yl)oxy)imino)-2-(2-(((tert-butoxycarbonyl)amino)thiazol-4-yl)acetamido)-7-oxo-4-thia-1-azabicyclo[3.2.0]heptane-3-carboxylate (500 mg) and THF (10 mL) were added to the reaction mixture, and the reaction mixture was stirred at room temperature for 3 hours and 30 minutes. The reaction mixture was added to a mixture of water (15 mL), dichloromethane (15 mL), and 1 mol/L hydrochloric acid (1.5 mL), and the organic layer was separated. The organic layer was washed twice with a 5% aqueous sodium chloride solution and then dehydrated and dried over anhydrous sodium sulfate. The solvent was distilled away under reduced pressure, and dichloromethane (10 mL) and 2-chloro-3,4-bis((4-methoxybenzyl)oxy)benzohydrazine (512 mg) were added to the residue, and the mixture was stirred at room temperature for 2 hours and 40 minutes. Dichloromethane (15.3 mL) was added to the reaction mixture, and the reaction mixture was stirred at a temperature equal to or lower than −20° C. At the same temperature, anisole (3.8 mL) and aluminum chloride (1.15 g) were sequentially added to the reaction mixture. The reaction mixture was stirred at a temperature equal to or lower than −20° C. for 2 hours. At the same temperature, aluminum chloride (383 mg) was added to the reaction mixture, and the reaction mixture was stirred at the same temperature for 30 minutes. Then, aluminum chloride (383 mg) was added to the reaction mixture, and the reaction mixture was stirred at the same temperature for 30 minutes. The reaction mixture was added to a mixture of acetonitrile (25 mL), water (20 mL), and trisodium citrate dihydrate (3.80 g) under ice cooling. A saturated aqueous sodium hydrogen carbonate solution was added to the reaction mixture such that the pH was adjusted to 5.0, and the aqueous layer was separated. The aqueous layer was concentrated under reduced pressure, and the residue was purified by medium-pressure reverse-phase silica gel column chromatography [eluent; water:acetonitrile=100:0→85:15]. The aqueous solution containing a target substance was lyophilized, thereby obtaining (3R,5R,6R)-6-((Z)-2-(2-aminothiazol-4-yl)-2-(((2-carboxypropan-2-yl)oxy)imino)acetamido)-3-(3-(((1E,2E)-2-(2-(2-chloro-3,4-dihydroxybenzoyl)hydrazono)ethylidene)amino)-2-oxoimidazolidin-1-yl)-7-oxo-4-thia-1-azabicyclo[3.2.0]heptane-3-carboxylate (32.5 mg) as light yellow solids.

NMR: 1.41 (3H, s), 1.43 (3H, s), 3.48 (1H, d, J=13.2 Hz), 3.75-3.86 (4H, m), 5.63 (1H, d, J=3.4 Hz), 5.67 (1H, d, J=3.4 Hz), 6.85 (1H, d, J=8.4 Hz), 6.95 (1H, s), 7.00 (1H, d, J=8.4 Hz), 7.38 (1H, d, J=8.0 Hz), 7.91 (1H, d, J=8.0 Hz)

MS: 767.05 [M+H]⁺, 765.10 [M−H]⁻

The compounds shown in Table 21 were obtained in the same manner as in Example 49.

TABLE 21

| Example No | Structural Formula | Name |
|---|---|---|
| 50 | | (3R,5R,6R)-6-((Z)-2-(2-aminothiazol-4-yl)-2-(((2-carboxypropan-2-yl)oxy)imino)acetamido)-3-((S)-3-(((1E,2E)-2-(2-((2-(2-chloro-3,4-dihydroxybenzamido)ethyl)carbamoyl)hydrazono)ethylidene)amino)-5-methyl-2-oxoimidazolidin-1-yl)-7-oxo-4-thia-1-azabicyclo[3.2.0]heptane-3-carboxylate |
| 51 | | (3R,5R,6R)-6-((Z)-2-(2-aminothiazol-4-yl)-2-(((2-carboxypropan-2-yl)oxy)imino)acetamido)-3-((S)-3-(((1E,2E)-2-(2-((2-(2-chloro-3,4-dihydroxybenzamido)ethyl)carbamoyl)hydrazono)ethylidene)amino)-4-methyl-2-oxoimidazolidin-1-yl)-7-oxo-4-thia-1-azabicyclo[3.2.0]heptane-3-carboxylate |
| 52 | | (3R,5R,6R)-6-((Z)-2-(2-aminothiazol-4-yl)-2-(((2-carboxypropan-2-yl)oxy)imino)acetamido)-3-((S)-3-(((1E,2E)-2-(2-(2-chloro-3,4-dihydroxybenzoyl)hydrazono)ethylidene)amino)-5-methyl-2-oxoimidazolidin-1-yl)-7-oxo-4-thia-1-azabicyclo[3.2.0]heptane-3-carboxylate |
| 53 | | (3R,5R,6R)-6-((Z)-2-(2-aminothiazol-4-yl)-2-(((2-carboxypropan-2-yl)oxy)imino)acetamido)-3-(3-(((1E,2E)-2-(2-((2-(2-chloro-3,4-dihydroxybenzamido)ethyl)carbamoyl)hydrazono)ethylidene)amino)-2-oxoimidazolidin-1-yl)-7-oxo-4-thia-1-azabicyclo[3.2.0]heptane-3-carboxylate |

TABLE 21-continued

| Example No | Structural Formula | Name |
|---|---|---|
| 54 | | (3R,5R,6R)-6-((Z)-2-(2-aminothiazol-4-yl)-2-(((2-carboxypropan-2-yl)oxy)imino)acetamido)-3-(3-(((1E,2E)-2-((2-(2-chloro-3,4-dihydroxybenzamido)ethoxy)imino)ethylidene)amino)-2-oxoimidazolidin-1-yl)-7-oxo-4-thia-1-azabicyclo[3.2.0]heptane-3-carboxylate |

The measured values of NMR and MS of the compounds in the table are as follows.

Example 50

NMR: 1.26 (3H, d, J=4.8 Hz), 1.42 (3H, s), 1.44 (3H, s), 3.35 (1H, d, J=12.0 Hz), 3.39-3.52 (5H, m), 3.71-3.81 (1H, m), 4.30-4.42 (1H, m), 5.65-5.72 (2H, m), 6.82 (1H, d, J=8.4 Hz), 6.90 (1H, d, J=8.4 Hz), 6.98 (1H, s), 7.25 (1H, d, J=8.0 Hz), 7.59 (1H, d, J=8.0 Hz)

MS: 867.05 [M+H]⁺, 865.00 [M−H]⁻

Example 51

NMR: 1.31 (3H, d, J=5.6 Hz), 1.50 (6H, s), 3.42-3.62 (7H, m), 3.85-4.00 (1H, t, J=8.4 Hz), 4.37-4.48 (1H, m), 5.67-5.72 (1H, m), 5.72-5.78 (1H, m), 6.88 (1H, d, J=8.0 Hz), 6.96 (1H, d, J=8.0 Hz), 7.46-7.58 (2H, m), 7.62 (1H, d, J=6.0 Hz)

MS: 867.10 [M+H]⁺, 865.00 [M−H]⁻

Example 52

NMR: 1.27 (3H, d, J=4.8 Hz), 1.40 (3H, s), 1.43 (3H, s), 3.34 (1H, d, J=12.8 Hz), 3.50-3.57 (1H, m), 3.79-3.88 (1H, m), 4.35-4.45 (1H, m), 5.63-5.71 (2H, m), 6.86 (1H, d, J=8.4 Hz), 6.96 (1H, s), 7.01 (1H, d, J=8.4 Hz), 7.37 (1H, d, J=8.0 Hz), 7.92 (1H, d, J=8.0 Hz)

MS: 781.05 [M+H]⁺, 779.05 [M−H]⁻

Example 53

NMR: 1.49 (3H, s), 1.51 (3H, s), 3.44-3.62 (5H, m), 3.73-3.91 (4H, m), 4.71 (1H, d, J=12.4 Hz), 5.71 (1H, d, J=3.6 Hz), 5.75 (1H, d, J=3.6 Hz), 6.88 (1H, d, J=8.4 Hz), 6.95 (1H, d, J=8.4 Hz), 7.03 (1H, s), 7.33 (1H, d, J=8.0 Hz), 7.65 (1H, d, J=8.0 Hz)

MS: 853.10 [M+H]⁺, 850.95 [M−H]⁻

Example 54

NMR: 1.49 (3H, s), 1.51 (3H, s), 3.56 (1H, d, J=12.4 Hz), 3.64-3.93 (6H, m), 4.34-4.42 (2H, m), 4.72 (1H, d, J=12.4 Hz), 5.71 (1H, d, J=3.6 Hz), 5.75 (1H, d, J=3.6 Hz), 6.86-6.99 (2H, m), 7.03 (1H, s), 7.29 (1H, d, J=8.4 Hz), 7.97 (1H, d, J=8.4 Hz)

MS: 811.05 [M+H]⁺, 808.95 [M−H]⁻

Example 55

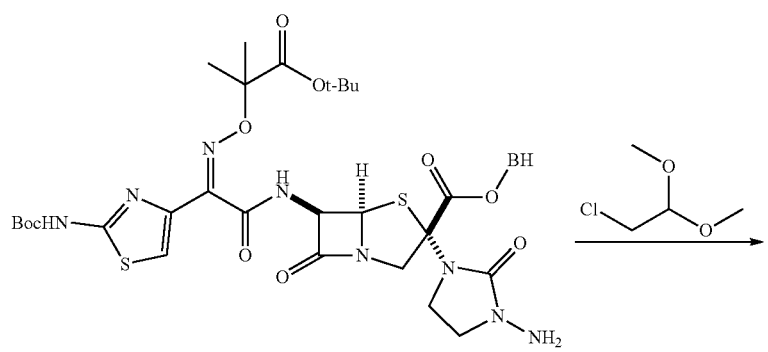

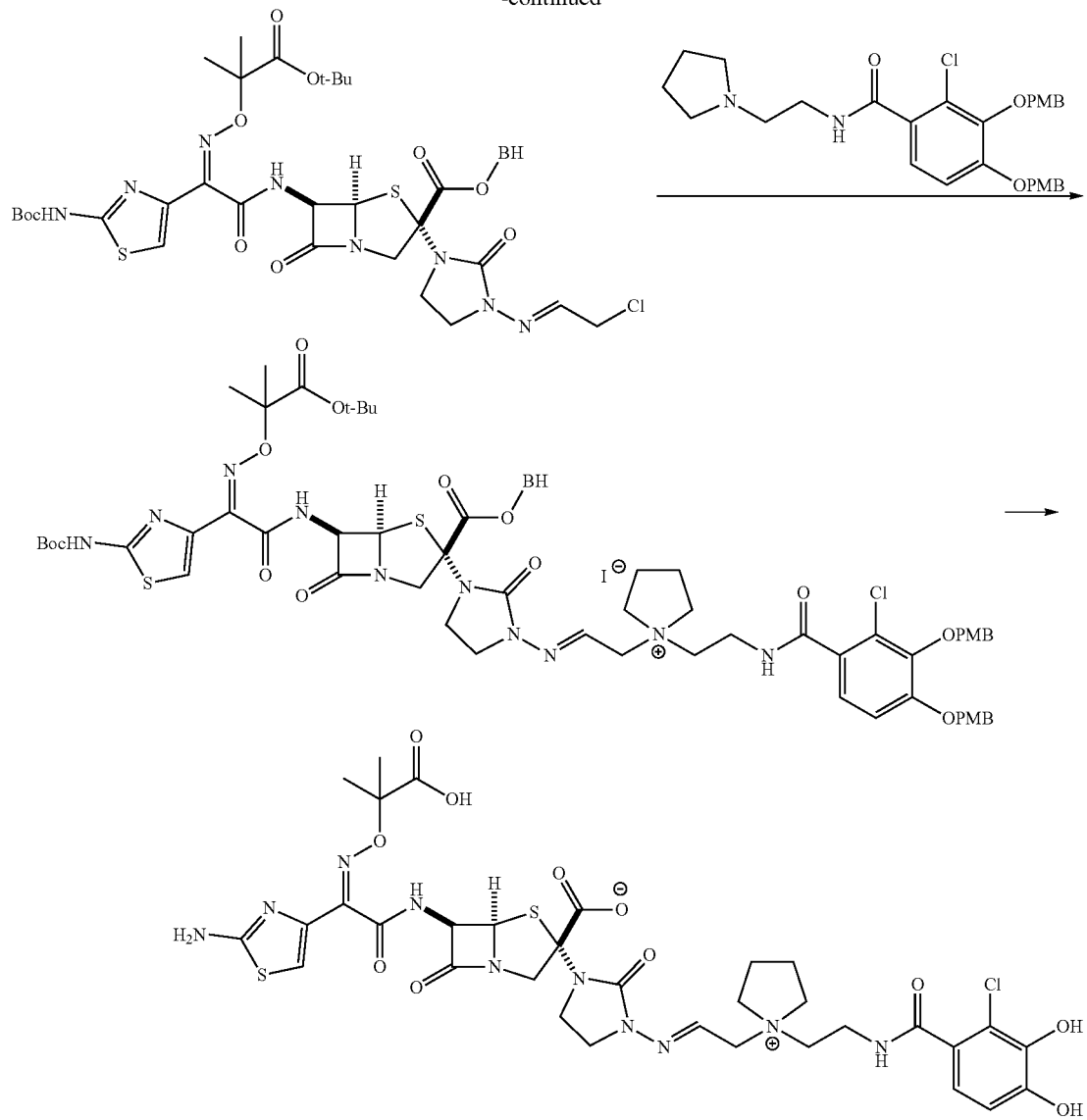

Example 55 (1)

Dichloromethane (10 mL) were added to benzhydryl (3R,5R,6R)-3-(3-amino-2-oxoimidazolidin-1-yl)-6-((Z)-2-(((1-(tert-butoxy)-2-methyl-1-oxopropan-2-yl)oxy)imino)-2-(2-((tert-butoxycarbonyl)amino)thiazol-4-yl)acetamido)-7-oxo-4-thia-1-azabicyclo[3.2.0]heptane-3-carboxylate (1.00 g), and the mixture was stirred under ice cooling. At the same temperature, 2-chloro-1,1-dimethoxyethane (2.0 mL) and p-toluenesulfonic acid monohydrate (66 mg) were sequentially added to the reaction mixture, and the reaction mixture was stirred at room temperature for 3 hours and 30 minutes. At the same temperature, 2-chloro-1,1-dimethoxyethane (0.66 mL) and p-toluenesulfonic acid monohydrate (44 mg) were sequentially added to the reaction mixture, and the reaction mixture was stirred at room temperature for 1 hour. The reaction mixture was added to a mixture of water (30 mL), ethyl acetate (30 mL), and 1 mol/L hydrochloric acid (1.5 mL), and the organic layer was separated. The organic layer was washed with a 5% aqueous sodium chloride solution and then dehydrated and dried over anhydrous sodium sulfate. The solvent was distilled away under reduced pressure, and the residue was purified by silica gel column chromatography [eluent; ethyl acetate:hexane=40:60→70:30], thereby obtaining benzhydryl (3R,5R,6R)-6-((Z)-2-(((1-(tert-butoxy)-2-methyl-1-oxopropan-2-yl)oxy)imino)-2-(2-((tert-butoxycarbonyl)amino)thiazol-4-yl)acetamido)-3-(3-((E)-2-chloroethylidene)amino)-2-oxoimidazolidin-1-yl)-7-oxo-4-thia-1-azabicyclo[3.2.0]heptane-3-carboxylate (765 mg) as a yellow oily substance.

NMR (CDCl$_3$): 1.39 (9H, s), 1.49-1.56 (15H, m), 3.48-3.74 (4H, m), 3.76-3.86 (1H, m), 4.28 (1H, d, J=5.6 Hz), 5.10 (1H, d, J=13.2 Hz), 5.60 (1H, d, J=3.6 Hz), 5.76 (1H, dd, J=8.0, 3.6 Hz), 6.86 (1H, s), 6.88-6.95 (1H, m), 7.08-7.15 (1H, m), 7.17-7.32 (1H, m), 7.40 (1H, d, J=8.0 Hz), 8.08 (1H, s)

Example 55 (2)

DMF (7.0 mL) was added to benzhydryl (3R,5R,6R)-6-((Z)-2-(((1-(tert-butoxy)-2-methyl-1-oxopropan-2-yl)oxy)

imino)-2-(2-((tert-butoxycarbonyl)amino)thiazol-4-yl)acetamido)-3-(3-(((E)-2-chloroethylidene)amino)-2-oxoimidazolidin-1-yl)-7-oxo-4-thia-1-azabicyclo[3.2.0]heptane-3-carboxylate (705 mg), and the mixture was stirred under ice cooling. At the same temperature, 2-chloro-3,4-bis((4-methoxybenzyl)oxy)-N-(2-(pyrrolidin-1-yl)ethyl)benzamide (800 mg) and sodium iodide (57 mg) were sequentially added to the reaction mixture, and the reaction mixture was stirred at room temperature for 4 hours. Sodium iodide (57 mg) was added to the reaction mixture, and the reaction mixture was stirred at room temperature for 2 hours. Ethyl acetate (20 mL) and water (20 mL) were added to the reaction mixture. Hydrochloric acid (1 mol/L) was added to the reaction mixture such that the pH was adjusted to 2.6. The organic layer was separated, washed twice with a 5% aqueous sodium chloride solution, and then dehydrated and dried over anhydrous sodium sulfate. The solvent was distilled away under reduced pressure, thereby obtaining a target substance (1.175 g) as a light brown oily substance.

Example 55 (3)

Dichloromethane (10 mL) was added to the compound (1.175 g) obtained in Example 55 (2), and the mixture was stirred at a temperature equal to or lower than −20° C. At the same temperature, anisole (5.0 mL) and aluminum chloride (2.0 g) were sequentially added to the reaction mixture. The reaction mixture was stirred at a temperature equal to or lower than −20° C. for 40 minutes. At the same temperature, aluminum chloride (1.0 g) was added to the reaction mixture, and the reaction mixture was stirred at the same temperature for 30 minutes. The reaction mixture was added to a mixture of acetonitrile (20 mL), water (20 mL), and trisodium citrate dihydrate (6.72 g) under ice cooling. A saturated aqueous sodium hydrogen carbonate solution was added to the reaction mixture such that the pH was adjusted to 5.7, and the aqueous layer was separated. The aqueous layer was concentrated under reduced pressure, and the residue was purified by medium-pressure reverse-phase silica gel column chromatography [eluent; water:acetonitrile=100:0→85:15]. The aqueous solution containing a target substance was lyophilized, thereby obtaining (3R,5R,6R)-6-((Z)-2-(2-aminothiazol-4-yl)-2-(((2-carboxypropan-2-yl)oxy)imino)acetamido)-3-(3-(((E)-2-(1-(2-(2-chloro-3,4-dihydroxybenzamido)ethyl)pyrrolidin-1-ium-1-yl)ethylidene)amino)-2-oxoimidazolidin-1-yl)-7-oxo-4-thia-1-azabicyclo[3.2.0]heptane-3-carboxylate (60.3 mg) as white solids.

NMR: 1.40 (3H, s), 1.42 (3H, s), 2.12-2.24 (4H, m), 3.41 (1H, d, J=12.8 Hz), 3.50-3.88 (12H, m), 4.14-4.24 (2H, m), 5.59 (1H, d, J=3.8 Hz), 5.67 (1H, d, J=3.8 Hz), 6.74-7.07 (4H, m)

MS: 851.10 [M+H]$^+$, 849.00 [M−H]$^−$

The compounds shown in Table 22 were obtained in the same manner as in Example 55.

TABLE 22

| Example No | Structural Formula | Name |
|---|---|---|
| 56 | | (3R,5R,6R)-6-((Z)-2-(2-aminothiazol-4-yl)-2-(((2-carboxypropan-2-yl)oxy)imino)acetamido)-3-((S)-3-(((E)-2-(1-(2-(2-chloro-3,4 dihydroxybenzamido)ethyl)pyrrolidin-1-ium-1-yl)ethylidene)amino)-4-methyl-2-oxoimidazolidin-1-yl)-7-oxo-4-thia-1-azabicyclo[3.2.0]heptane-3-carboxylate |
| 57 | | (3R,5R,6R)-6-((Z)-2-(2-aminothiazol-4-yl)-2-(((2-carboxypropan-2-yl)oxy)imino)acetamido)-3-((S)-3-(((E)-2-(1-(2-(2-chloro-3,4-dihydroxybenzamido)ethyl)-1H-imidazol-3-ium-3-yl)ethylidene)amino)-4-methyl-2-oxoimidazolidin-1-yl)-7-oxo-4-thia-1-azabicyclo[3.2.0]heptane-3-carboxylate |

TABLE 22-continued

| Example No | Structural Formula | Name |
|---|---|---|
| 58 | | (3R,5R,6R)-6-((Z)-2-(2-aminothiazol-4-yl)-2-(((2-carboxypropan-2-yl)oxy)imino)acetamido)-3-(3-(((E)-2-(1-(2-(2-chloro-3,4-dihydroxybenzamido)ethyl)-1H-imidazol-3-ium-3-yl)ethylidene)amino)-2-oxoimidazolidin-1-yl)-7-oxo-4-thia-1-azabicyclo[3.2.0]heptane-3-carboxylate |

The measured values of NMR and MS of the compounds in the table are as follows.

Example 56

NMR: 1.31 (3H, d, J=6.0 Hz), 1.48 (3H, s), 1.50 (3H, s), 2.21-2.32 (4H, m), 3.51 (1H, d, J=12.0 Hz), 3.60-3.72 (5H, m), 3.73-3.82 (2H, m), 3.87-3.97 (3H, m), 4.23-4.31 (2H, m), 4.37-4.47 (1H, m), 4.68 (1H, d, J=12.8 Hz), 5.67 (1H, d, J=3.6 Hz), 5.76 (1H, d, J=3.2 Hz), 6.80-6.92 (1H, m), 7.02 (1H, s), 7.30 (1H, s), 7.34-7.40 (1H, m)

MS: 866.05 [M+H]$^+$, 864.15 [M−H]$^−$

Example 57

NMR: 1.16 (3H, d, J=6.0 Hz), 1.48 (3H, s), 1.50 (3H, s), 3.12-3.15 (1H, m), 3.30 (1H, d, J=12.8 Hz), 3.34 (1H, dd, J=9.0, 3.8 Hz), 3.78 (1H, t, J=8.8 Hz), 4.47 (2H, t, J=5.4 Hz), 4.52 (2H, t, J=5.2 Hz), 4.59 (1H, d, J=12.8 Hz), 5.13 (2H, d, J=3.6 Hz), 5.60 (1H, d, J=3.6 Hz), 5.74 (1H, d, J=3.2 Hz), 6.81 (1H, d, J=8.4 Hz), 6.84 (1H, d, J=8.4 Hz), 6.87 (1H, s), 7.03 (1H, s), 7.44 (1H, s), 7.61 (1H, s), 8.99 (1H, s)

MS: 863.05 [M+H]$^+$, 861.35 [M−H]$^−$

Example 58

NMR: 1.49 (3H, s), 1.50 (3H, s), 3.27 (1H, d, J=12.8 Hz), 3.27-3.42 (2H, m), 3.58-3.73 (2H, m), 3.79-3.89 (4H, m), 4.63 (1H, d, J=13.2 Hz), 5.11 (2H, d, J=4.0 Hz), 5.62 (1H, d, J=3.6 Hz), 5.72 (1H, d, J=3.6 Hz), 6.77-6.83 (2H, m), 6.97 (1H, t, J=4.2 Hz), 7.04 (1H, s), 7.46 (1H, s), 7.67 (1H, s), 9.01 (1H, s)

MS: 849.10 [M+H]$^+$, 846.90 [M−H]$^−$

Example 59

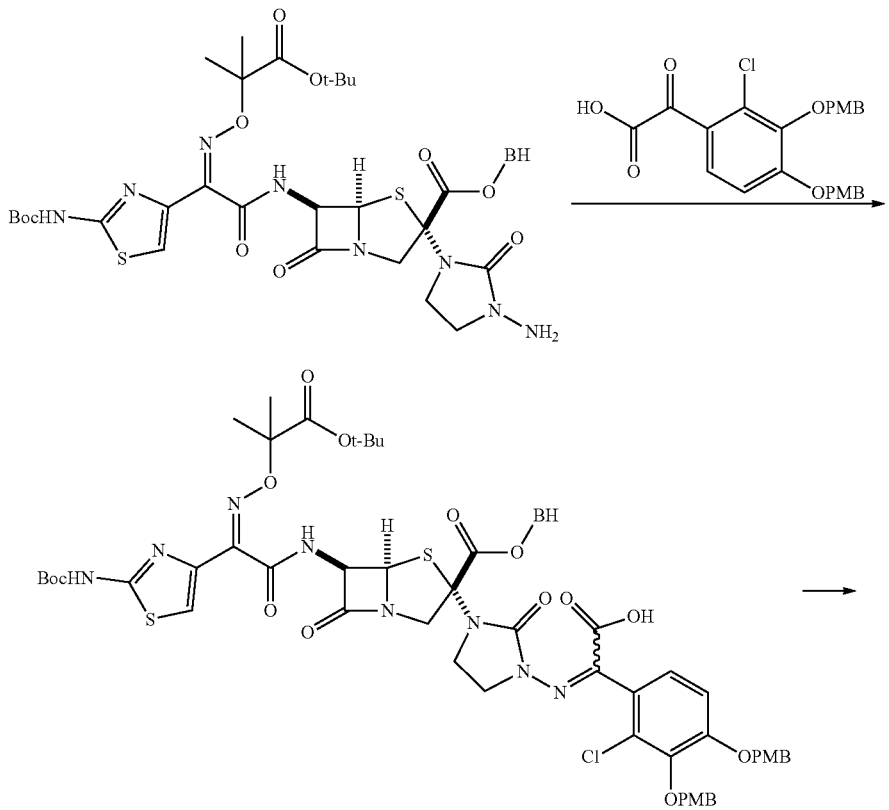

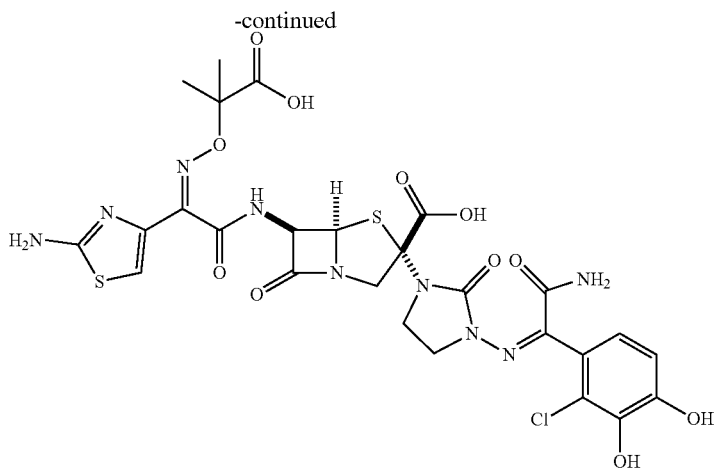

Example 59 (1)

Ethanol (4 mL) was added to 2-(2-chloro-3,4-bis((4-methoxybenzyl)oxy)phenyl)-2-oxoacetic acid (222 mg), and the mixture was stirred under ice cooling. At the same temperature, benzhydryl (3R,5R,6R)-3-(3-amino-2-oxoimidazolidin-1-yl)-6-((Z)-2-(((1-(tert-butoxy)-2-methyl-1-oxopropan-2-yl)oxy)imino)-2-(2-((tert-butoxycarbonyl)amino)thiazol-4-yl)acetamido)-7-oxo-4-thia-1-azabicyclo[3.2.0]heptane-3-carboxylate (400 mg) was added to the mixture, and the mixture was stirred at room temperature overnight. The reaction mixture was added to a mixture of ethyl acetate (40 mL) and water (40 mL). The organic layer was separated and washed twice with water (50 mL). The organic layer was washed with a saturated aqueous sodium chloride solution (10 mL) and then dehydrated and dried over anhydrous sodium sulfate. The solvent was distilled away under reduced pressure, thereby obtaining a target substance (500 mg) as light yellow solids.

Example 59 (2)

DMAC (5 mL) was added to the compound (500 mg) obtained in Example 59 (1), and the mixture was stirred under ice cooling. Ammonium chloride (45 mg), HOBt (106 mg), EDC (176 mg), and NMM (254 μL) were sequentially added to the reaction mixture under ice cooling. The reaction mixture was stirred at room temperature overnight. The reaction mixture was added to a mixture of ethyl acetate (30 mL) and water (30 mL), and 1 mol/L hydrochloric acid was added thereto such that the pH was adjusted to 5.4. The organic layer was separated, and the aqueous layer was extracted three times by using ethyl acetate (5 mL). The organic layers were combined, sequentially washed with water and a saturated aqueous sodium chloride solution, and then dehydrated and dried over anhydrous sodium sulfate. The solvent was distilled away under reduced pressure, thereby obtaining a target substance (499 mg) as yellow solids.

Example 59 (3)

Dichloromethane (10 mL) was added to the compound (499 mg) obtained in Example 59 (2), and the mixture was stirred at a temperature equal to or lower than −20° C. At the same temperature, anisole (2.5 mL) and aluminum chloride (766 mg) were sequentially added to the reaction mixture. The reaction mixture was stirred at a temperature equal to or lower than −20° C. for 40 minutes. The reaction mixture was added to a mixture of acetonitrile (40 mL), water (40 mL), and trisodium citrate dihydrate (2.53 g) under ice cooling. A saturated aqueous sodium hydrogen carbonate solution was added to the reaction mixture such that the pH was adjusted to 5.3, and the aqueous layer was separated. The aqueous layer was concentrated under reduced pressure, and the residue was purified by medium-pressure reverse-phase silica gel column chromatography [eluent; water:acetonitrile=100:0→75:25]. The aqueous solution containing a target substance was lyophilized, thereby obtaining (3R,5R,6R)-3-(3-(((Z)-2-amino-1-(2-chloro-3,4-dihydroxyphenyl)-2-oxoethylidene)amino)-2-oxoimidazolidin-1-yl)-6-((Z)-2-(2-aminothiazol-4-yl)-2-(((2-carboxypropan-2-yl)oxy)imino)acetamido)-7-oxo-4-thia-1-azabicyclo[3.2.0]heptane-3-carboxylate (24.9 mg) as yellow solids.

NMR: 1.48 (3H, s), 1.50 (3H, s), 3.14-3.40 (2H, m), 3.50 (1H, d, J=13.2 Hz), 3.53-3.65 (2H, m), 4.75 (1H, d, J=8.8 Hz), 5.67 (1H, d, J=3.6 Hz), 5.74 (1H, d, J=3.6 Hz), 6.82 (1H, d, J=8.0 Hz), 6.94 (1H, d, J=8.0 Hz), 7.02 (1H, s)

MS: 740.05 [M+H]$^+$, 738.00 [M−H]$^−$

The compounds shown in Table 23 were obtained in the same manner as in Example 59.

TABLE 23

| Example No | Structural Formula | Name |
|---|---|---|
| 60 | | (3R,5R,6R)-3-((R)-3-(((Z)-2-amino-1-(2-chloro-3,4-dihydiroxyphenyl)-2-oxoethylidene) amino)-4-methyl-2-oxoimidiazolidin-1-yl)-6-((Z)-2-(2-aminothiazol-4-yl)-2-(((2-carboxypropan-2-yl)oxy)imino) acetamido)-7-oxo-4-thia-1-azabicyclo [3.2.0]heptane-3-carboxylate |
| 61 | | (3R,5R,6R)-3-(3-(((Z)-2-amino-1-(2-chloro-3,4-dihydroxyphenyl)-2-oxoethylidene)amino)-2-oxoimidazolidin-1-yl)-6-((Z)-2-(2-aminothiazol-4-yl)-2-((1-carboxycyclobutoxy)imino) acetamido)-7-oxo-4-thia-1-azabicyclo [3.2.0]heptane-3-carboxylate |
| 62 | | (3R,5R,6R)-3-(3-(((Z)-2-amino-1-(2-chloro-3,4-dihydroxy phenyl)-2-oxoethylidene)amino)-2-oxoimidazolidin-1-yl)-6-((Z)-2-(2-amino-5-chlorothiazol-4-yl)-2-(((2-carboxypropan-2-yl)oxy) imino)acetamido)-7-oxo-4-thia-1-azabicyclo[3.2.0]heptane-3-carboxylate |

The measured values of NMR and MS of the compounds in the table are as follows.
Example 60
NMR: 0.98 (3H, d, J=6.0 Hz), 1.49 (3H, s), 1.51 (3H, s), 3.10-3.11 (1H, m), 3.29 (1H, d, J=8.0 Hz), 3.58-3.64 (2H, m), 4.61 (1H, d, J=12.4 Hz), 5.65 (1H, d, J=3.6 Hz), 5.75 (1H, d, J=3.6 Hz), 6.88-6.94 (1H, m), 6.97 (1H, d, J=8.0 Hz), 7.04 (1H, s)
MS: 754.15 [M+H]$^+$, 752.10 [M–H]$^-$
Example 61
NMR: 1.80-1.93 (1H, m), 1.94-2.07 (1H, m), 2.24-2.38 (2H, m), 2.39-2.49 (1H, m), 2.49-2.60 (1H, m), 3.13-3.37 (2H, m), 3.50 (1H, d, J=13.2 Hz), 3.55-3.66 (2H, m), 4.70 (1H, d, J=2.0 Hz), 5.69 (1H, d, J=3.6 Hz), 5.76 (1H, d, J=3.6 Hz), 6.82 (1H, d, J=8.4 Hz), 6.94 (1H, d, J=8.4 Hz), 7.06 (1H, s)
MS: 752.00 [M+H]$^+$, 750.15 [M–H]$^-$
Example 62
NMR: 1.50 (3H, s), 1.51 (3H, s), 3.15-3.37 (2H, m), 3.52 (1H, d, J=12.8 Hz), 3.55-3.65 (2H, m), 4.75 (1H, d, J=5.2 Hz), 5.65 (1H, d, J=4.0 Hz), 5.78 (1H, d, J=3.2 Hz), 6.82 (1H, d, J=8.4 Hz), 6.94 (1H, d, J=8.4 Hz)
MS: 774.20 [M+H]$^+$, 772.10 [M–H]$^-$
Example 63
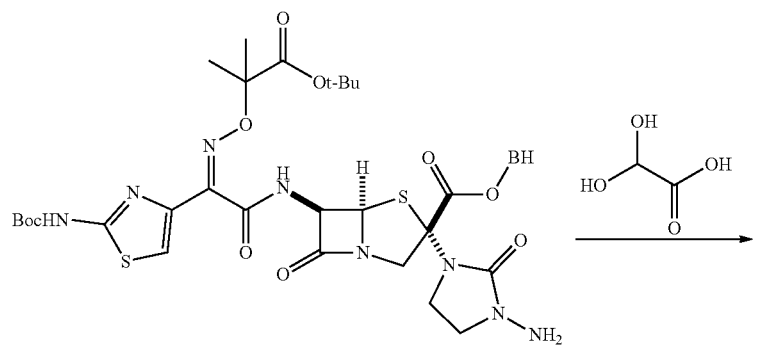
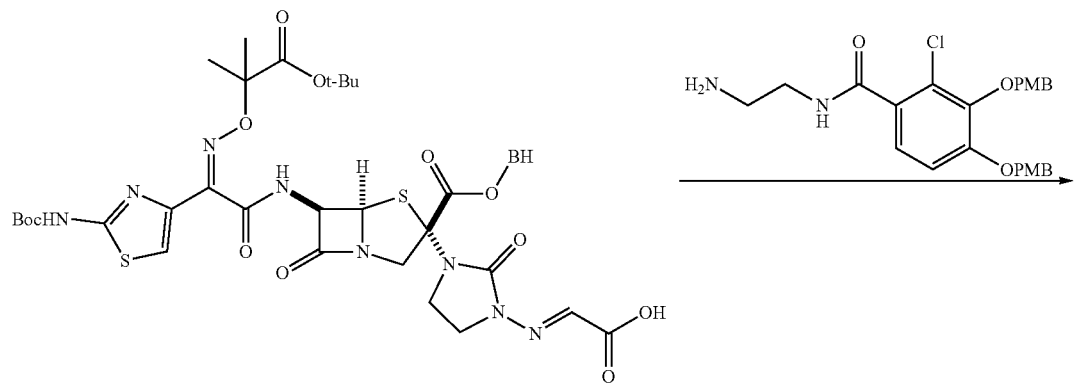
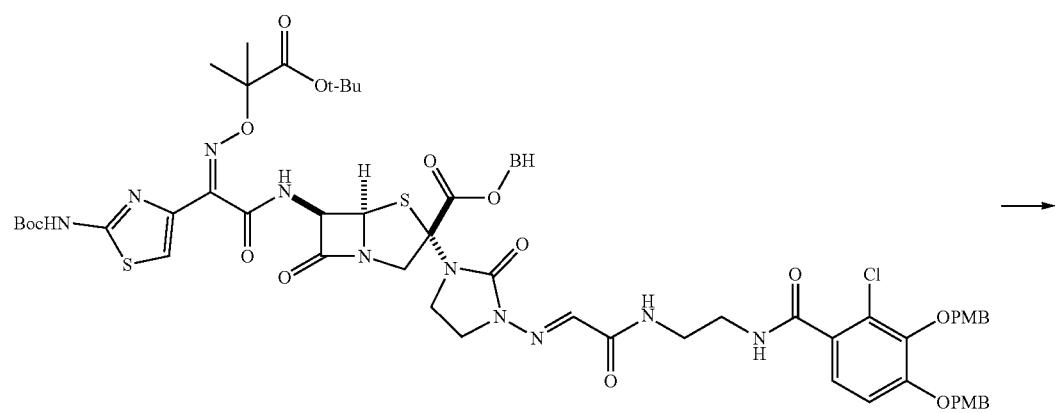

-continued

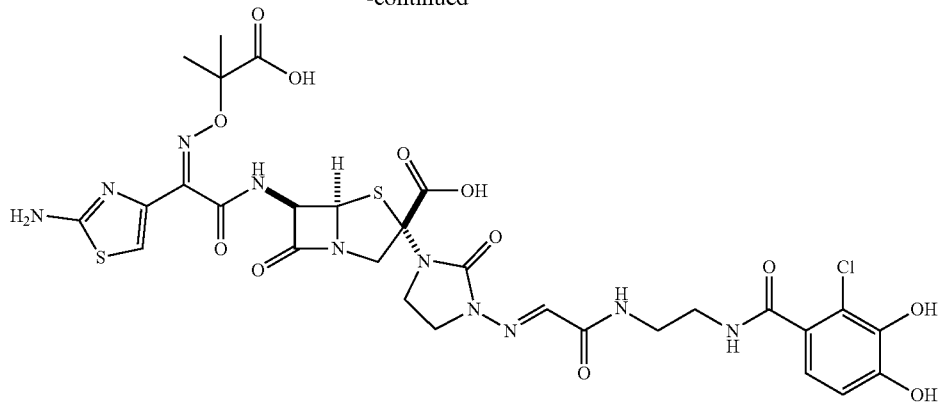

Example 63 (1)

THF (3 mL) was added to glyoxylic acid monohydrate (160 mg), and the mixture was stirred under ice cooling. At the same temperature, benzhydryl (3R,5R,6R)-3-(3-amino-2-oxoimidazolidin-1-yl)-6-((Z)-2-(((1-(tert-butoxy)-2-methyl-1-oxopropan-2-yl)oxy)imino)-2-(2-((tert-butoxycarbonyl)amino)thiazol-4-yl)acetamido)-7-oxo-4-thia-1-azabicyclo[3.2.0]heptane-3-carboxylate (300 mg) was added to the reaction mixture, and the reaction mixture was stirred at room temperature for 3 hours. The reaction mixture was added to a mixture of ethyl acetate (30 mL) and water (30 mL). The organic layer was separated and dehydrated and dried over anhydrous sodium sulfate. The solvent was distilled away under reduced pressure, thereby obtaining a target substance (340 mg) as yellow solids.

Example 63 (2)

DMAC (3.1 mL) was added to the compound (309 mg) obtained in Example 63 (1), and the mixture was stirred under ice cooling. At the same temperature, N-(2-aminoethyl)-2-chloro-3,4-bis((4-methoxybenzyl)oxy)benzamide (158 mg), HOBt (51 mg), EDC (71 mg), and NMM (81 μL) were sequentially added to the reaction mixture. The reaction mixture was stirred at room temperature overnight. At room temperature, the reaction mixture was added to a mixture of ethyl acetate (20 mL) and water (20 mL), and 1 mol/L hydrochloric acid was added thereto such that the pH was adjusted to 5.4. The organic layer was separated, and the aqueous layer was extracted three times by using ethyl acetate (5 mL). The organic layers were combined, sequentially washed with water and a saturated aqueous sodium chloride solution, and then dehydrated and dried over anhydrous sodium sulfate. The solvent was distilled away under reduced pressure, thereby obtaining benzhydryl (3R,5R,6R)-6-((Z)-2-(((1-(tert-butoxy)-2-methyl-1-oxopropan-2-yl)oxy)imino)-2-(2-((tert-butoxycarbonyl)amino)thiazol-4-yl)acetamido)-3-(3-(((E)-2-((2-(2-chloro-3,4-bis((4-methoxybenzyl)oxy)benzamido)ethyl)amino)-2-oxoethylidene)amino)-2-oxoimidazolidin-1-yl)-7-oxo-4-thia-1-azabicyclo[3.2.0]heptane-3-carboxylate (336 mg) as light yellow solids.

NMR (CDCl$_3$): 1.39 (9H, s), 1.51 (3H, s), 1.52 (3H, s), 1.54 (9H, s), 3.50 (1H, d, J=13.6 Hz), 3.55-3.69 (8H, m), 3.80 (3H, s), 3.83 (3H, s), 4.93 (2H, s), 5.06 (2H, s), 5.14 (1H, d, J=13.6 Hz), 5.60 (1H, d, J=4.0 Hz), 5.75 (1H, dd, J=7.8, 3.8 Hz), 6.77-6.85 (7H, m), 6.86 (1H, s), 6.86-6.94 (6H, m), 7.04-7.10 (1H, m), 7.21-7.45 (12H, m)

Example 63 (3)

Dichloromethane (3.4 mL) was added to the compound (168 mg) obtained in Example 63 (2), and the mixture was stirred at a temperature equal to or lower than −20° C. At the same temperature, anisole (799 μL) and aluminum chloride (244 mg) were sequentially added to the reaction mixture. The reaction mixture was stirred at a temperature equal to or lower than −20° C. for 30 minutes. The reaction mixture was added to a mixture of acetonitrile (10 mL), water (10 mL), and trisodium citrate dihydrate (809 mg) under ice cooling. A saturated aqueous sodium hydrogen carbonate solution was added to the reaction mixture such that the pH was adjusted to 5.2, and the aqueous layer was separated. The aqueous layer was concentrated under reduced pressure, and the residue was purified by medium-pressure reverse-phase silica gel column chromatography [eluent; water:acetonitrile=100:0→75:25]. The aqueous solution containing a target substance was lyophilized, thereby obtaining (3R,5R,6R)-6-((Z)-2-(2-aminothiazol-4-yl)-2-(((2-carboxypropan-2-yl)oxy)imino)acetamido)-3-(3-(((E)-2-((2-(2-chloro-3,4-dihydroxybenzamido)ethyl)amino)-2-oxoethylidene)amino)-2-oxoimidazolidin-1-yl)-7-oxo-4-thia-1-azabicyclo[3.2.0]heptane-3-carboxylate (20.5 mg) as white solids.

NMR: 1.49 (3H, s), 1.51 (3H, s), 3.55 (1H, d, J=13.6 Hz), 3.54-3.61 (4H, m), 3.76-3.84 (2H, m), 3.86-3.95 (2H, m), 4.73 (1H, d, J=12.8 Hz), 5.70 (1H, d, J=3.6 Hz), 5.75 (1H, d, J=3.6 Hz), 6.86-6.95 (3H, m), 7.04 (1H, s)

MS: 811.05 [M+H]$^+$, 809.30 [M−H]$^−$

Example 64

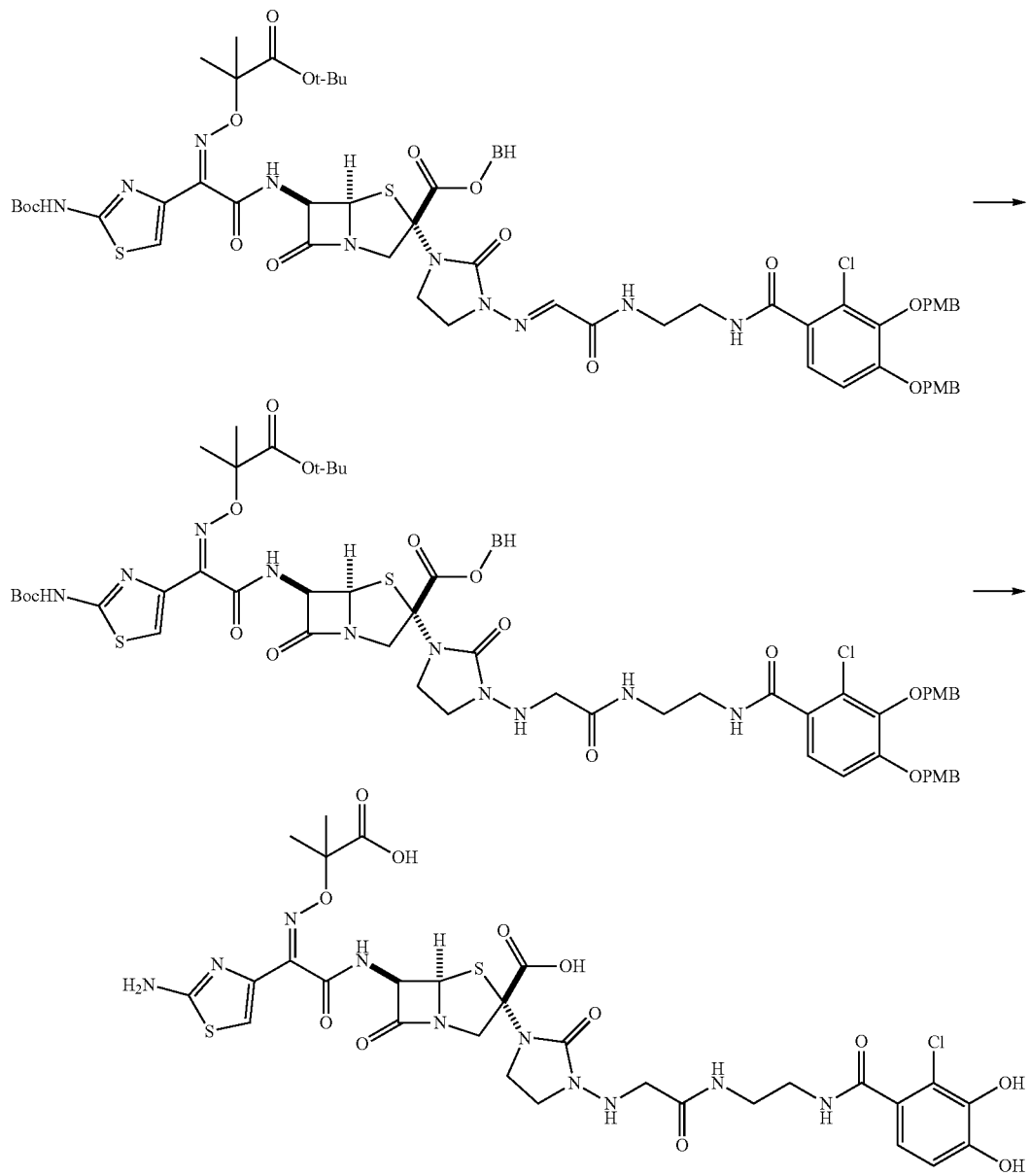

Example 64 (1)

Dichloromethane (3.4 mL) was added to benzhydryl (3R,5R,6R)-6-((Z)-2-(((1-(tert-butoxy)-2-methyl-1-oxopropan-2-yl)oxy)imino)-2-(2-((tert-butoxycarbonyl)amino)thiazol-4-yl)acetamido)-3-(3-(((E)-2-((2-(2-chloro-3,4-bis((4-methoxybenzyl)oxy)benzamido)ethyl)amino)-2-oxoethylidene)amino)-2-oxoimidazolidin-1-yl)-7-oxo-4-thia-1-azabicyclo[3.2.0]heptane-3-carboxylate (168 mg), and the mixture was stirred under ice cooling. At the same temperature, a 85% borane-2-picoline complex (19 mg) and p-toluenesulfonic acid monohydrate (47 mg) were sequentially added to the reaction mixture, and the reaction mixture was stirred at room temperature for 3 hours and 30 minutes. The reaction mixture was ice-cooled, and a 85% borane-2-picoline complex (12 mg) and p-toluenesulfonic acid monohydrate (23 mg) were sequentially added thereto, and the reaction mixture was stirred at room temperature overnight. At room temperature, the reaction mixture was added to a mixture of ethyl acetate (15 mL) and water (15 mL), and a saturated aqueous sodium hydrogen carbonate solution was added thereto such that the pH was adjusted to 4.6. The organic layer was separated, and the aqueous layer was extracted three times by using ethyl acetate. The organic layers were combined, sequentially washed with water and a saturated aqueous sodium chloride solution, and then dehydrated and dried over anhydrous sodium sulfate. The solvent was distilled away under reduced pressure, and the residue was purified by silica gel column chromatography [eluent; chloroform: 2-propanol=100:0→93:7], thereby obtaining a target substance (101 mg) as yellow solids.

Example 64 (2)

Dichloromethane (2.0 mL) was added to the compound (101 mg) obtained in Example 64 (1), and the mixture was stirred at a temperature equal to or lower than −20° C. At the same temperature, anisole (480 µL) and aluminum chloride (147 mg) were sequentially added to the reaction mixture. The reaction mixture was stirred at a temperature equal to or lower than −20° C. for 30 minutes. The reaction mixture was added to a mixture of acetonitrile (6 mL), water (6 mL), and trisodium citrate dihydrate (486 mg) under ice cooling. A saturated aqueous sodium hydrogen carbonate solution was added to the reaction mixture such that the pH was adjusted to 5.1, and the aqueous layer was separated. The aqueous layer was concentrated under reduced pressure, and the residue was purified by medium-pressure reverse-phase silica gel column chromatography [eluent; water:acetonitrile=100:0→80:20]. The aqueous solution containing a target substance was lyophilized, thereby obtaining (3R,5R,6R)-6-((Z)-2-(2-aminothiazol-4-yl)-2-(((2-carboxypropan-2-yl)oxy)imino)acetamido)-3-(3-((-2-((2-(2-chloro-3,4-dihydroxybenzamido)ethyl)amino)-2-oxoethyl)amino)-2-oxoimidazolidin-1-yl)-7-oxo-4-thia-1-azabicyclo[3.2.0]heptane-3-carboxylate (1.7 mg) as light yellow solids.

NMR: 1.47 (3H, s), 1.49 (3H, s), 3.14 (1H, d, J=13.2 Hz), 3.58 (2H, s), 3.34-3.65 (8H, m), 4.40 (1H, d, J=12.8 Hz), 5.38 (1H, d, J=3.6 Hz), 5.68 (1H, d, J=3.6 Hz), 6.90 (1H, d, J=8.0 Hz), 6.93 (1H, d, J=8.0 Hz), 6.99 (1H, s)

MS: 813.10 [M+H]⁺, 810.90 [M−H]⁻

Example 65

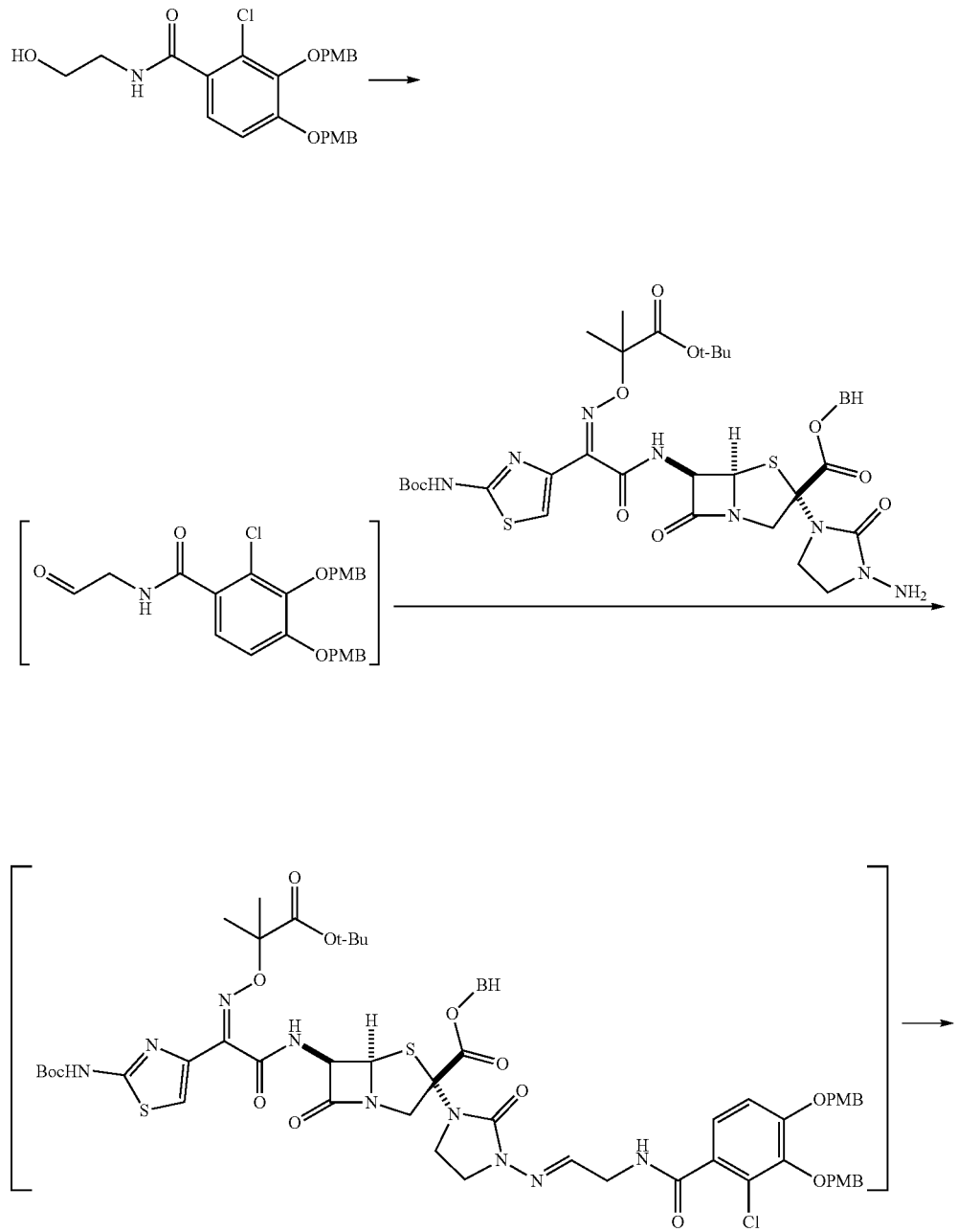

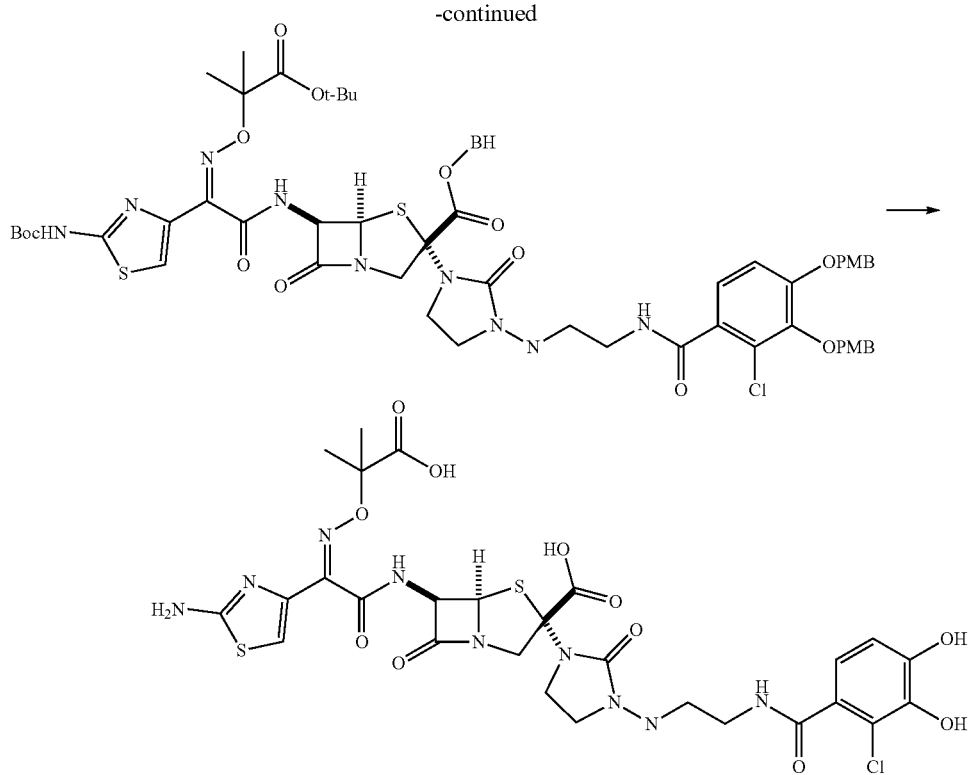

Example 65 (1)

Dichloromethane (3.6 mL) was added to 2-chloro-N-(2-hydroxyethyl)-3,4-bis ((4-methoxybenzyl)oxy)benzamide (0.36 g), and the mixture was stirred under ice cooling. Dess-Martin periodinane (0.65 g) was added to the reaction mixture, and the reaction mixture was stirred at room temperature for 1 hour. Dichloromethane (10 mL), water (5 mL), and a 1 mol/L aqueous sodium thiosulfate solution (5 mL) were sequentially added to the reaction mixture, and the organic layer was separated. The organic layer was washed with a saturated aqueous sodium chloride solution and dehydrated and dried over anhydrous sodium sulfate. The solvent was distilled away under reduced pressure, dichloromethane (10 mL) and benzhydryl (3R,5R,6R)-3-(3-amino-2-oxoimidazolidin-1-yl)-6-((Z)-2-(((1-(tert-butoxy)-2-methyl-1-oxopropan-2-yl)oxy)imino)-2-(2-((tert-butoxycarbonyl)amino)thiazol-4-yl)acetamido)-7-oxo-4-thia-1-azabicyclo[3.2.0]heptane-3-carboxylate (0.50 g) were added to the residue, and the mixture was stirred at room temperature for 1 hour. The reaction mixture was ice-cooled, and a 85% borane-2-picoline complex (91 mg) and p-toluenesulfonic acid monohydrate (220 mg) were sequentially added to the reaction mixture, and the reaction mixture was stirred at room temperature for 1 hour. At room temperature, dichloromethane (5 mL) and water (10 mL) were added to the reaction mixture, and a saturated aqueous sodium hydrogen carbonate solution was added thereto such that the pH was adjusted to 3.5. The organic layer was separated, washed with a saturated aqueous sodium chloride solution, and then dehydrated and dried over anhydrous sodium sulfate. The solvent was distilled away under reduced pressure, and the residue was purified by silica gel column chromatography [eluent; ethyl acetate:hexane=70:30→100:0], thereby obtaining benzhydryl (3R,5R,6R)-6-((Z)-2-(((1-(tert-butoxy)-2-methyl-1-oxopropan-2-yl)oxy)imino)-2-(2-((tert-butoxycarbonyl)amino)thiazol-4-yl)acetamido)-3-(3-((2-(2-chloro-3,4-bis((4-methoxybenzyl)oxy)benzamido)ethyl)amino)-2-oxoimidazolidin-1-yl)-7-oxo-4-thia-1-azabicyclo[3.2.0]heptane-3-carboxylate (625 mg) as a yellow oily substance.

NMR (CDCl$_3$): 1.37 (9H, s), 1.44-1.56 (15H, m), 2.86-3.04 (2H, m), 3.15-3.29 (1H, m), 3.48-3.52 (6H, m), 3.53-3.62 (1H, m), 3.80 (3H, s), 3.83 (3H, s), 4.23-4.33 (1H, m), 4.92 (1H, d, J=13.2 Hz), 4.95 (2H, s), 5.08 (2H, s), 5.56 (1H, d, J=3.6 Hz), 5.79 (1H, dd, J=8.4, 3.6 Hz), 6.80-6.87 (4H, m), 6.89-6.96 (4H, m), 7.13-7.29 (13H, m), 7.49 (1H, d, J=8.4 Hz), 8.17 (1H, s)

Example 65 (2)

Dichloromethane (12.5 mL) was added to benzhydryl (3R,5R,6R)-6-((Z)-2-(((1-(tert-butoxy)-2-methyl-1-oxopropan-2-yl)oxy)imino)-2-(2-((tert-butoxycarbonyl)amino)thiazol-4-yl)acetamido)-3-(3-((2-(2-chloro-3,4-bis((4-methoxybenzyl)oxy)benzamido)ethyl)amino)-2-oxoimidazolidin-1-yl)-7-oxo-4-thia-1-azabicyclo[3.2.0]heptane-3-carboxylate (625 mg), and the mixture was stirred at a temperature equal to or lower than −20° C. At the same temperature, anisole (3.1 mL) and aluminum chloride (0.95 g) were sequentially added to the reaction mixture. The reaction mixture was stirred at a temperature equal to or lower than −20° C. for 1 hour. The reaction mixture was added to a mixture of acetonitrile (30 mL), water (20 mL), and trisodium citrate dihydrate (3.14 g) under ice cooling. A saturated aqueous sodium hydrogen carbonate solution was added to the reaction mixture such that the pH was adjusted to 5.2, and the aqueous layer was separated. The aqueous layer was concentrated under reduced pressure, and the residue was purified by medium-pressure reverse-phase silica gel column chromatography [eluent; water:acetonitrile=100:0→85:15]. The aqueous solution containing a target substance was lyophilized, thereby obtaining (3R,5R,6R)-6-((Z)-2-(2-aminothiazol-4-yl)-2-(((2-carboxypropan-2-yl)oxy)imino)acetamido)-3-(3-((2-(2-chloro-3,4-dihydroxybenzamido)ethyl)amino)-2-oxoimidazolidin-1-yl)-7-oxo-4-thia-1-azabicyclo[3.2.0]heptane-3-carboxylate (112.5 mg) as white solids.

NMR: 1.47 (3H, s), 1.49 (3H, s), 3.05-3.19 (2H, m), 3.30 (1H, d, J=12.8 Hz), 3.43-3.66 (6H, m), 4.47 (1H, d, J=12.8 Hz), 5.52 (1H, d, J=3.6 Hz), 5.72 (1H, d, J=3.6 Hz), 6.90 (1H, d, J=8.0 Hz), 7.01 (1H, d, J=8.0 Hz), 7.02 (1H, s)

MS: 756.05 [M+H]$^+$, 754.10 [M–H]$^-$

Example 66

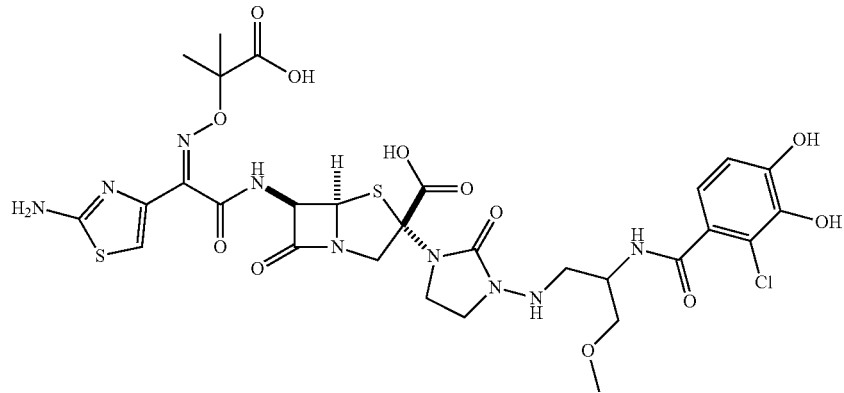

In the same manner as in Example 65, (3R,5R,6R)-6-((Z)-2-(2-aminothiazol-4-yl)-2-(((2-carboxypropan-2-yl)oxy)imino)acetamido)-3-(3-((2-(2-chloro-3,4-dihydroxybenzamido)-3-methoxypropyl)amino)-2-oxoimidazolidin-1-yl)-7-oxo-4-thia-1-azabicyclo[3.2.0]heptane-3-carboxylate was obtained.

NMR: 1.47 (3H, s), 1.49 (3H, s), 3.06-3.20 (2H, m), 3.24 (1H, d, J=11.6 Hz), 3.38-3.75 (6H, m), 3.43 (3H, s), 4.26-4.38 (1H, m), 4.46 [4.48](1H, d, J=12.8 Hz), 5.52 [5.55](1H, d, J=3.6 Hz), 5.69-5.76 (1H, m), 6.91 (1H, d, J=8.4 Hz), 6.99-7.06 (2H, m)

MS: 800.10 [M+H]$^+$, 797.95 [M–H]$^-$

Example 67

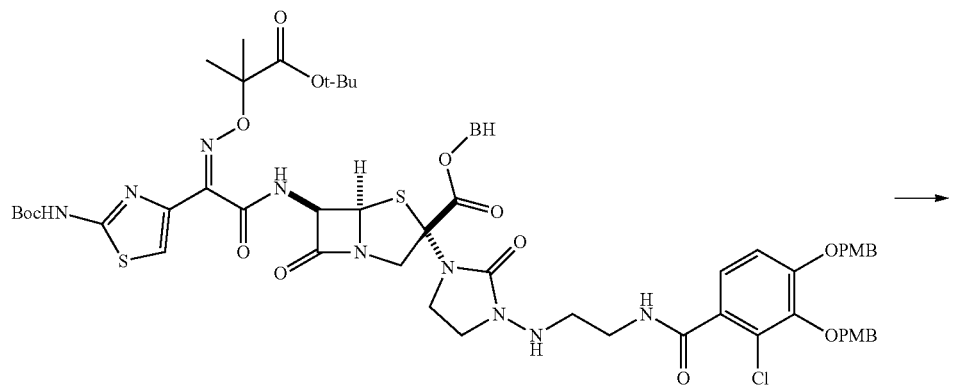

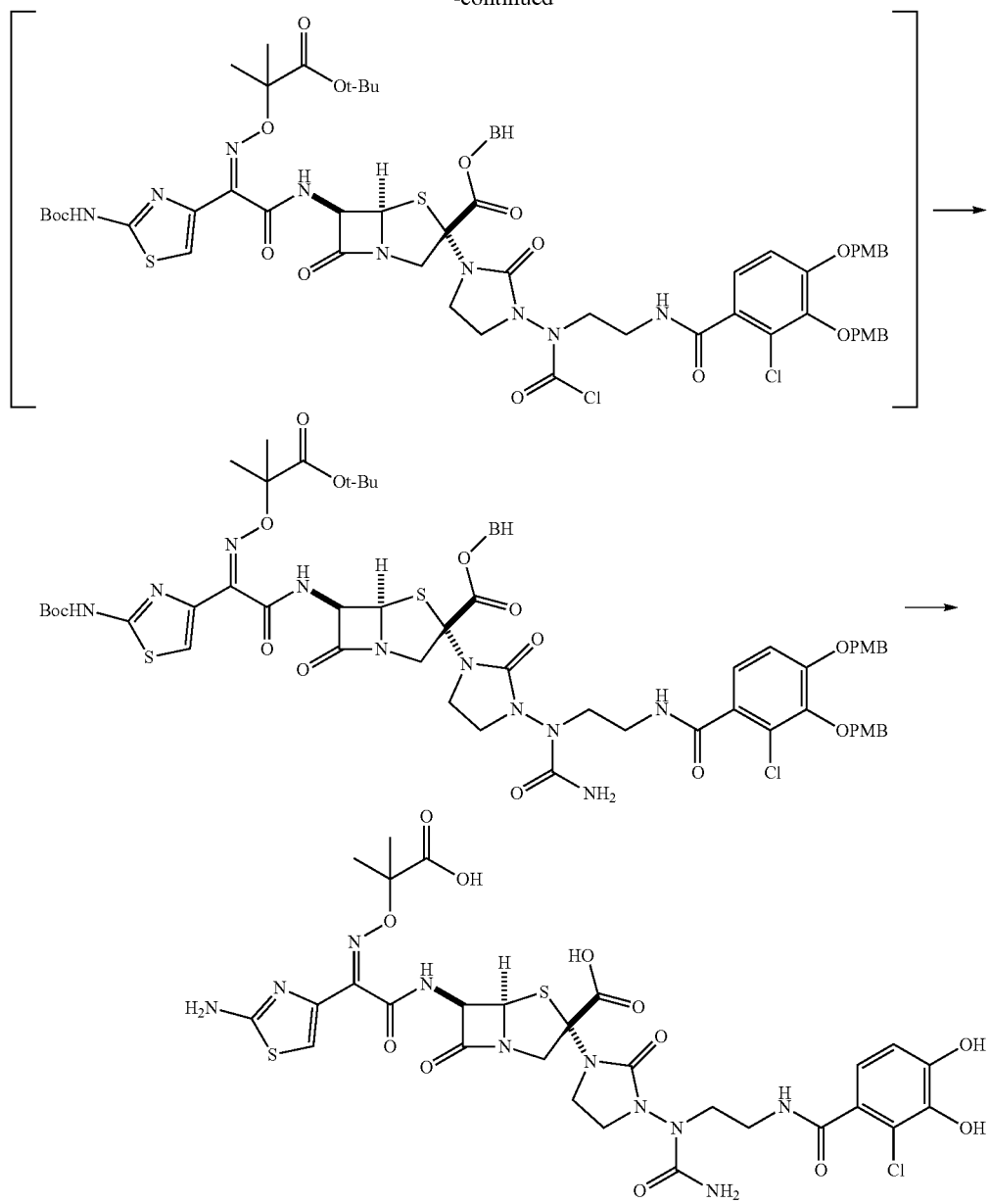

Example 67 (1)

Dichloromethane (2.2 mL) was added to benzhydryl (3R,5R,6R)-6-((Z)-2-(((1-(tert-butoxy)-2-methyl-1-oxopropan-2-yl)oxy)imino)-2-(2-(((tert-butoxycarbonyl)amino)thiazol-4-yl)acetamido)-3-(3-((2-(2-chloro-3,4-bis((4-methoxybenzyl)oxy)benzamido)ethyl)amino)-2-oxoimidazolidin-1-yl)-7-oxo-4-thia-1-azabicyclo[3.2.0]heptane-3-carboxylate (0.22 g), and the mixture was stirred under ice cooling. At the same temperature, triphosgene (20 mg) and N,N-diisopropylethylamine (35 µL) were sequentially added to the reaction mixture, and the reaction mixture was stirred at room temperature for 1 hour 30 minutes. At room temperature, ammonium chloride (13 mg) and triethylamine (46 µL) were added to the reaction mixture, and the reaction mixture was stirred for 1 hour. The reaction mixture was added to a mixture of ethyl acetate (10 mL), water (10 mL), and 1 mol/L hydrochloric acid (2 mL). The organic layer was separated, washed with a 5% aqueous sodium chloride solution, and then dehydrated and dried over anhydrous sodium sulfate. The solvent was distilled away under reduced pressure, and the residue was purified by silica gel column chromatography [eluent; ethyl acetate:hexane=100:0→chloroform: 2-propanol=90:10], thereby obtaining a target substance (99 mg) as a light brown oily substance.

Example 67 (2)

Dichloromethane (2 mL) was added to the compound (100 mg) obtained in Example 67 (1), and the mixture was stirred at a temperature equal to or lower than −20° C. At the same temperature, anisole (480 µL) and aluminum chloride (147 mg) were sequentially added to the reaction mixture. The reaction mixture was stirred at a temperature equal to or lower than −20° C. for 1 hour. The reaction mixture was added to a mixture of acetonitrile (10 mL), water (5 mL), and trisodium citrate dihydrate (486 mg) under ice cooling. A saturated aqueous sodium hydrogen carbonate solution was added to the reaction mixture such that the pH was adjusted to 5.1, and the aqueous layer was separated. The aqueous layer was concentrated under reduced pressure, and the residue was purified by medium-pressure reverse-phase silica gel column chromatography [eluent; water:acetonitrile=100:0→85:15]. The aqueous solution containing a target substance was lyophilized, thereby obtaining (3R,5R,6R)-6-((Z)-2-(2-aminothiazol-4-yl)-2-(((2-carboxypropan-2-yl)oxy)imino)acetamido)-3-(3-(1-(2-(2-chloro-3,4-dihydroxybenzamido)ethyl)ureido)-2-oxoimidazolidin-1-yl)-7-oxo-4-thia-1-azabicyclo[3.2.0]heptane-3-carboxylate (2.8 mg) as white solids.

NMR: 1.44-1.52 (6H, m), 3.32 (1H, d, J=12.4 Hz), 3.39-3.99 (8H, m), 4.41-4.51 (1H, m), 5.50 (1H, dd, J=6.0, 3.6 Hz), 5.68-5.73 (1H, m), 6.88-6.94 (1H, m), 6.97-7.06 (2H, m)

MS: 799.05 [M+H]$^+$, 796.90 [M−H]$^-$

Example 68

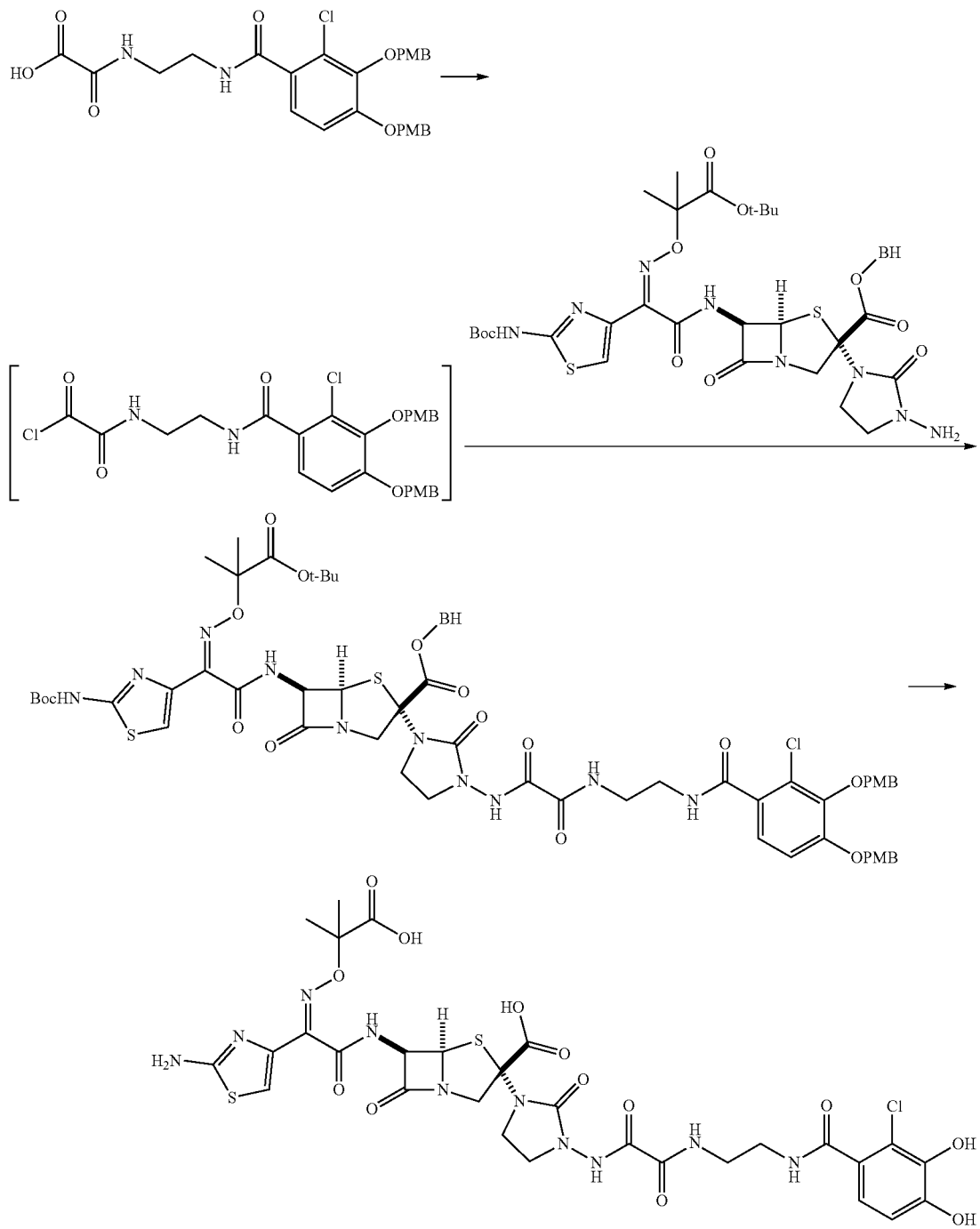

Example 68 (1)

Dichloromethane (1.3 mL) was added to the compound (70 mg) obtained in Reference Example 17, and the mixture was stirred under ice cooling. At the same temperature, oxalyl dichloride (13 µL) and DMF (7 µL) were sequentially added to the reaction mixture, and the reaction mixture was stirred for 1 hour. At the same temperature, oxalyl dichloride (7 µL) and DMF (3 µL) were sequentially added to the reaction mixture, and the reaction mixture was stirred for 1 hour, thereby obtaining a dichloromethane mixture containing the corresponding acid chloride.

THF (2.8 mL) and water (2.8 mL) were added to benzhydryl (3R,5R,6R)-3-(3-amino-2-oxoimidazolidin-1-yl)-6-((Z)-2-(((1-(tert-butoxy)-2-methyl-1-oxopropan-2-yl)oxy)imino)-2-(2-((tert-butoxycarbonyl)amino)thiazol-4-yl)acetamido)-7-oxo-4-thia-1-azabicyclo[3.2.0]heptane-3-carboxylate (111 mg), and the mixture was stirred under ice cooling. At the same temperature, sodium hydrogen carbonate (33 mg) was added to the reaction mixture. Then, at the same temperature, the prepared dichloromethane mixture containing the acid chloride was added dropwise to the reaction mixture. The reaction mixture was stirred at the same temperature for 15 minutes. Ethyl acetate (10 mL) and water (10 mL) were added to the reaction mixture, and the organic layer was separated. The organic layer was washed with a saturated aqueous sodium chloride solution and dehydrated and dried over anhydrous sodium sulfate. The solvent was distilled away under reduced pressure, thereby obtaining a target substance (179 mg) as yellow solids.

Example 68 (2)

Dichloromethane (3.6 mL) was added to the compound (179 mg) obtained in Example 68 (1), and the mixture was stirred at a temperature equal to or lower than −20° C. At the same temperature, anisole (841 µL) and aluminum chloride (258 mg) were sequentially added to the reaction mixture. The reaction mixture was stirred at a temperature equal to or lower than −20° C. for 30 minutes. The reaction mixture was added to a mixture of acetonitrile (11 mL), water (11 mL), and trisodium citrate dihydrate (852 mg) under ice cooling. A saturated aqueous sodium hydrogen carbonate solution was added to the reaction mixture such that the pH was adjusted to 5.1, and the aqueous layer was separated. The aqueous layer was concentrated under reduced pressure, and the residue was purified by medium-pressure reverse-phase silica gel column chromatography [eluent; water: acetonitrile=100:0→90:10]. The aqueous solution containing a target substance was lyophilized, thereby obtaining (3R,5R,6R)-6-((Z)-2-(2-aminothiazol-4-yl)-2-(((2-carboxypropan-2-yl)oxy)imino)acetamido)-3-(3-(2-((2-(2-chloro-3,4-dihydroxybenzamido)ethyl)amino)-2-oxoacetamido)-2-oxoimidazolidin-1-yl)-7-oxo-4-thia-1-azabicyclo[3.2.0]heptane-3-carboxylate (29.1 mg) as white solids.

NMR: 1.48 (3H, s), 1.50 (3H, s), 3.54-3.62 (5H, m), 3.62-3.67 (2H, m), 3.69-3.79 (2H, m), 4.65 (1H, d, J=12.4 Hz), 5.69 (1H, d, J=3.6 Hz), 5.75 (1H, d, J=3.2 Hz), 6.90 (1H, d, J=8.4 Hz), 6.94 (1H, d, J=8.0 Hz), 7.03 (1H, s)

MS: 827.10 [M+H]$^+$, 825.30 [M−H]$^−$

Example 69

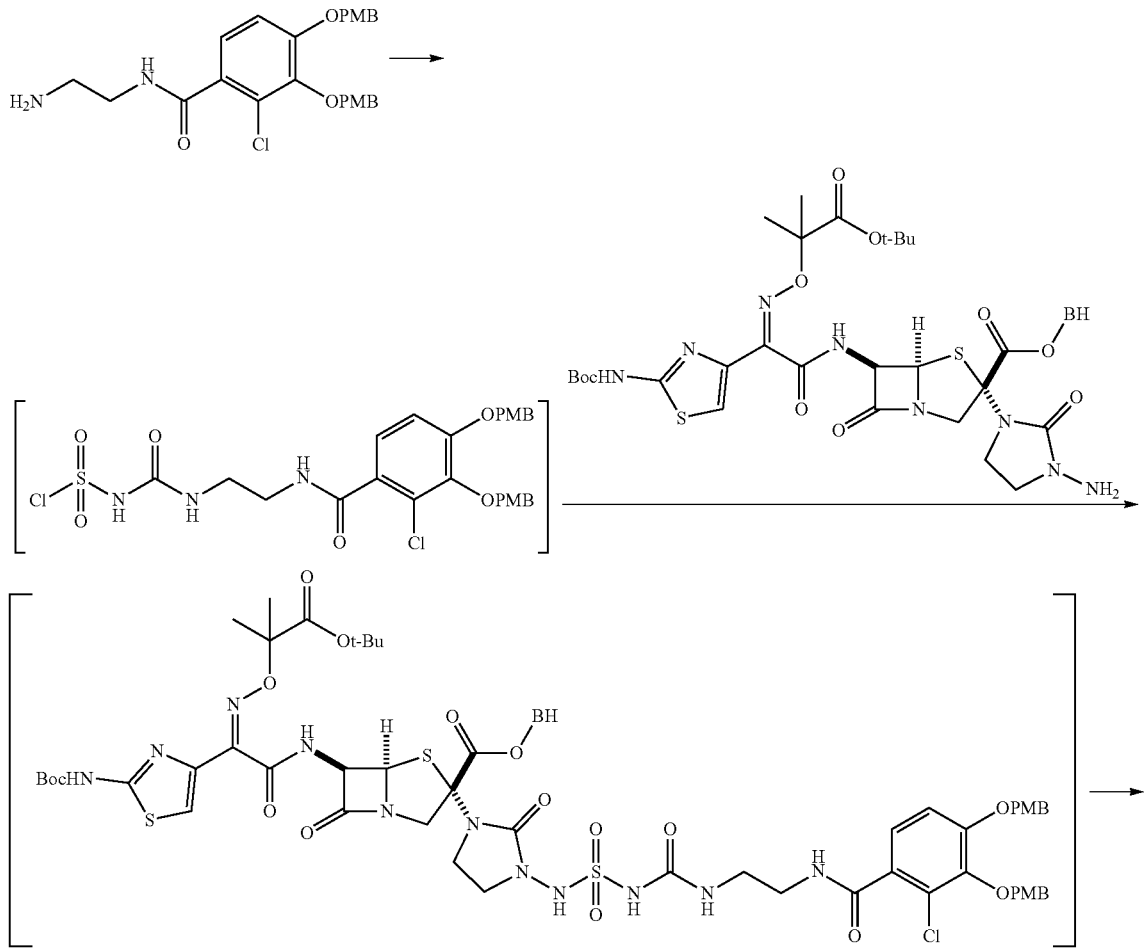

-continued

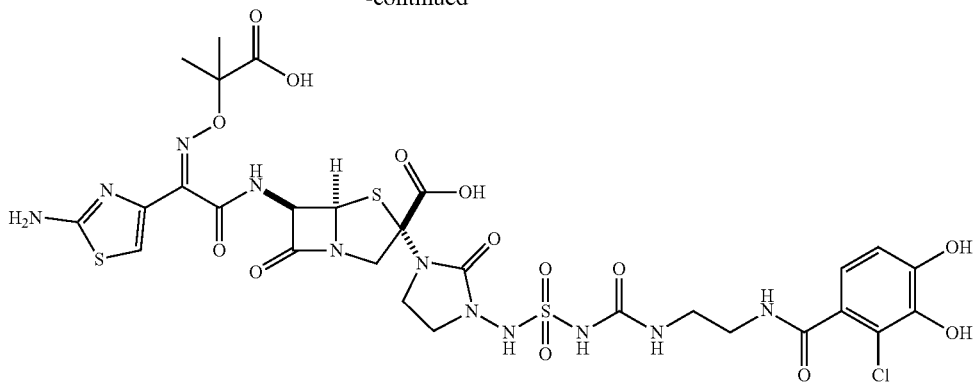

Example 69

Dichloromethane (1.9 mL) was added to N-(2-aminoethyl)-2-chloro-3,4-bis ((4-methoxybenzyl)oxy)benzamide (90 mg), and the mixture was stirred under ice cooling. At the same temperature, chlorosulfonyl isocyanate (17 μL) was added to the reaction mixture, and the reaction mixture was stirred at the same temperature for 40 minutes. At the same temperature, benzhydryl (3R,5R,6R)-3-(3-amino-2-oxoimidazolidin-1-yl)-6-((Z)-2-(((1-(tert-butoxy)-2-methyl-1-oxopropan-2-yl)oxy)imino)-2-(2-((tert-butoxycarbonyl)amino)thiazol-4-yl)acetamido)-7-oxo-4-thia-1-azabicyclo[3.2.0]heptane-3-carboxylate (150 mg) and N,N-diisopropylethylamine (36 μL) were sequentially added to the reaction mixture, and the reaction mixture was stirred for 2 hours. At the same temperature, anisole (1.1 mL) and aluminum chloride (347 mg) were sequentially added to the reaction mixture, and the reaction mixture was stirred for 30 minutes. At the same temperature, the reaction mixture was added to a mixture of acetonitrile (20 mL), water (15 mL), and trisodium citrate dihydrate (1.15 g). A saturated aqueous sodium hydrogen carbonate solution was added to the reaction mixture such that the pH was adjusted to 5.3, and the aqueous layer was separated. The aqueous layer was concentrated under reduced pressure, and the residue was purified by medium-pressure reverse-phase silica gel column chromatography [eluent; water:acetonitrile=100:0→85:15]. The aqueous solution containing a target substance was lyophilized, thereby obtaining (3R,5R,6R)-6-((Z)-2-(2-aminothiazol-4-yl)-2-(((2-carboxypropan-2-yl)oxy)imino)acetamido)-3-(3-((N-((2-(2-chloro-3,4-dihydroxybenzamido)ethyl)carbamoyl)sulfamoyl)amino)-2-oxoimidazolidin-1-yl)-7-oxo-4-thia-1-azabicyclo[3.2.0]heptane-3-carboxylate as white solids.

MS: 878.00 [M+H]$^+$, 875.90 [M−H]$^−$

Example 70

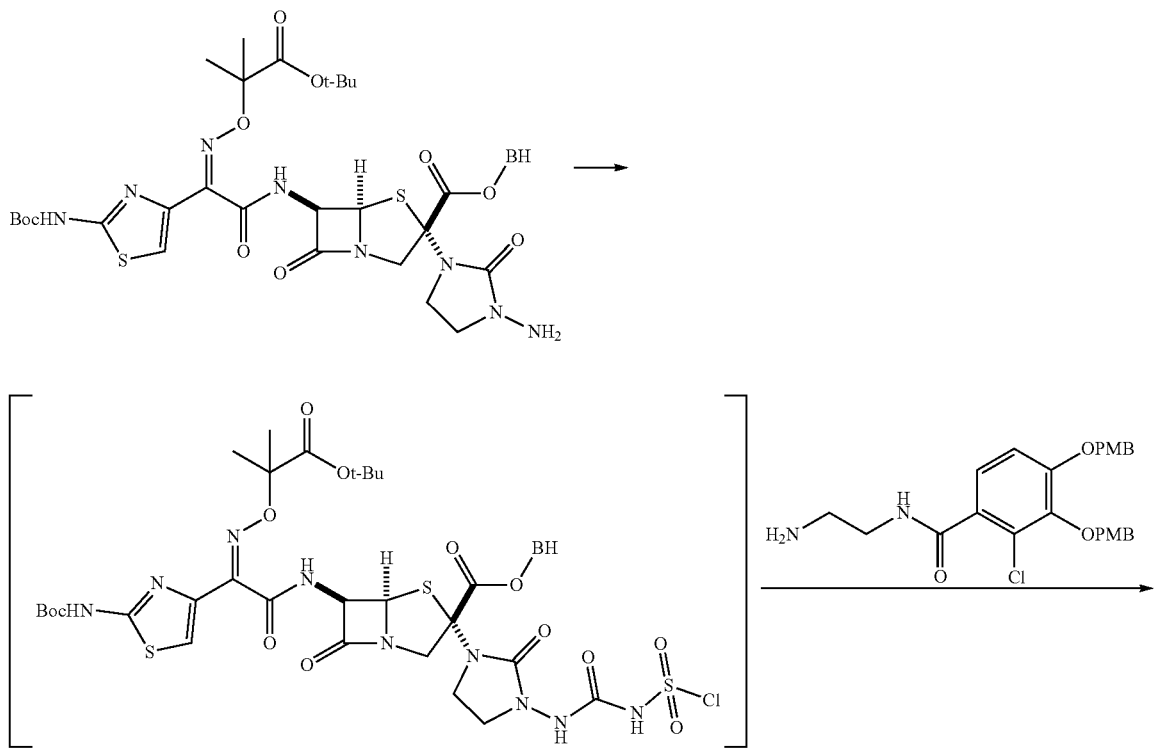

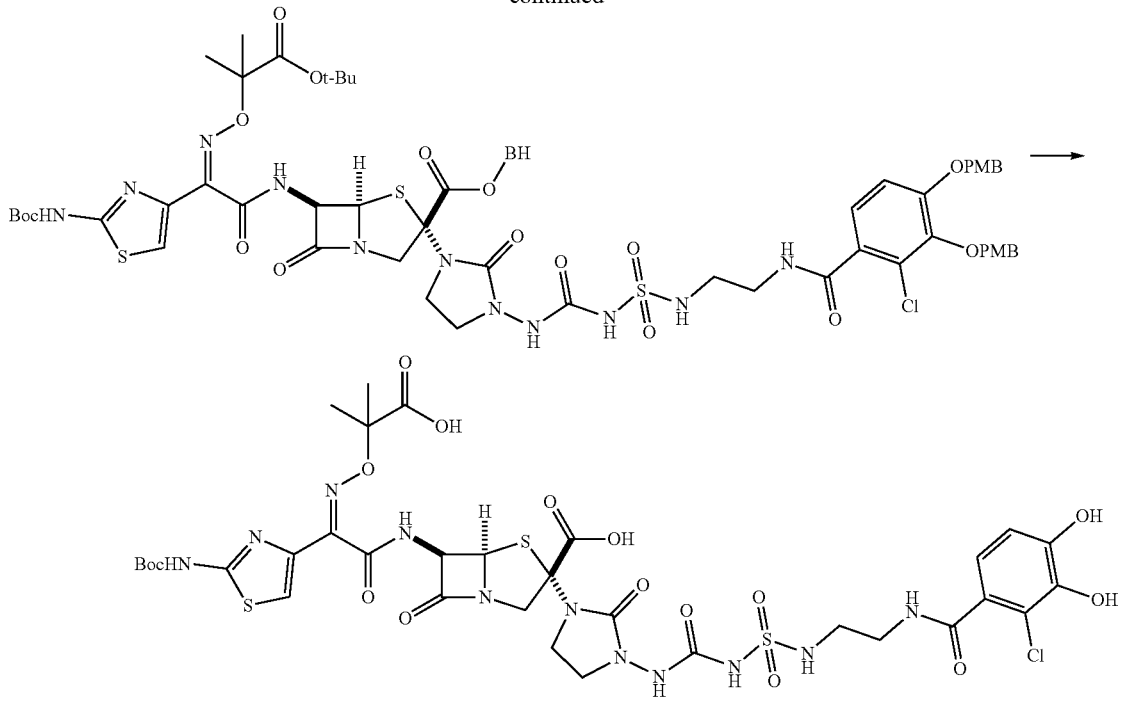

Example 70

Dichloromethane (1.7 mL) was added to benzhydryl (3R,5R,6R)-3-(3-amino-2-oxoimidazolidin-1-yl)-6-((Z)-2-(((1-(tert-butoxy)-2-methyl-1-oxopropan-2-yl)oxy)imino)-2-(2-((tert-butoxycarbonyl)amino)thiazol-4-yl)acetamido)-7-oxo-4-thia-1-azabicyclo[3.2.0]heptane-3-carboxylate (150 mg), and the mixture was stirred under ice cooling. At the same temperature, chlorosulfonyl isocyanate (15 μL) was added to the reaction mixture, and the reaction mixture was stirred at the same temperature for 40 minutes. At the same temperature, N-(2-aminoethyl)-2-chloro-3,4-bis((4-methoxybenzyl)oxy)benzamide (82 mg) and N,N-diisopropylethylamine (36 μL) were sequentially added to the reaction mixture, and the reaction mixture was stirred for 2 hours. At the same temperature, anisole (1.1 mL) and aluminum chloride (347 mg) were sequentially added to the reaction mixture, and the reaction mixture was stirred for 30 minutes. At the same temperature, the reaction mixture was added to a mixture of acetonitrile (20 mL), water (15 mL), and trisodium citrate dihydrate (1.15 g). A saturated aqueous sodium hydrogen carbonate solution was added to the reaction mixture such that the pH was adjusted to 5.3, and the aqueous layer was separated. The aqueous layer was concentrated under reduced pressure, and the residue was purified by medium-pressure reverse-phase silica gel column chromatography [eluent; water:acetonitrile=100:0→85:15]. The aqueous solution containing a target substance was lyophilized, thereby obtaining (3R,5R,6R)-6-((Z)-2-(2-aminothiazol-4-yl)-2-(((2-carboxypropan-2-yl)oxy)imino)acetamido)-3-(3-(3-(N-(2-(2-chloro-3,4-dihydroxybenzamido)ethyl)sulfamoyl)ureido)-2-oxoimidazolidin-1-yl)-7-oxo-4-thia-1-azabicyclo[3.2.0]heptane-3-carboxylate as white solids.

NMR: 1.48 (3H, s), 1.49 (3H, s), 3.23 (2H, t, J=6.2 Hz), 3.32-3.44 (1H, m), 3.49-3.60 (6H, m), 4.51 (1H, d, J=12.8 Hz), 5.58 (1H, d, J=3.6 Hz), 5.71 (1H, d, J=3.2 Hz), 6.92 (1H, d, J=8.0 Hz), 7.02 (1H, s), 7.07 (1H, d, J=8.4 Hz)

MS: 878.05 [M+H]$^+$, 875.90 [M−H]$^−$

Example 71

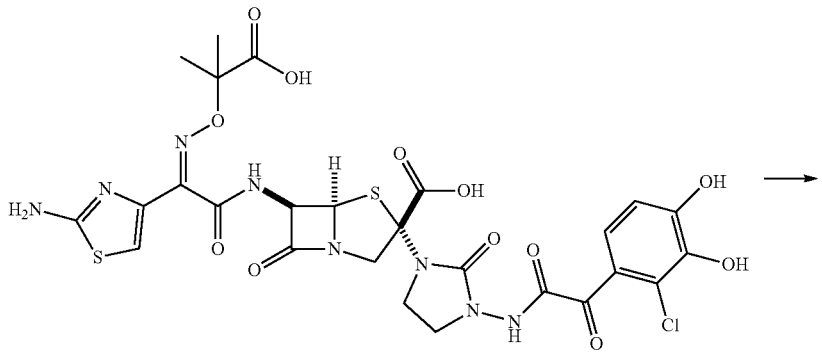

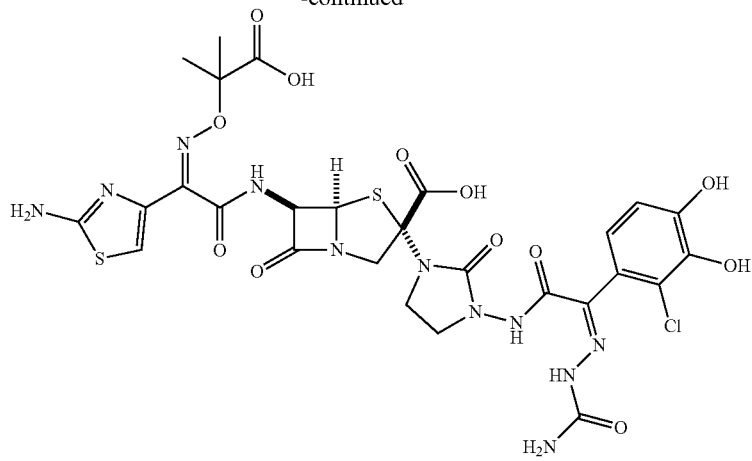

Water (1.0 mL) and semicarbazide hydrochloride (4.5 mg) were added to (3R,5R,6R)-6-((Z)-2-(2-aminothiazol-4-yl)-2-(((2-carboxypropan-2-yl)oxy)imino)acetamido)-3-(3-(2-(2-chloro-3,4-dihydroxyphenyl)-2-oxoacetamido)-2-oxoimidazolidin-1-yl)-7-oxo-4-thia-1-azabicyclo[3.2.0]heptane-3-carboxylate (30 mg), and the mixture was stirred. A saturated aqueous sodium hydrogen carbonate solution was added to the reaction mixture such that the pH was adjusted to 4.6, and the mixture was stirred at room temperature for 6 days. The reaction mixture was purified by medium-pressure reverse-phase silica gel column chromatography [eluent; water:acetonitrile=100:0→85:15]. The aqueous solution containing a target substance was lyophilized, thereby obtaining (3R,5R,6R)-6-((Z)-2-(2-aminothiazol-4-yl)-2-(((2-carboxypropan-2-yl)oxy)imino)acetamido)-3-(3-((Z)-2-(2-carbamoylhydrozono)-2-(2-chloro-3,4-dihydroxyphenyl)acetamido)-2-oxoimidazolidin-1-yl)-7-oxo-4-thia-1-azabicyclo[3.2.0]heptane-3-carboxylate (3.3 mg) as white solids.

NMR: 1.44-1.53 (6H, m), 3.52-3.80 (5H, m), 4.65 (1H, d, J=12.4 Hz), 5.69 (1H, d, J=3.6 Hz), 5.75 (1H, d, J=3.6 Hz), 6.98 (1H, d, J=8.4 Hz), 7.02 (1H, s), 7.07 (1H, d, J=8.4 Hz)

MS: 798.05 [M+H]$^+$, 795.90 [M−H]$^−$

The compounds shown in Table 24 were obtained in the same manner as in Example 1.

TABLE 24

| Example No | Structural Formula | Name |
|---|---|---|
| 72 | | (3R,5R,6R)-6-((Z)-2-(2-aminothiazol-4-yl)-2-(((2-carboxypropan-2-yl)oxy)imino)acetamido)-3-(3-(3-(2-chloro-3,4-dihydroxybenzamido)-2-oxoimidazolidin-1-carboxamido)-2-oxoimidazolidin-1-yl)-7-oxo-4-thia-1-azabicyclo[3.2.0]heptane-3-carboxylate |
| 73 | | (3R,5R,6R)-6-((Z)-2-(2-aminothiazol-4-yl)-2-(((2-carboxypropan-2-yl)oxy)imino)acetamido)-3-(5-((2-chloro-3,4-dihydroxybenzamido)methyl)-2-oxoimidazolidin-3-yl)-7-oxo-4-thia-1-azabicyclo[3.2.0]heptane-3-carboxylate |

TABLE 24-continued

| Example No | Structural Formula | Name |
|---|---|---|
| 74 | | (3R,5R,6R)-6-((Z)-2-(2-aminothiazol-4-yl)-2-(((2-carboxypropan-2-yl)oxy)imino)acetamido)-3-(4-((2-chloro-3,4-dihydroxybenzamido)methyl)-1H-1,2,3-triazol-1-yl)-7-oxo-4-thia-1-azabicyclo[3.2.0]heptane-3-carboxylate |

The measured values of NMR and MS of the compounds in the table are as follows.

Example 72

NMR: 1.49 (3H, s), 1.51 (3H, s), 3.57-3.75 (6H, m), 3.77-3.89 (2H, m), 3.93-4.02 (1H, m), 4.65 (1H, d, J=12.0 Hz), 5.70 (1H, d, J=3.6 Hz), 5.73-5.77 (1H, m), 6.95 (1H, d, J=8.4 Hz), 7.03 (1H, s), 7.15 (1H, d, J=8.4 Hz)

MS: 840.00 [M+H]$^+$, 837.85 [M−H]$^−$

Example 73

NMR: 1.43 (3H, s), 1.44 (3H, s), 3.72-3.89 (4H, m), 3.95-4.03 (1H, m), 4.60 (1H, d, J=12.8 Hz), 4.91-5.00 (1H, m), 5.64 (1H, d, J=3.6 Hz), 5.73 (1H, d, J=3.6 Hz), 6.90 (1H, d, J=8.4 Hz), 6.93 (1H, s), 7.00 (1H, d, J=8.8 Hz)

MS: 728.00 [M+H]$^+$, 726.00 [M−H]$^−$

Example 74

NMR: 1.47 (3H, s), 1.50 (3H, s), 4.10 (1H, dd, J=13.2, 1.2 Hz), 4.65-4.73 (3H, m), 5.59 (1H, d, J=3.6 Hz), 5.81 (1H, dd, J=3.8, 1.0 Hz), 6.91 (1H, d, J=8.4 Hz), 7.01 (1H, s), 7.01 (1H, d, J=8.4 Hz), 7.87 (1H, s)

MS: 710.05 [M+H]$^+$, 708.00 [M−H]$^−$

The compounds shown in Table 25 were obtained in the same manner as in Example 19.

TABLE 25

| Example No | Structural Formula | Name |
|---|---|---|
| 75 | | (3R,5R,6R)-6-((Z)-2-(2-aminothiazol-4-yl)-2-(((2-carboxypropan-2-yl)oxy)imino)acetamido)-3-(3-(2-(2-chloro-3,4-dihydroxyphenyl)-N-methyl-2-oxoacetamido)-2-oxoimidazolidin-1-yl)-7-oxo-4-thia-1-azabicyclo[3.2.0]heptane-3-carboxylate |
| 76 | | (3R,5R,6R)-6-((Z)-2-(2-amino-5-chlorothiazol-4-yl)-2-((1-carboxycyclopropoxy-)imino)acetamido)-3-(3-(2-(2-chloro-3,4-dihydroxyphenyl)-2-oxoacetamido)-2-oxoimidazolidin-1-yl)-7-oxo-4-thia-1-azabicyclo[3.2.0]heptane-3-carboxylate |

TABLE 25-continued

| Example No | Structural Formula | Name |
|---|---|---|
| 77 | | (3R,5R,6R)-6-((Z)-2-(5-amino-1,2,4-thiadiazol-3-yl)-2-((l-carboxycyclopropoxy-)imino)acetamido)-3-(3-(2-(2-chloro-3,4-dihydroxyphenyl)-2-oxoacetamido)-2-oxoimidazolidin-1-yl)-7-oxo-4-thia-1-azabicyclo[3.2.0]heptane-3-carboxylate |
| 78 | | (3R,5R,6R)-6-((Z)-2-(2-amino-5-chlorothiazol-4-yl)-2-((1-carboxycyclobutooxy)imino)acetamido)-3-(3-(2-(2-chloro-3,4-dihydroxyphenyl)-2-oxoacetamido)-2-oxoimidazolidin-1-yl)-7-oxo-4-thia-1-azabicyclo[3.2.0]heptane-3-carboxylate |
| 79 | | (3R,5R,6R)-6-((Z)-2-(5-amino-1,2,4-thiadiazol-3-yl)-2-((1-carboxycyclobutoxy)imino)acetamido)-3-(3-(2-(2-chloro-3,4-dihydroxyphenyl)-2-oxoacetamido)-2-oxoimidazolidin-1-yl)-7-oxo-4-thia-1-azabicyclo[3.2.0]heptane-3-carboxylate |
| 80 | | (3R,5R,6R)-6-((Z)-2-(2-amino-5-methylthiazol-4-yl)-2-(((2-carboxypropan-2-yl)oxy)imino)acetamido)-3-(3-(2-(2-chloro-3,4-dihydroxyphenyl)-2-oxoacetamido)-2-oxoimidazolidin-1-yl)-7-oxo-4-thia-1-azabicyclo[3.2.0]heptane-3-carboxylate |

TABLE 25-continued

| Example No | Structural Formula | Name |
|---|---|---|
| 81 | | (3R,5R,6R)-6-((Z)-2-(2-amino-5-bromothiazol-4-yl)-2-(((2-carboxypropan-2-yl)oxy)imino)acetamido)-3-(3-(2-chloro-3,4-dihydroxyphenyl)-2-oxoacetamido)-2-oxoimidazolidin-1-yl)-7-oxo-4-thia-1-azabicyclo[3.2.0]heptane-3-carboxylate |
| 82 | | (3R,5R,6R)-6-((Z)-2-(2-aminothiazol-4-yl)-2-(((2-carboxypropan-2-yl)oxy)imino)acetamido)-3-(4-(2-(2-chloro-3,4-dihydroxyphenyl)-2-oxoacetamido)-2,5-dioxopiperazin-1-yl)-7-oxo-4-thia-1-azabicyclo[3.2.0]heptane-3-carboxylate |
| 83 | | (3R,5R,6R)-6-((Z)-2-(2-aminothiazol-4-yl)-2-(((2-carboxypropan-2-yl)oxy)imino)acetamido)-3-(3-(2,5-dichloro-3,4-dihydroxybenzamido)-2-oxoimidazolidin-1-yl)-7-oxo-4-thia-1-azabicyclo[3.2.0]heptane-3-carboxylate |
| 84 | | (3R,5R,6R)-6-((Z)-2-(2-aminothiazol-4-yl)-2-(((2-carboxypropan-2-yl)oxy)imino)acetamido)-3-((S)-3-(2-(2-chloro-3,4-dihydroxyphenyl)-2-oxoacetamido)-2-oxopyrrolidin-1-yl)-7-oxo-4-thia-1-azabicyclo[3.2.0]heptane-3-carboxylate |

TABLE 25-continued

| Example No | Structural Formula | Name |
|---|---|---|
| 85 | | (3R,5R,6R)-6-((Z)-2-(2-aminothiazol-4-yl)-2-(((2-carboxypropan-2-yl)oxy)imino)acetamido)-3-((R)-3-(2-(2-chloro-3,4-dihydroxyphenyl)-2-oxoacetamido)-2-oxopyrrolidin-1-yl)-7-oxo-4-thia-1-azabicyclo[3.2.0]heptane-3-carboxylate |
| 86 | | (3R,5R,6R)-6-((Z)-2-(2-aminothiazol-4-yl)-2-(((2-carboxypropan-2-yl)oxy)imino)acetamido)-3-(3-(2-(2-chloro-3,4-dihydroxyphenyl)-2-oxoacetamido)-2-oxotetrahydropyrrolidin-1(2H)-yl)-7-oxo-4-thia-1-azabicyclo[3.2.0]heptane-3-carboxylate |

The measured values of NMR and MS of the compounds in the table are as follows.

Example 75

NMR: 1.49 (3H, s), 1.50 (3H, s), 3.18 (3H, s), 3.20-3.37 (2H, m), 3.44-3.52 (1H, m), 3.59-3.73 (2H, m), 4.29 (1H, d, J=12.8 Hz), 4.99 (1H, d, J=3.6 Hz), 5.71 (1H, d, J=3.2 Hz), 6.94 (1H, d, J=8.8 Hz), 7.04 (1H, s), 7.39 (1H, d, J=8.4 Hz)
MS: 754.95 [M+H]$^+$, 752.95 [M−H]$^−$

Example 76

NMR: 1.22-1.46 (4H, m), 3.64 (1H, d, J=12.8 Hz), 3.67-3.82 (4H, m), 4.66 (1H, d, J=12.8 Hz), 5.67 (1H, d, J=3.6 Hz), 5.79 (1H, d, J=2.8 Hz), 6.87 (1H, d, J=8.8 Hz), 7.44 (1H, d, J=8.4 Hz)
MS: 772.90 [M+H]$^+$, 771.00 [M−H]$^−$

Example 77

NMR: 1.24-1.47 (4H, m), 3.62 (1H, dd, J=13.0, 1.0 Hz), 3.67-3.82 (4H, m), 4.66 (1H, d, J=12.8 Hz), 5.68 (1H, d, J=3.6 Hz), 5.80 (1H, d, J=2.8 Hz), 6.90 (1H, d, J=8.8 Hz), 7.44 (1H, d, J=8.4 Hz)
MS: 739.90 [M+H]$^+$, 737.90 [M−H]$^−$

Example 78

NMR: 1.81-1.93 (1H, m), 2.05-2.10 (1H, m), 2.26-2.40 (2H, m), 2.40-2.50 (1H, m), 2.51-2.61 (1H, m), 3.41-3.47 (1H, m), 3.65 (1H, d, J=12.8 Hz), 3.65-3.81 (3H, m), 4.68 (1H, d, J=12.4 Hz), 5.71 (1H, d, J=2.8 Hz), 5.83 (1H, d, J=3.6 Hz), 6.93 (1H, d, J=8.8 Hz), 7.44 (1H, d, J=8.4 Hz)
MS: 786.95 [M+H]$^+$, 785.15 [M−H]$^−$

Example 79

NMR: 1.85-1.95 (1H, m), 1.98-2.12 (1H, m), 2.28-2.43 (2H, m), 2.44-2.64 (2H, m), 3.41-3.46 (1H, m), 3.63 (1H, d, J=12.8 Hz), 3.67-3.81 (3H, m), 4.68 (1H, d, J=12.8 Hz), 5.72 (1H, d, J=3.6 Hz), 5.84 (1H, d, J=2.8 Hz), 6.95 (1H, d, J=8.4 Hz), 7.44 (1H, d, J=8.4 Hz)
MS: 754.25 [M+H]$^+$, 752.00 [M−H]$^−$

Example 80

NMR: 1.49 (3H, s), 1.50 (3H, s), 2.36 (3H, s), 3.58-3.62 (1H, m), 3.62-3.65 (1H, m), 3.68-3.80 (3H, m), 4.67 (1H, d, J=12.4 Hz), 5.69 (1H, d, J=3.6 Hz), 5.79 (1H, d, J=4.0 Hz), 6.93 (1H, d, J=8.4 Hz), 7.44 (1H, d, J=8.4 Hz)
MS: 755.00 [M+H]$^+$, 753.05 [M−H]$^−$

Example 81

NMR: 1.52 (3H, s), 1.53 (3H, s), 3.64 (1H, d, J=12.4 Hz), 3.69-3.79 (4H, m), 4.67 (1H, d, J=12.4 Hz), 5.69 (1H, d, J=4.0 Hz), 5.80 (1H, d, J=2.8 Hz), 6.94 (1H, d, J=8.4 Hz), 7.44 (1H, d, J=8.8 Hz)
MS: 818.90 [M+H]$^+$, 816.90 [M−H]$^−$

Example 82

NMR: 1.49 (3H, s), 1.50 (3H, s), 3.26 (1H, d, J=11.8 Hz), 4.32-4.62 (4H, m), 5.13 (1H, d, J=12.8 Hz), 5.71 (1H, d, J=3.6 Hz), 5.74 (1H, dd, J=3.6, 0.8 Hz), 6.81 (1H, d, J=8.8 Hz), 7.02 (1H, s), 7.48 (1H, d, J=8.8 Hz)

MS: 769.05 [M+H]$^+$, 767.00 [M−H]$^−$

Example 83

NMR: 1.49 (3H, s), 1.51 (3H, s), 3.64 (1H, d, J=12.8 Hz), 3.70-3.77 (4H, m), 4.68 (1H, d, J=12.8 Hz), 5.71 (1H, d, J=3.6 Hz), 5.76 (1H, d, J=2.8 Hz), 6.97 (1H, s), 7.05 (1H, s)

MS: 746.95 [M+H]$^+$, 745.05 [M−H]$^−$

Example 84

NMR: 1.49 (3H, s), 1.50 (3H, s), 2.14-2.28 (1H, m), 2.56-2.68 (1H, m), 3.40 (1H, dd, J=12.8, 1.2 Hz), 3.74-3.84 (1H, m), 3.84-3.93 (1H, m), 4.69 (1H, t, J=9.4 Hz), 4.87 (1H, d, J=12.8 Hz), 5.69 (1H, d, J=3.6 Hz), 5.72 (1H, dd, J=3.6, 0.8 Hz), 6.92 (1H, d, J=8.4 Hz), 7.03 (1H, s), 7.38 (1H, d, J=8.4 Hz)

MS: 740.05 [M+H]$^+$, 738.10 [M−H]$^−$

Example 85

NMR: 1.48 (3H, s), 1.51 (3H, s), 2.09-2.24 (1H, m), 2.58-2.71 (1H, m), 3.44 (1H, d, J=12.8 Hz), 3.67-3.78 (1H, m), 3.80-3.90 (1H, m), 4.78-4.82 (2H, m), 5.70 (1H, d, J=3.6 Hz), 5.74 (1H, d, J=3.6 Hz), 6.90 (1H, d, J=8.4 Hz), 7.04 (1H, s), 7.39 (1H, d, J=8.8 Hz)

MS: 740.05 [M+H]$^+$, 738.00 [M−H]$^−$

Example 86

NMR: 1.48 (3H, s), 1.50 (3H, s), 2.15-2.34 (2H, m), 3.25 (1H, d, J=12.4 Hz), 3.44-3.53 (1H, m), 3.59-3.71 (2H, m), 3.84-3.96 (1H, m), 4.96 (1H, d, J=12.8 Hz), 5.65 (1H, d, J=3.2 Hz), 5.72 (1H, d, J=2.8 Hz), 6.62 (1H, d, J=8.4 Hz), 7.04 (1H, s), 7.32 (1H, d, J=8.4 Hz)

MS: 755.05 [M+H]$^+$, 752.95 [M−H]$^−$

The compounds shown in Table 26 were obtained in the same manner as in Example 27.

TABLE 26

| Example No | Structural Formula | Name |
|---|---|---|
| 87 | | (3R,5R,6R)-6-((Z)-2-(2-aminothiazol-4-yl)-2-(((2-carboxypropan-2-yl)oxy)imino)acetamido)-3-(3-(2-(2-2-chloro-3,4-dihydroxybenzoyl)hydrazinyl)-2-oxoacetamido)-2-oxoimidazolidin-1-yl)-7-oxo-4-thia-1-azabicyclo[3.2.0]heptane-3-carboxylate |
| 88 | | (3R,5R,6R)-6-((Z)-2-(2-aminothiazol-4-yl)-2-(((2-carboxypropan-2-yl)oxy)imino)acetamido)-3-(3-(2-(2-(2-chloro-3,4-dihydroxyphenyl)-2-oxoacetyl)hydrazinyl)-2-oxoacetamido)-2-oxoimidazolidin-1-yl)-7-oxo-4-thia-1-azabicyclo[3.2.0]heptane-3-carboxylate |
| 89 | | (3R,5R,6R)-6-((Z)-2-(2-amino-5-bromothiazol-4-yl)-2-(((2-carboxypropan-2-yl)oxy)imino)acetamido)-3-(3-(2-(2-(2-chloro-3,4-dihydroxyphenyl)-2-oxoacetyl)hydrazinyl)-2-oxoacetamido)-2-oxoimidazolidin-1-yl)-7-oxo-4-thia-1-azabicyclo[3.2.0]heptane-3-carboxylate |

TABLE 26-continued

| Example No | Structural Formula | Name |
|---|---|---|
| 90 | | (3R,5R,6R)-6-((Z)-2-(2-amino-5-methylthiazol-4-yl)-2-(((2-carboxypropan-2-yl)oxy)imino)acetamido)-3-(3-(2-(2-(2-chloro-3,4-dihydroxyphenyl)-2-oxoacetyl)hydrazinyl)-2-oxoacetamido)-2-oxoimidazolidin-1-yl)-7-oxo-4-thia-1-azabicyclo[3.2.0]heptane-3-carboxylate |
| 91 | | (3R,5R,6R)-6-((Z)-2-(2-aminothiazol-4-yl)-2-(((2-carboxypropan-2-yl)oxy)imino)acetamido)-3-(3-(2-(2-((Z)-(2-(2-chloro-3,4-dihydroxyphenyl)-2-hydroxyimino)acetyl)hydrazinyl)-2-oxoacetamido)-2-odazolidin-1-yl)-7-oxo-4-thia-1-azabicyclo[3.2.0]heptane-3-carboxylate |
| 92 | | (3R,5R,6R)-6-((Z)-2-(2-aminothiazol-4-yl)-2-(((2-carboxypropan-2-yl)oxy)imino)acetamido)-3-(3-(2-((3-(2-(2-chloro-3,4-dihydroxyphenyl)-2-oxoacetamido)propyl)amino)-2-oxoacetamido)-2-oxoimidazolidin-1-yl)-7-oxo-4-thia-1-azabicyclo[3.2.0]heptane-3-carboxylate |
| 93 | | (3R,5R,6R)-6-((Z)-2-(2-aminothiazol-4-yl)-2-(((2-carboxypropan-2-yl)oxy)imino)acetamido)-3-(3-(2-((4-(2-(2-chloro-3,4-dihydroxyphenyl)-2-oxoacetamido)butyl)amino)-oxoacetamido)-2-oxoimidazolidin-1-yl)-7-oxo-4-thia-1-azabicyclo[3.2.0]heptane-3-carboxylate |
| 94 | | (3R,5R,6R)-6-((Z)-2-(2-aminothiazol-4-yl)-2-(((2-carboxypropan-2-yl)oxy)imino)acetamido)-3-(3-(2-((2-(2-chloro-N,3,4-trihydroxybenzamido)ethyl)amino)-2-oxoacetamido)-2-oxoimidazolidin-1-yl)-7-oxo-4-thia-1-azabicyclo[3.2.0]heptane-3-carboxylate |

The measured values of NMR and MS of the compounds in the table are as follows.

Example 87

NMR: 1.49 (3H, s), 1.51 (3H, s), 3.61 (1H, d, J=12.8 Hz), 3.64-3.79 (4H, m), 4.67 (1H, d, J=12.4 Hz), 5.70 (1H, d, J=3.6 Hz), 5.75 (1H, d, J=2.8 Hz), 6.95 (1H, d, J=8.4 Hz), 7.04 (1H, s), 7.15 (1H, d, J=8.4 Hz)

MS: 799.05 [M+H]$^+$, 797.00 [M−H]$^−$

Example 88

NMR: 1.49 (3H, s), 1.51 (3H, s), 3.61 (1H, d, J=12.8 Hz), 3.64-3.79 (4H, m), 4.67 (1H, d, J=12.4 Hz), 5.70 (1H, d, J=3.6 Hz), 5.75 (1H, d, J=2.8 Hz), 6.92 (1H, d, J=8.4 Hz), 7.03 (1H, s), 7.42 (1H, d, J=8.4 Hz)

MS: 827.05 [M+H]$^+$, 824.90 [M−H]$^−$

Example 89

NMR: 1.52 (3H, s), 1.53 (3H, s), 3.60-3.70 (3H, m), 3.70-3.78 (2H, m), 4.66 (1H, d, J=13.6 Hz), 5.68 (1H, d, J=4.0 Hz), 5.80 (1H, d, J=3.6 Hz), 6.95 (1H, d, J=8.4 Hz), 7.43 (1H, d, J=8.8 Hz)

MS: 904.90 [M+H]$^+$, 902.60 [M−H]$^−$

Example 90

NMR: 1.50 (3H, s), 1.52 (3H, s), 2.34 (3H, s), 3.48-3.80 (5H, m), 4.65 (1H, d, J=12.8 Hz), 5.68 (1H, d, J=3.6 Hz), 5.78 (1H, d, J=2.8 Hz), 6.97 (1H, d, J=8.8 Hz), 7.44 (1H, d, J=8.4 Hz)

MS: 841.00 [M+H]$^+$, 838.90 [M−H]$^−$

Example 91

NMR: 1.49 (3H, s), 1.51 (3H, s), 3.59 (1H, d, J=12.4 Hz), 3.62-3.78 (4H, m), 4.66 (1H, d, J=12.8 Hz), 5.69 (1H, d, J=3.6 Hz), 5.75 (1H, d, J=4.0 Hz), 6.88 (1H, d, J=8.4 Hz), 6.98 (1H, d, J=8.4 Hz), 7.03 (1H, s)

MS: 842.05 [M+H]$^+$, 839.90 [M−H]$^−$

Example 92

NMR: 1.49 (3H, s), 1.50 (3H, s), 1.92 (2H, t, J=6.4 Hz), 3.38-3.46 (4H, m), 3.54-3.65 (3H, m), 3.68-3.76 (2H, m), 4.64 (1H, d, J=12.4 Hz), 5.68 (1H, d, J=4.0 Hz), 5.74 (1H, d, J=2.8 Hz), 6.96 (1H, d, J=8.4 Hz), 7.03 (1H, s), 7.33 (1H, d, J=8.8 Hz)

MS: 869.10 [M+H]$^+$, 867.00 [M−H]$^−$

Example 93

NMR: 1.49 (3H, s), 1.50 (3H, s), 1.62-1.70 (4H, m), 3.31-3.42 (4H, m), 3.53-3.66 (3H, m), 3.66-3.76 (2H, m), 4.65 (1H, d, J=12.8 Hz), 5.68 (1H, d, J=4.0 Hz), 5.74 (1H, d, J=3.2 Hz), 6.96 (1H, d, J=8.4 Hz), 7.04 (1H, s), 7.31 (1H, d, J=8.4 Hz)

MS: 883.05 [M+H]$^+$, 880.95 [M−H]$^−$

Example 94

NMR: 1.49 (3H, s), 1.51 (3H, s), 3.48-3.56 (2H, m), 3.60 (1H, d, J=13.2 Hz), 3.63-3.83 (6H, m), 4.67 (1H, d, J=12.8 Hz), 5.71 (1H, d, J=4.0 Hz), 5.75 (1H, d, J=2.8 Hz), 6.77 (1H, d, J=8.4 Hz), 6.93 (1H, d, J=8.4 Hz), 7.04 (1H, s)

MS: 843.10 [M+H]$^+$, 840.90 [M−H]$^−$

The compounds shown in Table 27 were obtained in the same manner as in Example 49.

TABLE 27

| Example No | Structural Formula | Name |
|---|---|---|
| 95 | 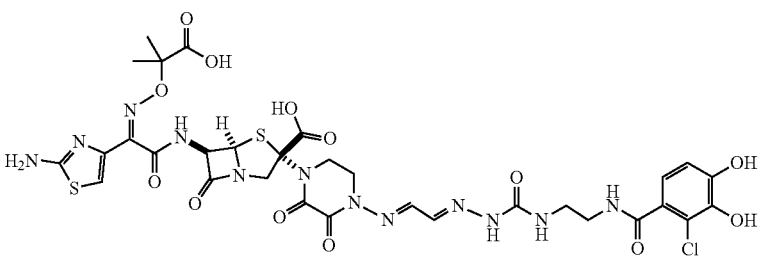 | (3R,5R,6R)-6-((Z)-2-(2-aminothiazol-4-yl)-2-(((2-carboxypropan-2-yl)oxy)imino)acetamido)-3-(4-(((1E,2E)-2-(2-((2-(2-chloro-3,4-dihydroxybenzamido)ethyl)carbamoyl)hydrazinylidene)ethyl)amino)-2,3-dioxopiperazin-1-yl)-7-oxo-4-thia-1-azabicyclo[3.2.0]heptane-3-carboxylate |

The measured values of NMR and MS of the compounds in the table are as follows.

Example 95

NMR: 1.49 (3H, s), 1.51 (3H, s), 3.26 (1H, d, J=12.8 Hz), 3.49-3.60 (4H, m), 4.05-4.35 (4H, m), 5.08 (1H, d, J=13.2 Hz), 5.71 (1H, d, J=4.0 Hz), 5.75 (1H, d, J=2.8 Hz), 6.90 (1H, d, J=8.4 Hz), 6.97 (1H, d, J=8.4 Hz), 7.03 (1H, s), 7.70 (1H, d, J=8.0 Hz), 7.95 (1H, d, J=8.0 Hz)

MS: 881.15 [M+H]$^+$, 878.90 [M−H]$^−$

The compounds shown in Table 28 were obtained in the same manner as in Example 59.

TABLE 28

| Example No | Structural Formula | Name |
|---|---|---|
| 96 | | (3R,5R,6R)-6-((Z)-2-(2-aminothiazol-4-yl)-2-(((2-carboxypropan-2-yl)oxy)imino)acetamido)-3-(3-(((Z)-1-(2-chloro-3,4-dihydroxyphenyl)-2-(methylamino)-2-oxoethylidene)amino)-2-oxoimidazolidin-1-yl)-7-oxo-4-thia-1-azabicyclo[3.2.0]heptane-3-carboxylate |
| 97 | | (3R,5R,6R)-3-(3-(((Z)-2((2-aminoethyl)amino)-1-(2-chloro-3,4-dihydroxyphenyl)-2-oxoethylidene)amino)-2-oxoimidazolidin-1-yl)-6-((Z)-2-(2-aminothiazol-4-yl)-2-(((2-carboxypropan-2-yl)oxy)imino)acetamido)-7-oxo-4-thia-1-azabicyclo[3.2.0]heptane-3-calboxylate |
| 98 | | (3R,5R,6R)-6-((Z)-2-(2-aminothiazol-4-yl)-2-(((2-carboxypropan-2-yl)oxy)imino)acetamido)-3-(3-(((Z)-carboxy(2-chloro-3,4-dihydroxyphenyl)methylene)amino)-2-oxoimidazolidin-1-yl)-7-oxo-4-thia-1-azabicyclo[3.2.0]heptane-3-carboxylate |

The measured values of NMR and MS of the compounds in the table are as follows.

Example 96

NMR: 1.48 (3H, s), 1.50 (3H, s), 2.86 (3H, s), 3.11-3.35 (2H, m), 3.49 (1H, d, J=12.4 Hz), 3.53-3.65 (2H, m), 5.67 (1H, d, J=3.6 Hz), 5.74 (1H, d, J=3.2 Hz), 6.81 (1H, d, J=8.0 Hz), 6.94 (1H, d, J=8.0 Hz), 7.02 (1H, s)

MS: 754.05 [M+H]$^+$, 752.05 [M−H]$^−$

Example 97

NMR: 1.57 (3H, s), 1.61 (3H, s), 3.18-3.25 (4H, m), 3.55-3.69 (5H, m), 4.93-5.09 (1H, m), 5.42-5.49 (1H, m), 5.69-5.73 (1H, m), 6.81 (1H, d, J=8.4 Hz), 6.93 (1H, d, J=8.4 Hz), 7.20-7.24 (1H, m)

MS: 783.10 [M+H]$^+$, 781.05 [M−H]$^−$

Example 98

NMR: 1.48 (3H, s), 1.49 (3H, s), 3.12-3.24 (2H, m), 3.51-3.60 (3H, m), 4.67 (1H, d, J=12.8 Hz), 5.64 (1H, d, J=4.0 Hz), 5.73 (1H, d, J=3.2 Hz), 6.79 (1H, d, J=8.4 Hz), 6.93 (1H, d, J=8.0 Hz), 7.02 (1H, s)

MS: 741.05 [M+H]$^+$, 739.10 [M−H]$^−$

Example 99

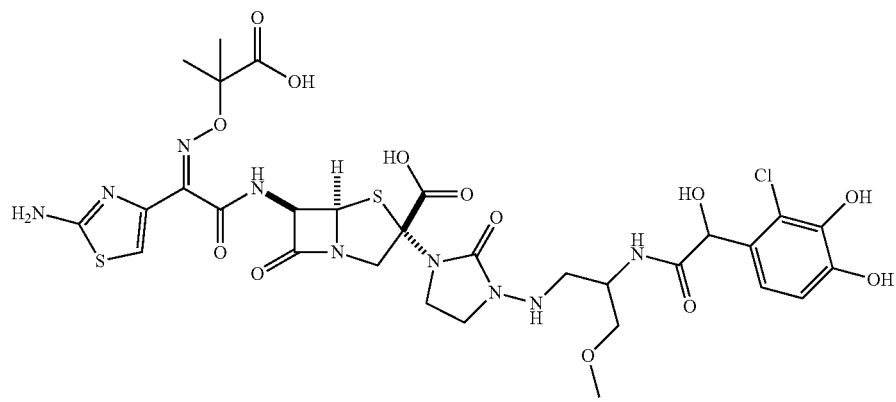

In the same manner as in Example 65, (3R,5R,6R)-6-((Z)-2-(2-aminothiazol-4-yl)-2-(((2-carboxypropan-2-yl)oxy)imino)acetamido)-3-(3-((2-(2-(2-chloro-3,4-dihydroxyphenyl)-2-hydroxyacetamido)-3-methoxypropyl)amino)-2-oxoimidazolidin-1-yl)-7-oxo-4-thia-1-azabicyclo[3.2.0]heptane-3-carboxylate was obtained.

NMR: 1.42-1.56 (6H, m), 3.03-3.13 (1H, m), 3.16-3.99 (11H, m), 4.12-4.34 (1H, m), 4.45-4.56 (1H, m), 5.10-5.39 (1H, m), 5.45-5.63 (1H, m), 5.64-5.78 (1H, m), 6.82-6.97 (2H, m), 6.98-7.06 (1H, m)

MS: 830.10 [M+H]$^+$, 827.90 [M−H]$^−$

The compounds shown in Table 29 were obtained in the same manner as in Example 68.

TABLE 29

| Example No | Structural Formula | Name |
|---|---|---|
| 100 | | (3R,5R,6R)-6-((Z)-2-(2-amino-5-chlorothiazol-4-yl)-2-((1-carboxycyclopropoxy-)imino)acetamido)-3-(3-(2-((2-(2-chloro-3,4-dihydroxybenzamido)ethyl)amino)-2-oxoacetamido)-2-oxoimidazolidin-1-yl)-7-oxo-4-thia-1-azabicyclo[3.2.0]heptane-3-carboxylate |
| 101 | | (3R,5R,6R)-6-((Z)-2-(5-amino-1,2,4-thiadiazol-3-yl)-2-((1-carboxycyclopropoxy-)imino)acetamido)-3-(3-(2-((2-(2-chloro-3,4-dihydroxybenzamido)ethyl)amino)-2-oxoacetamido)-2-oxoimidazolidin-1-yl)-7-oxo-4-thia-1-azabicyclo[3.2.0]heptane-3-carboxylate |

TABLE 29-continued

| Example No | Structural Formula | Name |
|---|---|---|
| 102 | | (3R,5R,6R)-6-((Z)-2-(2-amino-5-chlorothiazol-4-yl)-2-((1-carboxycyclobutoxy)imino)acetamido)-3-(3-(2-((2-(2-chloro-3,4-dihydroxybenzamido)ethyl)amino)-2-oxoacetamido)-2-oxoimidazolidin-1-yl)-7-oxo-4-thia-1-azabicyclo[3.2.0]heptane-3-carboxylate |
| 103 | | (3R,5R,6R)-6-((Z)-2-(5-amino-1,2,4-thiadiazol-3-yl)-2-((1-carboxycyclopropoxy-)imino)acetamido)-3-(3-(2-((2-(2-chloro-3,4-dihydroxybenzamido)ethyl)amino)-2-oxoacetamido)-2-oxoimidazolidin-1-yl)-7-oxo-4-thia-1-azabicyclo[3.2.0]heptane-3-carboxylate |
| 104 | | (3R,5R,6R)-6-((Z)-2-(2-aminothiazol-4-yl)-2-(((2-carboxypropan-2-yl)oxy)imino)acetamido)-3-(3-(2-(2-(2-chloro-3,4-dihydroxybenzamido)ethyl)hydroxy)amino)-2-oxoacetamido)-2-oxoimidazolidin-1-yl)-7-oxo-4-thia-1-azabicyclo[3.2.0]heptane-3-carboxylate |

The measured values of NMR and MS of the compounds in the table are as follows.

Example 100

NMR: 1.23-1.44 (4H, m), 3.53-3.67 (8H, m), 3.72 (1H, d, J=6.8 Hz), 4.63 (1H, d, J=12.8 Hz), 5.65 (1H, d, J=4.0 Hz), 5.78 (1H, d, J=3.2 Hz), 6.89 (1H, d, J=8.0 Hz), 6.94 (1H, d, J=8.4 Hz)

MS: 858.95 [M+H]$^+$, 856.95 [M−H]$^−$

Example 101

NMR: 1.27-1.46 (4H, m), 3.50-3.69 (7H, m), 3.69-3.77 (2H, m), 4.63 (1H, d, J=12.8 Hz), 5.66 (1H, d, J=3.6 Hz), 5.79 (1H, d, J=3.6 Hz), 6.90 (1H, d, J=8.4 Hz), 6.94 (1H, d, J=8.4 Hz)

MS: 826.15[M+H]$^+$, 824.10[M−H]$^−$

Example 102

NMR: 1.82-1.95 (1H, m), 1.96-2.09 (1H, m), 2.27-2.40 (2H, m), 2.40-2.50 (1H, m), 2.51-2.60 (1H, m), 3.54-3.67 (7H, m), 3.70-3.75 (2H, m), 4.65 (1H, d, J=12.8 Hz), 5.69 (1H, d, J=3.6 Hz), 5.82 (1H, d, J=3.6 Hz), 6.90 (1H, d, J=8.4 Hz), 6.94 (1H, d, J=8.4 Hz)

MS: 873.00 [M+H]$^+$, 871.00 [M−H]$^−$

Example 103

NMR: 1.84-1.97 (1H, m), 1.98-2.11 (1H, m), 2.28-2.44 (2H, m), 2.44-2.53 (1H, m), 2.53-2.63 (1H, m), 3.54-3.68 (7H, m), 3.70-3.77 (2H, m), 4.66 (1H, d, J=12.4 Hz), 5.70 (1H, d, J=3.6 Hz), 5.83 (1H, dd, J=3.6, 1.2 Hz), 6.89 (1H, d, J=8.4 Hz), 6.94 (1H, d, J=8.4 Hz)

MS: 840.25 [M+H]$^+$, 838.25 [M−H]$^−$

Example 104

NMR: 1.45 (3H, s), 1.46 (3H, s), 3.42-3.73 (9H, m), 4.55 (1H, d, J=12.4 Hz), 5.65 (1H, d, J=3.6 Hz), 5.70 (1H, dd, J=10.2, 3.0 Hz), 6.88 (1H, s), 6.93 (1H, d, J=8.8 Hz), 6.99 (1H, d, J=6.4 Hz)

MS: 843.05 [M+H]$^+$, 841.05 [M−H]$^−$

Example 105

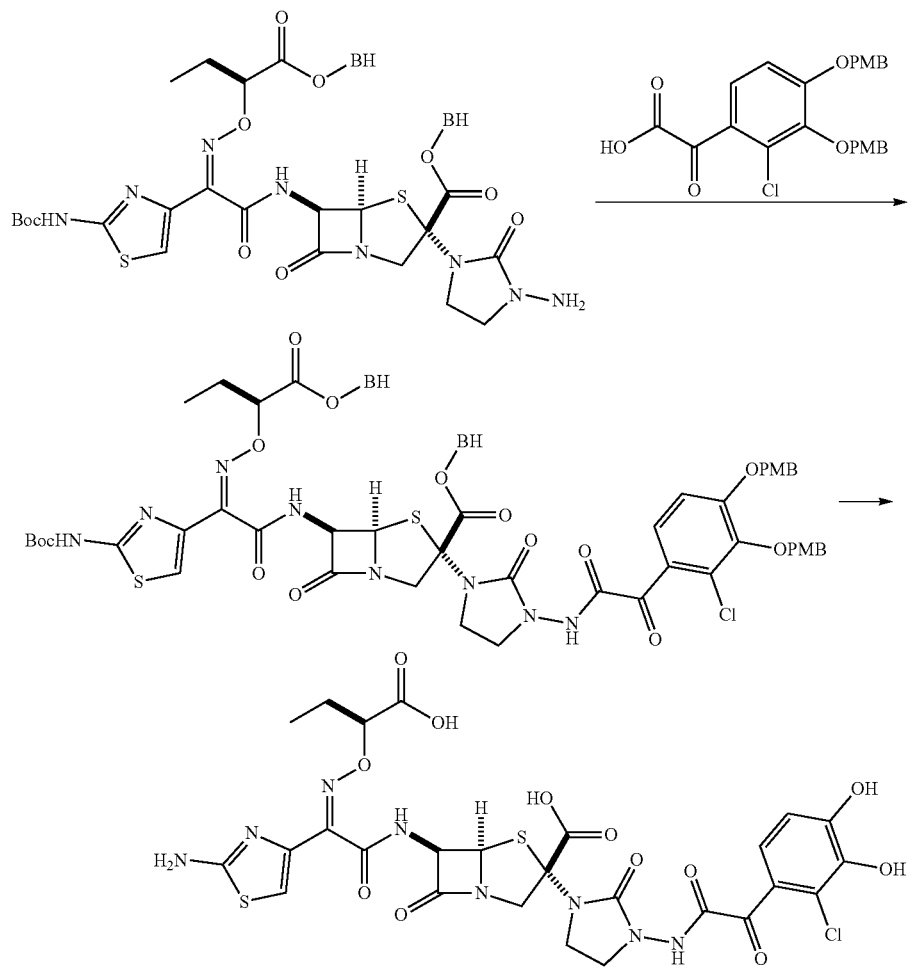

Example 105 (1)

2-(2-Chloro-3,4-bis((4-methoxybenzyl)oxy)phenyl)-2-oxoacetic acid (155 mg), HATU (129 mg), DMAC (3 mL), and NMM (75 μL) were sequentially added to benzhydryl (3R,5R,6R)-3-(3-amino-2-oxoimidazolidin-1-yl)-6-(((Z)-2-((((S)-1-(benzhydryloxy)-1-oxobutan-2-yl)oxy)imino)-2-(2-((tert-butoxycarbonyl)amino)thiazol-4-yl)acetamido)-7-oxo-4-thia-1-azabicyclo[3.2.0]heptane-3-carboxylate (300 mg). The reaction mixture was stirred at room temperature for 2 hours. Ethyl acetate (10 mL) and water (10 mL) were added to the reaction mixture, and the organic layer was separated. The organic layer was washed with a saturated aqueous sodium chloride solution and dehydrated and dried over anhydrous sodium sulfate. The solvent was distilled away under reduced pressure. The residue was purified by silica gel column chromatography [eluent; ethyl acetate:hexane=30:70→70:30], thereby obtaining a target substance (374 mg) as light yellow solids.

Example 105 (2)

Dichloromethane (5.6 mL) was added to the compound (374 mg) obtained in Example 105 (1), and the mixture was stirred at −20° C. At the same temperature, anisole (1.7 mL) and aluminum chloride (529 mg) were sequentially added to the reaction mixture. The reaction mixture was stirred at a temperature equal to or lower than −20° C. for 30 minutes. The reaction mixture was added to a mixture of acetonitrile (15 mL), water (15 mL), and trisodium citrate dihydrate (1.75 g) under ice cooling. A saturated aqueous sodium hydrogen carbonate solution was added to the reaction mixture such that the pH was adjusted to 5.3, and the aqueous layer was separated. The aqueous layer was concentrated under reduced pressure, and the residue was purified by medium-pressure reverse-phase silica gel column chromatography [eluent; water: acetonitrile=100:0→90:10]. The aqueous solution containing a target substance was lyophilized, thereby obtaining (3R,5R,6R)-6-((Z)-2-(2-aminothiazol-4-yl)-2-(((S)-1-carboxypropoxy)imino)acetamido)-3-(3-(2-(2-chloro-3,4-dihydroxyphenyl)-2-oxoacetamido)-2-oxoimidazolidin-1-yl)-7-oxo-4-thia-1-azabicyclo[3.2.0]heptane-3-carboxylate (90 mg) as yellow solids.

NMR: 0.97 (3H, t, J=7.4 Hz), 1.77-1.94 (2H, m), 3.63 (1H, d, J=12.8 Hz), 3.67-3.87 (4H, m), 4.49-4.56 (1H, m), 4.68 (1H, d, J=12.8 Hz), 5.71 (1H, d, J=4.0 Hz), 5.79 (1H, d, J=3.6 Hz), 6.83 (1H, d, J=8.4 Hz), 7.05-7.08 (1H, m), 7.44 (1H, d, J=8.8 Hz)

MS: 741.05 [M+H]+, 738.95 [M−H]−

The compounds shown in Table 30 were obtained in the same manner as in Example 105.

TABLE 30

| Example No | Structural Formula | Name |
|---|---|---|
| 106 | | (3R,5R,6R)-6-((Z)-2-(5-amino-1,2,4-thiadiazol-3-yl)-2-((1-carboxycyclopropoxy-)imino)acetamido)-3-(3-(3-(2-(2-chloro-3,4-dihydroxyphenyl)-2-oxoacetamido)propanamido)-2-oxoimidazolidin-1-yl)-7-oxo-4-thia-1-azabicyclo[3.2.0]heptane-3-carboxylate |
| 107 | | (3R,5R,6R)-6-((Z)-2-(2-amino-5-chlorothiazol-4-yl)-2-((1-carboxycyclopropoxy-)imino)acetamido)-3-(3-(3-(2-(2-chloro-3,4-dihydroxyphenyl)-2-oxoacetamido)propanamido)-2-oxoimidazolidin-1-yl)-7-)oxo-4-thia-1-azabicyclo[3.2.0]heptane-3-carboxylate |
| 108 | | (3R,5R,6R)-6-((Z)-2-(2-amino-5-chlorothiazol-4-yl)-2-((1-carboxycyclobutoxy)imino)acetamido)-3-(3-(3-(2-(2-chloro-3,4-dihydroxyphenyl)-2-oxoacetamido)propanamido)-2-oxoimidazolidin-1-yl)-7-oxo-4-thia-1-azabicyclo[3.2.0]heptane-3-carboxylate |
| 109 | | (3R,5R,6R)-6-((Z)-2-(5-amino-1,2,4-thiadiazol-3-yl)-2-((1-carboxycyclobutoxy)imino)acetamido)-3-(3-(3-(2-(2-chloro-3,4-dihydroxyphenyl)-2-oxoacetamido)propanamido)-2-oxoimidazolidin-1-yl)-7-oxo-4-thia-1-azabicyclo[3.2.0]heptane-3-carboxylate |
| 110 | | (3R,5R,6R)-6-((Z)-2-(2-amino-5-methylthiazol-4-yl)-2-(((2-carboxypropan-2-yl)oxy)imino)acetamido)-3-(3-(3-(2-(2-chloro-3,4-dihydroxyphenyl)-2-oxoacetamido)propanamido)-2-oxoimidazolidin-1-yl)-7-oxo-4-thia-1-azabicyclo[3.2.0]heptane-3-carboxylate |

TABLE 30-continued

| Example No | Structural Formula | Name |
|---|---|---|
| 111 | | (3R,5R,6R)-6-((Z)-2-(2-amino-5-bromothiazol-4-yl)-2-(((2-carboxypropan-2-yl)oxy)imino)acetamido)-3-(3-(2-chloro-3,4-dihydroxyphenyl)-2-oxoacetamido)propanamido)-2-oxoimidazolidin-1-yl)-7-oxo-4-thia-1-azabicyclo[3.2.0]heptane-3-carboxylate |
| 112 | | (3R,5R,6R)-6-((Z)-2-(2-aminothiazol-4-yl)-2-(((2-carboxypropan-2-yl)oxy)imino)acetamido)-3-(3-(2-(2,5-dichloro-3,4-dihydroxyphenyl)-2-oxoacetamido)-2-oxoimidazolidin-1-yl)-7-oxo-4-thia-1-azabicyclo[3.2.0]heptane-3-carboxylate |
| 113 | | (3R,5R,6R)-6-((Z)-2-(2-aminothiazol-4-yl)-2-(((S)-1-carboxy-2-hydroxyethoxy)imino)acetamido)-3-(3-(2-(2-chloro-3,4-dihydroxyphenyl)-2-oxoacetamido)-2-oxoimidazolidin-1-yl)-7-oxo-4-thia-1-azabicyclo[3.2.0]heptane-3-carboxylate |
| 114 | | (3R,5R,6R)-6-((Z)-2-(2-aminothiazol-4-yl)-2-(((S)-1-carboxy-2-methylpropoxy)imino)acetamido)-3-(3-(2-(2-chloro-3,4-dihydroxyphenyl)-2-oxoacetamido)-2-oxoimidazolidin-1-yl)-7-oxo-4-thia-1-azabiclyclo[3.2.0]heptane-3-carboxylate |
| 115 | | (3R,5R,6R)-6-((Z)-2-(2-aminothiazol-4-yl)-2-(((S)-1-carboxybutoxy)imino)acetamido)-3-(3-(2-(2-chloro-3,4-dihydroxyphenyl)-2-oxoacetamido)-2-oxoimidazolidin-1-yl)-7-oxo-4-thia-1-azabicyclo[3.2.0]heptane-3-carboxylate |

TABLE 30-continued

| Example No | Structural Formula | Name |
|---|---|---|
| 116 | | (3R,5R,6R)-6-((Z)-2-(2-aminothiazol-4-yl)-2-(((R)-1-carboxy-2-hydroxyethoxy)imino)acetamido)-3-(3-(2-(2-chloro-3,4-dihydroxyphenyl)-2-oxoacetamido)-2-oxoimidazolidin-1-yl)-7-oxo-4-thia-1-azabicyclo[3.2.0]heptane-3-carboxylate |
| 117 | | (3R,5R,6R)-6-((Z)-2-(2-aminothiazol-4-yl)-2-(((2-arboxypropan-2-yl)oxy)imino)acetamido)-3-(3-((Z-2-(2-chloro-3,4-dihydroxyphenyl)-2-(hydroxyimino)acetamido)-2-oxoimidazolidin-1-yl)-7-oxo-4-thia-1-azabicyclo[3.2.0]heptane-3-carboxylate |
| 118 | | (3R,5R,6R)-6-((Z)-2-(2-aminothiazol-4-yl)-2-(((2-carboxypropan-2-yl)oxy)imino)acetamido)-3-(3-((Z-2-(3,4-dihydroxyphenyl)-2-(hydroxyimino)acetamido)-2-oxoimidazolidin-1-yl)-7-oxo-4-thia-1-azabicyclo[3.2.0]heptane-3-carboxylate |
| 119 | | (3R,5R,6R)-6-((Z)-2-(2-aminothiazol-4-yl)-2-(((2-carboxypropan-2-yl)oxy)imino)acetamido)-3-(3-((Z-2-(2-chloro-3,4-dihydroxyphenyl)-2-hydrazinylideneacetamido)-2-oxoimidazolidin-1-yl)-7-oxo-4-thia-1-azabicyclo[3.2.0]heptane-3-carboxylate |

TABLE 30-continued

| Example No | Structural Formula | Name |
|---|---|---|
| 120 | | (3R,5R,6R)-6-((Z)-2-(2-aminothiazol-4-yl)-2-(((2-carboxypropan-2-yl)oxy)imino)acetamido)-3-(3-((Z)-2-(2-chloro-3,4-dihydroxyphenyl)-2-(2-piperidine-4-carbonyl)hydrazinylidene)acetamido)-2-oxoimidazolidin-1-yl)-7-oxo-4-thia-1-azabicyclo[3.2.0]heptane-3-carboxylate |
| 121 | | (3R,5R,6R)-6-((Z)-2-(2-aminothiazol-4-yl)-2-(((2-carboxypropan-2-yl)oxy)imino)acetamido)-3-(3-(2-((2-(2-(2-chloro-3,4-dihydroxyphenyl)-2-oxoacetamido)ethyl)amino)-2-oxoacetamido)-2-oxoimidazolidin-1-yl)-7-oxo-4-thia-1-azabicyclo[3.2.0]heptane-3-carboxylate |
| 122 | | (3R,5R,6R)-6-((Z)-2-(2-aminothiazol-4-yl)-2-(((2-carboxypropan-2-yl)oxy)imino)acetamido)-3-(3-(3-((Z)-2-(2-chloro-3,4-dihydroxyphenyl)-2-(hydroxyimino)acetamido)propanamido)-2-oxoimidazolidin-1-yl)-7-oxo-4-thia-1-azabicyclo[3.2.0]heptane-3-carboxylate |
| 123 | | (3R,5R,6R)-6-((Z)-2-(2-aminothiazol-4-yl)-2-(((2-carboxypropan-2-yl)oxy)imino)acetamido)-3-(3-(3-((Z)-2-(2-chloro-3,4-dihydroxyphenyl)-2-hydrazinylideneacetamido)propanamido)-2-oxoimidazolidin-1-yl)-7-oxo-4-thia-1-azabicyclo[3.2.0]heptane-3-carboxylate |

TABLE 30-continued

| Example No | Structural Formula | Name |
|---|---|---|
| 124 | | (3R,5R,6R)-6-((Z)-2-(2-aminothiazol-4-yl)-2-(((2-carboxypropan-2-yl)oxy)imino)acetamido)-3-(3-(5-hydroxy-4-oxo-1,4-dihydropyridine-2-carboxamido)-2-oxoimidazolidin-1-yl)-7-oxo-4-thia-1-azabicyclo[3.2.0]heptane-3-carboxylate |
| 125 | | (3R,5R,6R)-6-((Z)-2-(2-aminothiazol-4-yl)-2-(((2-carboxypropan-2-yl)oxy)imino)acetamido)-3-(3-(1,5-dihydroxy-4-oxo-1,4-dihydropyridine-2-carboxamido)-2-oxoimidazolidin-1-yl)-7-oxo-4-thia-1-azabicyclo[3.2.0]heptane-3-carboxylate |
| 126 | | (3R,5R,6R)-6-((Z)-2-(2-aminothiazol-4-yl)-2-(((2-carboxypropan-2-yl)oxy)imino)acetamido)-3-(4-(2-(2-chloro-3,4-dihydroxyphenyl)-2-oxoacetamido)-2,3-dioxopiperazin-1-yl)-7-oxo-4-thia-1-azabicyclo[3.2.0]heptane-3-carboxylate |
| 127 | | (3R,5R,6R)-6-((Z)-2-(2-aminothiazol-4-yl)-2-(((2-carboxypropan-2-yl)oxy)imino)acetamido)-3-(4-(2-(2-(2-chloro-3,4-dihydroxybenzamido)ethyl)amino)-2-oxoacetamido)-2,3-dioxopiperazin-1-yl)-7-oxo-4-thia-1-azabicyclo[3.2.0]heptane-3-carboxylate |

TABLE 30-continued

| Example No | Structural Formula | Name |
|---|---|---|
| 128 | | (3R,5R,6R)-6-((Z)-2-(2-aminothiazol-4-yl)-2-(((2-carboxypropan-2-yl)oxy)imino)acetamido)-3-(4-(3-((Z)-(2-(2-chloro-3,4-dihydroxyphenyl)-2-(hydroxyimino)acetamido)propanamido)-2,3-dioxopiperazin-1-yl)-7-oxo-4-thia-1-azabicyclo[3.2.0]heptane-3-carboxylate |
| 129 | | (3R,5R,6R)-6-((Z)-2-(2-aminothiazol-4-yl)-2-(((2-carboxypropan-2-yl)oxy)imino)acetamido)-3-(4-(3-((E)-2-(2-chloro-3,4-dihydroxyphenyl)-2-(hydroxyimino)acetamido)propanamido)-2,3-dioxopiperazin-1-yl)-7-oxo-4-thia-1-azabicyclo[3.2.0]heptane-3-carboxylate |
| 130 | | (3R,5R,6R)-6-((Z)-2-(2-aminothiazol-4-yl)-2-(((2-carboxypropan-2-yl)oxy)imino)acetamido)-3-(4-(3-((Z)-2-(2-chloro-3,4-dihydroxyphenyl)-2-hydrazinylideneacetamido)propanamido)-2,3-dioxopiperazin-1-yl)-7-oxo-4-thia-1-azabicyclo[3.2.0]heptane-3-carboxylate |

TABLE 30-continued

| Example No | Structural Formula | Name |
|---|---|---|
| 131 | | (3R,5R,6R)-6-((Z)-2-(2-aminothiazol-4-yl)-2-(((2-carboxypropan-2-yl)oxy)imino)acetamido)-3-(4-((Z)-2-(2-chloro-3,4-dihydroxyphenyl)-2-(hydroxyimino)acetamido)-2,3-dioxopiperazin-1-yl)-7-oxo-4-thia-1-azabicyclo[3.2.0]heptane-3-carboxylate |
| 132 | | (3R,5R,6R)-6-((Z)-2-(2-aminothiazol-4-yl)-2-(((2-carboxypropan-2-yl)oxy)imino)acetamido)-3-(4-(2-chloro-3,4-dihydroxybenzamido)-2,3-dioxopiperazin-1-yl)-7-oxo-4-thia-1-azabicyclo[3.2.0]heptane-3-carboxylate |
| 133 | | (3R,5R,6R)-6-((Z)-2-(2-amino-5-bromothiazol-4-yl)-2-(((2-carboxypropan-2-yl)oxy)imino)acetamido)-3-(4-(2-(2-chloro-3,4-dihydroxyphenyl)-2-oxoacetamido)-2,3-dioxopiperazin-1-yl)-7-oxo-4-thia-1-azabicyclo[3.2.0]heptane-3-carboxylate |

TABLE 30-continued

| Example No | Structural Formula | Name |
|---|---|---|
| 134 | | (3R,5R,6R)-6-((Z)-2-(5-amino-1,2,4-thiadiazol-3-yl)-2-(((2-carboxypropan-2-yl)oxy)imino)acetamido)-3-(4-(2-(2-chloro-3,4-dihydroxyphenyl)-2-oxoacetamido)-2,3-dioxopiperazin-1-yl)-7-oxo-4-thia-1-azabicyclo[3.2.0]heptane-3-carboxylate |
| 135 | | (3R,5R,6R)-6-((Z)-2-(2-amino-5-chlorothiazol-4-yl)-2-(((2-carboxypropan-2-yl)oxy)imino)acetamido)-3-(4-(2-(2-chloro-3,4-dihydroxyphenyl)-2-oxoacetamido)-2,3-dioxopiperazin-1-yl)-7-oxo-4-thia-1-azabicyclo[3.2.0]heptane-3-carboxylate |
| 136 | | (3R,5R,6R)-6-((Z)-2-(2-amino-5-chlorothiazol-4-yl)-2-(((2-carboxypropan-2-yl)oxy)imino)acetamido)-3-(3-(2-(2-(2-chloro-3,4-dihydroxyphenyl)-2-oxoacetyl)hydrazinyl)-2-oxoacetamido)-2-oxoimidazolidin-1-yl)-7-oxo-4-thia-1-azabicyclo[3.2.0]heptane-3-carboxylate |

The measured values of NMR and MS of the compounds in the table are as follows.

Example 106

NMR: 1.23-1.46 (4H, m), 2.65 (2H, t, J=6.2 Hz), 3.52-3.62 (3H, m), 3.62-3.74 (4H, m), 4.59 (1H, d, J=12.4 Hz), 5.39 (1H, d, J=3.6 Hz), 5.77 (1H, d, J=4.0 Hz), 6.95 (1H, d, J=8.4 Hz), 7.34 (1H, d, J=8.8 Hz)

MS: 810.95 [M+H]$^+$, 809.10 [M–H]$^-$

Example 107

NMR: 1.22-1.45 (4H, m), 2.66 (2H, t, J=6.4 Hz), 3.53-3.72 (7H, m), 4.58 (1H, d, J=12.8 Hz), 5.60 (1H, d, J=4.0 Hz), 5.75 (1H, d, J=4.0 Hz), 6.95 (1H, d, J=8.8 Hz), 7.34 (1H, d, J=8.8 Hz)

MS: 843.95 [M+H]$^+$, 842.05 [M–H]$^-$

Example 108

NMR: 1.81-1.95 (1H, m), 1.95-2.08 (1H, m), 2.27-2.39 (2H, m), 2.39-2.49 (1H, m), 2.50-2.60 (1H, m), 2.66 (2H, t, J=6.4 Hz), 3.54-3.72 (7H, m), 4.61 (1H, d, J=12.8 Hz), 5.64 (1H, d, J=4.0 Hz), 5.79 (1H, d, J=3.6 Hz), 6.95 (1H, d, J=8.8 Hz), 7.34 (1H, d, J=8.4 Hz)

MS: 858.00 [M+H]$^+$, 855.95 [M–H]$^-$

Example 109

NMR: 1.83-1.96 (1H, m), 1.96-2.10 (1H, m), 2.27-2.41 (2H, m), 2.43-2.53 (1H, m), 2.53-2.62 (1H, m), 2.65 (2H, t, J=6.2 Hz), 3.53-3.73 (7H, m), 4.61 (1H, d, J=12.4 Hz), 5.66 (1H, d, J=3.6 Hz), 5.81 (1H, d, J=3.6 Hz), 6.95 (1H, d, J=8.4 Hz), 7.34 (1H, d, J=8.4 Hz)

MS: 825.20 [M+H]$^+$, 822.95 [M–H]$^-$

Example 110

NMR: 1.49 (3H, s), 1.50 (3H, s), 2.34 (3H, s), 2.66 (2H, t, J=6.2 Hz), 3.52-3.62 (3H, m), 3.64-3.71 (4H, m), 4.59 (1H, d, J=12.4 Hz), 5.63 (1H, d, J=4.0 Hz), 5.75 (1H, d, J=3.2 Hz), 6.96 (1H, d, J=8.4 Hz), 7.34 (1H, d, J=8.4 Hz)
MS: 826.00 [M+H]$^+$, 824.00 [M−H]$^-$

Example 111

NMR: 1.50 (3H, s), 1.52 (3H, s), 2.66 (2H, t, J=6.2 Hz), 3.54-3.63 (3H, m), 3.63-3.71 (4H, m), 4.59 (1H, d, J=12.4 Hz), 5.62 (1H, d, J=4.0 Hz), 5.76 (1H, d, J=2.8 Hz), 6.96 (1H, d, J=8.4 Hz), 7.34 (1H, d, J=8.8 Hz)
MS: 889.90 [M+H]$^+$, 887.75 [M−H]$^-$

Example 112

NMR: 1.49 (3H, s), 1.51 (3H, s), 3.54-3.68 (2H, m), 3.68-3.80 (3H, m), 4.68 (1H, d, J=13.2 Hz), 5.71 (1H, d, J=4.0 Hz), 5.75 (1H, d, J=3.6 Hz), 7.05 (1H, s), 7.40 (1H, s)
MS: 774.95 [M+H]$^+$, 773.00 [M−H]$^-$

Example 113

NMR: 3.61 (1H, d, J=12.8 Hz), 3.68-3.80 (4H, m), 3.93-4.02 (2H, m), 4.64-4.73 (2H, m), 5.71 (1H, d, J=4.0 Hz), 5.80 (1H, d, J=2.8 Hz), 6.96 (1H, d, J=8.8 Hz), 7.10 (1H, s), 7.44 (1H, d, J=8.4 Hz)
MS: 743.00 [M+H]$^+$, 741.00 [M−H]$^-$

Example 114

NMR: 0.98 (3H, d, J=6.8 Hz), 1.01 (3H, d, J=7.2 Hz), 2.15-2.22 (1H, m), 3.64 (1H, d, J=12.8 Hz), 3.68-3.87 (4H, m), 4.30-4.36 (1H, m), 4.67 (1H, dd, J=12.6, 4.6 Hz), 5.71 (1H, d, J=3.6 Hz), 5.77-5.82 (1H, m), 6.84 (1H, d, J=8.4 Hz), 7.06 (1H, s), 7.44 (1H, d, J=8.8 Hz)
MS: 755.05 [M+H]$^+$, 752.95 [M−H]$^-$

Example 115

NMR: 0.94 (3H, t, J=7.4 Hz), 1.35-1.49 (2H, m), 1.75-1.86 (2H, m), 3.66 (1H, d, J=12.4 Hz), 3.70-3.87 (4H, m), 4.55-4.61 (1H, m), 4.66 (1H, d, J=12.8 Hz), 5.70 (1H, d, J=3.6 Hz), 5.80 (1H, d, J=3.6 Hz), 6.81 [6.88](1H, d, J=8.8 Hz), 7.06 [7.06](1H, s), 7.44 [7.45](1H, d, J=8.6 Hz)
MS: 755.05 [M+H]$^+$, 752.95 [M−H]$^-$

Example 116

NMR: 3.61 (1H, d, J=12.8 Hz), 3.68-3.80 (4H, m), 3.91-4.02 (2H, m), 4.64-4.73 (2H, m), 5.71 (1H, d, J=4.0 Hz), 5.80 (1H, d, J=3.6 Hz), 6.92 (1H, d, J=8.4 Hz), 7.08 (1H, s), 7.44 (1H, d, J=8.4 Hz)
MS: 743.00 [M+H]$^+$, 740.90 [M−H]$^-$

Example 117

NMR: 1.48 (3H, s), 1.50 (3H, s), 3.60 (1H, d, J=12.8 Hz), 3.61-3.78 (4H, m), 4.65 [4.66](1H, d, J=12.6 Hz), 5.69 [5.69](1H, d, J=3.6 Hz), 5.75 (1H, d, J=3.6 Hz), 6.87 (1H, d, J=8.0 Hz), 6.98 (1H, d, J=8.4 Hz), 7.03 [7.03](1H, s)
MS: 756.05 [M+H]$^+$, 753.95 [M−H]$^-$

Example 118

NMR: 1.49 (3H, s), 1.51 (3H, s), 3.61 (1H, d, J=12.8 Hz), 3.63-3.81 (4H, m), 4.66 (1H, d, J=12.8 Hz), 5.70 (1H, d, J=3.6 Hz), 5.75 (1H, d, J=4.0 Hz), 6.94-7.07 (3H, m), 7.12 (1H, s)
MS: 722.10 [M+H]$^+$, 720.00 [M−H]$^-$

Example 119

NMR: 1.48 (3H, s), 1.50 (3H, s), 3.54-3.77 (5H, m), 4.64 (1H, d, J=12.8 Hz), 5.68 (1H, d, J=3.6 Hz), 5.74 (1H, dd, J=3.6, 0.8 Hz), 6.79 (1H, d, J=8.0 Hz), 7.01 (1H, d, J=8.4 Hz), 7.02 (1H, s)
MS: 755.10 [M+H]$^+$, 752.95 [M−H]$^-$

Example 120

NMR: 1.48 (3H, s), 1.50 (3H, s), 1.70-2.18 (4H, m), 2.90-3.18 (1H, m), 3.18-3.41 (2H, m), 3.41-3.62 (2H, m), 3.62-3.81 (4I, m), 3.81-3.92 (1H, m), 4.64 (1H, d, J=12.8 Hz), 5.67-5.78 (2H, m), 6.76-6.90 (1H, m), 6.92-7.09 (2H, m)
MS: 866.15 [M+H]$^+$, 864.10 [M−H]$^-$

Example 121

NMR: 1.49 (3H, s), 1.50 (3H, s), 3.51-3.68 (8H, m), 3.70-3.77 (1H, m), 4.63 (1H, d, J=12.8 Hz), 5.69 (1H, d, J=3.6 Hz), 5.74 (1H, d, J=3.2 Hz), 6.95 (1H, d, J=8.8 Hz), 7.05 (1H, s), 7.28 (1H, d, J=8.4 Hz)
MS: 855.00 [M+H]$^+$, 853.25 [M−H]$^-$

Example 122

NMR: 1.48 (3H, s), 1.50 (3H, s), 2.58 (2H, t, J=6.2 Hz), 3.62-3.73 (7H, m), 4.63 (1H, d, J=12.8 Hz), 5.68 (1H, d, J=3.6 Hz), 5.75 (1H, dd, J=3.6, 1.2 Hz), 6.81 (1H, d, J=8.4 Hz), 6.97 (1H, d, J=8.4 Hz), 7.03 (1H, s)
MS: 827.10 [M+H]$^+$, 824.95 [M−H]$^-$

Example 123

NMR: 1.49 (3H, s), 1.50 (3H, s), 2.56 (2H, t, J=6.4 Hz), 3.50-3.73 (7H, m), 4.63 (1H, d, J=12.8 Hz), 5.68 (1H, d, J=3.6 Hz), 5.75 (1H, dd, J=3.8, 1.0 Hz), 6.74 (1H, d, J=8.4 Hz), 7.00 (1H, d, J=8.4 Hz), 7.03 (1H, s)
MS: 826.10 [M+H]$^+$, 824.00 [M−H]$^-$

Example 124

NMR: 1.49 (3H, s), 1.51 (3H, s), 3.62 (1H, dd, J=12.8, 1.2 Hz), 3.66-3.82 (4H, m), 4.67 (1H, d, J=12.4 Hz), 5.71 (1H, d, J=4.0 Hz), 5.76 (1H, dd, J=3.6, 0.8 Hz), 7.03 (1H, s), 7.16 (1H, s), 7.82 (1H, s)
MS: 680.10 [M+H]$^+$, 678.00 [M−H]$^-$

Example 125

NMR: 1.49 (3H, s), 1.51 (3H, s), 3.65 (1H, dd, J=12.8, 1.2 Hz), 3.68-3.79 (4H, m), 4.66 (1H, d, J=12.8 Hz), 5.71 (1H, d, J=3.6 Hz), 5.76 (1H, dd, J=3.6, 1.2 Hz), 7.03 (1H, s), 7.42 (1H, s), 7.59 (1H, s)
MS: 696.10 [M+H]$^+$, 694.00 [M−H]$^-$

Example 126

NMR: 1.49 (3H, s), 1.50 (3H, s), 3.28 (1H, d, J=13.2 Hz), 4.01-4.13 (2H, m), 4.18-4.36 (2H, m), 5.09 (1H, d, J=13.2 Hz), 5.71 (1H, d, J=3.6 Hz), 5.74 (1H, d, J=3.6 Hz), 6.81 (1H, d, J=8.8 Hz), 7.03 (1H, s), 7.47 (1H, d, J=8.4 Hz)
MS: 769.05 [M+H]$^+$, 766.90 [M−H]$^-$

Example 127

NMR: 1.49 (3H, s), 1.50 (3H, s), 3.18 [3.26](1H, dd, J=12.8, 1.2 Hz), 3.53-3.67 (4H, m), 3.76-4.33 (4H, m), 5.05

[5.08](1H, d, J=13.0 Hz), 5.67 [5.69](1H, d, J=3.6 Hz), 5.74 (1H, dd, J=3.6, 1.2 Hz), 6.77-6.87 (2H, m), 7.02 [7.03](1H, s)
MS: 855.20 [M+H]+, 852.95 [M−H]−

Example 128

NMR: 1.49 (3H, s), 1.50 (3H, s), 2.64 (2H, t, J=6.2 Hz), 3.25 (1H, dd, J=13.0, 1.0 Hz), 3.66 (2H, t, J=6.4 Hz), 3.82-3.95 (2H, m), 4.09-4.27 (2H, m), 5.07 (1H, d, J=12.8 Hz), 5.69 (1H, d, J=3.6 Hz), 5.74 (1H, dd, J=3.2, 0.8 Hz), 6.80 (1H, d, J=8.0 Hz), 6.97 (1H, d, J=8.0 Hz), 7.02 (1H, s)
MS: 855.10 [M+H]+, 852.90 [M−H]−

Example 129

NMR: 1.49 (3H, s), 1.50 (3H, s), 2.61-2.73 (2H, m), 3.25 (1H, d, J=12.8 Hz), 3.62-3.92 (4H, m), 4.07-4.27 (2H, m), 5.07 (1H, d, J=12.8 Hz), 5.70 (1H, d, J=3.2 Hz), 5.74 (1H, d, J=3.2 Hz), 6.93 (1H, d, J=8.4 Hz), 6.97 (1H, d, J=8.0 Hz), 7.02 (1H, s)
MS: 855.10 [M+H]+, 852.90 [M−H]−

Example 130

NMR: 1.49 (3H, s), 1.50 (3H, s), 2.62 (2H, t, J=6.4 Hz), 3.25 (1H, dd, J=12.8, 1.2 Hz), 3.58-3.94 (2H, m), 3.83-3.94 (2H, m), 4.10-4.28 (2H, m), 5.07 (1H, d, J=13.2 Hz), 5.70 (1H, d, J=3.6 Hz), 5.73 (1H, dd, J=3.6, 1.2 Hz), 6.74 (1H, d, J=8.4 Hz), 7.01 (1H, d, J=8.4 Hz), 7.02 (1H, s)
MS: 854.20 [M+H]+, 852.00 [M−H]−

Example 131

NMR: 1.48 (3H, s), 1.50 (3H, s), 3.26 (1H, dd, J=12.8, 0.8 Hz), 3.97-4.08 (2H, m), 4.16-4.33 (2H, m), 5.08 (1H, d, J=13.2 Hz), 5.69 (1H, d, J=3.6 Hz), 5.74 (1H, dd, J=3.6, 1.2 Hz), 6.87 (1H, d, J=8.4 Hz), 6.98 (1H, d, J=8.4 Hz), 7.02 (1H, s)
MS: 784.05 [M+H]+, 781.85 [M−H]−

Example 132

NMR: 1.49 (3H, s), 1.51 (3H, s), 3.29 (1H, dd, J=13.0, 1.0 Hz), 4.05-4.15 (2H, m), 4.20-4.36 (2H, m), 5.10 (1H, d, J=12.8 Hz), 5.71 (1H, d, J=3.6 Hz), 5.75 (1H, dd, J=3.6, 1.2 Hz), 6.95 (1H, d, J=8.8 Hz), 7.03 (1H, s), 7.17 (1H, d, J=8.4 Hz)
MS: 741.05 [M+H]+, 739.05 [M−H]−

Example 133

NMR: 1.52 (3H, s), 1.53 (3H, s), 3.28 (1H, d, J=12.4 Hz), 4.01-4.13 (2H, m), 4.17-4.37 (2H, m), 5.09 (1H, d, J=13.2 Hz), 5.67 (1H, d, J=3.2 Hz), 5.76-5.82 (1H, m), 6.90-7.07 (1H, m), 7.42-7.51 (1H, m)
MS: 846.90 [M+H]+, 844.90 [M−H]−

Example 134

NMR: 1.53 (3H, s), 1.54 (3H, s), 3.28 (1H, d, J=12.8 Hz), 4.02-4.15 (2H, m), 4.16-4.37 (2H, m), 5.08 (1H, d, J=12.8 Hz), 5.68 (1H, d, J=2.8 Hz), 5.80 (1H, d, J=2.8 Hz), 6.98 (1H, d, J=8.4 Hz), 7.46 (1H, d, J=7.6 Hz)
MS: 770.05 [M+H]+, 767.95 [M−H]−

Example 135

NMR: 1.50 (3H, s), 1.52 (3H, s), 3.29 (1H, d, J=13.2 Hz), 4.01-4.15 (2H, m), 4.15-4.37 (2H, m), 5.09 (1H, d, J=12.8 Hz), 5.67 (1H, d, J=3.6 Hz), 5.78 (1H, d, J=2.0 Hz), 6.98 (1H, d, J=8.4 Hz), 7.46 (1H, d, J=8.4 Hz)
MS: 802.95 [M+H]+, 800.90 [M−H]−

Example 136

NMR: 1.51 (3H, s), 1.52 (3H, s), 3.57-3.80 (5H, m), 4.65 (1H, d, J=12.8 Hz), 5.68 (1H, d, J=4.0 Hz), 5.79 (1H, d, J=3.6 Hz), 6.96 (1H, d, J=8.4 Hz), 7.43 (1H, d, J=8.4 Hz)
MS: 861.00 [M+H]+, 858.95 [M−H]−

Example 137

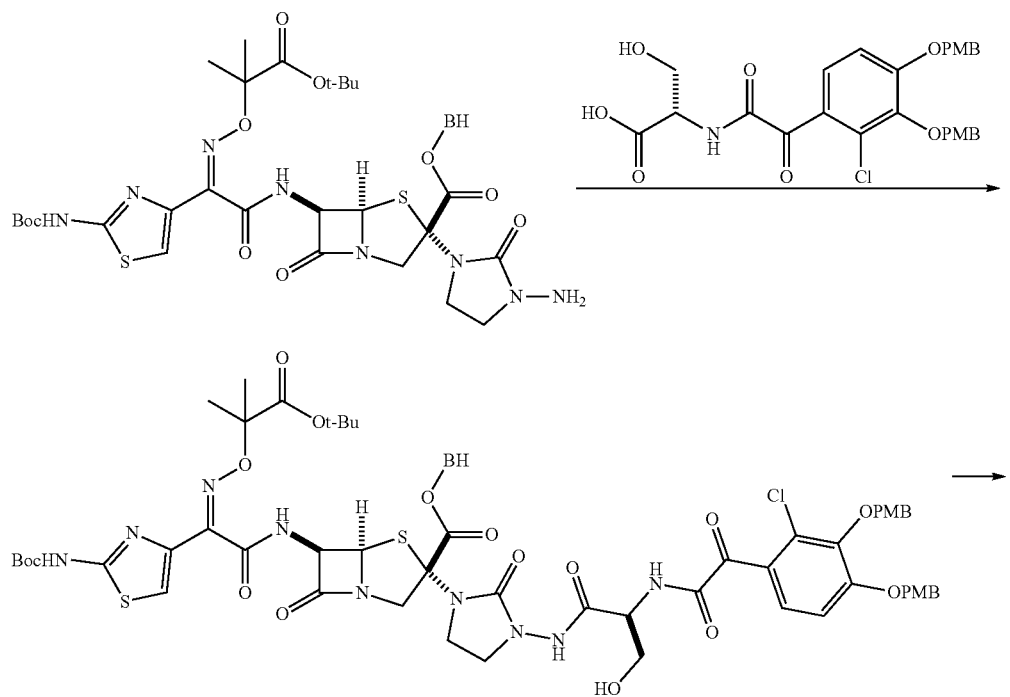

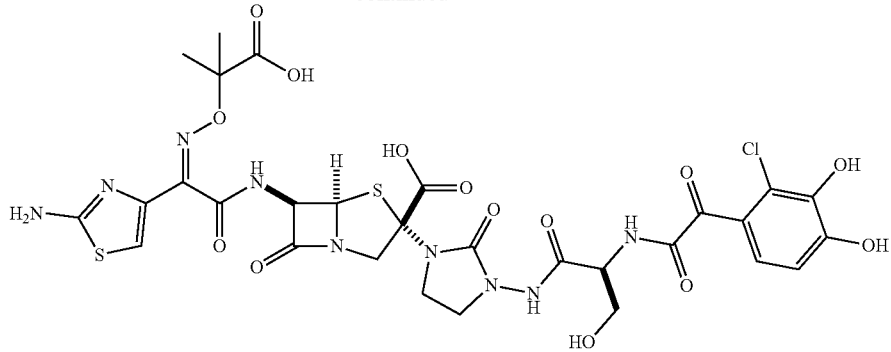

Example 137 (1)

(2-(2-Chloro-3,4-bis((4-methoxybenzyl)oxy)phenyl)-2-oxoacetyl)-L-serine (166 mg), 4-(4,6-dimethoxy-1,3,5-triazin-2-yl)-4-methylmorpholinium chloride (137 mg), and THF (3.6 mL) were sequentially added to benzhydryl (3R,5R,6R)-3-(3-amino-2-oxoimidazolidin-1-yl)-6-((Z)-2-(((1-(tert-butoxy)-2-methyl-1-oxopropan-2-yl)oxy)imino)-2-(2-((tert-butoxycarbonyl)amino)thiazol-4-yl)acetamido)-7-oxo-4-thia-1-azabicyclo[3.2.0]heptane-3-carboxylate (120 mg). The reaction mixture was stirred at room temperature overnight. Ethyl acetate (6 mL) and water (6 mL) were added to the reaction mixture, and the organic layer was separated. The aqueous layer was extracted twice by using ethyl acetate (10 mL). The organic layer was washed a saturated aqueous sodium chloride solution (20 mL) and dehydrated and dried over anhydrous sodium sulfate. The solvent was distilled away under reduced pressure. The residue was purified by silica gel column chromatography [eluent; ethyl acetate:hexane=50:50→100:0], thereby obtaining a target substance (200 mg) as brown solids.

Example 137 (2)

Dichloromethane (4 mL) was added to the compound (200 mg) obtained in Example 137 (1), and the mixture was stirred at −20° C. At the same temperature, anisole (940 μL) and aluminum chloride (288 mg) were sequentially added to the reaction mixture. The reaction mixture was stirred at a temperature equal to or lower than −20° C. for 30 minutes. The reaction mixture was added to a mixture of acetonitrile (15 mL), water (15 mL), and trisodium citrate dihydrate (952 mg) under ice cooling. A saturated aqueous sodium hydrogen carbonate solution was added to the reaction mixture such that the pH was adjusted to 5.2, and the aqueous layer was separated. The aqueous layer was concentrated under reduced pressure, and the residue was purified by medium-pressure reverse-phase silica gel column chromatography [eluent; water:acetonitrile=100:0→85:15]. The aqueous solution containing a target substance was lyophilized, thereby obtaining (3R,5R,6R)-6-((Z)-2-(2-aminothiazol-4-yl)-2-(((2-carboxypropan-2-yl)oxy)imino)acetamido)-3-(3-((S)-2-(2-(2-chloro-3,4-dihydroxyphenyl)-2-oxoacetamido)-3-hydroxypropanamido)-2-oxoimidazolidin-1-yl)-7-oxo-4-thia-1-azabicyclo[3.2.0]heptane-3-carboxylate (35 mg) as yellow solids.

NMR: 1.49 (3H, s), 1.50 (3H, s), 3.54-3.68 (3H, m), 3.68-3.76 (2H, m), 3.99 (2H, d, J=5.6 Hz), 4.66 (1H, d, J=13.2 Hz), 5.69 (1H, d, J=3.6 Hz), 5.75 (1H, d, J=4.0 Hz), 6.95 (1H, d, J=8.4 Hz), 7.04 (1H, s), 7.40 (1H, d, J=8.8 Hz)

MS: 828.00 [M+H]$^+$, 826.15 [M−H]$^-$

The compounds shown in Table 31 were obtained in the same manner as in Example 137.

TABLE 31

| Example No | Structural Formula | Name |
|---|---|---|
| 138 | | (3R,5R,6R)-6-((Z)-2-(2-aminothiazol-4-yl)-2-(((2-carboxypropan-2-yl)oxy)imino)acetamido)-3-(3-((R)-2-(2-(2-chloro-3,4-dihydroxyphenyl)-2-oxoacetamido)-3-hydroxypropanamido)-2-oxoimidazolidin-1-yl)-7-oxo-4-thia-1-azabicyclo[3.2.0]heptane-3-carboxylate |

TABLE 31-continued

| Example No | Structural Formula | Name |
|---|---|---|
| 139 | | (3R,5R,6R)-6-((Z)-2-(2-aminothiazol-4-yl)-2-(((2-carboxypropan-2-yl)oxy)imino)acetamido)-3-(3-((R)-2-(2-(2-chloro-3,4-dihydroxyphenyl)-2-oxoacetamido)-3-hydroxypropanamido)-2-oxoimidazolidin-1-yl)-7-oxo-4-thia-1-azabicyclo[3.2.0]heptane-3-carboxylate |
| 140 | | (3R,5R,6R)-6-((Z)-2-(2-aminothiazol-4-yl)-2-(((2-carboxypropan-2-yl)oxy)imino)acetamido)-3-(3-(2-(2-chloro-N,3,4-trihydroxybenzamido)-2-oxoimidazolidin-1-yl)-7-oxo-4-thia-1-azabicyclo[3.2.0]heptane-3-carboxylate |

The measured values of NMR and MS of the compounds in the table are as follows.

Example 138

NMR: 1.48 (3H, s), 1.50 (3H, s), 3.53-3.67 (3H, m), 3.67-3.75 (2H, m), 3.99 (2H, d, J=6.0 Hz), 4.67 (1H, d, J=5.6 Hz), 5.69 (1H, d, J=4.0 Hz), 5.74 (1H, d, J=3.2 Hz), 6.94 (1H, d, J=8.8 Hz), 7.03 (1H, s), 7.39 (1H, d, J=8.8 Hz)
MS: 828.00 [M+H]$^+$, 826.15 [M−H]$^−$

Example 139

NMR: 1.46 (3H, s), 1.47 (3H, s), 3.40 (3H, s), 3.42-3.47 (1H, m), 3.51-3.64 (3H, m), 3.64-3.71 (2H, m), 3.84 (2H, d, J=5.6 Hz), 4.62 (1H, d, J=12.8 Hz), 5.65 (1H, d, J=4.0 Hz), 5.71 (1H, d, J=3.2 Hz), 6.94 (1H, d, J=8.4 Hz), 7.01 (1H, s), 7.36 (1H, d, J=8.4 Hz)
MS: 841.95 [M+H]$^+$, 840.05 [M−H]$^−$

Example 140

NMR: 1.49 (3H, s), 1.51 (3H, s), 3.54-3.86 (7H, m), 4.66 (1H, dd, J=12.6, 3.0 Hz), 5.69 (1H, d, J=3.6 Hz), 5.75 (1H, d, J=3.2 Hz), 6.93 (1H, d, J=8.4 Hz), 7.03 (1H, s), 7.07 (1H, d, J=8.4 Hz)
MS: 786.05 [M+H]$^+$, 783.95 [M−H]$^−$

Example 141

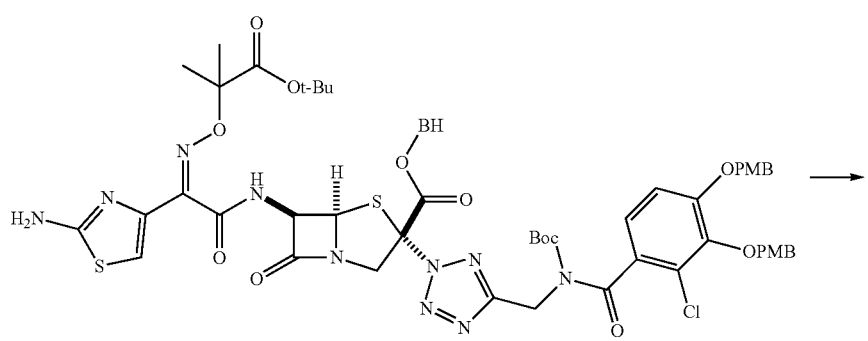

-continued

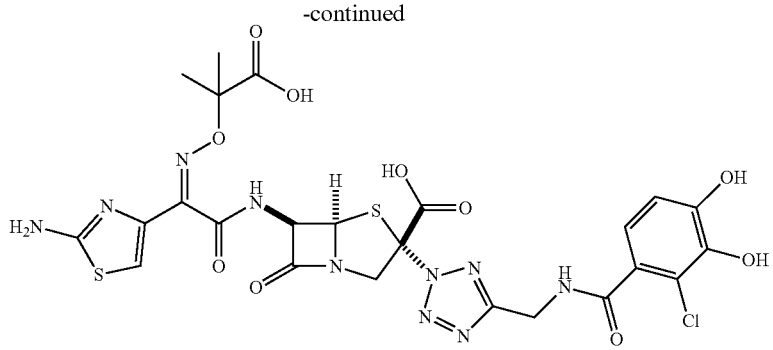

Dichloromethane (1.1 mL) was added to benzhydryl (3R,5R,6R)-6-((Z)-2-(2-aminothiazol-4-yl)-2-(((1-(tert-butoxy)-2-methyl-1-oxopropan-2-yl)oxy)imino)acetamido)-3-(5-((N-(tert-butoxycarbonyl)-2-chloro-3,4-bis((4-methoxybenzyl)oxy)benzamido)methyl)-2H-tetrazol-2-yl)-7-oxo-4-thia-1-azabicyclo[3.2.0]heptane-3-carboxylate (71 mg), and the mixture was stirred at −20° C. At the same temperature, anisole (0.36 mL) and aluminum chloride (110 mg) were sequentially added to the reaction mixture. The reaction mixture was stirred at a temperature equal to or lower than −20° C. for 50 minutes. The reaction mixture was added to a mixture of acetonitrile (5 mL), water (5 mL), and trisodium citrate dihydrate (0.37 g) under ice cooling. A saturated aqueous sodium hydrogen carbonate solution was added to the reaction mixture such that the pH was adjusted to 5.1, and the aqueous layer was separated. The aqueous layer was concentrated under reduced pressure, and the residue was purified by medium-pressure reverse-phase silica gel column chromatography [eluent; water:acetonitrile=100:0→75:25]. The aqueous solution containing a target substance was lyophilized, thereby obtaining (3R,5R,6R)-6-((Z)-2-(2-aminothiazol-4-yl)-2-(((2-carboxypropan-2-yl)oxy)imino)acetamido)-3-(5-((2-chloro-3,4-dihydroxybenzamido)methyl)-2H-tetrazol-2-yl)-7-oxo-4-thia-1-azabicyclo[3.2.0]heptane-3-carboxylate (7.6 mg) as white solids.

NMR: 1.45 (3H, s), 1.46 (3H, s), 4.16 (1H, d, J=12.8 Hz), 4.67 (1H, dd, J=16.4, 5.6 Hz), 4.78 (1H, dd, J=16.4, 5.6 Hz), 4.90 (1H, d, J=12.8 Hz), 5.70 (1H, d, J=4.0 Hz), 5.77 (1H, dd, J=8.0, 4.0 Hz), 6.78 (1H, d, J=8.0 Hz), 6.84 (1H, s), 6.86 (1H, d, J=8.0 Hz), 7.70 (1H, d, J=1.2 Hz), 8.86 (1H, t, J=5.6 Hz), 9.34 (1H, d, J=8.0 Hz), 10.08-10.09 (1H, brs)

MS: 711.05 [M+H]$^+$, 708.90 [M−H]$^-$

Test Example 1 Antibacterial Activity Evaluation Test

The minimum inhibitory concentration (MIC) was measured according to the Clinical and Laboratory Standards Institute (CLSI) standard method by using the following broth microdilution method.

As bacteria, a *Pseudomonas aeruginosa* strain ATCC27853, an AmpC-derepressed *Pseudomonas aeruginosa* mutant strain (S-3028), an IMP-1-containing *Pseudomonas aeruginosa* strain (S-2838), a VIM-2-containing *Pseudomonas aeruginosa* strain (S-3779), a GES-19 and GES-20-containing *Pseudomonas aeruginosa* strain (S-3759), a CTX-M-15-containing *Escherichia coli* strain (TK-1747), a KPC-2-containing *Klebsiella pneumoniae* strain (Y-995), an OXA-48-containing *Klebsiella pneumoniae* strain (Y-1062), and an NDM-1-containing *Klebsiella pneumoniae* strain (Y-1007) were used. The test bacterial cells that had been cultured overnight on a Mueller Hinton agar medium were scraped off, suspended at a density equivalent to 0.5 McFarland standard, and diluted 10-fold, thereby obtaining an inoculum. A cation-adjusted Mueller Hinton medium containing a test compound was inoculated with 0.005 mL of the inoculum, and the cells were cultured at 35° C. for 16 to 20 hours. The minimum drug concentration at which the growth of bacteria was not visually observed was defined as MIC (g/mL).

As test compounds, the compounds obtained in Examples 2, 8, 19, 20, 21, 22, 23, 28, 29, 30, 31, 45, 47, 53, and 68 were used.

The results are shown in Table 32.

TABLE 32

| Example No. | Pseudomonas aeruginosa ATCC 27853 | Pseudomonas aeruginosa S-3028 | Pseudomonas aeruginosa S-2838 | Pseudomonas aeruginosa S-3779 | Pseudomonas aeruginosa S3759 |
|---|---|---|---|---|---|
| 2 | 1 | 1 | 0.5 | 0.25 | 4 |
| 8 | 0.25 | 0.5 | 4 | 1 | 2 |
| 19 | 0.25 | 2 | 0.25 | 0.25 | 0.25 |
| 20 | 0.5 | 0.25 | 0.12 | 0.25 | 0.5 |
| 21 | 0.25 | 4 | 2 | 0.5 | 1 |
| 22 | 0.5 | 0.5 | 0.5 | 0.25 | 0.5 |
| 23 | 0.25 | 0.5 | 1 | 0.25 | 1 |
| 28 | 0.5 | 0.25 | 0.25 | 0.5 | 2 |
| 29 | 0.25 | <0.06 | 1 | 0.5 | 0.5 |
| 30 | 0.25 | <0.06 | 0.5 | 0.5 | 0.5 |
| 31 | 0.25 | <0.06 | 1 | 0.25 | 0.5 |
| 45 | 1 | 2 | 2 | 1 | 2 |
| 47 | 0.5 | 0.12 | 4 | 1 | 1 |

TABLE 32-continued

| | | | | | |
|---|---|---|---|---|---|
| 53 | 0.5 | 1 | 4 | 0.5 | 2 |
| 68 | 1 | 0.25 | 1 | 2 | 4 |

| Example No. | Escherichia coli TK-1747 | Klebsiella pneumoniae Y-1007 | Klebsiella pneumoniae Y-995 | Klebsiella pneumoniae Y-1062 |
|---|---|---|---|---|
| 2 | 0.25 | <0.06 | 0.12 | 2 |
| 8 | 0.12 | <0.06 | 0.06 | 16 |
| 19 | 0.5 | <0.06 | 0.25 | 0.12 |
| 20 | <0.06 | <0.06 | 0.12 | 0.5 |
| 21 | 0.12 | <0.06 | <0.06 | 2 |
| 22 | <0.06 | <0.06 | 0.06 | 0.06 |
| 23 | 0.25 | <0.06 | 0.25 | 0.5 |
| 28 | 2 | <0.06 | 1 | 0.25 |
| 29 | 2 | <0.06 | 0.5 | 1 |
| 30 | 0.25 | <0.06 | 0.25 | 0.5 |
| 31 | 1 | 0.12 | 0.12 | 1 |
| 45 | 0.12 | <0.06 | 0.25 | 1 |
| 47 | <0.06 | <0.06 | 0.5 | 0.25 |
| 53 | 2 | 0.12 | 2 | 0.5 |
| 68 | 1 | <0.06 | 0.5 | 1 |

Test Example 2 Test for Protection Against Systemic Infection in Mouse with Multidrug-Resistant *Pseudomonas aeruginosa*

As mice, ICR male SPF mice (4 weeks old: 10 mice per group) were used. Clinically isolated multidrug-resistant *Pseudomonas aeruginosa* strain (S-2838 strain) cultured overnight on a Mueller-Hinton agar plate at 37° C. was cultured on a cation-adjusted Mueller Hinton medium for 5 hours, and then diluted 20-fold with a 10% mucin/phosphate buffer, thereby preparing an inoculum. An infection was induced by intraperitoneally inoculating the mice with the inoculum at 0.5 mL (about $10^6$ CFU/mouse). Each test compound was dissolved in physiological saline, and 1 hour after the infection, the compound was subcutaneously administered once to the mice at 40 mg/kg. The control group was administered with the same amount of physiological saline used as a vehicle. The number of surviving mice was recorded 3 days after the infection.

As the test compounds, the compounds obtained in Examples 19, 20, 21, 22, 23, and 31 were used.

As a result, it has been revealed that while all the control groups not being administered with the test compounds die, the mice in the groups administered with the test compounds of Examples 19, 20, 21, 22, 23, and 31 show a survival rate equal to or higher than 90% 3 days after the inoculation with bacteria, which tells that the test compounds have in-vivo antibacterial activity against multidrug-resistant *Pseudomonas aeruginosa*.

Test Example 3

An antibacterial activity evaluation test was performed in the same manner as in Test Example 1.

As test compounds, the compounds obtained in Examples 26, 73, 74, 76, 78, 82, 83, 84, 85, 86, 88, 104, 105, 107, 113, 114, 115, 117, 121, 122, 126, 136, 139, and 141 were used.

The results are shown in Table 33.

TABLE 33

| Example No. | Pseudomonas aeruginosa ATCC 27853 | Pseudomonas aeruginosa S-3028 | Pseudomonas aeruginosa S-2838 | Pseudomonas aeruginosa S-3779 | Pseudomonas aeruginosa S3759 |
|---|---|---|---|---|---|
| 26 | 1 | 0.12 | 0.25 | 0.25 | 0.25 |
| 73 | 0.5 | 0.25 | 0.5 | 1 | 0.5 |
| 74 | 0.5 | 0.5 | 0.25 | 1 | 1 |
| 76 | 0.5 | 0.12 | 0.5 | 0.25 | 0.25 |
| 78 | 0.5 | <0.06 | 1 | 0.25 | 1 |
| 82 | 0.5 | 4 | 4 | 1 | 2 |
| 83 | 0.25 | 0.5 | 0.5 | 0.5 | 1 |
| 84 | 0.5 | 0.5 | 0.5 | 0.5 | 1 |
| 85 | 0.5 | 0.12 | 0.25 | 0.25 | 0.25 |
| 86 | 4 | 1 | 1 | 2 | 2 |
| 88 | 0.5 | 0.5 | 0.5 | 0.5 | 0.5 |
| 104 | 2 | 2 | 0.5 | 1 | 4 |
| 105 | 0.25 | <0.06 | 0.25 | 0.25 | 0.5 |
| 107 | 0.25 | 2 | 0.5 | 0.25 | 0.5 |
| 113 | 4 | 0.25 | 0.5 | 0.5 | 1 |
| 114 | 2 | 1 | 4 | 1 | 2 |
| 115 | 0.5 | 0.12 | 1 | 0.5 | 0.5 |
| 117 | 2 | 0.25 | 2 | 0.5 | 2 |
| 121 | 2 | 2 | 4 | 1 | 2 |
| 122 | 1 | 2 | 2 | 2 | 2 |
| 126 | 1 | 0.5 | 2 | 1 | 0.5 |
| 136 | 0.5 | 0.12 | 0.12 | 0.5 | 0.5 |

TABLE 33-continued

| | | | | |
|---|---|---|---|---|
| 139 | 1 | 0.5 | 0.5 | 1 | 2 |
| 141 | 1 | 0.5 | 0.25 | 1 | 4 |

| Example No. | Escherichia coli TK-1747 | Klebsiella pneumoniae Y-1007 | Klebsiella pneumoniae Y-995 | Klebsiella pneumoniae Y-1062 |
|---|---|---|---|---|
| 26 | 0.12 | <0.06 | 0.12 | 0.5 |
| 73 | 0.25 | 0.12 | 16 | 1 |
| 74 | 1 | 0.25 | 2 | 4 |
| 76 | 0.06 | 0.25 | 0.25 | 0.25 |
| 78 | 0.25 | <0.06 | 0.25 | 0.25 |
| 82 | 1 | 0.5 | 4 | 2 |
| 83 | 0.5 | <0.06 | 0.25 | 2 |
| 84 | <0.06 | <0.06 | 0.5 | <0.06 |
| 85 | <0.06 | <0.06 | <0.06 | 0.12 |
| 86 | 1 | <0.06 | 0.5 | 1 |
| 88 | 2 | <0.06 | 0.25 | 0.5 |
| 104 | 1 | <0.06 | 2 | 2 |
| 105 | 0.5 | <0.06 | 0.12 | 0.5 |
| 107 | 0.25 | <0.06 | 2 | 0.25 |
| 113 | <0.06 | <0.06 | 0.12 | 0.25 |
| 114 | 0.25 | <0.06 | 0.25 | 0.25 |
| 115 | 0.25 | <0.06 | 0.25 | 1 |
| 117 | 0.12 | <0.06 | 0.25 | 0.5 |
| 121 | <0.06 | 0.12 | 0.25 | 0.5 |
| 122 | 0.5 | <0.06 | 0.5 | 1 |
| 126 | <0.06 | <0.06 | 0.12 | 1 |
| 136 | <0.06 | 0.12 | 0.25 | 0.12 |
| 139 | 2 | 0.12 | 1 | 4 |
| 141 | 0.5 | 0.25 | >32 | 1 |

Test Example 4

A test for protection against systemic infection in a mouse with multidrug-resistant *Pseudomonas aeruginosa* was performed in the same manner as in Test Example 2.

As test compounds, the compounds obtained in Examples 83, 105, 114, 117, 122, 126, and 139 were used.

As a result, it has been revealed that while all the control groups not being administered with the test compounds die, the mice in the groups administered with the test compounds of Examples 83, 105, 114, 117, 122, 126, and 139 show a survival rate equal to or higher than 90% 3 days after the inoculation with bacteria, which tells that the test compounds have in-vivo antibacterial activity against multidrug-resistant *Pseudomonas aeruginosa*.

The compound represented by General Formula [1] or a salt thereof has a strong antibacterial activity against Gram-negative bacteria such as *Pseudomonas aeruginosa* and drug-resistant Gram-negative bacteria including multidrug-resistant *Pseudomonas aeruginosa*, for example, enterobacteria or *Pseudomonas aeruginosa* producing carbapenemase. Therefore, the compound or a salt thereof is useful as an antibacterial agent.

What is claimed is:

1. A compound represented by General Formula [1] or a salt thereof,

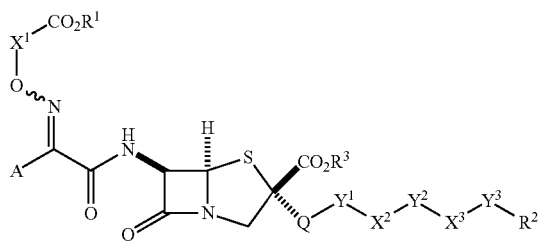

[1]

in the formula, $R^1$ represents a hydrogen atom or a carboxyl protecting group;

$R^2$ represents an aryl group which may be substituted or a heterocyclic group which may be substituted;

$R^3$ represents a hydrogen atom or a carboxyl protecting group;

$X^1$ represents a $C_{1-6}$ alkylene group which may be substituted, a $C_{2-6}$ alkenylene group which may be substituted, a $C_{2-6}$ alkynylene group which may be substituted, a divalent cyclic hydrocarbon group which may be substituted, or a divalent monocyclic saturated heterocyclic group which may be substituted;

A represents a heterocyclic group which may be substituted;

Q represents a divalent cyclic amino group which may be substituted or a divalent heterocyclic group which may be substituted;

$Y^1$ represents a $C_{1-6}$ alkylene group which may be substituted, a $C_{2-6}$ alkenylene group which may be substituted, a $C_{2-6}$ alkynylene group which may be substituted, a group represented by Formula —N=CH—CH=N—, a group represented by Formula —N=CH—CH=N—O—, a group represented by Formula —N=CH—CH$_2$—, a group represented by Formula —N=CHC(=O)—, a group represented by Formula —NHC(=O)—, a group represented by Formula —NHC(=O)CH$_2$—, a group represented by Formula —NHC(=O)NH—, a group represented by Formula —NHC(=O)NH—O—, a group represented by Formula —NHC(=O)C(=O)NH—, a group represented by Formula —NHC(=O)C(=O)N(OH)—, a group represented by Formula —NHCH$_2$C(=O)—, a group represented by Formula —NHS(=O)$_2$NHC(=O)—, a group represented by Formula —NHC(=O)NHS(=O)$_2$—, or a bond;

$X^2$ represents a group represented by General Formula —NR$^4$— (where R$^4$ represents a hydrogen atom, a carbamoyl group, a $C_{1-6}$ alkyl group which may be substituted, or a hydroxyl group which may be protected), a group represented by General Formula —N$^+$R$^5$R$^6$— (where R$^5$ and R$^6$ are the same as or different from each other and each represent a $C_{1-6}$ alkyl group which may be substituted, or in combination represent a $C_{2-6}$ alkylene group which may be substituted or a $C_{2-6}$ alkenylene group which may be substituted), a group represented by General Formula —NR$^7$—C(=O)—NR$^8$— (where R$^7$ and R$^8$ are the same as or different from each other and each represent a hydrogen atom, a $C_{1-6}$ alkyl group which may be substituted, or a hydroxyl group which may be protected), a divalent cyclic amino group which may be substituted, a divalent heterocyclic group which may be substituted, or a bond;

Y$^2$ represents a $C_{1-6}$ alkylene group which may be substituted, a $C_{2-6}$ alkenylene group which may be substituted, a $C_{2-6}$ alkynylene group which may be substituted, or a bond; X$^3$ represents a group represented by General Formula —NR$^9$— (where R$^9$ represents a hydrogen atom, a $C_{1-6}$ alkyl group which may be substituted, or a hydroxyl group which may be protected) or a bond; and Y$^3$ represents a group represented by Formula —C(=O)—, a group represented by Formula —C(=O)—C(=O)—, a group represented by General Formula —C(=O)—C(=NR$^{10a}$)— (where R$^{10a}$ represents a $C_{1-6}$ alkoxy group which may be substituted, a hydroxyl group which may be protected, or a ureido group), or a group represented by Formula —N=CR$^{11a}$— (where R$^{11a}$ represents a carbamoyl group which may be substituted or a carboxyl group which may be protected).

2. The compound or a salt thereof according to claim 1, wherein R$^2$ represents an aryl group which may be substituted.

3. The compound or a salt thereof according to claim 1, wherein A represents a monocyclic heterocyclic group which may be substituted.

4. The compound or a salt thereof according to claim 1, wherein X$^1$ represents a $C_{1-6}$ alkylene group which may be substituted or a divalent cyclic hydrocarbon group which may be substituted.

5. The compound or a salt thereof according to claim 1, wherein Q represents a divalent heterocyclic group which may be substituted.

6. The compound or a salt thereof according to claim 1, wherein Y$^1$ represents a $C_{1-6}$ alkylene group which may be substituted, a group represented by Formula —N=CH—CH=N—, a group represented by Formula —N=CH—CH$_2$—, a group represented by Formula —N=CHC(=O)—, a group represented by Formula —NHC(=O)—, a group represented by Formula —NHC(=O)CH$_2$—, a group represented by Formula —NHC(=O)NH—, a group represented by Formula —NHC(=O)NH—O—, a group represented by Formula —NHC(=O)C(=O)NH—, a group represented by Formula —NHCH$_2$C(=O)—, or a bond.

7. The compound or a salt thereof according to claim 1, wherein X$^2$ represents a group represented by General Formula —NR$^{4a}$— (where R$^{4a}$ represents a hydrogen atom or a carbamoyl group), a group represented by General Formula —N$^+$R$^{5a}$R$^{6a}$— (where R$^{5a}$ and R$^{6a}$ in combination represent a $C_{2-6}$ alkylene group which may be substituted), a group represented by General Formula —NR$^{7a}$—C(=O)—NR$^{8a}$— (where R$^{7a}$ and R$^{8a}$ each represent a hydrogen atom), a divalent cyclic amino group which may be substituted, a divalent heterocyclic group which may be substituted, or a bond.

8. The compound or a salt thereof according to claim 1, wherein Y$^2$ represents a $C_{1-6}$ alkylene group which may be substituted or a bond.

9. The compound or a salt thereof according to claim 1, wherein X$^3$ represents a group represented by General Formula —NR$^{9a}$— (where R$^{9a}$ represents a hydrogen atom) or a bond.

10. The compound or a salt thereof according to claim 1, wherein R$^3$ represents a hydrogen atom.

11. The compound or a salt thereof according to claim 1, wherein R$^1$ represents a hydrogen atom.

12. The compound or a salt thereof according to claim 1, wherein R$^2$ represents a phenyl group which may be substituted;

A represents a monocyclic nitrogen and sulfur-containing heterocyclic group which may be substituted;

Q represents a divalent monocyclic heterocyclic group which may be substituted;

Y$^1$ represents a group represented by Formula —NHC(=O)—, a group represented by Formula —NHC(=O)C(=O)NH—, or a bond;

X$^2$ represents a group represented by General Formula —NR$^{4b}$— (where R$^{4b}$ represents a hydrogen atom) or a bond;

Y$^2$ represents a $C_{1-3}$ alkylene group or a bond; and

Y$^3$ represents a group represented by Formula —C(=O)— or a group represented by Formula —C(=O)—C(=O)—.

13. The compound or a salt thereof according to claim 1, wherein the compound is a compound selected from (3R,5R,6R)-6-((Z)-2-(2-aminothiazol-4-yl)-2-((1-carboxycyclobutoxy)imino)acetamido)-3-(3-(2-(2-chloro-3,4-dihydroxyphenyl)-2-oxoacetamido)-2-oxoimidazolidin-1-yl)-7-oxo-4-thia-1-azabicyclo[3.2.0]heptane-3-carboxylate, (3R,5R,6R)-6-((Z)-2-(2-aminothiazol-4-yl)-2-(((2-carboxypropan-2-yl)oxy)imino)acetamido)-3-(3-(2-(2-chloro-3,4-dihydroxyphenyl)-2-oxoacetamido)-2-oxoimidazolidin-1-yl)-7-oxo-4-thia-1-azabicyclo[3.2.0]heptane-3-carboxylate, (3R,5R,6R)-6-((Z)-2-(2-amino-5-chlorothiazol-4-yl)-2-(((2-carboxypropan-2-yl)oxy)imino)acetamido)-3-(3-(2-(2-chloro-3,4-dihydroxyphenyl)-2-oxoacetamido)-2-oxoimidazolidin-1-yl)-7-oxo-4-thia-1-azabicyclo[3.2.0]heptane-3-carboxylate, (3R,5R,6R)-6-((Z)-2-(2-aminothiazol-4-yl)-2-(((2-carboxypropan-2-yl)oxy)imino)acetamido)-3-((S)-3-(2-(2-chloro-3,4-dihydroxyphenyl)-2-oxoacetamido)-2-oxopyrrolidin-1-yl)-7-oxo-4-thia-1-azabicyclo[3.2.0]heptane-3-carboxylate, (3R,5R,6R)-6-((Z)-2-(2-aminothiazol-4-yl)-2-(((2-carboxypropan-2-yl)oxy)imino)acetamido)-3-((R)-3-(2-(2-chloro-3,4-dihydroxyphenyl)-2-oxoacetamido)-2-oxopyrrolidin-1-yl)-7-oxo-4-thia-1-azabicyclo[3.2.0]heptane-3-carboxylate, (3R,5R,6R)-6-((Z)-2-(2-aminothiazol-4-yl)-2-(((2-carboxypropan-2-yl)oxy)imino)acetamido)-3-(4-(2-(2-chloro-3,4-dihydroxyphenyl)-2-oxoacetatamido)-2,3-dioxopiperazin-1-yl)-7-oxo-4-thia-1-azabicyclo[3.2.0]heptane-3-carboxylate, and (3R,5R,6R)-6-((Z)-2-(2-amino-5-chlorothiazol-4-yl)-2-(((2-carboxypropan-2-yl)oxy)imino)acetamido)-3-(3-(2-(2-(2-chloro-3,4-dihydroxyphenyl)-2-oxoacetyl)hydradienyl)-2-oxoacetamido)-2-oxoimidazolidin-1-yl)-7-oxo-4-thia-1-azabicyclo[3.2.0]heptane-3-carboxylate.

14. A pharmaceutical composition comprising:
the compound or a salt thereof according to claim 1.

15. A method for treating infections caused by Gram-negative bacteria or drug-resistant Gram-negative bacteria, comprising administering an effective amount of the compound or a salt thereof according to claim 1 to a subject that has a Gram-negative bacteria or drug-resistant Gram-negative bacteria infection.

\* \* \* \* \*